United States Patent
Ahrendt et al.

(10) Patent No.: US 8,394,795 B2
(45) Date of Patent: Mar. 12, 2013

(54) PYRAZOLE [3, 4-B] PYRIDINE RAF INHIBITORS

(75) Inventors: Kateri A. Ahrendt, Boulder, CO (US); Alexandre J. Buckmelter, Boulder, CO (US); Jason De Meese, Boulder, CO (US); Jonas Grina, Boulder, CO (US); Joshua D. Hansen, Boulder, CO (US); Ellen R. Laird, Boulder, CO (US); Paul Lunghofer, Boulder, CO (US); David Moreno, Boulder, CO (US); Brad Newhouse, Boulder, CO (US); Li Ren, Boulder, CO (US); Jeongbeob Seo, Boulder, CO (US); Hongqi Tian, Boulder, CO (US); Steven Mark Wenglowsky, Boulder, CO (US); Bainian Feng, South San Francisco, CA (US); Janet Gunzner, South San Francisco, CA (US); Kim Malesky, South San Francisco, CA (US); Simon Mathieu, South San Francisco, CA (US); Joachim Rudolph, South San Francisco, CA (US); Zhaoyang Wen, South San Francisco, CA (US); Wendy B. Young, South San Francisco, CA (US)

(73) Assignees: Array BioPharma Inc., Boulder, CO (US); Genentech, Inc., South San Francisco, CA (US)

( * ) Notice: Subject to any disclaimer, the term of this patent is extended or adjusted under 35 U.S.C. 154(b) by 120 days.

(21) Appl. No.: 12/920,050

(22) PCT Filed: Feb. 27, 2009

(86) PCT No.: PCT/US2009/035381
§ 371 (c)(1),
(2), (4) Date: Dec. 22, 2010

(87) PCT Pub. No.: WO2009/111279
PCT Pub. Date: Sep. 11, 2009

(65) Prior Publication Data
US 2011/0092479 A1     Apr. 21, 2011

Related U.S. Application Data

(60) Provisional application No. 61/032,813, filed on Feb. 29, 2008.

(51) Int. Cl.
*A61K 31/535* (2006.01)
*A61K 31/44* (2006.01)
*C07D 413/14* (2006.01)
*C07D 471/04* (2006.01)

(52) U.S. Cl. .................. 514/234.2; 514/303; 544/127; 546/119

(58) Field of Classification Search ............ 544/127; 546/119; 514/234.2, 303
See application file for complete search history.

(56) References Cited

U.S. PATENT DOCUMENTS

| | | | |
|---|---|---|---|
| 3,542,793 A * | 11/1970 | Eichenberger et al. ....... 546/119 |
| 4,328,155 A | 5/1982 | Masaru et al. |
| 7,235,576 B1 | 6/2007 | Riedl et al. |
| 7,351,834 B1 | 4/2008 | Riedl et al. |
| 2001/0011135 A1 | 8/2001 | Riedl et al. |
| 2002/0137774 A1 | 9/2002 | Riedl et al. |
| 2002/0165394 A1 | 11/2002 | Dumas et al. |
| 2003/0105091 A1 | 6/2003 | Riedl et al. |
| 2003/0139605 A1 | 7/2003 | Riedl et al. |
| 2003/0181442 A1 | 9/2003 | Riedl et al. |
| 2003/0207914 A1 | 11/2003 | Dumas et al. |
| 2004/0087626 A1 | 5/2004 | Renhowe et al. |
| 2005/0085482 A1 | 4/2005 | Ramurthy et al. |
| 2005/0187230 A1 | 8/2005 | Ding et al. |
| 2005/0192287 A1 | 9/2005 | Costales et al. |
| 2006/0189627 A1 | 8/2006 | Laird et al. |
| 2006/0281751 A1 | 12/2006 | Laird et al. |
| 2006/0281762 A1 | 12/2006 | Staehle et al. |
| 2006/0293340 A1 | 12/2006 | Batt et al. |
| 2007/0010560 A1 | 1/2007 | Buchstaller et al. |
| 2007/0021456 A1 | 1/2007 | Mitjans et al. |

(Continued)

FOREIGN PATENT DOCUMENTS

| | | | |
|---|---|---|---|
| WO | WO 99/30710 A1 | 6/1999 |
| WO | WO 99/32106 A1 | 7/1999 |

(Continued)

OTHER PUBLICATIONS

European Office Action for EP App. No. 09718306.5, 4 pages, dated Feb. 2, 2011.

(Continued)

*Primary Examiner* — Rebecca Anderson
(74) *Attorney, Agent, or Firm* — Viksnins Harris & Padys PLLP

(57) ABSTRACT

Compounds of Formula I are useful for inhibition of Raf kinases. Methods of using compounds of Formula I and stereoisomers, tautomers, prodrugs and pharmaceutically acceptable salts thereof, for in vitro, in situ, and in vivo diagnosis, prevention or treatment of such disorders in mammalian cells, or associated pathological conditions are disclosed.

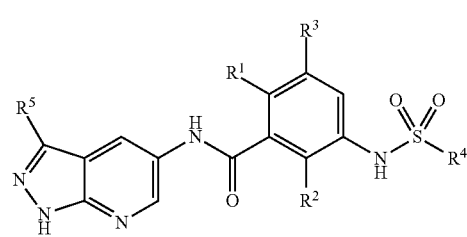

45 Claims, No Drawings

U.S. PATENT DOCUMENTS

| | | |
|---|---|---|
| 2007/0032519 A1 | 2/2007 | Zhang et al. |
| 2007/0049603 A1 | 3/2007 | Miknis et al. |
| 2007/0049615 A1 | 3/2007 | Ibrahim et al. |
| 2007/0054916 A1 | 3/2007 | Patel et al. |
| 2007/0060607 A1 | 3/2007 | Bartkovitz et al. |
| 2007/0078121 A1 | 4/2007 | Flynn et al. |
| 2007/0093532 A1 | 4/2007 | Buchstaller et al. |
| 2007/0142440 A1 | 6/2007 | Burgdorf et al. |
| 2007/0149533 A1 | 6/2007 | Calderwood et al. |
| 2007/0155746 A1 | 7/2007 | Lang et al. |
| 2007/0155764 A1 | 7/2007 | Lang et al. |
| 2007/0259849 A1 | 11/2007 | Aquila et al. |
| 2007/0287838 A1 | 12/2007 | Niculescu-Duvaz et al. |
| 2008/0114006 A1 | 5/2008 | Flynn et al. |
| 2008/0146570 A1 | 6/2008 | Aquila et al. |
| 2008/0167338 A1 | 7/2008 | Spevak et al. |
| 2008/0188514 A1 | 8/2008 | Wu et al. |
| 2008/0207616 A1 | 8/2008 | Aquila et al. |
| 2008/0221148 A1 | 9/2008 | Ibrahim et al. |
| 2008/0255184 A1 | 10/2008 | Tang |
| 2008/0300246 A1 | 12/2008 | Xie et al. |
| 2008/0306096 A1 | 12/2008 | Aquila et al. |
| 2009/0054469 A1 | 2/2009 | Aquila et al. |
| 2009/0099190 A1 | 4/2009 | Flynn et al. |
| 2009/0105250 A1 | 4/2009 | Sim et al. |
| 2009/0118261 A1 | 5/2009 | Aquila et al. |
| 2009/0118273 A1 | 5/2009 | Nagle et al. |
| 2009/0149484 A1 | 6/2009 | Aquila et al. |
| 2009/0163525 A1 | 6/2009 | Aquila et al. |
| 2009/0170849 A1 | 7/2009 | Aquila et al. |
| 2009/0286782 A1 | 11/2009 | Ibrahim et al. |
| 2009/0286783 A1 | 11/2009 | Ibrahim et al. |
| 2009/0298815 A1 | 12/2009 | Adams et al. |
| 2009/0306086 A1 | 12/2009 | Ibrahim et al. |
| 2009/0306087 A1 | 12/2009 | Ibrahim et al. |
| 2009/0306107 A1 | 12/2009 | Perez et al. |
| 2009/0318428 A1 | 12/2009 | Honold et al. |
| 2010/0029605 A1 | 2/2010 | Albaugh et al. |
| 2010/0184765 A1 | 7/2010 | Huang et al. |
| 2010/0190777 A1 | 7/2010 | Wu et al. |
| 2010/0249119 A1 | 9/2010 | Hirose et al. |
| 2011/0003809 A1 | 1/2011 | Ahrendt et al. |
| 2011/0003859 A1 | 1/2011 | Ahrendt et al. |
| 2011/0053932 A1 | 3/2011 | Sim et al. |
| 2011/0053946 A1 | 3/2011 | Niculescu-Duvaz et al. |
| 2011/0110889 A1 | 5/2011 | Ahrendt et al. |
| 2011/0118245 A1 | 5/2011 | Abraham et al. |
| 2011/0172245 A1 | 7/2011 | Hirose et al. |
| 2011/0201594 A1 | 8/2011 | Murthi et al. |
| 2012/0130069 A1 | 5/2012 | Sim et al. |

FOREIGN PATENT DOCUMENTS

| | | |
|---|---|---|
| WO | WO 99/32436 A1 | 7/1999 |
| WO | WO 99/32455 A1 | 7/1999 |
| WO | WO 03/068773 A1 | 8/2003 |
| WO | WO 2005/009958 A1 | 2/2005 |
| WO | WO 2005/062795 A2 | 7/2005 |
| WO | WO 2006/040039 A1 | 4/2006 |
| WO | WO 2006/042599 A1 | 4/2006 |
| WO | WO 2006/066913 A2 | 6/2006 |
| WO | WO 2006/067446 A1 | 6/2006 |
| WO | WO 2006/124731 A2 | 11/2006 |
| WO | WO 2006/124731 A3 | 11/2006 |
| WO | WO 2006/124780 A2 | 11/2006 |
| WO | WO 2007/002325 A1 | 1/2007 |
| WO | WO 2007/002433 A1 | 1/2007 |
| WO | WO 2007/013896 A2 | 2/2007 |
| WO | WO 2007/017143 A1 | 2/2007 |
| WO | WO 2007/070398 A1 | 6/2007 |
| WO | WO 2007/076460 A2 | 7/2007 |
| WO | WO 2008/028617 A1 | 3/2008 |
| WO | WO 2008/044688 A1 | 4/2008 |
| WO | WO 2008/079906 A1 | 7/2008 |
| WO | WO 2008/079909 A1 | 7/2008 |
| WO | WO 2008/112695 A2 | 9/2008 |
| WO | WO 2008/124393 A1 | 10/2008 |
| WO | WO 2008/144253 A1 | 11/2008 |
| WO | WO 2009/012283 A1 | 1/2009 |

OTHER PUBLICATIONS

European Office Action for EP App. No. 09718306.5, 4 pages, dated Oct. 10, 2011.

Li et al., "B-Raf Kinase Inhibitors for Cancer Treatment", *Current Opinion in Investigational Drugs*, vol. 8, No. 6, 452-456 (2007).

Patent Cooperation Treaty, International Search Report and Written Opinion for PCT/US2009/035381, 15 pages, dated Jun. 16, 2009.

Smith et al., "Recent Advances in the Research and Development of RAF Kinase Inhibitors", Current Topics in Medicinal Chemistry. vol. 6, No. 11, 1071-1089 (2006).

* cited by examiner

PYRAZOLE [3, 4-B] PYRIDINE RAF INHIBITORS

RELATED APPLICATIONS

This application claims priority to U.S. Provisional Application No. 61/032,813 that was filed on Feb. 29, 2008.

BACKGROUND OF THE INVENTION

1. Field of the Invention

The present invention relates to novel compounds, to pharmaceutical compositions comprising the compounds, to a process for making the compounds and to the use of the compounds in therapy. More particularly, it relates to certain substituted 1H-pyrazolo[3,4-b]pyridine compounds useful for inhibiting Raf kinase and for treating disorders mediated thereby.

2. Description of the State of the Art

The Raf/MEK/ERK pathway is critical for cell survival, growth, proliferation and tumorigenesis. Li, Nanxin, et al. "B-Raf kinase inhibitors for cancer treatment." *Current Opinion in Investigational Drugs*. Vol. 8, No. 6 (2007): 452-456. Raf kinases exist as three isoforms, A-Raf, B-Raf and C-Raf. Among the three isoforms, studies have shown that B-Raf functions as the primary MEK activator. B-Raf is one of the most frequently mutated genes in human cancers. B-Raf kinase represents an excellent target for anticancer therapy based on preclinical target validation, epidemiology and drugability.

Small molecule inhibitors of B-Raf are being developed for anticancer therapy. Nexavar® (sorafenib tosylate) is a multikinase inhibitor, which includes inhibition of B-Raf, and is approved for the treatment of patients with advanced renal cell carcinoma and unresectable hepatocellular carcinoma. Other Raf inhibitors have also been disclosed or have entered clinical trials, for example SB-590885, RAF-265, PLX-4032 and XL-281. Other B-Raf inhibitors are also known, see for example, U.S. Patent Application Publication 2006/0189627, U.S. Patent Application Publication 2006/0281751, U.S. Patent Application Publication 2007/0049603, International Patent Application Publication WO 2007/002325 and International Patent Application Publication WO 2007/002433.

Pyrazolopyridines are known, see for example, International Patent Application Publication WO 03/068773 and International Patent Application Publication WO 2007/013896.

Kinase inhibitors are known, see for example, International Patent Application Publication WO 2005/062795.

International Patent Application Publication WO 2008/079906 and International Patent Application Publication WO 2008/079909 also disclose kinase inhibitors.

International Patent Application Publication WO 2006/066913, International Patent Application WO 2008/028617 and International Patent Application Publication WO 2009/012283 also disclose kinase inhibitors.

SUMMARY OF THE INVENTION

In one aspect, the invention relates to compounds that are inhibitors of Raf kinases, particularly B-Raf inhibitors. Certain hyperproliferative disorders are characterized by the over activation of Raf kinase function, for example by mutations or over expression of the protein. Accordingly, the compounds of the invention are useful in the treatment of hyperproliferative disorders, such as cancer.

More specifically, one aspect of the present invention provides compounds of Formula I:

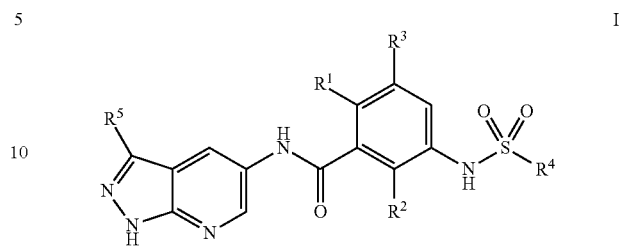

I and stereoisomers, tautomers, prodrugs and pharmaceutically acceptable salts thereof, wherein $R^1$, $R^2$, $R^3$, $R^4$ and $R^5$ are as defined herein.

More specifically, one aspect of the present invention provides compounds of Formula I:

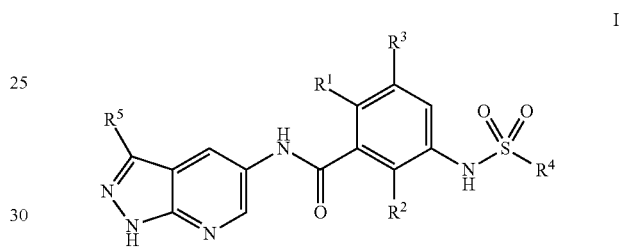

I and stereoisomers, tautomers and pharmaceutically acceptable salts thereof, wherein $R^1$, $R^2$, $R^3$, $R^4$ and $R^5$ are as defined herein.

Another aspect of the present invention provides intermediate compounds of Formula III:

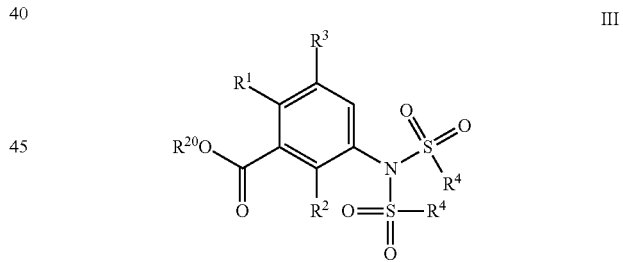

III wherein $R^1$, $R^2$, $R^3$, $R^4$ and $R^{20}$ are as defined herein.

Another aspect of the present invention provides intermediate compounds of Formula IV:

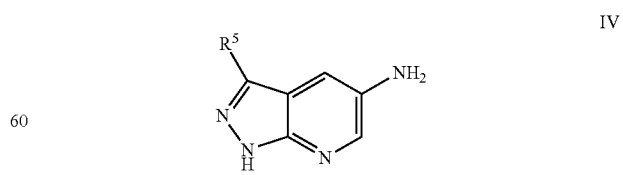

IV wherein $R^5$ is defined herein.

Another aspect of the present invention provides methods of preventing or treating a disease or disorder modulated by B-Raf, comprising administering to a mammal in need of such treatment an effective amount of a compound of this invention or a stereoisomer, prodrug or pharmaceutically acceptable salt thereof. Examples of such diseases and disorders include, but are not limited to, hyperproliferative disorders (such as cancer, including melanoma and other cancers of the skin), neurodegeneration, cardiac hypertrophy, pain, migraine and neurotraumatic disease.

Another aspect of the present invention provides methods of preventing or treating a disease or disorder modulated by B-Raf, comprising administering to a mammal in need of such treatment an effective amount of a compound of this invention or a stereoisomer or pharmaceutically acceptable salt thereof. Examples of such diseases and disorders include, but are not limited to, hyperproliferative disorders (such as cancer, including melanoma and other cancers of the skin), neurodegeneration, cardiac hypertrophy, pain, migraine and neurotraumatic disease.

Another aspect of the present invention provides methods of preventing or treating cancer, comprising administering to a mammal in need of such treatment an effective amount of a compound of this invention, or a stereoisomer, prodrug or pharmaceutically acceptable salt thereof, alone or in combination with one or more additional compounds having anti-cancer properties.

Another aspect of the present invention provides methods of preventing or treating cancer, comprising administering to a mammal in need of such treatment an effective amount of a compound of this invention, or a stereoisomer or pharmaceutically acceptable salt thereof, alone or in combination with one or more additional compounds having anti-cancer properties.

Another aspect of the present invention provides a method of treating a hyperproliferative disease in a mammal comprising administering a therapeutically effective amount of a compound of this invention to the mammal.

Another aspect of the present invention provides methods of preventing or treating kidney disease, comprising administering to a mammal in need of such treatment an effective amount of a compound of this invention, or a stereoisomer, prodrug or pharmaceutically acceptable salt thereof, alone or in combination with one or more additional compounds.

Another aspect of the present invention provides methods of preventing or treating polycystic kidney disease, comprising administering to a mammal in need of such treatment an effective amount of a compound of this invention, or a stereoisomer, prodrug or pharmaceutically acceptable salt thereof, alone or in combination with one or more additional compounds.

Another aspect of the present invention provides the compounds of the present invention for use in therapy.

Another aspect of the present invention provides the compounds of the present invention for use in the treatment of a hyperproliferative disease. In a further embodiment, the hyperproliferative disease may be cancer (or still further, a specific cancer as defined herein).

Another aspect of the present invention provides the compounds of the present invention for use in the treatment of a kidney disease. In a further embodiment, the kidney disease may be polycystic kidney disease.

Another aspect of the present invention provides the use of a compound of this invention in the manufacture of a medicament for the treatment of a hyperproliferative disease. In a further embodiment, the hyperproliferative disease may be cancer (or still further, a specific cancer as defined herein).

Another aspect of the present invention provides the use of a compound of this invention in the manufacture of a medicament for the treatment of a kidney disease. In a further embodiment, the kidney disease may be polycystic kidney disease.

Another aspect of the present invention provides the use of a compound of the present invention in the manufacture of a medicament, for use as a B-Raf inhibitor in the treatment of a patient undergoing cancer therapy.

Another aspect of the present invention provides the use of a compound of the present invention in the manufacture of a medicament, for use as a B-Raf inhibitor in the treatment of a patient undergoing polycystic kidney disease therapy.

Another aspect of the present invention provides a pharmaceutical composition comprising a compound of the present invention for use in the treatment of a hyperproliferative disease.

Another aspect of the present invention provides a pharmaceutical composition comprising a compound of the present invention for use in the treatment of cancer.

Another aspect of the present invention provides a pharmaceutical composition comprising a compound of the present invention for use in the treatment of polycystic kidney disease.

Another aspect of the present invention provides a pharmaceutical composition comprising a compound of this invention, a stereoisomer, prodrug or a pharmaceutically acceptable salt thereof, and a pharmaceutically acceptable carrier or excipient.

Another aspect of the present invention provides a pharmaceutical composition comprising a compound of this invention or a pharmaceutically acceptable salt thereof, and a pharmaceutically acceptable carrier or excipient.

Another aspect of the present invention includes methods of preparing, methods of separation, and methods of purification of the compounds of this invention.

Another aspect of the present invention provides intermediates for preparing compounds of Formula I. Certain compounds of Formula I may be used as intermediates for other compounds of Formula I.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

DEFINITIONS

The term "alkyl" includes linear or branched-chain radicals of carbon atoms. In one example, the alkyl radical is one to six carbon atoms ($C_1$-$C_6$). In other examples, the alkyl radical is $C_1$-$C_5$, $C_1$-$C_4$ or $C_1$-$C_3$. Some alkyl moieties have been abbreviated, for example, methyl ("Me"), ethyl ("Et"), propyl ("Pr") and butyl ("Bu"), and further abbreviations are used to designate specific isomers of compounds, for example, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu") and the like. Other examples of alkyl groups include 1-pentyl (n-pentyl, —$CH_2CH_2CH_2CH_2CH_3$), 2-pentyl (—$CH(CH_3)$ $CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH$ $(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)$ $CH_2CH_2CH_2CH_3$), 3-hexyl (—$CH(CH_2CH_3)$ $(CH_2CH_2CH_3)$), 2-methyl-2-pentyl (—$C(CH_3)_2$ $CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C$ $(CH_3)_2CH(CH_3)_2$) and 3,3-dimethyl-2-butyl (—$CH(CH_3)C$ $(CH_3)_3$. The abbreviations are sometimes used in conjunction with elemental abbreviations and chemical structures, for example, methanol ("MeOH") or ethanol ("EtOH").

Additional abbreviations used throughout the application include, for example, benzyl ("Bn"), phenyl ("Ph") and acetyl ("Ac").

The term "alkenyl" refers to linear or branched-chain monovalent hydrocarbon radical with at least one site of unsaturation, i.e., a carbon-carbon double bond, wherein the alkenyl radical may be optionally substituted independently with one or more substituents described herein, and includes radicals having "cis" and "trans" orientations, or alternatively, "E" and "Z" orientations. In one example, the alkenyl radical is two to six carbon atoms ($C_2$-$C_6$). In other examples, the alkenyl radical is $C_2$-$C_3$. Examples include, but are not limited to, ethenyl or vinyl (—$CH=CH_2$), prop-1-enyl (—$CH=CHCH_3$), prop-2-enyl (—$CH_2CH=CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, hexa-1,3-dienyl.

The term "alkynyl" refers to a linear or branched monovalent hydrocarbon radical with at least one site of unsaturation, i.e., a carbon-carbon, triple bond, wherein the alkynyl radical may be optionally substituted independently with one or more substituents described herein. In one example, the alkynyl radical is two to eighteen carbon atoms ($C_2$-$C_6$). In other examples, the alkynyl radical is $C_2$-$C_3$. Examples include, but are not limited to, ethynyl (—$C\equiv CH$), prop-1-ynyl (—$C\equiv CCH_3$), prop-2-ynyl (propargyl, $CH_2C\equiv CH$), but-1-ynyl, but-2-ynyl and but-3-ynyl.

The terms "alkenyl" and "alkynyl" also include linear or branched-chain radicals of carbon atoms containing at least one unsaturated bond.

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 6 carbon atoms ($C_3$-$C_6$). In other examples, cycloalkyl is $C_3$-$C_4$ or $C_3$-$C_5$. In other examples, the cycloalkyl group, as a monocycle, is $C_3$-$C_6$ or $C_5$-$C_6$. In another example, the cycloalkyl group, as a bicycle, is $C_7$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo [2.2.2]octane, and bicyclo[3.2.2]nonane.

The terms "heterocyclic" or "heterocycle" or "heterocyclyl" refers to a saturated or a partially unsaturated (i.e., having one or more double and/or triple bonds within the ring) cyclic group in which at least one ring atom is a heteroatom independently selected from nitrogen, oxygen, and sulfur, the remaining ring atoms being carbon. In one embodiment, heterocyclyl includes saturated or partially unsaturated 4-6 membered heterocyclyl groups. The heterocyclyl group may be optionally substituted with one or more substituents described herein. Exemplary heterocyclyl groups include, but are not limited to, oxiranyl, aziridinyl, thiiranyl, azetidinyl, oxetanyl, thietanyl, 1,2-dithietanyl, 1,3-dithietanyl, pyrrolidinyl, piperidinyl, dihydropyridinyl, tetrahydropyridinyl, morpholinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinylimidazolinyl, imidazolidinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. Heterocycles include 4 to 6 membered rings containing one or two heteroatoms selected from oxygen, nitrogen and sulfur.

The term "heteroaryl" refers to an aromatic cyclic group in which at least one ring atom is a heteroatom independently selected from nitrogen, oxygen and sulfur, the remaining ring atoms being carbon. Heteroaryl groups may be optionally substituted with one or more substituents described herein. In one example, heteroaryl includes 5-6 membered heteroaryl groups. Other examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, and furopyridinyl. Heteroaryls include 5 to 6 membered aromatic rings containing one, two or three heteroatoms selected from oxygen, nitrogen and sulfur.

"Halogen" refers to F, Cl, Br or I.

The abbreviation "TLC" stands for thin layer chromatography.

The terms "treat" or "treatment" refer to therapeutic, prophylactic, palliative or preventative measures. In one example, treatment includes therapeutic and palliative treatment. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrases "therapeutically effective amount" or "effective amount" mean an amount of a compound of the present invention that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art.

The terms "cancer" and "cancerous" refer to or describe the physiological condition in mammals that is typically characterized by abnormal or unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. The term cancer may be used generically to include various types of cancer or specifically (as listed above).

The phrase "pharmaceutically acceptable" indicates that the substance or composition is compatible chemically and/or toxicologically, with the other ingredients comprising a formulation, and/or the mammal being treated therewith.

The phrase "pharmaceutically acceptable salt," as used herein, refers to pharmaceutically acceptable organic or inorganic salts of a compound of the invention.

The compounds of this invention also include other salts of such compounds which are not necessarily pharmaceutically acceptable salts, and which may be useful as intermediates for preparing and/or purifying compounds of this invention and/or for separating enantiomers of compounds of this invention.

The term "mammal" means a warm-blooded animal that has or is at risk of developing a disease described herein and includes, but is not limited to, guinea pigs, dogs, cats, rats, mice, hamsters, and primates, including humans.

B-Raf Inhibitor Compounds

The present invention provides compounds, and pharmaceutical formulations thereof, that are potentially useful in the treatment of diseases, conditions and/or disorders modulated by B-Raf.

One embodiment of this invention provides compounds of Formula I:

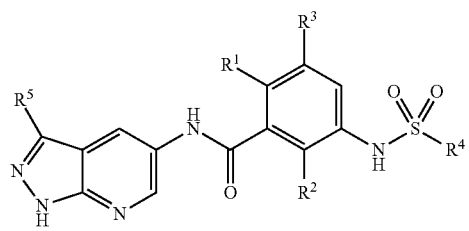

and stereoisomers, prodrugs, tautomers and pharmaceutically acceptable salts thereof, wherein:

$R^1$ and $R^2$ are independently selected from hydrogen, halogen, CN, $C_1$-$C_3$ alkyl and $C_1$-$C_3$ alkoxy;

$R^3$ is hydrogen, halogen or $C_1$-$C_3$ alkyl;

$R^4$ is $C_3$-$C_5$ cycloalkyl, $C_1$-$C_6$ alkyl, $C_2$-$C_6$ alkenyl, $C_2$-$C_6$ alkynyl, phenyl, a 5-6 membered heteroaryl, or $NR^gR^h$, wherein the cycloalkyl, alkyl, alkenyl, alkynyl, phenyl and heteroaryl are optionally substituted with $OR^e$, halogen, phenyl, $C_3$-$C_4$ cycloalkyl, or $C_1$-$C_4$ alkyl optionally substituted with halogen;

$R^5$ is:
hydrogen,
halogen,
CN,
$NR^cR^d$,
$OR^e$,
$SR^f$,
phenyl optionally substituted with one to three $R^a$ groups,
a 5-6 membered heteroaryl optionally substituted with $C_1$-$C_4$ alkyl,
a saturated or partially unsaturated $C_3$-$C_6$ cycloalkyl optionally substituted with halogen or $C_1$-$C_4$ alkyl,
a saturated or partially unsaturated 4-6 membered heterocyclyl optionally substituted with $C_1$-$C_4$ alkyl,
$C_2$-$C_6$ alkynyl optionally substituted with halogen, $OR^c$ or $NR^cR^d$,
$C_2$-$C_6$ alkenyl optionally substituted with halogen, $OR^c$ or $NR^cR^d$, or
$C_1$-$C_6$ alkyl optionally substituted with one to three $R^b$ groups;

each $R^a$ is independently selected from halogen, $CF_3$, $C_1$-$C_4$ alkyl or —O($C_1$-$C_4$ alkyl), wherein the alkyl or alkoxy are optionally substituted with OH, $NR^cR^d$ or a 5-6 membered heterocyclyl optionally substituted with $C_1$-$C_3$ alkyl;

each $R^b$ is independently selected from halogen, OH, $OCH_3$, oxo, —$NR^cR^d$, or $C_3$-$C_6$ cycloalkyl;

each $R^c$ and $R^d$ are independently selected from hydrogen, phenyl and $C_1$-$C_4$ alkyl optionally substituted with oxo;

$R^e$ is selected from a 4-6 membered heterocyclyl and $C_1$-$C_6$ alkyl optionally substituted with halogen, OH, $OCH_3$, $C_3$-$C_6$ cycloalkyl or a 4-6 membered heterocyclyl;

$R^f$ is $C_1$-$C_6$ alkyl; and $R^g$ and $R^h$ are independently selected from hydrogen and $C_1$-$C_5$ alkyl optionally substituted with halogen, or $R^g$ and $R^h$ together with the nitrogen to which they are attached form a 4 to 6 membered heterocyclic ring.

Compounds of Formula I include compounds wherein:

$R^1$, $R^2$ and $R^3$ are independently selected from hydrogen, halogen or $C_1$-$C_3$ alkyl;

$R^4$ is $C_3$-$C_4$ cycloalkyl; $C_1$-$C_6$ alkyl optionally substituted with OH, halogen, phenyl or $C_3$-$C_4$ cycloalkyl; phenyl optionally substituted with halogen or $C_1$-$C_4$ alkyl optionally substituted with halogen; a 5-6 membered heteroaryl optionally substituted with $C_1$-$C_4$ alkyl; or $NR^gR^h$;

$R^5$ is hydrogen, halogen, CN, $NR^cR^d$, $OR^e$, $SR^f$, phenyl optionally substituted with one to three $R^a$ groups, a 5-6 membered heteroaryl optionally substituted with $C_1$-$C_4$ alkyl, $C_3$-$C_6$ cycloalkyl optionally substituted with halogen or $C_1$-$C_4$ alkyl, a saturated or partially unsaturated 4-6 membered heterocyclyl optionally substituted with $C_1$-$C_4$ alkyl, $C_2$-$C_6$ alkynyl optionally substituted with $NR^cR^d$, $C_2$-$C_6$ alkenyl, or $C_1$-$C_6$ alkyl optionally substituted with one to three $R^b$ groups;

each $R^a$ is independently selected from halogen, $CF_3$, $C_1$-$C_4$ alkyl or —O($C_1$-$C_4$ alkyl), wherein the alkyl or alkoxy are optionally substituted with OH, $NR^cR^d$ or a 5-6 membered heterocyclyl optionally substituted with $C_1$-$C_3$ alkyl;

each $R^b$ is independently selected from halogen, OH, $OCH_3$, oxo, —$NR^cR^d$, or $C_3$-$C_6$ cycloalkyl;

each $R^c$ and $R^d$ are independently selected from hydrogen, phenyl and $C_1$-$C_4$ alkyl optionally substituted with oxo;

$R^e$ is selected from a 4-6 membered heterocyclyl and $C_1$-$C_6$ alkyl optionally substituted with halogen, $OCH_3$, $C_3$-$C_6$ cycloalkyl or a 4-6 membered heterocyclyl;

$R^f$ is $C_1$-$C_6$ alkyl; and $R^g$ and $R^h$ are independently selected from hydrogen and $C_1$-$C_5$ alkyl optionally substituted with halogen, or $R^g$ and $R^h$ together with the nitrogen to which they are attached form a 4 to 6 membered heterocyclic ring.

One embodiment of this invention provides compounds of Formula I:

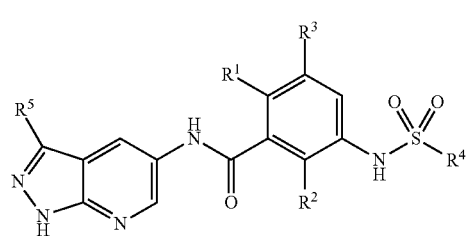

I and stereoisomers, tautomers and pharmaceutically acceptable salts thereof, wherein:

$R^1$ and $R^2$ are independently selected from hydrogen, halogen, CN, $C_1$-$C_3$ alkyl and $C_1$-$C_3$ alkoxy;

$R^3$ is hydrogen, halogen or $C_1$-$C_3$ alkyl;

$R^4$ is $C_3$-$C_5$ cycloalkyl, $C_1$-$C_6$ alkyl, $C_2$-$C_6$ alkenyl, or $C_2$-$C_6$ alkynyl, wherein the cycloalkyl, alkyl, alkenyl and alkynyl are optionally substituted with $OR^c$, halogen or $C_3$-$C_4$ cycloalkyl;

$R^5$ is hydrogen, halogen, CN, $NR^cR^d$, $OR^e$, phenyl optionally substituted with one to three $R^a$ groups, a 5-6 membered heteroaryl optionally substituted with $C_1$-$C_4$ alkyl, a saturated or partially unsaturated $C_3$-$C_6$ cycloalkyl optionally substituted with halogen or $C_1$-$C_4$ alkyl, a saturated or partially unsaturated 5-6 membered heterocyclyl, $C_2$-$C_6$ alkynyl optionally substituted with $OR^c$, $C_2$-$C_6$ alkenyl optionally substituted with $OR^c$, or $C_1$-$C_6$ alkyl optionally substituted with one to three $R^b$ groups;

each $R^a$ is independently selected from halogen, $CF_3$, $C_1$-$C_4$ alkyl or —O($C_1$-$C_4$ alkyl), wherein the alkyl or alkoxy are optionally substituted with OH, $NR^cR^d$ or a 5-6 membered heterocyclyl optionally substituted with $C_1$-$C_3$ alkyl;

each $R^b$ is independently selected from halogen, OH, $OCH_3$, oxo or —$NR^cR^d$; each $R^c$ and $R^d$ are independently selected from hydrogen and $C_1$-$C_4$ alkyl; and $R^e$ is $C_1$-$C_6$ alkyl optionally substituted with halogen or $C_3$-$C_6$ cycloalkyl.

Compounds of Formula I include compounds wherein:

$R^1$, $R^2$ and $R^3$ are independently selected from hydrogen, halogen or $C_1$-$C_3$ alkyl;

$R^4$ is $C_3$-$C_4$ cycloalkyl or $C_1$-$C_6$ alkyl optionally substituted with OH, halogen or $C_3$-$C_4$ cycloalkyl;

$R^5$ is hydrogen, halogen, CN, $NR^cR^d$, $OR^e$, phenyl optionally substituted with one to three $R^a$ groups, 5-6 membered heteroaryl optionally substituted with $C_1$-$C_4$ alkyl, $C_3$-$C_6$ cycloalkyl, 5-6 membered heterocyclyl, $C_2$-$C_6$ alkenyl, or $C_1$-$C_6$ alkyl optionally substituted with one to three $R^b$ groups;

each $R^a$ is independently selected from halogen, $CF_3$, $C_1$-$C_4$ alkyl or —O($C_1$-$C_4$ alkyl), wherein the alkyl or alkoxy are optionally substituted with OH, $NR^cR^d$ or a 5-6 membered heterocyclyl optionally substituted with $C_1$-$C_3$ alkyl;

each $R^b$ is independently selected from halogen, OH, $OCH_3$, oxo or —$NR^cR^d$;

$R^c$ and $R^d$ are independently selected from hydrogen and $C_1$-$C_4$ alkyl; and $R^e$ is $C_1$-$C_6$ alkyl optionally substituted with halogen or $C_3$-$C_6$ cycloalkyl.

In certain embodiments, $R^1$ and $R^2$ are independently selected from hydrogen, halogen, CN, $C_1$-$C_3$ alkyl or $C_1$-$C_3$ alkoxy.

In certain embodiments, $R^1$, $R^2$ and $R^3$ are independently selected from hydrogen, halogen or $C_1$-$C_3$ alkyl.

In certain embodiments, $R^1$, $R^2$ and $R^3$ are independently selected from hydrogen, F and Cl.

In certain embodiments, $R^1$ is hydrogen, halogen, CN, $C_1$-$C_3$ alkyl or $C_1$-$C_3$ alkoxy.

In certain embodiments, $R^1$ is hydrogen, halogen or $C_1$-$C_3$ alkyl.

In certain embodiments, $R^1$ is hydrogen.

In certain embodiments, $R^1$ is halogen. In certain embodiments, $R^1$ is F or Cl.

In certain embodiments, $R^1$ is $C_1$-$C_3$ alkyl. In certain embodiments, $R^1$ is methyl.

In certain embodiments, $R^2$ is hydrogen, halogen, CN, $C_1$-$C_3$ alkyl or $C_1$-$C_3$ alkoxy.

In certain embodiments, $R^2$ is hydrogen, halogen or $C_1$-$C_3$ alkyl.

In certain embodiments, $R^2$ is hydrogen.

In certain embodiments, $R^2$ is halogen. In certain embodiments, $R^2$ is F or Cl.

In certain embodiments, $R^2$ is $C_1$-$C_3$ alkyl. In certain embodiments, $R^2$ is methyl.

In certain embodiments of Formula I, $R^2$ is Cl.

In certain embodiments of Formula I, $R^2$ is hydrogen.

In certain embodiments, $R^3$ is hydrogen, halogen or $C_1$-$C_3$ alkyl.

In certain embodiments, $R^3$ is hydrogen.

In certain embodiments, $R^3$ is halogen. In certain embodiments, $R^3$ is F or Cl.

In certain embodiments, $R^1$ and $R^2$ are F and $R^3$ is hydrogen.

In certain embodiments, $R^1$ is F and $R^2$ is Cl and $R^3$ is hydrogen.

In certain embodiments, $R^1$ is Cl and $R^2$ is F and $R^3$ is hydrogen.

In certain embodiments, $R^1$ is F and $R^2$ and $R^3$ are hydrogen.

In certain embodiments, $R^1$ and $R^3$ are hydrogen and $R^2$ is F.

In certain embodiments, $R^2$ and $R^3$ are F and $R^1$ is hydrogen.

In certain embodiments, $R^1$ is Cl and $R^2$ and $R^3$ are hydrogen.

In certain embodiments, $R^1$, $R^2$ and $R^3$ are F.

In certain embodiments, $R^1$ is F and $R^2$ is methyl and $R^3$ is hydrogen.

In certain embodiments, $R^1$ is methyl and $R^2$ is F and $R^3$ is hydrogen.

In certain embodiments, $R^1$ is F and $R^2$ and $R^3$ are hydrogen.

In certain embodiments, $R^1$ is Cl and $R^2$ and $R^3$ are hydrogen.

In certain embodiments, $R^2$ is F and $R^1$ and $R^3$ are hydrogen.

In certain embodiments, the residue:

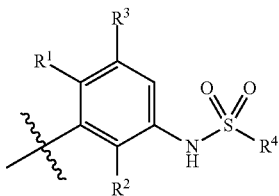

of Formula I, wherein the wavy line represents the point of attachment of the residue in Formula I, is selected from:

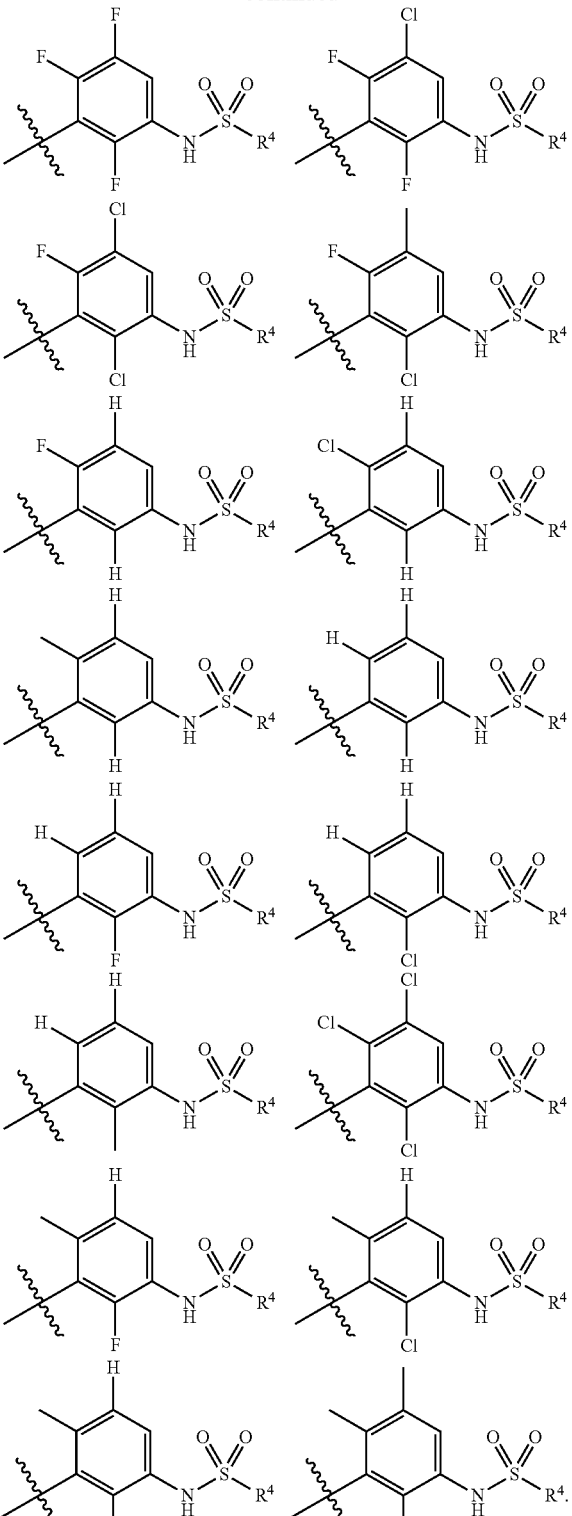

In certain embodiments, $R^4$ is $C_3$-$C_5$ cycloalkyl, $C_1$-$C_6$ alkyl, $C_2$-$C_6$ alkenyl, $C_2$-$C_6$ alkynyl, phenyl, a 5-6 membered heteroaryl, or $NR^gR^h$, wherein the cycloalkyl, alkyl, alkenyl, alkynyl and phenyl are optionally substituted with $OR^e$, halogen, phenyl, $C_3$-$C_4$ cycloalkyl or $C_1$-$C_4$ alkyl optionally substituted with halogen.

In certain embodiments, $R^c$ is independently selected from hydrogen, phenyl and $C_1$-$C_4$ alkyl optionally substituted with oxo. In certain embodiments, $R^c$ is hydrogen.

In certain embodiments, $R^4$ is $C_3$-$C_5$ cycloalkyl, $C_1$-$C_6$ alkyl, $C_2$-$C_6$ alkenyl, $C_2$-$C_6$ alkynyl, phenyl, a 5-6 membered heteroaryl, or $NR^gR^h$, wherein the cycloalkyl, alkyl, alkenyl, alkynyl and phenyl are optionally substituted with OH, halogen, phenyl, $C_3$-$C_4$ cycloalkyl or $C_1$-$C_4$ alkyl optionally substituted with halogen.

In certain embodiments, $R^4$ is $C_3$-$C_5$ cycloalkyl, $C_1$-$C_6$ alkyl, $C_2$-$C_6$ alkenyl, or $C_2$-$C_6$ alkynyl, wherein the cycloalkyl, alkyl, alkenyl and alkynyl are optionally substituted with $OR^c$, halogen or $C_3$-$C_4$ cycloalkyl.

In certain embodiments, $R^4$ is cyclopropyl, ethyl, propyl, butyl, isobutyl, —CH$_2$CH$_2$CH$_2$OH, —CH$_2$Cl, —CH$_2$CF$_3$, —CH$_2$CH$_2$CH$_2$F, —CH$_2$CH$_2$CF$_3$, phenylmethyl, cyclopropylmethyl, phenyl, 2-fluorophenyl, 3-fluorophenyl, 4-fluorophenyl, 2,5-difluorophenyl, 4-chloro-3-trifluoromethylphenyl, 1-methyl-1H-imidazol-4-yl, furan-2-yl, pyridin-2-yl, pyridin-3-yl, thiophen-2-yl, —NHCH$_2$CH$_3$, —NHCH$_2$CH$_2$CH$_3$, —N(CH$_3$)CH$_2$CH$_3$, —NHCH(CH$_3$)$_2$, —NHCH$_2$CHF$_2$, —N(CH$_3$)$_2$ or pyrrolidin-1-yl.

In certain embodiments, $R^4$ is cyclopropyl, ethyl, propyl, isobutyl, —CH$_2$CH$_2$CH$_2$OH, —CH$_2$CH$_2$CH$_2$F, phenylmethyl, cyclopropylmethyl, phenyl, 2-fluorophenyl, 3-fluorophenyl, 4-fluorophenyl, 2,5-difluorophenyl, 4-chloro-3-trifluoromethylphenyl, 1-methyl-1H-imidazol-4-yl, furan-2-yl, pyridin-2-yl, thiophen-2-yl or —NHCH$_2$CH$_3$.

In certain embodiments, $R^4$ is propyl, butyl, isobutyl, —CH$_2$CH$_2$CH$_2$F, —CH$_2$CH$_2$CF$_3$ or cyclopropylmethyl.

In certain embodiments, $R^4$ is $C_3$-$C_5$ cycloalkyl or $C_1$-$C_6$ alkyl optionally substituted with OH, halogen or $C_3$-$C_4$ cycloalkyl.

In certain embodiments, $R^4$ is $C_3$-$C_5$ cycloalkyl. In certain embodiments, $R^4$ is $C_3$-$C_4$ cycloalkyl. In certain embodiments, $R^4$ is cyclopropyl or cyclobutyl.

In certain embodiments, $R^4$ is $C_3$-$C_5$ cycloalkyl. In certain embodiments, $R^4$ is $C_3$-$C_4$ cycloalkyl. In certain embodiments, $R^4$ is cyclopropyl.

In certain embodiments, $R^4$ is $C_1$-$C_6$ alkyl. In certain embodiments, $R^4$ is ethyl, propyl, butyl or isobutyl.

In certain embodiments, $R^4$ is $C_1$-$C_6$ alkyl. In certain embodiments, $R^4$ is propyl, butyl or isobutyl.

In certain embodiments, $R^4$ is $C_1$-$C_6$ alkyl optionally substituted with $OR^c$. In certain embodiments, $R^c$ is hydrogen. In certain embodiments, $R^4$ is $C_1$-$C_6$ alkyl optionally substituted with OH. In certain embodiments, $R^4$ is —CH$_2$CH$_2$CH$_2$OH.

In certain embodiments, $R^4$ is $C_1$-$C_6$ alkyl optionally substituted with halogen. In certain embodiments, $R^4$ is —CF$_3$, —CH$_2$Cl, —CH$_2$CF$_3$, —CH$_2$CH$_2$CH$_2$F, —CH$_2$CH$_2$CF$_3$, —CF$_2$CF$_3$ or —CF$_2$CF$_2$CF$_3$.

In certain embodiments, $R^4$ is $C_1$-$C_6$ alkyl optionally substituted with halogen. In certain embodiments, $R^4$ is —CF$_3$, —CH$_2$CF$_3$, —CH$_2$CH$_2$CH$_2$F, —CH$_2$CH$_2$CF$_3$, —CF$_2$CF$_3$ or —CF$_2$CF$_2$CF$_3$. In certain embodiments, $R^4$ is —CH$_2$CH$_2$CH$_2$F or —CH$_2$CH$_2$CF$_3$.

In certain embodiments, $R^4$ is $C_1$-$C_6$ alkyl optionally substituted with OH, halogen or $C_3$-$C_4$ cycloalkyl. In certain embodiments, $R^4$ is cyclopropylmethyl (—CH$_2$-cyclopropyl) or cyclobutylmethyl (—CH$_2$-cyclobutyl). In certain embodiments, $R^4$ is cyclopropylmethyl (—CH$_2$-cyclopropyl).

In certain embodiments, $R^4$ is $C_1$-$C_6$ alkyl optionally substituted with phenyl. In certain embodiments, $R^4$ is phenylmethyl.

In certain embodiments, $R^4$ is phenyl optionally substituted with $OR^c$, halogen, $C_3$-$C_4$ cycloalkyl or $C_1$-$C_4$ alkyl optionally substituted with halogen. In certain embodiments, $R^4$ is phenyl optionally substituted with halogen. In certain embodiments, $R^4$ is phenyl optionally substituted with $C_1$-$C_4$ alkyl optionally substituted with halogen. In certain embodiments, $R^4$ is phenyl optionally substituted with halogen and $C_1$-$C_4$ alkyl optionally substituted with halogen. In certain embodiments, $R^4$ is phenyl. In certain embodiments, $R^4$ is phenyl, 2-fluorophenyl, 3-fluorophenyl, 4-fluorophenyl, 2,5-difluorophenyl or 4-chloro-3-trifluoromethylphenyl.

In certain embodiments, $R^4$ is a 5-6 membered heteroaryl optionally substituted with $OR^c$, halogen, $C_3$-$C_4$ cycloalkyl or $C_1$-$C_4$ alkyl optionally substituted with halogen. In certain embodiments, $R^4$ is a 5-6 membered heteroaryl optionally substituted with $C_1$-$C_4$ alkyl. In certain embodiments, $R^4$ is a 5-6 membered heteroaryl optionally substituted with $OR^c$, halogen, $C_3$-$C_4$ cycloalkyl or $C_1$-$C_4$ alkyl optionally substituted with halogen, wherein the heteroaryl contains one or two heteroatoms selected from the group consisting of oxygen, nitrogen and sulfur. In certain embodiments, $R^4$ is a 5-6 membered heteroaryl optionally substituted with $OR^c$, halogen, $C_3$-$C_4$ cycloalkyl or $C_1$-$C_4$ alkyl optionally substituted with halogen, wherein the heteroaryl is imidazolyl, furanyl, pyridinyl or thiophenyl. In certain embodiments, $R^4$ is 1-methyl-1H-imidazol-4-yl, furan-2-yl, pyridin-2-yl, pyridin-3-yl or thiophen-2-yl.

In certain embodiments, $R^4$ is $NR^gR^h$. In certain embodiments, $R^g$ and $R^h$ are independently selected from hydrogen and $C_1$-$C_5$ alkyl optionally substituted with halogen. In certain embodiments, $R^h$ is hydrogen or methyl. In certain embodiments, $R^g$ is $C_1$-$C_5$ alkyl optionally substituted with halogen. In certain embodiments, $R^g$ is methyl, ethyl, propyl, isopropyl, or 2,2-difluoroethyl. In certain embodiments, $R^4$ is selected from the group consisting of —NHCH$_2$CH$_3$, —NHCH$_2$CH$_2$CH$_3$, —N(CH$_3$)CH$_2$CH$_3$, —NHCH(CH$_3$)$_2$, —NHCH$_2$CHF$_2$, and —N(CH$_3$)$_2$.

In certain embodiments, $R^4$ is $NR^gR^h$, wherein $R^g$ and $R^h$ together with the nitrogen to which they are attached form a 4 to 6 membered heterocyclic ring. In certain embodiments, $R^4$ is $NR^gR^h$, wherein $R^g$ and $R^h$ together with the nitrogen to which they are attached form a 4 to 6 membered heterocyclic ring, wherein the heterocyclic ring contains one or two heteroatoms selected from nitrogen and oxygen. In certain embodiments, $R^4$ is $NR^gR^h$, wherein $R^g$ and $R^h$ together with the nitrogen to which they are attached form a 5 membered heterocyclic ring. In certain embodiments, $R^4$ is $NR^gR^h$, wherein $R^g$ and $R^h$ together with the nitrogen to which they are attached form a 5 membered heterocyclic ring, wherein the heterocyclic ring contains one nitrogen heteroatom. In certain embodiments, $R^4$ is pyrrolidin-1-yl.

In certain embodiments, $R^1$ and $R^2$ are F, $R^3$ is hydrogen and $R^4$ is propyl, such that compounds of Formula I have the structure of Formula Ia (a subset of Formula I):

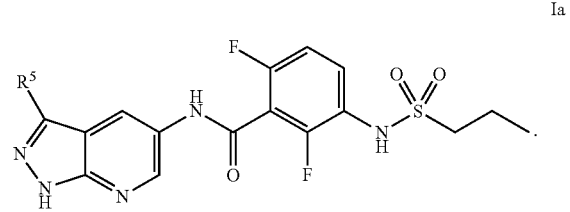

Ia

In certain embodiments of Formula Ia, $R^5$ is selected from —O($C_1$-$C_3$ alkyl), phenyl optionally substituted with one or two halogens, and a saturated $C_3$-$C_5$ cycloalkyl optionally substituted with halogen or methyl. In certain embodiments of Formula Ia, $R^5$ is selected from methoxy, ethoxy, propoxy, isopropoxy, phenyl, 3-chlorophenyl, 4-chlorophenyl, 3-fluorophenyl, 4-fluorophenyl, 2,3-difluorophenyl, 3,4-difluorophenyl, 3,5-difluorophenyl, cyclopropyl, 2,2-difluorocyclopropyl, 2-methylcyclopropyl, cyclobutyl and cyclopentyl.

In certain embodiments of Formula Ia, $R^5$ is —O($C_1$-$C_3$ alkyl). In certain embodiments of Formula Ia, $R^5$ is selected from methoxy, ethoxy, propoxy, isopropoxy. In certain embodiments of Formula Ia, $R^5$ is selected from methoxy and ethoxy. In certain embodiments of Formula Ia, $R^5$ is methoxy. In certain embodiments of Formula Ia, $R^5$ is ethoxy.

In certain embodiments of Formula Ia, $R^5$ is phenyl optionally substituted with one or two halogens. In certain embodiments of Formula Ia, $R^5$ is selected from phenyl, 3-chlorophenyl, 4-chlorophenyl, 3-fluorophenyl, 4-fluorophenyl, 2,3-difluorophenyl, 3,4-difluorophenyl, and 3,5-difluorophenyl.

In certain embodiments of Formula Ia, $R^5$ is a saturated $C_3$-$C_5$ cycloalkyl optionally substituted with halogen or methyl. In certain embodiments of Formula Ia, $R^5$ is selected from cyclopropyl, 2,2-difluorocyclopropyl, 2-methylcyclopropyl, cyclobutyl and cyclopentyl. In certain embodiments of Formula Ia, $R^5$ is selected from cyclopropyl, 2,2-difluorocyclopropyl, and 2-methylcyclopropyl. In certain embodiments of Formula Ia, $R^5$ is cyclopropyl. In certain embodiments of Formula Ia, $R^5$ is 2,2-difluorocyclopropyl. In certain embodiments of Formula Ia, $R^5$ is 2-methylcyclopropyl.

In certain embodiments, $R^1$ is Cl, $R^2$ is F, $R^3$ is hydrogen and $R^4$ is propyl, such that compounds of Formula I have the structure of Formula Ia1 (a subset of Formula I):

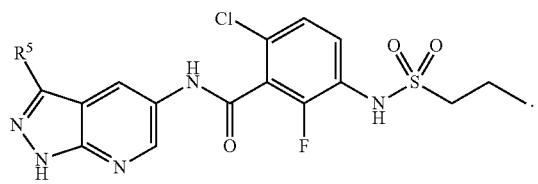

Ia1

In certain embodiments of Formula Ia1, $R^5$ is selected from —O($C_1$-$C_3$ alkyl), phenyl optionally substituted with one or two halogens, and a saturated $C_3$-$C_5$ cycloalkyl optionally substituted with halogen or methyl. In certain embodiments of Formula Ia1, $R^5$ is selected from methoxy, ethoxy, isopropoxy and cyclopropyl.

In certain embodiments of Formula Ia1, $R^5$ is —O($C_1$-$C_3$ alkyl). In certain embodiments of Formula Ia1, $R^5$ is selected from methoxy, ethoxy, and isopropoxy. In certain embodiments of Formula Ia1, $R^5$ is selected from methoxy and ethoxy. In certain embodiments of Formula Ia1, $R^5$ is methoxy. In certain embodiments of Formula Ia1, $R^5$ is ethoxy.

In certain embodiments of Formula Ia1, $R^5$ is a saturated $C_3$-$C_5$ cycloalkyl optionally substituted with halogen or methyl. In certain embodiments of Formula Ia1, $R^5$ is cyclopropyl.

In certain embodiments, $R^1$ is F, $R^2$ is Cl, $R^3$ is hydrogen and $R^4$ is propyl, such that compounds of Formula I have the structure of Formula Ia2 (a subset of Formula I):

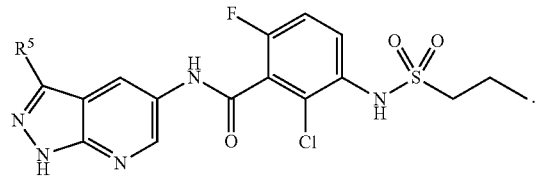

Ia2

In certain embodiments of Formula Ia2, $R^5$ is selected from —O($C_1$-$C_3$ alkyl), phenyl optionally substituted with one or two halogens, and a saturated $C_3$-$C_5$ cycloalkyl optionally substituted with halogen or methyl. In certain embodiments of Formula Ia2, $R^5$ is selected from methoxy and cyclopropyl.

In certain embodiments of Formula Ia2, $R^5$ is —O($C_1$-$C_3$ alkyl). In certain embodiments of Formula Ia2, $R^5$ is methoxy.

In certain embodiments of Formula Ia2, $R^5$ is a saturated $C_3$-$C_5$ cycloalkyl optionally substituted with halogen or methyl. In certain embodiments of Formula Ia2, $R^5$ is cyclopropyl.

In certain embodiments, $R^3$ is hydrogen and $R^4$ is propyl, such that compounds of Formula I have the structure of Formula Ib (a subset of Formula I):

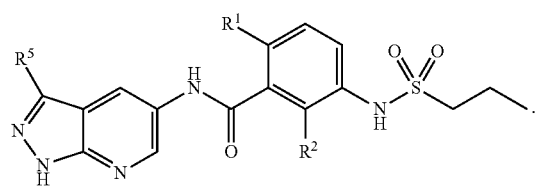

Ib wherein $R^1$ and $R^2$ are independently selected from F and Cl, and $R^5$ is selected from —O($C_1$-$C_3$ alkyl), phenyl optionally substituted with one or two halogens, and a saturated $C_3$-$C_5$ cycloalkyl optionally substituted with halogen or methyl.

In certain embodiments of Formula Ib, $R^5$ is selected from methoxy, ethoxy, propoxy, isopropoxy, phenyl, 3-chlorophenyl, 4-chlorophenyl, 3-fluorophenyl, 4-fluorophenyl, 2,3-difluorophenyl, 3,4-difluorophenyl, 3,5-difluorophenyl, cyclopropyl, 2,2-difluorocyclopropyl, 2-methylcyclopropyl, cyclobutyl and cyclopentyl.

In certain embodiments of Formula Ib, $R^5$ is selected from methoxy and ethoxy. In certain embodiments of Formula Ib, $R^5$ is methoxy. In certain embodiments of Formula Ib, $R^5$ is ethoxy.

In certain embodiments of Formula Ib, $R^5$ is selected from cyclopropyl, 2,2-difluorocyclopropyl, and 2-methylcyclopropyl. In certain embodiments of Formula Ib, $R^5$ is cyclopropyl. In certain embodiments of Formula Ib, $R^5$ is 2,2-difluorocyclopropyl. In certain embodiments of Formula Ib, $R^5$ is 2-methylcyclopropyl.

In certain embodiments, $R^5$ is hydrogen, halogen, CN, $NR^cR^d$, $OR^e$, $SR^f$, phenyl optionally substituted with one to three $R^a$ groups, a 5-6 membered heteroaryl optionally substituted with $C_1$-$C_4$ alkyl, a saturated or partially unsaturated $C_3$-$C_6$ cycloalkyl optionally substituted with halogen or $C_1$-$C_4$ alkyl, a saturated or partially unsaturated 4-6 membered heterocyclyl optionally substituted with $C_1$-$C_4$ alkyl, $C_2$-$C_6$ alkynyl optionally substituted with halogen, $OR^e$ or $NR^cR^d$, $C_2$-$C_6$ alkenyl optionally substituted with halogen, $OR^e$ or $NR^cR^d$, or $C_1$-$C_6$ alkyl optionally substituted with one to three $R^b$ groups.

In certain embodiments, $R^5$ is hydrogen, halogen, CN, $NR^cR^d$, $OR^e$, phenyl optionally substituted with one to three $R^a$ groups, a 5-6 membered heteroaryl optionally substituted with $C_1$-$C_4$ alkyl, saturated or partially unsaturated $C_3$-$C_6$ cycloalkyl optionally substituted with $C_1$-$C_4$ alkyl, a saturated or partially unsaturated 5-6 membered heterocyclyl, $C_2$-$C_6$ alkynyl optionally substituted with $OR^e$, $C_2$-$C_6$ alkenyl optionally substituted with $OR^e$, or $C_1$-$C_6$ alkyl optionally substituted with one to three $R^b$ groups.

In certain embodiments, $R^5$ is hydrogen, CN, $NR^cR^d$, $OR^e$, $SR^f$, phenyl optionally substituted with one to three $R^a$ groups, a 5-6 membered heteroaryl optionally substituted with $C_1$-$C_4$ alkyl, a saturated or partially unsaturated $C_3$-$C_6$ cycloalkyl optionally substituted with halogen or $C_1$-$C_4$ alkyl, a saturated or partially unsaturated 4-6 membered heterocyclyl optionally substituted with $C_1$-$C_4$ alkyl, $C_2$-$C_6$ alkynyl optionally substituted with halogen, $OR^e$ or $NR^cR^d$, $C_2$-$C_6$ alkenyl optionally substituted with halogen, $OR^e$ or $NR^cR^d$, or $C_1$-$C_6$ alkyl optionally substituted with one to three $R^b$ groups.

In certain embodiments, $R^5$ is hydrogen, CN, $NR^cR^d$, $OR^e$, phenyl optionally substituted with one to three $R^a$ groups, a 5-6 membered heteroaryl optionally substituted with $C_1$-$C_4$ alkyl, saturated or partially unsaturated $C_3$-$C_6$ cycloalkyl optionally substituted with $C_1$-$C_4$ alkyl, a saturated or partially unsaturated 5-6 membered heterocyclyl, $C_2$-$C_6$ alkynyl optionally substituted with $OR^e$, $C_2$-$C_6$ alkenyl optionally substituted with $OR^e$, or $C_1$-$C_6$ alkyl optionally substituted with one to three $R^b$ groups.

In certain embodiments, $R^5$ is CN, $NR^cR^d$, $OR^e$, $SR^f$, phenyl optionally substituted with one to three $R^a$ groups, a 5-6 membered heteroaryl optionally substituted with $C_1$-$C_4$ alkyl, a saturated or partially unsaturated $C_3$-$C_6$ cycloalkyl optionally substituted with halogen or $C_1$-$C_4$ alkyl, a saturated or partially unsaturated 4-6 membered heterocyclyl optionally substituted with $C_1$-$C_4$ alkyl, $C_2$-$C_6$ alkynyl optionally substituted with halogen, $OR^e$ or $NR^cR^d$, $C_2$-$C_6$ alkenyl optionally substituted with halogen, $OR^e$ or $NR^cR^d$, or $C_1$-$C_6$ alkyl optionally substituted with one to three $R^b$ groups.

In certain embodiments, $R^5$ is CN, $NR^cR^d$, $OR^e$, phenyl optionally substituted with one to three $R^a$ groups, a 5-6 membered heteroaryl optionally substituted with $C_1$-$C_4$ alkyl, saturated or partially unsaturated $C_3$-$C_6$ cycloalkyl optionally substituted with $C_1$-$C_4$ alkyl, a saturated or partially unsaturated 5-6 membered heterocyclyl, $C_2$-$C_6$ alkynyl optionally substituted with $OR^e$, $C_2$-$C_6$ alkenyl optionally substituted with $OR^e$, or $C_1$-$C_6$ alkyl optionally substituted with one to three $R^b$ groups.

In certain embodiments, each $R^a$ is independently selected from halogen, $CF_3$, $C_1$-$C_4$ alkyl or —$O(C_1$-$C_4$ alkyl), wherein the alkyl or alkoxy are optionally substituted with OH, $NR^cR^d$ or a 5-6 membered heterocyclyl optionally substituted with $C_1$-$C_3$ alkyl.

In certain embodiments, each $R^b$ is independently selected from halogen, OH, $OCH_3$, oxo, —$NR^cR^d$, or $C_3$-$C_6$ cycloalkyl.

In certain embodiments, each $R^b$ is independently selected from halogen, OH, $OCH_3$, oxo or —$NR^cR^d$.

In certain embodiments, each $R^b$ is independently selected from halogen, OH, $OCH_3$, or —$NR^cR^d$.

In certain embodiments, each $R^c$ is independently selected from hydrogen, phenyl, and $C_1$-$C_4$ alkyl optionally substituted with oxo.

In certain embodiments, each $R^c$ is independently selected from hydrogen and $C_1$-$C_4$ alkyl.

In certain embodiments, each $R^d$ is independently selected from hydrogen, phenyl, and $C_1$-$C_4$ alkyl optionally substituted with oxo.

In certain embodiments, each $R^d$ is independently selected from hydrogen and $C_1$-$C_4$ alkyl.

In certain embodiments, $R^e$ is a 4-6 membered heterocyclyl or $C_1$-$C_6$ alkyl optionally substituted with halogen, OH, $OCH_3$, $C_3$-$C_6$ cycloalkyl or a 4-6 membered heterocyclyl.

In certain embodiments, $R^e$ is $C_1$-$C_6$ alkyl optionally substituted with halogen or $C_3$-$C_6$ cycloalkyl.

In certain embodiments, $R^f$ is $C_1$-$C_6$ alkyl.

In certain embodiments, $R^5$ is hydrogen, halogen, CN, $NR^cR^d$, $OR^e$, $SR^f$, phenyl optionally substituted with one to three $R^a$ groups, a 5-6 membered heteroaryl optionally substituted with $C_1$-$C_4$ alkyl, $C_3$-$C_6$ cycloalkyl optionally substituted with halogen or $C_1$-$C_4$ alkyl, a saturated or partially unsaturated 4-6 membered heterocyclyl optionally substituted with $C_1$-$C_4$ alkyl, $C_2$-$C_6$ alkynyl optionally substituted with $NR^cR^d$, $C_2$-$C_6$ alkenyl, or $C_1$-$C_6$ alkyl optionally substituted with one to three $R^b$ groups.

In certain embodiments, $R^5$ is hydrogen, halogen, CN, $NR^cR^d$, $OR^e$, phenyl optionally substituted with one to three $R^a$ groups, 5-6 membered heteroaryl optionally substituted with $C_1$-$C_4$ alkyl, $C_3$-$C_6$ cycloalkyl, 5-6 membered heterocyclyl, $C_2$-$C_6$ alkenyl, or $C_1$-$C_6$ alkyl optionally substituted with one to three $R^b$ groups.

In certain embodiments, $R^5$ is hydrogen, CN, $NR^cR^d$, $OR^e$, $SR^f$, phenyl optionally substituted with one to three $R^a$ groups, a 5-6 membered heteroaryl optionally substituted with $C_1$-$C_4$ alkyl, $C_3$-$C_6$ cycloalkyl optionally substituted with halogen or $C_1$-$C_4$ alkyl, a saturated or partially unsaturated 4-6 membered heterocyclyl optionally substituted with $C_1$-$C_4$ alkyl, $C_2$-$C_6$ alkynyl optionally substituted with $NR^cR^d$, $C_2$-$C_6$ alkenyl, or $C_1$-$C_6$ alkyl optionally substituted with one to three $R^b$ groups.

In certain embodiments, $R^5$ is hydrogen, CN, $NR^cR^d$, $OR^e$, phenyl optionally substituted with one to three $R^a$ groups, 5-6 membered heteroaryl optionally substituted with $C_1$-$C_4$ alkyl, $C_3$-$C_6$ cycloalkyl, 5-6 membered heterocyclyl, $C_2$-$C_6$ alkenyl, or $C_1$-$C_6$ alkyl optionally substituted with one to three $R^b$ groups.

In certain embodiments, $R^5$ is CN, $NR^cR^d$, $OR^e$, $SR^f$, phenyl optionally substituted with one to three $R^a$ groups, a 5-6 membered heteroaryl optionally substituted with $C_1$-$C_4$ alkyl, $C_3$-$C_6$ cycloalkyl optionally substituted with halogen or $C_1$-$C_4$ alkyl, a saturated or partially unsaturated 4-6 membered heterocyclyl optionally substituted with $C_1$-$C_4$ alkyl, $C_2$-$C_6$ alkynyl optionally substituted with $NR^cR^d$, $C_2$-$C_6$ alkenyl, or $C_1$-$C_6$ alkyl optionally substituted with one to three $R^b$ groups.

In certain embodiments, $R^5$ is CN, $NR^cR^d$, $OR^e$, phenyl optionally substituted with one to three $R^a$ groups, 5-6 membered heteroaryl optionally substituted with $C_1$-$C_4$ alkyl, $C_3$-$C_6$ cycloalkyl, 5-6 membered heterocyclyl, $C_2$-$C_6$ alkenyl, or $C_1$-$C_6$ alkyl optionally substituted with one to three $R^b$ groups.

In certain embodiments, $R^5$ is selected from hydrogen, Br, I, CN, methylamino, dimethylamino, diethylamino, isopropylamino, phenylamino, —NHC(=O)$CH_3$, methoxy, ethoxy, propoxy, isopropoxy, 2-methoxyethoxy, 2-fluoroethoxy, 2,2,2-trifluoroethoxy, 2-hydroxyethoxy, oxetan-3-yloxy, 3-hydroxypropoxy, cyclobutylmethoxy, oxetan-3-ylmethoxy, tetrahydrofuran-3-yloxy, methylthio, ethylthio, phenyl, 3-chlorophenyl, 4-chlorophenyl, 3-fluorophenyl, 4-fluorophenyl, 4-trifluoromethylphenyl, 3-((dimethylamino)methyl)phenyl, 3-(2-(dimethylamino)ethoxy)phenyl, 4-(2-(dimethylamino)ethoxy)phenyl, 3-((2,2-dimethyl- 1,3-dioxolan-4-yl)methoxy)phenyl, 3-(2,3-dihydroxypropoxy)phenyl, 3-(morpholinomethyl)phenyl, 3-(piperidin-1-ylmethyl)phenyl, 2,3-difluorophenyl, 3,4-difluorophenyl, 3,5-difluorophenyl, pyridin-2-yl, pyridin-3-yl, pyridin-4-yl, 1-methyl-1H-pyrazol-4-yl, furan-2-yl, 1H-imidazol-1-yl, cyclopropyl, cyclobutyl, cyclopentyl, 2,2-difluorocyclopropyl, 2-methylcyclopropyl, azetidin-3-yl, 1-methylazetidin-3-yl, tetrahydrofuran-3-yl, pyrrolidin-1-yl, piperidin-4-yl, morpholino, 4-methylpiperazin-1-yl, 1-methyl-1,2,3,6-tetrahydropyridin-4-yl, —C≡CCH$_2$N(CH$_2$CH$_3$)$_2$, —CH═CH$_2$, methyl, ethyl, propyl, isopropyl, isobutyl, —CH$_2$CH$_2$CH$_2$OH, —CH$_2$CH$_2$CH$_2$N(CH$_3$)$_2$, —CH$_2$C(═O)OCH$_3$, CF$_3$, —CH$_2$OH, 2,2,2-trifluoroethyl, —C(═O)CH$_3$, and —C(═O)cyclopropyl.

In certain embodiments, R$^5$ is selected from hydrogen, Br, I, methylamino, dimethylamino, methoxy, phenyl, 3-chlorophenyl, 4-chlorophenyl, 3-fluorophenyl, 4-fluorophenyl, 4-trifluoromethylphenyl, 3-((dimethylamino)methyl)phenyl, 3-(2-(dimethylamino)ethoxy)phenyl, 4-(2-(dimethylamino)ethoxy)phenyl, 3-((2,2-dimethyl-1,3-dioxolan-4-yl)methoxy)phenyl, 3-(2,3-dihydroxypropoxy)phenyl, 3-(morpholinomethyl)phenyl, 2,3-difluorophenyl, 3,4-difluorophenyl, 3,5-difluorophenyl, pyridin-3-yl, pyridin-4-yl, 1-methyl-1H-pyrazol-4-yl, furan-2-yl, cyclopropyl, cyclobutyl, cyclopentyl, piperidin-4-yl, morpholino, —CH═CH$_2$, methyl, ethyl, propyl, isopropyl, isobutyl, —CH$_2$CH$_2$CH$_2$OH, —CH$_2$CH$_2$CH$_2$N(CH$_3$)$_2$, —CH$_2$C(═O)OCH$_3$ and CF$_3$.

In certain embodiments, R$^5$ is hydrogen.

In certain embodiments, R$^5$ is halogen. In certain embodiments, R$^5$ is F, Cl, Br or I. In certain embodiments, R$^5$ is Br. In certain embodiments, R$^5$ is I.

In certain embodiments, R$^5$ is CN.

In certain embodiments, R$^5$ is NR$^c$R$^d$. In certain embodiments, R$^c$ and R$^d$ are independently selected from hydrogen, phenyl, and C$_1$-C$_4$ alkyl optionally substituted with oxo. In certain embodiments, R$^5$ is methylamino, dimethylamino, diethylamino, isopropylamino, phenylamino or —NHC(═O)CH$_3$.

In certain embodiments, R$^5$ is NR$^c$R$^d$. In certain embodiments, R$^c$ and R$^d$ are independently selected from hydrogen, phenyl, and C$_1$-C$_4$ alkyl. In certain embodiments, R$^5$ is methylamino, dimethylamino, diethylamino, isopropylamino or phenylamino.

In certain embodiments, R$^5$ is NR$^c$R$^d$. In certain embodiments, R$^c$ and R$^d$ are independently selected from hydrogen and C$_1$-C$_4$ alkyl. In certain embodiments, R$^5$ is methylamino or dimethylamino.

In certain embodiments, R$^5$ is OR$^e$. In certain embodiments, R$^e$ is a 4-6 membered heterocyclyl or C$_1$-C$_6$ alkyl optionally substituted with halogen, OH, OCH$_3$, C$_3$-C$_6$ cycloalkyl or a 4-6 membered heterocyclyl. In certain embodiments, R$^e$ is C$_1$-C$_6$ alkyl optionally substituted with OH or OCH$_3$. In certain embodiments, R$^e$ is C$_1$-C$_6$ alkyl optionally substituted with C$_3$-C$_6$ cycloalkyl. In certain embodiments, R$^e$ is C$_1$-C$_6$ alkyl optionally substituted with cyclobutyl. In certain embodiments, R$^e$ is a 4-6 membered heterocyclyl. In certain embodiments, R$^e$ is a 4-6 membered heterocyclyl, wherein the heterocyclyl contains one or two heteroatoms selected from the group consisting of oxygen, nitrogen and sulfur. In certain embodiments, R$^e$ is a 4-6 membered heterocyclyl, wherein the heterocyclyl contains one heteroatom selected from the group consisting of oxygen, nitrogen and sulfur. In certain embodiments, R$^e$ is a 4-6 membered heterocyclyl, wherein the heterocyclyl contains one oxygen heteroatom. In certain embodiments, R$^e$ is a 4-6 membered heterocyclyl, wherein the heterocyclyl is oxetanyl or tetrahydrofuranyl. In certain embodiments, R$^e$ is methyl, ethyl, propyl, isopropyl, 2-methoxyethyl, 2-fluoroethyl, 2,2,2-trifluoroethyl, 2-hydroxyethyl, oxetan-3-yl, 3-hydroxypropyl, cyclobutylmethyl, oxetan-3-ylmethyl or tetrahydrofuran-3yl. In certain embodiments, R$^5$ is methoxy, ethoxy, propoxy, isopropoxy, 2-methoxyethoxy, 2-fluoroethoxy, 2,2,2-trifluoroethoxy, 2-hydroxyethoxy, oxetan-3-yloxy, 3-hydroxypropoxy, cyclobutylmethoxy, oxetan-3ylmethoxy or tetrahydrofuran-3 yloxy.

In certain embodiments, R$^5$ is OR$^e$. In certain embodiments, R$^e$ is C$_1$-C$_6$ alkyl optionally substituted with halogen or C$_3$-C$_6$ cycloalkyl. In certain embodiments, R$^e$ is methyl. In certain embodiments, R$^5$ is methoxy.

In certain embodiments, R$^5$ is SR$^f$. In certain embodiments, R$^f$ is C$_1$-C$_6$ alkyl. In certain embodiments, R$^5$ is methylthio or ethylthio.

In certain embodiments, R$^5$ is phenyl optionally substituted with one to three R$^a$ groups. In certain embodiments, each R$^a$ is independently selected from halogen, CF$_3$, C$_1$-C$_4$ alkyl or —O(C$_1$-C$_4$ alkyl), wherein the alkyl or alkoxy are optionally substituted with OH, NR$^c$R$^d$ or a 5-6 membered heterocyclyl optionally substituted with C$_1$-C$_3$ alkyl. In certain embodiments, R$^c$ and R$^d$ are independently selected from hydrogen and C$_1$-C$_4$ alkyl.

In certain embodiments, R$^5$ is phenyl.

In certain embodiments, R$^5$ is phenyl substituted by one R$^a$ group. In certain embodiments, R$^a$ is selected from halogen, CF$_3$, C$_1$-C$_4$ alkyl or —O(C$_1$-C$_4$ alkyl), wherein the alkyl or alkoxy are optionally substituted with OH, NR$^c$R$^d$ or a 5-6 membered heterocyclyl optionally substituted with C$_1$-C$_3$ alkyl. In certain embodiments, R$^c$ and R$^d$ are methyl. In certain embodiments, R$^a$ is —O(C$_1$-C$_4$ alkyl) optionally substituted with OH or a 5-6 membered heterocyclyl optionally substituted with C$_1$-C$_3$ alkyl. In certain embodiments, R$^a$ is —O(C$_1$-C$_4$ alkyl) substituted with a 5-6 membered heterocyclyl optionally substituted with C$_1$-C$_3$ alkyl, wherein the heterocyclyl is 1,3-dioxolane. In certain embodiments, R$^b$ is C$_1$-C$_4$ alkyl substituted with a 5-6 membered heterocyclyl, wherein the heterocyclyl is morpholinyl. In certain embodiments, R$^5$ is selected from 3-chlorophenyl, 4-chlorophenyl, 3-fluorophenyl, 4-fluorophenyl, 4-trifluoromethylphenyl, 3-((dimethylamino)methyl)phenyl, 3-(2-(dimethylamino)ethoxy)phenyl, 4-(2-(dimethylamino)ethoxy)phenyl, 3-((2,2-dimethyl-1,3-dioxolan-4-yl)methoxy)phenyl, 3-(2,3-dihydroxypropoxy)phenyl, 3-(morpholinomethyl)phenyl and 3-(piperidin-1-ylmethyl)phenyl.

In certain embodiments, R$^5$ is phenyl substituted by one R$^a$ group. In certain embodiments, R$^a$ is selected from halogen, CF$_3$, C$_1$-C$_4$ alkyl or —O(C$_1$-C$_4$ alkyl), wherein the alkyl or alkoxy are optionally substituted with OH, NR$^c$R$^d$ or a 5-6 membered heterocyclyl optionally substituted with C$_1$-C$_3$ alkyl. In certain embodiments, R$^c$ and R$^d$ are methyl. In certain embodiments, R$^a$ is —O(C$_1$-C$_4$ alkyl) optionally substituted with OH or a 5-6 membered heterocyclyl optionally substituted with C$_1$-C$_3$ alkyl. In certain embodiments, R$^a$ is —O(C$_1$-C$_4$ alkyl) substituted with a 5-6 membered heterocyclyl optionally substituted with C$_1$-C$_3$ alkyl, wherein the heterocyclyl is 1,3-dioxolane. In certain embodiments, R$^a$ is C$_1$-C$_4$ alkyl substituted with a 5-6 membered heterocyclyl, wherein the heterocyclyl is morpholinyl. In certain embodiments, R$^5$ is selected from 3-chlorophenyl, 4-chlorophenyl, 3-fluorophenyl, 4-fluorophenyl, 4-trifluoromethylphenyl, 3-((dimethylamino)methyl)phenyl, 3-(2-(dimethylamino)ethoxy)phenyl, 4-(2-(dimethylamino)ethoxy)phenyl, 3-((2,2-dimethyl-1,3-dioxolan-4-yl)methoxy)phenyl, 3-(2,3-dihydroxypropoxy)phenyl and 3-(morpholinomethyl)phenyl.

In certain embodiments, R$^5$ is phenyl substituted by a halogen. In certain embodiments, R$^5$ is phenyl substituted with F or Cl. In certain embodiments, $R^5$ is selected from 3-chlorophenyl, 4-chlorophenyl, 3-fluorophenyl and 4-fluorophenyl.

In certain embodiments, $R^5$ is phenyl substituted by $CF_3$. In certain embodiments, $R^5$ is 4-trifluoromethylphenyl.

In certain embodiments, $R^5$ is phenyl substituted with $C_1$-$C_4$ alkyl optionally substituted with $NR^cR^d$. In certain embodiments, $R^c$ and $R^d$ are methyl. In certain embodiments, $R^5$ is 3-((dimethylamino)methyl)phenyl.

In certain embodiments, $R^5$ is phenyl substituted with —O($C_1$-$C_4$ alkyl) optionally substituted with OH, $NR^cR^d$ or a 5-6 membered heterocyclyl optionally substituted with $C_1$-$C_3$ alkyl. In certain embodiments, $R^c$ and $R^d$ are methyl. In certain embodiments, $R^5$ is phenyl substituted with —O($C_1$-$C_4$ alkyl) substituted with a 5-6 membered heterocyclyl optionally substituted with $C_1$-$C_3$ alkyl, wherein the heterocyclyl is 1,3-dioxolane. In certain embodiments, $R^5$ is selected from 3-(2-(dimethylamino)ethoxy)phenyl, 4-(2-(dimethylamino)ethoxy)phenyl, 3-((2,2-dimethyl-1,3-dioxolan-4-yl)methoxy)phenyl and 3-(2,3-dihydroxypropoxy)phenyl.

In certain embodiments, $R^5$ is phenyl optionally substituted with two $R^a$ groups. In certain embodiments, each $R^a$ is halogen. In certain embodiments, each $R^a$ is F. In certain embodiments, $R^5$ is 2,3-difluorophenyl, 3,4-difluorophenyl and 3,5-difluorophenyl.

In certain embodiments, $R^5$ is phenyl optionally substituted with one or two $R^a$ groups. In certain embodiments, each $R^a$ is halogen. In certain embodiments, $R^5$ is selected from 3-chlorophenyl, 4-chlorophenyl, 3-fluorophenyl, 4-fluorophenyl, 2,3-difluorophenyl, 3,4-difluorophenyl and 3,5-difluorophenyl.

In certain embodiments, $R^5$ is phenyl optionally substituted with one or two $R^a$ groups. In certain embodiments, $R^a$ is selected from halogen, $CF_3$, $C_1$-$C_4$ alkyl or —O($C_1$-$C_4$ alkyl) wherein the alkyl or alkoxy are optionally substituted with OH, $NR^cR^d$ or a 5-6 membered heterocyclyl optionally substituted with $C_1$-$C_3$ alkyl. In certain embodiments, $R^c$ and $R^d$ are methyl. In certain embodiments, $R^5$ is selected from 3-chlorophenyl, 4-chlorophenyl, 3-fluorophenyl, 4-fluorophenyl, 4-trifluoromethylphenyl, 3-((dimethylamino)methyl)phenyl, 3-(2-(dimethylamino)ethoxy)phenyl, 4-(2-(dimethylamino)ethoxy)phenyl, 2,3-difluorophenyl, 3,4-difluorophenyl, 3,5-difluorophenyl, 3-((2,2-dimethyl-1,3-dioxolan-4-yl)methoxy)phenyl, 3-(2,3-dihydroxypropoxy)phenyl and 3-(morpholinomethyl)phenyl.

In certain embodiments, $R^5$ is a 5-6 membered heteroaryl optionally substituted with $C_1$-$C_4$ alkyl. In certain embodiments, $R^5$ is a 5-6 membered heteroaryl optionally substituted with $C_1$-$C_4$ alkyl, wherein the heteroaryl contains one or two heteroatoms selected from oxygen, nitrogen and sulfur. In certain embodiments, $R^5$ is a 5-6 membered heteroaryl optionally substituted with $C_1$-$C_4$ alkyl, wherein the heteroaryl contains one or two heteroatoms selected from oxygen and nitrogen. In certain embodiments, $R^5$ is a 5-6 membered heteroaryl optionally substituted with $C_1$-$C_4$ alkyl, wherein the heteroaryl is selected from pyridinyl, pyrazolyl, furanyl and imidazolyl. In certain embodiments, $R^5$ is selected from pyridin-2-yl, pyridin-3-yl, pyridin-4-yl, 1-methyl-1H-pyrazol-4-yl, furan-2-yl and 1H-imidazol-1-yl.

In certain embodiments, $R^5$ is a 5-6 membered heteroaryl optionally substituted with $C_1$-$C_4$ alkyl. In certain embodiments, $R^5$ is a 5-6 membered heteroaryl optionally substituted with $C_1$-$C_4$ alkyl, wherein the heteroaryl is selected from pyridinyl, pyrazolyl and furanyl. In certain embodiments, $R^5$ is selected from pyridin-3-yl, pyridine-4-yl, 1-methyl-1H-pyrazol-4-yl and furan-2-yl.

In certain embodiments, $R^5$ is a saturated or partially unsaturated $C_3$-$C_6$ cycloalkyl optionally substituted with halogen or $C_1$-$C_4$ alkyl. In certain embodiments, $R^5$ is a saturated $C_3$-$C_6$ cycloalkyl optionally substituted with halogen or $C_1$-$C_4$ alkyl. In certain embodiments, $R^5$ is a saturated $C_3$-$C_6$ cycloalkyl optionally substituted with halogen or $C_1$-$C_4$ alkyl, wherein the cycloalkyl is selected from cyclopropyl, cyclobutyl and cyclopentyl. In certain embodiments, $R^5$ is a saturated $C_3$-$C_6$ cycloalkyl. In certain embodiments, $R^5$ is a saturated $C_3$-$C_6$ cycloalkyl, wherein the cycloalkyl is selected from cyclopropyl, cyclobutyl and cyclopentyl. In certain embodiments, $R^5$ is selected from cyclopropyl, cyclobutyl and cyclopentyl. In certain embodiments, $R^5$ is cyclopropyl, 2,2-difluorocyclopropyl or 2-methylcyclopropyl.

In certain embodiments, $R^5$ is a saturated or partially unsaturated $C_3$-$C_6$ cycloalkyl optionally substituted with halogen or $C_1$-$C_4$ alkyl. In certain embodiments, $R^5$ is a saturated $C_3$-$C_6$ cycloalkyl optionally substituted with halogen or $C_1$-$C_4$ alkyl. In certain embodiments, $R^5$ is a saturated $C_3$-$C_6$ cycloalkyl. In certain embodiments, $R^5$ is selected from cyclopropyl, cyclobutyl and cyclopentyl. In certain embodiments, $R^5$ is cyclopropyl.

In certain embodiments, $R^5$ is a saturated or partially unsaturated 4-6 membered heterocyclyl optionally substituted with $C_1$-$C_4$ alkyl. In certain embodiments, $R^5$ is a saturated 4-6 membered heterocyclyl optionally substituted with $C_1$-$C_4$ alkyl. In certain embodiments, $R^5$ is a saturated 4-6 membered heterocyclyl. In certain embodiments, $R^5$ is a 4-6 membered heterocyclyl optionally substituted with $C_1$-$C_4$ alkyl, wherein the heterocyclyl contains one or two heteroatoms selected from oxygen, nitrogen and sulfur. In certain embodiments, $R^5$ is a 4-6 membered heterocyclyl optionally substituted with $C_1$-$C_4$ alkyl, wherein the heterocyclyl is azetidinyl, tetrahydrofuranyl, pyrrolidinyl, piperidinyl, piperazinyl or morpholinyl. In certain embodiments, $R^5$ is a partially unsaturated 4-6 membered heterocyclyl optionally substituted with $C_1$-$C_4$ alkyl. In certain embodiments, $R^5$ is a partially unsaturated 4-6 membered heterocyclyl optionally substituted with $C_1$-$C_4$ alkyl, wherein the heterocyclyl contains one or two heteroatoms selected from oxygen, nitrogen and sulfur. In certain embodiments, $R^5$ is a partially unsaturated 4-6 membered heterocyclyl optionally substituted with $C_1$-$C_4$ alkyl, wherein the heterocyclyl is 1,2,3,6-tetrahydropyridinyl. In certain embodiments, $R^5$ is a 4-6 membered heterocyclyl optionally substituted with $C_1$-$C_4$ alkyl, wherein the heterocyclyl contains one or two heteroatoms selected from nitrogen and oxygen. In certain embodiments, $R^5$ is azetidin-3-yl, 1-methylazetidin-3-yl, tetrahydrofuran-3-yl, pyrrolidin-1-yl, piperidin-4-yl, morpholino, 4-methylpiperazin-1-yl or 1-methyl-1,2,3,6-tetrahydropyridin-4-yl.

In certain embodiments, $R^5$ is a saturated or partially unsaturated 4-6 membered heterocyclyl optionally substituted with $C_1$-$C_3$ alkyl. In certain embodiments, $R^5$ is a saturated 4-6 membered heterocyclyl optionally substituted with $C_1$-$C_3$ alkyl. In certain embodiments, $R^5$ is a 4-6 membered heterocyclyl optionally substituted with $C_1$-$C_3$ alkyl, wherein the heterocyclyl contains one or two heteroatoms selected from oxygen and nitrogen. In certain embodiments, $R^5$ is a 4-6 membered heterocyclyl optionally substituted with $C_1$-$C_3$ alkyl, wherein the heterocyclyl is azetidinyl, tetrahydrofuranyl, pyrrolidinyl, piperidinyl, piperazinyl or morpholinyl. In certain embodiments, $R^5$ is azetidin-3-yl, 1-methylazetidin-3-yl, tetrahydrofuran-3-yl, pyrrolidin-1-yl, piperidin-4-yl, morpholino or 4-methylpiperazin-1-yl.

In certain embodiments, $R^5$ is a saturated or partially unsaturated 5-6 membered heterocyclyl. In certain embodiments, $R^5$ is a saturated 5-6 membered heterocyclyl. In certain embodiments, $R^5$ is a 5-6 membered heterocyclyl, wherein the heterocyclyl is piperidinyl or morpholinyl. In certain embodiments, $R^5$ is piperidin-4-yl or morpholino.

In certain embodiments, $R^5$ is a saturated or partially unsaturated 4-6 membered heterocyclyl optionally substituted with $C_1$-$C_3$ alkyl. In certain embodiments, $R^5$ is a partially unsaturated 4-6 membered heterocyclyl optionally substituted with $C_1$-$C_3$ alkyl. In certain embodiments, $R^5$ is a partially unsaturated 4-6 membered heterocyclyl, wherein the heterocyclyl contains one or two nitrogen heteroatoms. In certain embodiments, $R^5$ is a partially unsaturated 4-6 membered heterocyclyl, wherein the heterocyclyl is 1,2,3,6-tetrahydropyridinyl. In certain embodiments, $R^5$ is 1-methyl-1,2,3,6-tetrahydropyridin-4-yl.

In certain embodiments, $R^5$ is $C_2$-$C_6$ alkynyl optionally substituted with $OR^c$ or $NR^cR^d$. In certain embodiments, $R^5$ is $C_2$-$C_6$ alkynyl optionally substituted with $NR^cR^d$. In certain embodiments, $R^c$ and $R^d$ are hydrogen or $C_1$-$C_4$ alkyl. In certain embodiments, $R^5$ is —C≡CCH$_2$N(CH$_2$CH$_3$)$_2$.

In certain embodiments, $R^5$ is $C_2$-$C_6$ alkenyl optionally substituted with $OR^c$. In certain embodiments, $R^5$ is $C_2$-$C_6$ alkenyl. In certain embodiments, $R^5$ is —CH=CH$_2$.

In certain embodiments, $R^5$ is $C_1$-$C_6$ alkyl optionally substituted with one to three $R^b$ groups. In certain embodiments, each $R^b$ is independently selected from halogen, OH, OCH$_3$, oxo, —NR$^c$R$^d$, or $C_3$-$C_6$ cycloalkyl. In certain embodiments, $R^c$ and $R^d$ are independently selected from hydrogen, phenyl, and $C_1$-$C_4$ alkyl optionally substituted with oxo. In certain embodiments, $R^5$ is selected from methyl, ethyl, isopropyl, isobutyl, —CH$_2$CH$_2$CH$_2$OH, —CH$_2$CH$_2$CH$_2$N(CH$_3$)$_2$, —CH$_2$C(=O)OCH$_3$, CF$_3$, —CH$_2$OH, 2,2,2-trifluoroethyl, —C(=O)CH$_3$, and —C(=O)cyclopropyl.

In certain embodiments, $R^5$ is $C_1$-$C_6$ alkyl optionally substituted with one to three $R^b$ groups. In certain embodiments, each $R^b$ is independently selected from halogen, OH, OCH$_3$, oxo or —NR$^c$R$^d$. In certain embodiments, $R^c$ and $R^d$ are independently selected from hydrogen and $C_1$-$C_4$ alkyl. In certain embodiments, $R^5$ is selected from methyl, ethyl, isopropyl, isobutyl, —CH$_2$CH$_2$CH$_2$OH, —CH$_2$CH$_2$CH$_2$N(CH$_3$)$_2$, —CH$_2$C(=O)OCH$_3$ and CF$_3$.

In certain embodiments, $R^5$ is $C_1$-$C_6$ alkyl optionally substituted with one to three $R^b$ groups. In certain embodiments, each $R^b$ is independently selected from halogen, OH, OCH$_3$, oxo, —NR$^c$R$^d$, and $C_3$-$C_6$ cycloalkyl. In certain embodiments, $R^b$ is $C_3$-$C_6$ cycloalkyl, wherein the cycloalkyl is cyclopropyl. In certain embodiments, $R^c$ and $R^d$ are independently selected from hydrogen and $C_1$-$C_4$ alkyl. In certain embodiments, $R^5$ is selected from methyl, ethyl, isopropyl, isobutyl, —CH$_2$CH$_2$CH$_2$OH, —CH$_2$CH$_2$CH$_2$N(CH$_3$)$_2$, CF$_3$, —CH$_2$OH, 2,2,2-trifluoroethyl, —C(=O)CH$_3$, and —C(=O)cyclopropyl.

In certain embodiments, $R^5$ is $C_1$-$C_6$ alkyl optionally substituted with one to three $R^b$ groups. In certain embodiments, each $R^b$ is independently selected from halogen, OH, OCH$_3$, or —NR$^c$R$^d$. In certain embodiments, $R^c$ and $R^d$ are independently selected from hydrogen and $C_1$-$C_4$ alkyl. In certain embodiments, $R^5$ is selected from methyl, ethyl, isopropyl, isobutyl, —CH$_2$CH$_2$CH$_2$OH, —CH$_2$CH$_2$CH$_2$N(CH$_3$)$_2$, and CF$_3$.

In certain embodiments, $R^5$ is $C_1$-$C_6$ alkyl. In certain embodiments, $R^5$ is selected from methyl, ethyl, propyl, isopropyl and isobutyl.

In certain embodiments, $R^5$ is $C_1$-$C_6$ alkyl substituted with one $R^b$ group. In certain embodiments, $R^b$ is selected from OH, oxo and NR$^c$R$^d$. In certain embodiments, $R^5$ is selected from —CH$_2$CH$_2$CH$_2$OH, —CH$_2$CH$_2$CH$_2$N(CH$_3$)$_2$, —CH$_2$OH, and —C(=O)CH$_3$.

In certain embodiments, $R^5$ is $C_1$-$C_6$ alkyl substituted with one $R^b$ group. In certain embodiments, $R^b$ is selected from OH and NR$^c$R$^d$. In certain embodiments, $R^5$ is selected from —CH$_2$CH$_2$CH$_2$OH and —CH$_2$CH$_2$CH$_2$N(CH$_3$)$_2$.

In certain embodiments, $R^5$ is $C_1$-$C_6$ alkyl substituted with two $R^b$ groups. In certain embodiments, each $R^b$ is selected from oxo and $C_3$-$C_6$ cycloalkyl. In certain embodiments, $R^5$ is —C(=O)cyclopropyl.

In certain embodiments, $R^5$ is $C_1$-$C_6$ alkyl substituted with two $R^b$ groups. In certain embodiments, each $R^b$ is selected from oxo and OCH$_3$. In certain embodiments, $R^5$ is —CH$_2$C(=O)OCH$_3$.

In certain embodiments, $R^5$ is $C_1$-$C_6$ alkyl substituted with three $R^b$ groups. In certain embodiments, $R^b$ is halogen. In certain embodiments, $R^5$ is CF$_3$ or 2,2,2-trifluoroethyl.

In certain embodiments, $R^5$ is $C_1$-$C_6$ alkyl substituted with three $R^b$ groups. In certain embodiments, $R^b$ is halogen. In certain embodiments, $R^5$ is CF$_3$.

It will be appreciated that certain compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

It will also be appreciated that compounds of Formula I include tautomeric forms. Tautomers are compounds that are interconvertible by tautomerization. This commonly occurs due to the migration of a hydrogen atom or proton, accompanied by the switch of a single bond and adjacent double bond. For instance, 1H-pyrazolo[3,4-b]pyridine is one tautomeric form, while 7H-pyrazolo[3,4-b]pyridine is another tautomeric form. Other tautomers of Formula I may also form at other positions, including, but not limited to, the sulfonamide or $R^5$ position depending on the substitution. The compounds of Formula I are intended to include all tautomeric forms.

The compounds of Formula I include the tautomer 7H-pyrazolo[3,4-b]pyridine, shown as Formula II:

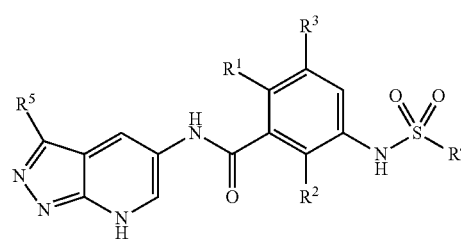

wherein $R^1$, $R^2$, $R^3$, $R^4$ and $R^5$ are as defined herein.

In another embodiment of the present invention, intermediates of Formula III are provided:

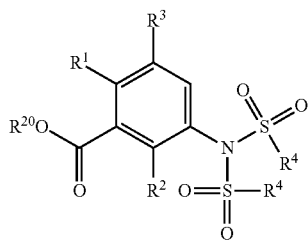

wherein $R^{20}$ is hydrogen, $C_1$-$C_6$ alkyl, benzyl or phenyl and $R^1$, $R^2$, $R^3$ and $R^4$ are as defined herein.

In one embodiment of Formula III, $R^{20}$ is $C_1$-$C_6$ alkyl, benzyl or phenyl.

In another embodiment of the present invention, intermediates of Formula IV are provided:

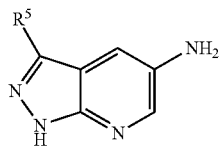

wherein $R^5$ is as defined herein.

In certain embodiments of Formula IV, $R^5$ is CN.
In certain embodiments of Formula IV, $R^5$ is $OR^e$.
In certain embodiments of Formula IV, $R^5$ is $SR^f$.
In certain embodiments of Formula IV, $R^5$ is phenyl optionally substituted with one to three $R^a$ groups.
In certain embodiments of Formula IV, $R^5$ is a 5-6 membered heteroaryl optionally substituted with $C_1$-$C_4$ alkyl.
In certain embodiments of Formula IV, $R^5$ is a saturated or partially unsaturated $C_3$-$C_6$ cycloalkyl optionally substituted with halogen or $C_1$-$C_4$ alkyl.
In certain embodiments of Formula IV, $R^5$ is a saturated or partially unsaturated 4-6 membered heterocyclyl optionally substituted with $C_1$-$C_4$ alkyl.
In certain embodiments of Formula IV, $R^5$ is $C_2$-$C_6$ alkynyl optionally substituted with halogen, $OR^c$ or $NR^cR^d$.
In certain embodiments of Formula IV, $R^5$ is $C_2$-$C_6$ alkenyl optionally substituted with halogen, $OR^c$ or $NR^cR^d$.
In certain embodiments of Formula IV, $R^5$ is $C_1$-$C_6$ alkyl optionally substituted with one to three $R^b$ groups.

In another embodiment of the present invention, intermediates of Formula IVa (a subset of Formula IV) are provided:

wherein $R^e$ is selected from a 4-6 membered heterocyclyl and $C_1$-$C_6$ alkyl optionally substituted with halogen, OH, $OCH_3$, $C_3$-$C_6$ cycloalkyl or a 4-6 membered heterocyclyl.

In certain embodiments of Formula IVa, $R^e$ is selected from a 4-6 membered heterocyclyl and $C_1$-$C_6$ alkyl optionally substituted with halogen, OH, $OCH_3$, $C_3$-$C_6$ cycloalkyl or a 4-6 membered heterocyclyl, wherein the heterocyclyls contain one or two heteroatoms selected from oxygen, nitrogen and sulfur. In certain embodiments of Formula IVa, $R^e$ is selected from a 4-6 membered heterocyclyl and $C_1$-$C_6$ alkyl optionally substituted with halogen, OH, $OCH_3$, $C_3$-$C_6$ cycloalkyl or a 4-6 membered heterocyclyl, wherein the heterocyclyls contain one oxygen heteroatom. In certain embodiments of Formula IVa, $R^e$ is selected from a 4-6 membered heterocyclyl and $C_1$-$C_6$ alkyl optionally substituted with halogen, OH, $OCH_3$, $C_3$-$C_6$ cycloalkyl or a 4-6 membered heterocyclyl, wherein the heterocyclyls are selected from oxetanyl and tetrahydrofuran.

In certain embodiments of Formula IVa, $R^e$ is $C_1$-$C_6$ alkyl optionally substituted with halogen, OH, $OCH_3$, $C_3$-$C_6$ cycloalkyl or a 4-6 membered heterocyclyl. In certain embodiments of Formula IVa, $R^e$ is $C_1$-$C_6$ alkyl optionally substituted with halogen, OH, $OCH_3$, $C_3$-$C_6$ cycloalkyl or a 4-6 membered heterocyclyl, wherein the heterocyclyl contains one oxygen heteroatom. In certain embodiments of Formula IVa, $R^e$ is $C_1$-$C_6$ alkyl optionally substituted with halogen, OH, $OCH_3$, $C_3$-$C_6$ cycloalkyl or a 4-6 membered heterocyclyl, wherein the heterocyclyl is selected from oxetanyl and tetrahydrofuran. In certain embodiments of Formula IVa, $R^e$ is selected from methyl, ethyl, propyl, isopropyl, —$CH_2CF_3$, —$CH_2CH_2F$, —$CH_2CH_2OH$, —$CH_2CH_2OCH_3$, —$CH_2CH_2CH_2OCH_3$, oxetan-3-yl, tetrahydropyran-3-yl, —$CH_2$(cyclobutyl) and —$CH_2$(oxetan-3-yl).

Compounds of Formula IVa include 3-methoxy-1H-pyrazolo[3,4-b]pyridin-5-amine, 3-ethoxy-1H-pyrazolo[3,4-b]pyridin-5-amine, 3-propoxy-1H-pyrazolo[3,4-b]pyridin-5-amine, 3-isopropoxy-1H-pyrazolo[3,4-b]pyridin-5-amine, 3-(2-methoxyethoxy)-1H-pyrazolo[3,4-b]pyridin-5-amine, 3-(2-fluoroethoxy)-1H-pyrazolo[3,4-b]pyridin-5-amine, 3-(2,2,2-trifluoroethoxy)-1H-pyrazolo[3,4-b]pyridin-5-amine, 3-(5-amino-1H-pyrazolo[3,4-b]pyridin-3-yloxy)propan-1-ol, 2-(5-amino-1H-pyrazolo[3,4-b]pyridin-3-yloxy)ethanol, 3-(oxetan-3-yloxy)-1H-pyrazolo[3,4-b]pyridin-5-amine, 3-(tetrahydrofuran-3-yloxy)-1H-pyrazolo[3,4-b]pyridin-5-amine, 3-(oxetan-3-ylmethoxy)-1H-pyrazolo[3,4-b]pyridin-5-amine and 3-(cyclobutylmethoxy)-1H-pyrazolo[3,4-b]pyridin-5-amine.

In another embodiment of the present invention, intermediates of Formula IVb (a subset of Formula IV) are provided:

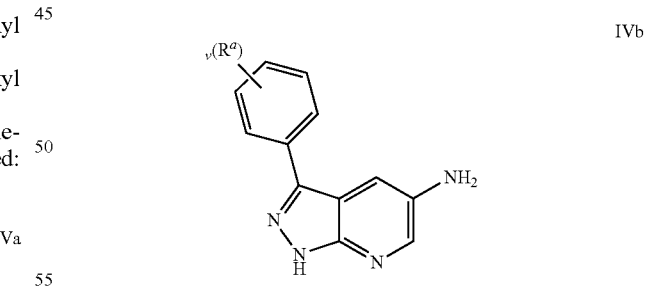

wherein v is 0, 1, 2 or 3 and $R^a$ is as defined herein.
In certain embodiments of Formula IVb, v is 0.
In certain embodiments of Formula IVb, v is 1.
In certain embodiments of Formula IVb, v is 2.
In certain embodiments of Formula IVb, v is 3.
In certain embodiments of Formula IVb, $R^a$ is halogen. In certain embodiments of Formula IVb, $R^a$ is F or Cl. In certain embodiments of Formula IVb, $R^a$ is F or Cl and v is 1 or 2.

Compounds of Formula IVb include 3-phenyl-1H-pyrazolo[3,4-b]pyridin-5-amine, 3-(3-chlorophenyl)-1H-pyrazolo[3,4-b]pyridin-5-amine, 3-(4-chlorophenyl)-1H-pyrazolo[3,4-b]pyridin-5-amine, 3-(3-fluorophenyl)-1H-pyrazolo[3,4-b]pyridin-5-amine, 3-(4-fluorophenyl)-1H-pyrazolo[3,4-b]pyridin-5-amine, 3-(2,3-difluorophenyl)-1H-pyrazolo[3,4-b]pyridin-5-amine, 3-(3,4-difluorophenyl)-1H-pyrazolo[3,4-b]pyridin-5-amine, and 3-(3,5-difluorophenyl)-1H-pyrazolo[3,4-b]pyridin-5-amine.

Compounds of Formula IVb include 3-(4-(trifluoromethyl)phenyl)-1H-pyrazolo[3,4-b]pyridin-5-amine, 3-(3-(2-(dimethylamino)ethoxy)phenyl)-1H-pyrazolo[3,4-b]pyridin-5-amine, 3-(4-(2-(dimethylamino)ethoxy)phenyl)-1H-pyrazolo[3,4-b]pyridin-5-amine, 3-(3-((dimethylamino)methyl)phenyl)-1H-pyrazolo[3,4-b]pyridin-5-amine, 3-(3-(5-amino-1H-pyrazolo[3,4-b]pyridin-3-yl)phenoxy)propane-1,2-diol, 3-(3-((2,2-dimethyl-1,3-dioxolan-4-yl)methoxy)phenyl)-1H-pyrazolo[3,4-b]pyridin-5-amine, 3-(3-(morpholinomethyl)phenyl)-1H-pyrazolo[3,4-b]pyridin-5-amine, and 3-(3-(piperidin-1-ylmethyl)phenyl)-1H-pyrazolo[3,4-b]pyridin-5-amine.

In another embodiment of the present invention, intermediates of Formula IVc (a subset of Formula IV) are provided:

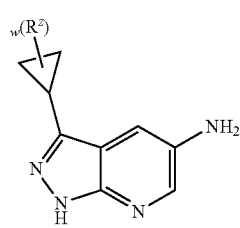

IVc wherein $R^z$ is halogen or $C_1$-$C_4$ alkyl and w is 0, 1 or 2.

In certain embodiments of Formula IVc, w is 0.
In certain embodiments of Formula IVc, w is 1.
In certain embodiments of Formula IVc, w is 2.
In certain embodiments of Formula IVc, $R^z$ is halogen. In certain embodiments of Formula IVc, $R^z$ is F. In certain embodiments of Formula IVc, $R^z$ is F and w is 2.
In certain embodiments of Formula IVc, $R^z$ is $C_1$-$C_4$ alkyl. In certain embodiments of Formula IVc, $R^z$ is methyl. In certain embodiments of Formula IVc, $R^z$ is methyl and w is 1.

Compounds of Formula IVc include 3-cyclopropyl-1H-pyrazolo[3,4-b]pyridin-5-amine, 3-(2,2-difluorocyclopropyl)-1H-pyrazolo[3,4-b]pyridin-5-amine, (R)-3-(2,2-difluorocyclopropyl)-1H-pyrazolo[3,4-b]pyridin-5-amine, (S)-3-(2,2-difluorocyclopropyl)-1H-pyrazolo[3,4-b]pyridin-5-amine, 3-(2-methylcyclopropyl)-1H-pyrazolo[3,4-b]pyridin-5-amine, and 3-((cis)-2-methylcyclopropyl)-1H-pyrazolo[3,4-b]pyridin-5-amine.

It will also be appreciated that certain compounds of Formula I may be used as intermediates for further compounds of Formula I.

It will be further appreciated that the compounds of the present invention may exist in unsolvated, as well as solvated forms with pharmaceutically acceptable solvents, such as water, ethanol, and the like, and it is intended that the invention embrace both solvated and unsolvated forms.

The term "prodrug" as used in this application refers to a precursor or derivative form of a compound of the invention that is less active or inactive compared to the parent compound or drug and is capable of being metabolized in vivo into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug.

Prodrugs of compounds of Formula I are not as active as the compounds of Formula I in the assay as described in Example A. However, the prodrugs are capable of being converted in vivo into more active metabolites, i.e., compounds of Formula I. Prodrugs of compounds of Formula I include compounds having Formula V:

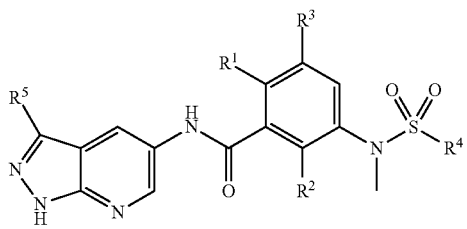

V wherein $R^1$, $R^2$, $R^3$, $R^4$ and $R^5$ are as defined herein.

Synthesis of Compounds

Compounds of the present invention may be synthesized by synthetic routes that include processes analogous to those well-known in the chemical arts, particularly in light of the description contained herein. The starting materials are generally available from commercial sources such as Sigma-Aldrich (St. Louis, Mo.), Alfa Aesar (Ward Hill, Mass.), or TCI (Portland, Oreg.), or are readily prepared using methods well known to those skilled in the art (e.g., prepared by methods generally described in Louis F. Fieser and Mary Fieser, *Reagents for Organic Synthesis*. v. 1-23, New York: Wiley 1967-2006 ed. (also available via the Wiley InterScience® website), or *Beilsteins Handbuch der organischen Chemie*, 4, Aufl. ed. Springer-Verlag, Berlin, including supplements (also available via the Beilstein online database)).

For illustrative purposes, Schemes 1-18 show general methods for preparing the compounds of the present invention, as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

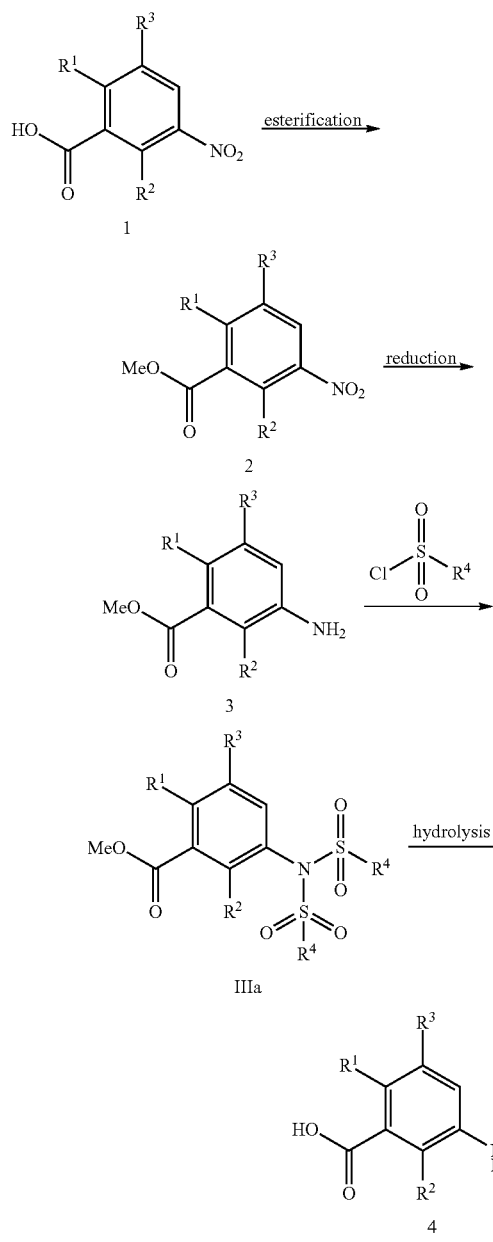

Scheme 2

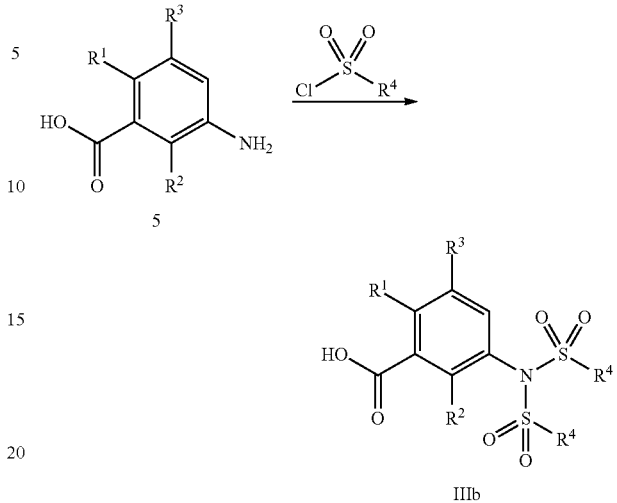

Scheme 2 shows a general method for preparing compounds of Formula IIIb (a subset of Formula III), wherein $R^1$, $R^2$, $R^3$ and $R^4$ are as defined herein. Aniline 5 is sulfonylated in an organic solvent, such as DCM, in the presence of a base, such as $NEt_3$, to provide a compound of Formula IIIb.

Scheme 3

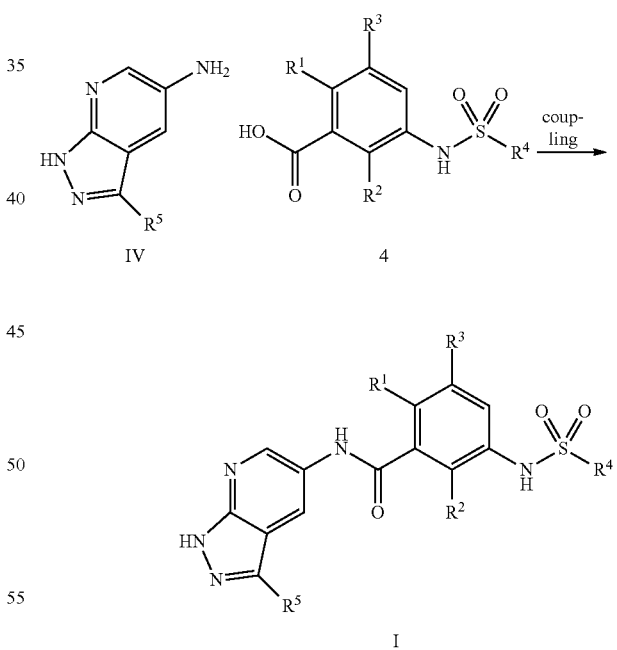

Scheme 1 shows a general method for preparing compound 4, wherein $R^1$, $R^2$, $R^3$ and $R^4$ are as defined herein. Benzoic acid 1 is esterified to methyl benzoate 2 by treatment with trimethylsilyl diazomethane in MeOH or via Fischer esterification conditions, such as treatment with trimethylsilyl chloride ("TMSCl") in MeOH. Reduction of ester 2 is performed using a standard condition, such as treatment with Pd/C and $H_2$. Bis-sulfonamide of Formula IIIa (a subset of Formula III) is obtained by treatment of aniline 3 with a sulfonyl chloride in the presence of a base, such as $NEt_3$, in an organic solvent, such as dichloromethane ("DCM"). Hydrolysis of Formula IIIa is accomplished under basic conditions, such as aqueous NaOH in the appropriate solvent system such as THF and/or MeOH, to provide compound 4.

Scheme 3 illustrates a general method for preparing compounds of Formula I, wherein $R^1$, $R^2$, $R^3$, $R^4$ and $R^5$ are as defined herein. Coupling of 5-aminopyrazolopyridine of Formula IV with acid 4 is performed with an activating reagent, such as N-(3-dimethylaminopropyl)-N'-ethylcarbodiimide hydrochloride ("EDCI"), in the presence of an additive, such as hydroxybenzotriazole ("HOBt"), in a suitable solvent, such as dimethylformamide ("DMF").

Scheme 4

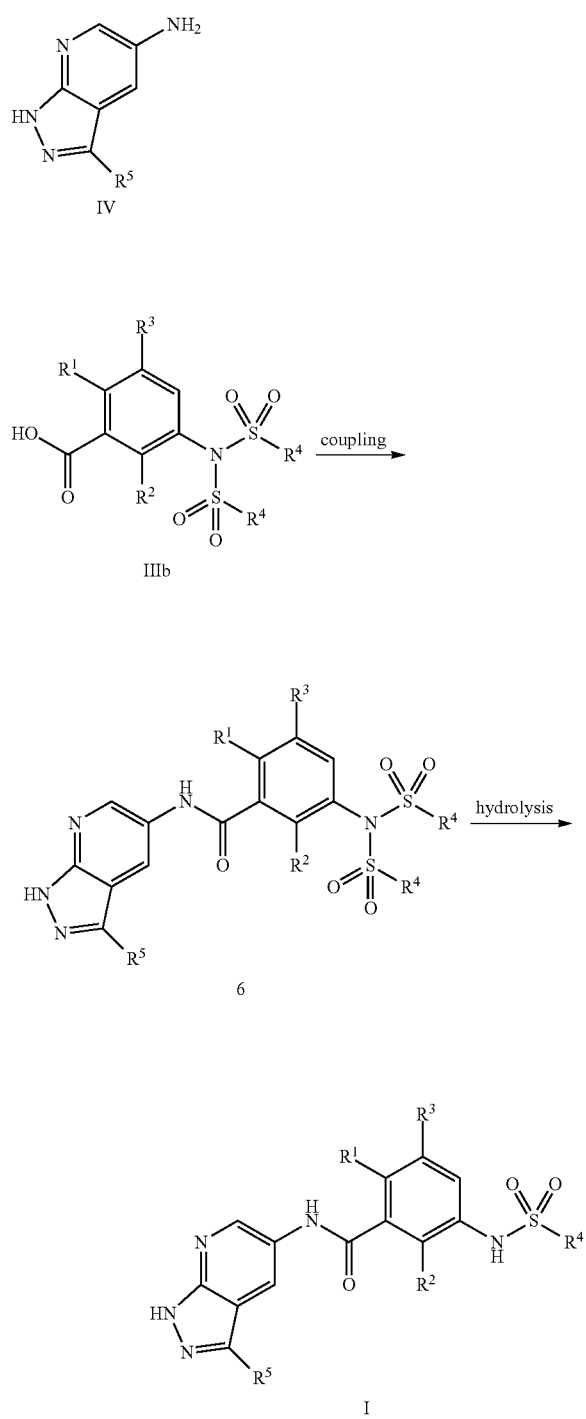

Scheme 4 illustrates another general method for preparing compounds of Formula I, wherein $R^1$, $R^2$, $R^3$, $R^4$ and $R^5$ are as defined herein. Coupling of 5-aminopyrazolopyridine of Formula IV with bis-sulfonamido acid of Formula IIIb is performed with an activating reagent, such as EDCI, in the presence of an additive, such as HOBt, in a suitable solvent, such as DMF. Hydrolysis of compound 6 is accomplished with an aqueous base, such as NaOH, in a solvent system, such as tetrahydrofuran ("THF") and/or MeOH.

Scheme 5

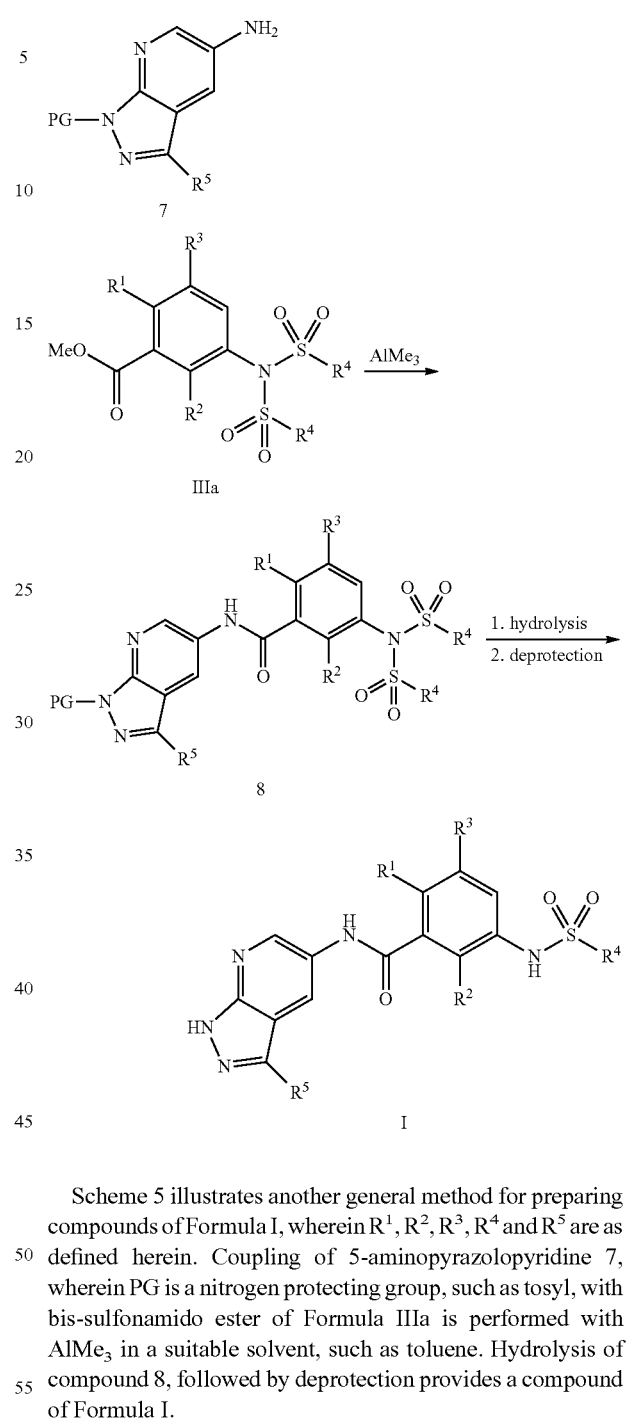

Scheme 5 illustrates another general method for preparing compounds of Formula I, wherein $R^1$, $R^2$, $R^3$, $R^4$ and $R^5$ are as defined herein. Coupling of 5-aminopyrazolopyridine 7, wherein PG is a nitrogen protecting group, such as tosyl, with bis-sulfonamido ester of Formula IIIa is performed with AlMe$_3$ in a suitable solvent, such as toluene. Hydrolysis of compound 8, followed by deprotection provides a compound of Formula I.

Scheme 6

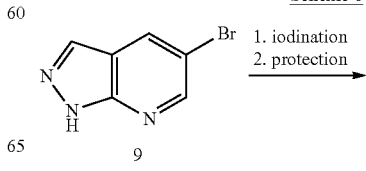

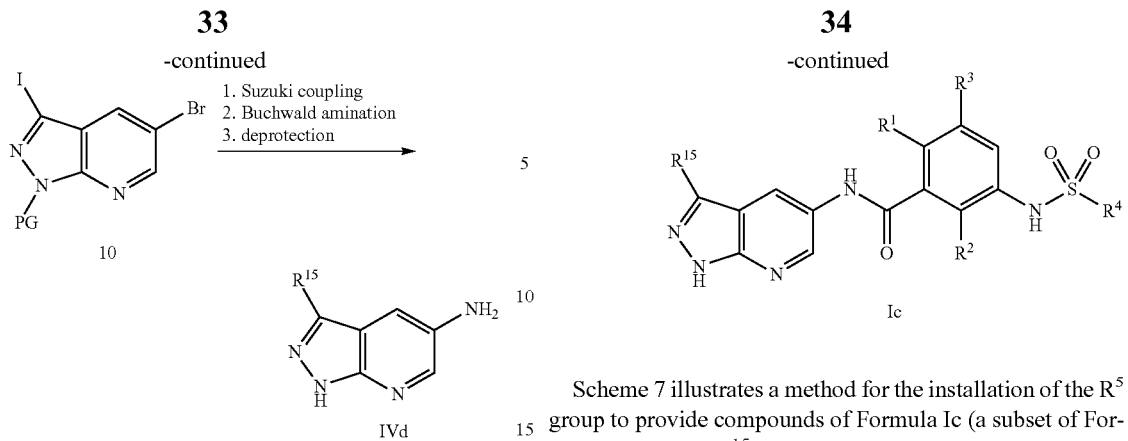

Scheme 6 shows a general method for preparing compounds of Formula IVd (a subset of Formula IV), wherein $R^{15}$ is aryl or heteroaryl. Pyrazolopyridine 9 is iodinated, for example, by n-iodosuccinimide, and the pyrazole nitrogen may be protected, for example with 2-(trimethylsilyl)ethoxymethyl chloride ("SEMCl"), in a solvent, such as DMF, in the presence of a base, such as NaH, to provide compound 10, wherein PG is a nitrogen protecting group. A Suzuki cross coupling reaction with compound 10 in the presence of a catalyst, such as tetrakis(triphenylphosphine)palladium, is used to install $R^{15}$. A subsequent Buchwald coupling reaction with an aminating reagent, such as tert-butyl carbamate, followed by global deprotection in the presence of an acid, such as HCl, provides aniline of Formula IVd.

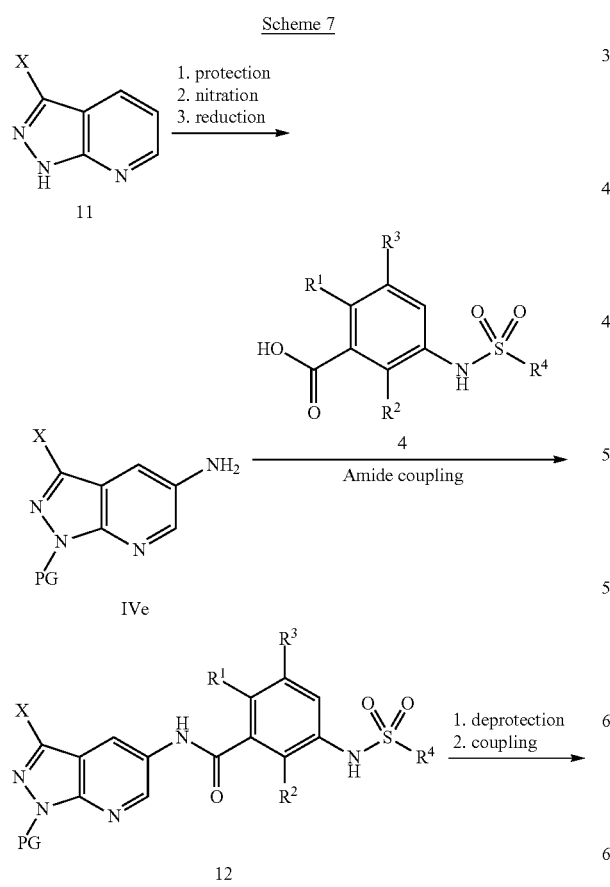

Scheme 7 illustrates a method for the installation of the $R^5$ group to provide compounds of Formula Ic (a subset of Formula I), wherein $R^{15}$ is aryl or heteroaryl. Pyrazolopyridine 11, wherein X is halogen, may be protected, for example with a tosyl group by using tosyl chloride, in a solvent, such as dichloromethane or THF, in the presence of a base, such as $K_2CO_3$ or NaH. Nitration, for example with tetrabutylammonium nitrate, followed by reduction of the nitro group under standard conditions, such as $SnCl_2$ dihydrate, provides compounds of Formula IVe (a subset of Formula IV), wherein PG is a nitrogen protecting group, such as a tosyl group. Aniline of Formula IVe and benzoic acid 4 are coupled under standard conditions to provide amide 12. Removal of the protecting group under basic conditions, for example with $K_2CO_3$, at an appropriate temperature, for example 0° C. to reflux, followed by a cross-coupling reaction, for example the Suzuki, Stille or Negishi reactions, in the presence of a catalyst, such as tetrakis(triphenylphosphine)palladium, can be used to install a variety of aryl and heteroaryl groups.

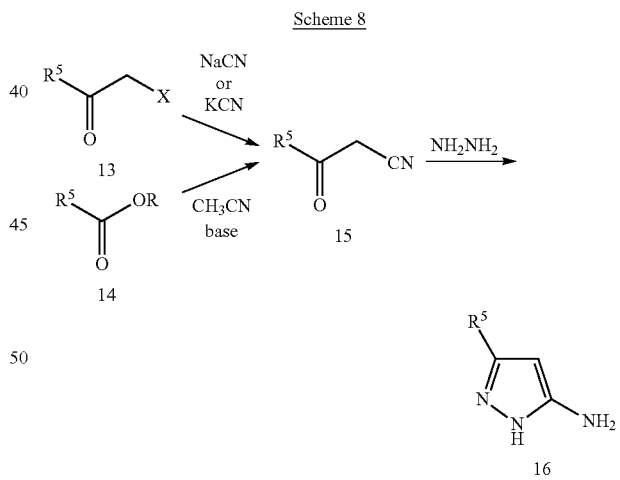

Scheme 8 shows a general method for preparing compound 16, wherein $R^5$ is as defined herein. α-Cyanoketone 15 is prepared by reaction of an α-substituted ketone 13, wherein X is halogen or a suitable leaving group such as mesylate or tosylate, with NaCN or KCN in a suitable organic solvent, such as DMF. Alternatively, α-cyanoketone 15 is prepared by treatment of ester 14 with $CH_3CN$ and a suitable base, such as NaH or NaOtBu. Subjection of α-cyanoketone 15 to hydrazine in a solvent, such as EtOH, at about 80° C. provides 3-substituted-1H-pyrazol-5-amine 16.

Scheme 9

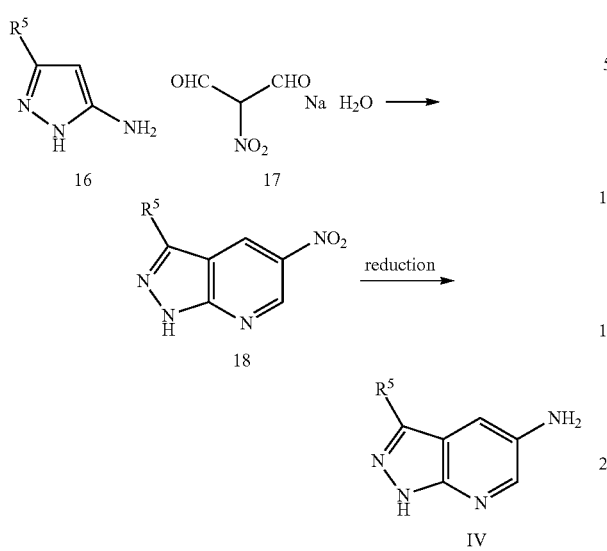

Scheme 9 shows a general method for preparing compounds of Formula IV, wherein $R^5$ is as defined herein. Treatment of 3-substituted-1H-pyrazol-5-amine 16 with sodium nitromalonaldehyde monohydrate 17 in a suitable solvent, such as AcOH, at about 90° C. affords 3-substituted-5-nitro-1H-pyrazolo[3,4-b]pyridine 18. Standard reduction of the nitro functionality in compound 18, such as by treatment with Pd/C and $H_2$, affords 3-substituted-1H-pyrazolo[3,4-b]pyridin-5-amine of Formula IV.

Scheme 10

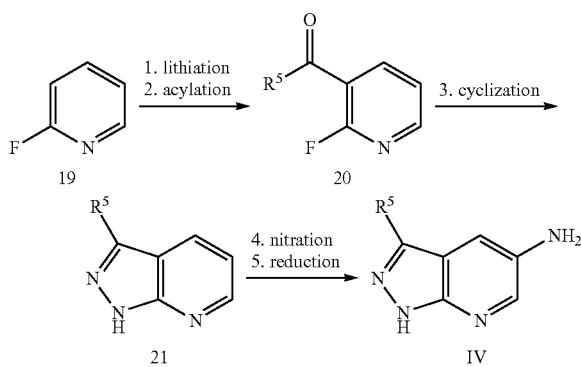

Scheme 10 provides an alternative route to preparing analogs of $R^5$ in compounds of Formula IV, wherein $R^5$ is as defined herein. 2-Fluoropyridine 19 may be lithiated with a suitable base, such as lithium diisopropylamide ("LDA"), in a solvent, such as tetrahydrofuran, at low temperature. This is followed by a reaction with an ester to provide the acylated pyridine 20. Compound 21 is prepared by cyclization of pyridine 20 with hydrazine at elevated temperature in a solvent, such as ethanol. Compound 21 may be nitrated by standard nitrating conditions, such as mixed nitric and sulfuric acids or tetrabutylammonium nitrate and trifluoroacetic anhydride in dichloromethane. Subsequent reduction with $SnCl_2 \cdot 2H_2O$ in ethyl acetate or hydrogenation with palladium on carbon catalyst in a solvent, such as ethanol, provides the 5-amino derivative of Formula IV.

Scheme 11

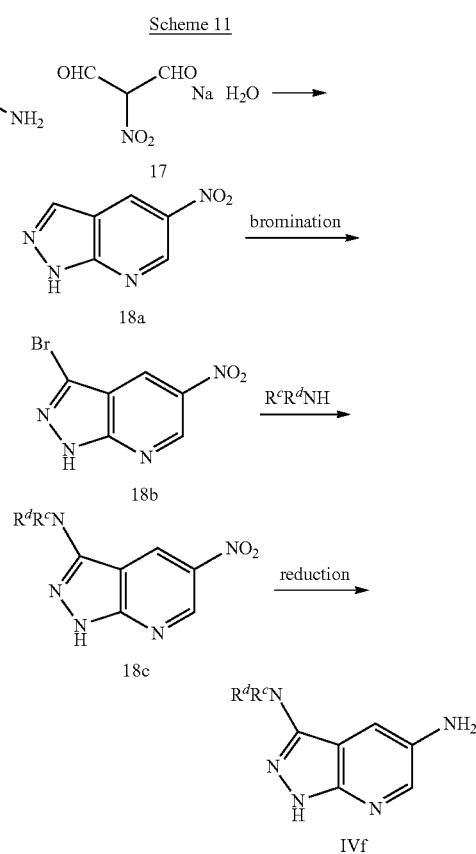

Scheme 11 shows a general method for preparing compounds of Formula IVf (a subset of Formula IV), wherein $R^c$ and $R^d$ are as defined herein. Treatment of 1H-pyrazol-5-amine 16a (a subset of compound 16) with sodium nitromalonaldehyde monohydrate 17 in a suitable solvent, such as AcOH, at 90° C. affords 5-nitro-1H-pyrazolo[3,4-b]pyridine 18a (a subset of compound 18). Pyrazolopyridine 18a is brominated, for example, by bromine, in the presence of a base, such as NaOH, to give bromonitropyrazole 18b (a subset of compound 18). Treatment of compound 18b with a nitrogen nucleophile at an elevated temperature, for example 120° C. to 160° C., affords 3-aminopyrazolo[3,4-b]pyridine 18c (a subset of compound 18). Standard reduction of the nitro functionality in compound 18c, such as by treatment with Pd/C and $H_2$, affords 3-N-substituted-1H-pyrazolo[3,4-b]pyridin-5-amine of Formula IVf.

Scheme 12

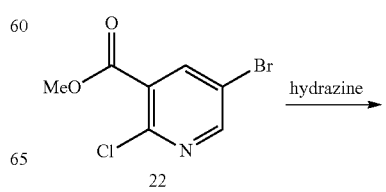

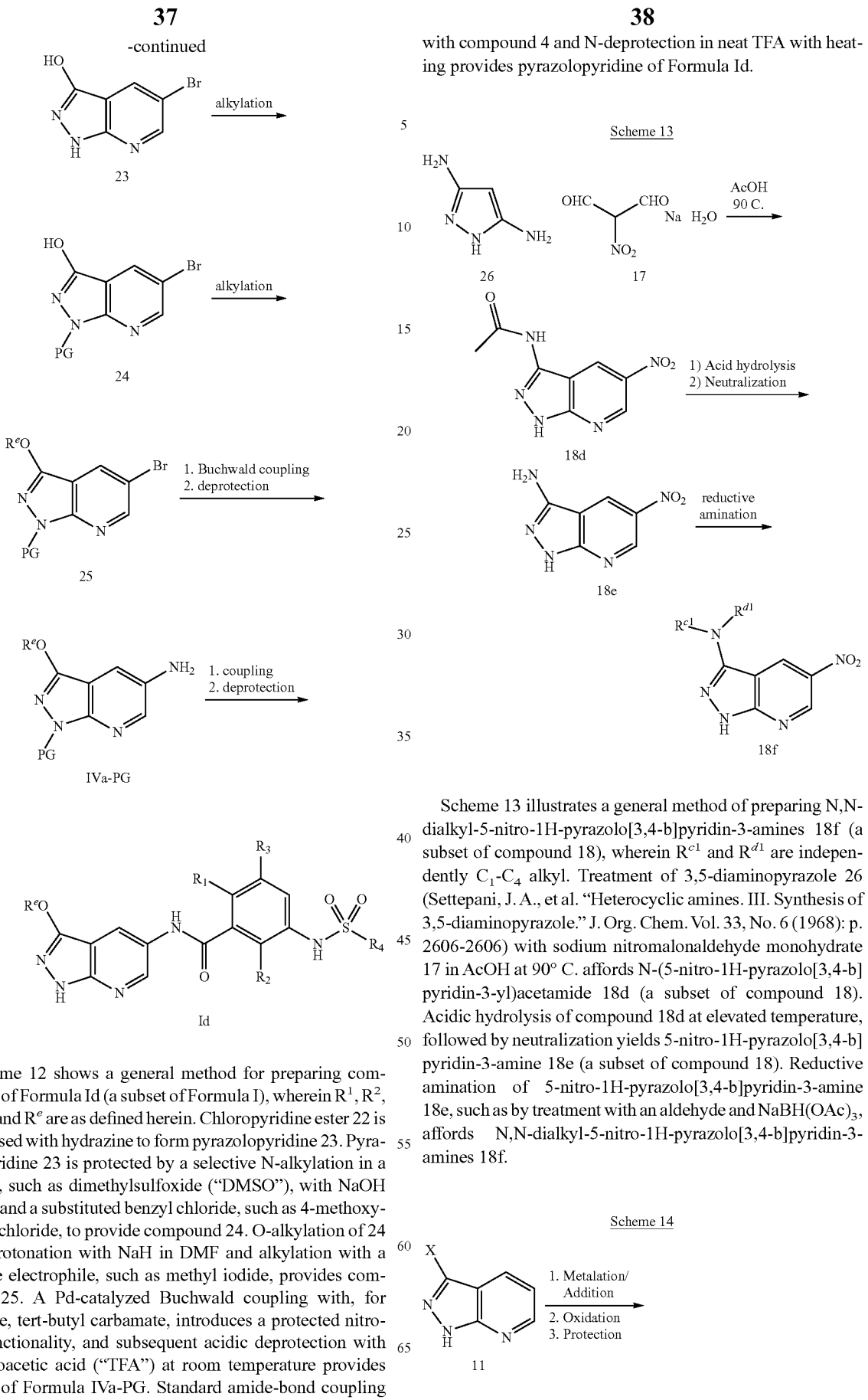

Scheme 12 shows a general method for preparing compounds of Formula Id (a subset of Formula I), wherein $R^1$, $R^2$, $R^3$, $R^4$ and $R^e$ are as defined herein. Chloropyridine ester 22 is condensed with hydrazine to form pyrazolopyridine 23. Pyrazolopyridine 23 is protected by a selective N-alkylation in a solvent, such as dimethylsulfoxide ("DMSO"), with NaOH as base and a substituted benzyl chloride, such as 4-methoxybenzyl chloride, to provide compound 24. O-alkylation of 24 by deprotonation with NaH in DMF and alkylation with a suitable electrophile, such as methyl iodide, provides compound 25. A Pd-catalyzed Buchwald coupling with, for example, tert-butyl carbamate, introduces a protected nitrogen functionality, and subsequent acidic deprotection with trifluoroacetic acid ("TFA") at room temperature provides aniline of Formula IVa-PG. Standard amide-bond coupling with compound 4 and N-deprotection in neat TFA with heating provides pyrazolopyridine of Formula Id.

Scheme 13 illustrates a general method of preparing N,N-dialkyl-5-nitro-1H-pyrazolo[3,4-b]pyridin-3-amines 18f (a subset of compound 18), wherein $R^{c1}$ and $R^{d1}$ are independently $C_1$-$C_4$ alkyl. Treatment of 3,5-diaminopyrazole 26 (Settepani, J. A., et al. "Heterocyclic amines. III. Synthesis of 3,5-diaminopyrazole." J. Org. Chem. Vol. 33, No. 6 (1968): p. 2606-2606) with sodium nitromalonaldehyde monohydrate 17 in AcOH at 90° C. affords N-(5-nitro-1H-pyrazolo[3,4-b]pyridin-3-yl)acetamide 18d (a subset of compound 18). Acidic hydrolysis of compound 18d at elevated temperature, followed by neutralization yields 5-nitro-1H-pyrazolo[3,4-b]pyridin-3-amine 18e (a subset of compound 18). Reductive amination of 5-nitro-1H-pyrazolo[3,4-b]pyridin-3-amine 18e, such as by treatment with an aldehyde and $NaBH(OAc)_3$, affords N,N-dialkyl-5-nitro-1H-pyrazolo[3,4-b]pyridin-3-amines 18f.

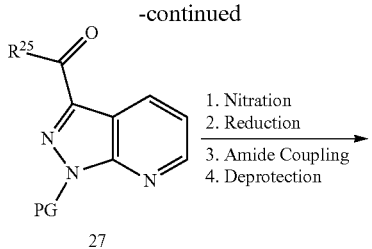

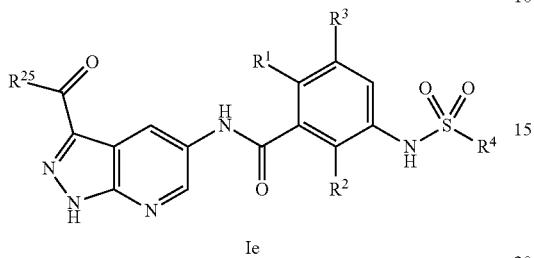

Scheme 14 shows a general method of preparing compounds of Formula Ie, wherein $R^{25}$ is $C_1$-$C_6$ cycloalkyl or $C_1$-$C_5$ alkyl optionally substituted with halogen, OH, $OCH_3$, $NR^cR^d$ or $C_1$-$C_6$ cycloalkyl, and $R^1$, $R^2$, $R^3$ and $R^4$ are as defined herein. Compound 11, wherein X is halogen, can be metalated and added to an electrophile, such as an aldehyde. Oxidation of the resulting alcohol with an oxidizing agent, such as Dess-Martin periodidane, followed blocking of the N—H group can be used to prepare compound 27, wherein PG is a protecting group, such as 4-methoxybenzyl. Compound 27 may then undergo nitration, reduction, coupling with compound 4 and deprotection as discussed above and elaborated in the Examples to provide compounds of Formula Ie.

Scheme 15

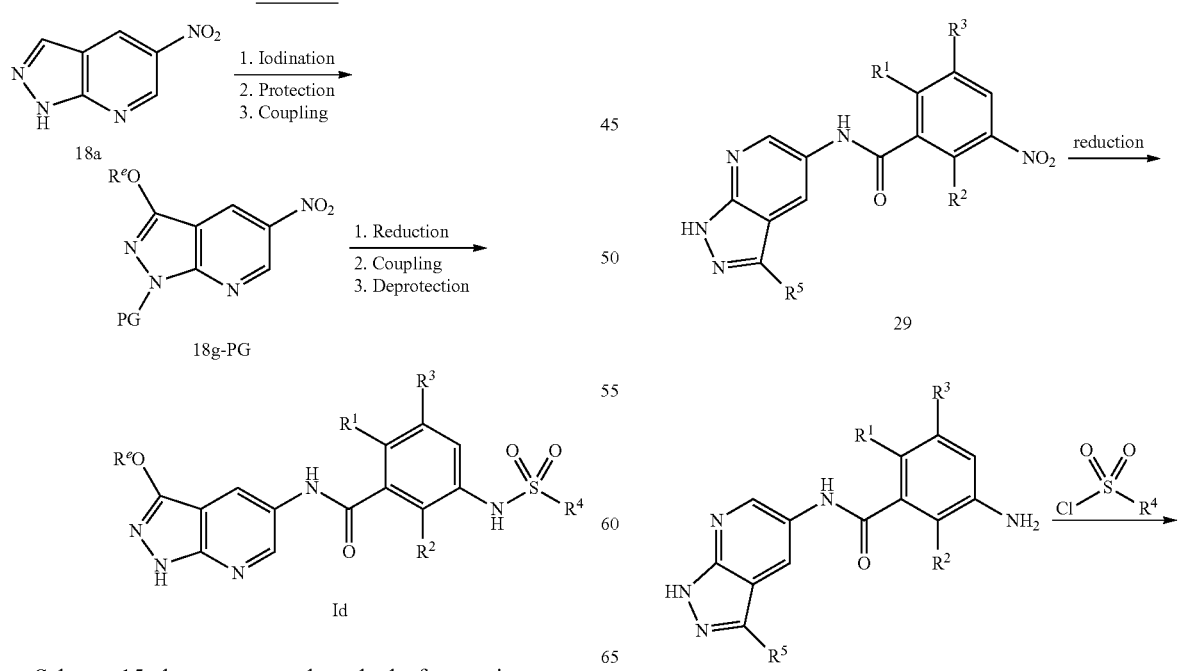

Scheme 15 shows a general method of preparing compounds of Formula Id, wherein $R^1$, $R^2$, $R^3$, $R^4$ and $R^e$ are as defined herein. Compound 18a may be treated with iodine, protected with a reagent, such as 4-methoxybenzyl chloride, following which treatment with appropriate catalysts, such as copper iodide and phenanthroline, in a solvent, such as toluene, creates conditions whereby alcohols can be coupled to yield compound 18g-PG, wherein PG is a protecting group, such as 4-methoxybenzyl. Compound 18g-PG may then be reduced, coupled with compound 4 and deprotected as discussed above and elaborated in the Examples to provide compounds of Formula Id.

Scheme 16

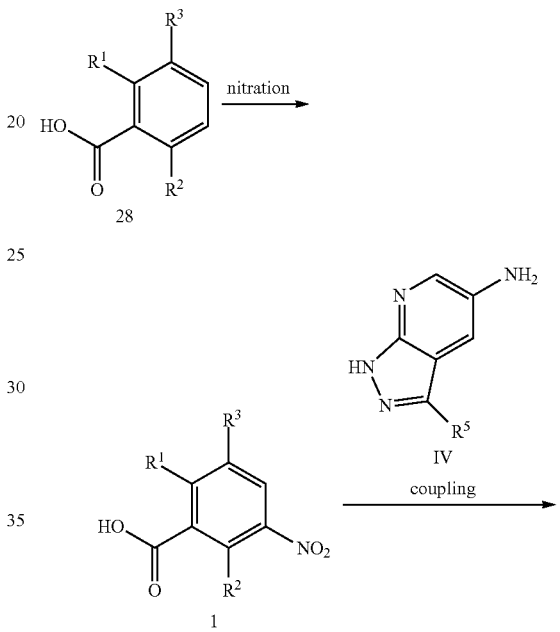

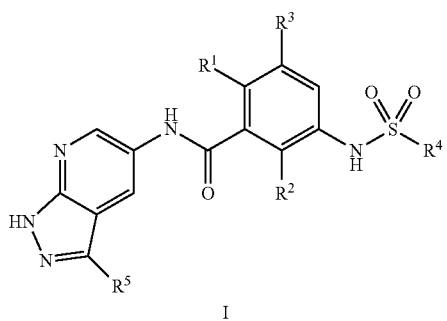

I

Scheme 16 shows a general method for preparing compounds of Formula I, wherein $R^1$, $R^2$, $R^3$, $R^4$ and $R^5$ are as defined herein. Benzoic acid 28 is nitrated in the presence of nitric acid, either neat or in the presence of another acid, such as sulfuric acid or trifluoroacetic acid, to provide nitrated benzoic acid 1. Compound I may be coupled with a compound of Formula IV with an activating reagent, such as EDCI, in the presence of an additive, such as HOBt, in a suitable solvent, such as DMF or DCM, to provide compound 29. Compound 29 may be reduced to aniline 30 in a number of ways, for example, by $SnCl_2$ dihydrate, Zn/acid, or by hydrogenation. Sulfonamide of Formula I is obtained by treatment of aniline 30 with a sulfonyl chloride in the presence of a base, such as pyridine, in an organic solvent, such as DCM.

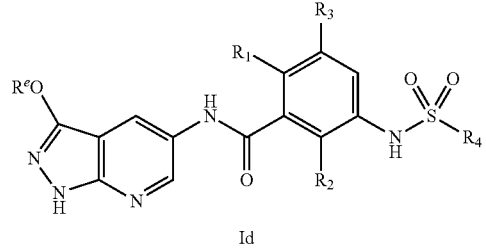

Id

Scheme 17 shows a general method for preparing compounds of Formula Id, wherein $R^1$, $R^2$, $R^3$, $R^4$ and $R^e$ are as defined herein. Malononitrile 31 is converted to imino ester HCl salt 32 by treatment with alcohol $R^eOH$ in the presence of HCl in an organic solvent, such as diethyl ether. Compound 32 is then condensed with hydrazine monohydrochloride in a suitable solvent, such as MeOH, to provide 3-alkoxyl-1H-pyrazol-5-amine 16b (a subset of compound 16). Cyclization of 16b with sodium nitromalonaldehyde monohydrate 17 in a suitable solvent, such as $H_2O$, at 90° C. affords 3-alkoxyl-5-nitro-1H-pyrazolo[3,4-b]pyridine 18g (a subset of compound 18). Standard reduction of the nitro functionality in compound 18g, such as by treatment with Pd/C and $H_2$, affords 3-substituted-1H-pyrazolo[3,4-b]pyridin-5-amine of Formula IVa. Standard amide-bond coupling provides pyrazolopyridine of Formula Id.

Scheme 17

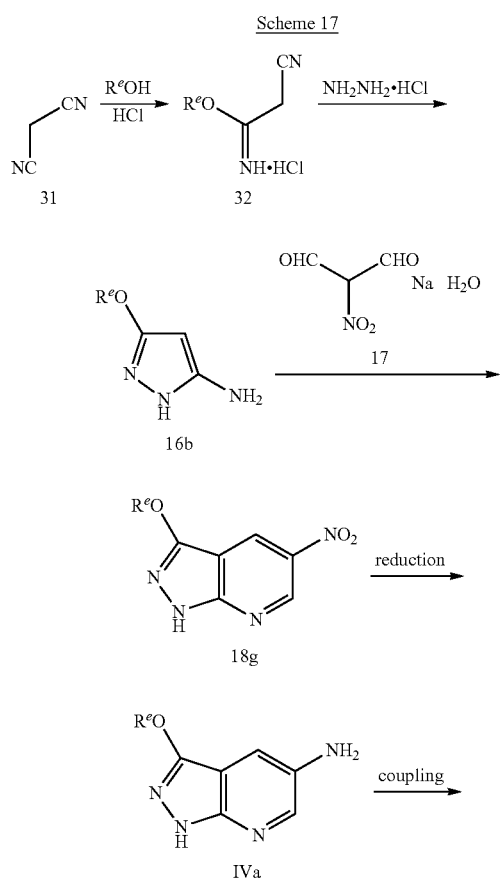

Scheme 18

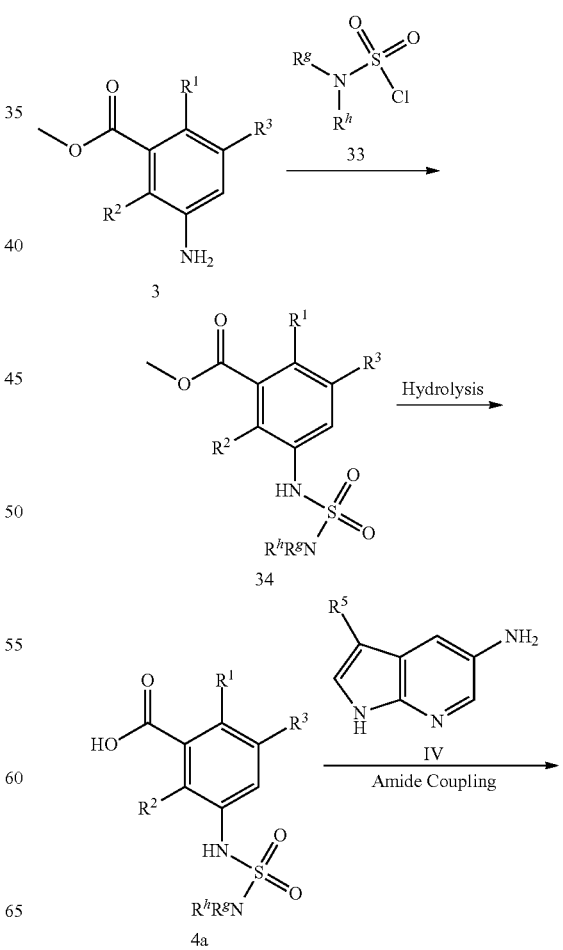

-continued

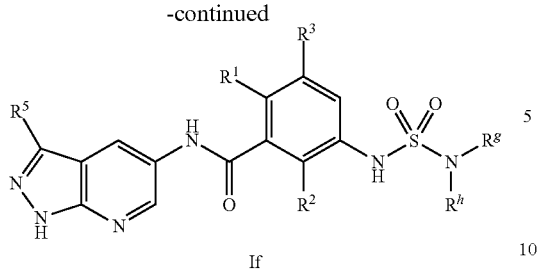

If

Scheme 18 illustrates a general method for the preparation of compound of Formula If (a subset of Formula I), wherein $R^1$, $R^2$, $R^3$, $R^5$, $R^g$ and $R^h$ are defined herein. Compound 3 can be treated with a base, such as triethylamine, and sulfamyl chloride 33 in a solvent, such as DCM, to produce the sulfamide 34. Hydrolysis can be carried out on 34 with a base, such as sodium hydroxide, in a suitable solvent or mixture of solvents, such as THF and MeOH, to provide the acid 4a (a subset of compound 4). Amide bond coupling of 4a and a compound of Formula IV can be carried out with a coupling agent, such as EDCI, in a solvent, such as DMF, to provide a compound of Formula If.

Accordingly, another embodiment of the present invention provides a process for preparing compounds of Formula I (or subsets of Formula I), comprising (a) coupling a compound of Formula IV:

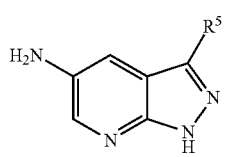

IV wherein $R^5$ is as defined herein;
with compound 4:

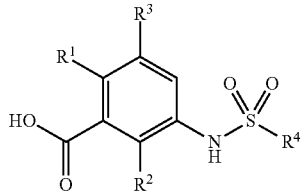

4 wherein $R^1$, $R^2$, $R^3$ and $R^4$ are as defined herein;
to provide a compound of Formula I;
(b) coupling a compound of Formula IV:

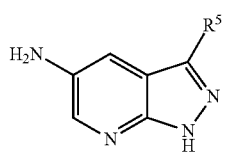

IV wherein $R^5$ is as defined herein;

with a compound of Formula III:

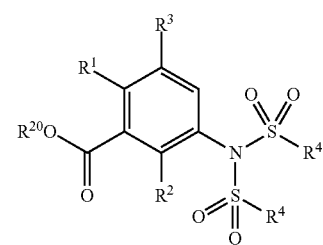

III wherein $R^{20}$ is hydrogen, $C_1$-$C_6$ alkyl, benzyl or phenyl and $R^1$, $R^2$, $R^3$ and $R^4$ are as defined herein;
to provide compound 6:

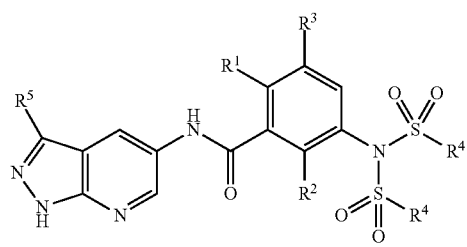

6 followed by hydrolysis to provide a compound of Formula I;

(c) coupling a compound of Formula IVe:

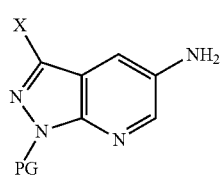

IVe wherein X is halogen and PG is an amine protecting group;
with compound 4:

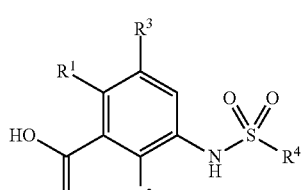

4 wherein $R^1$, $R^2$, $R^3$ and $R^4$ are as defined herein;

to provide compound 12:

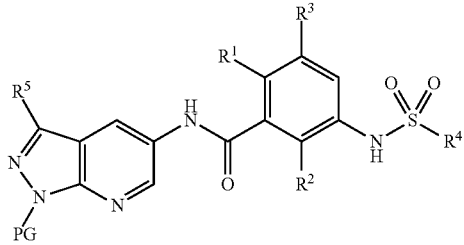

12 followed by deprotection and a cross-coupling reaction provides compounds of Formula Ic:

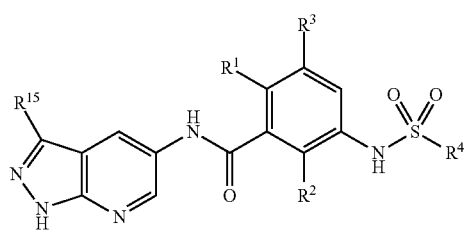

Ic wherein $R^{15}$ is phenyl optionally substituted with one to three $R^a$ groups or 5 or 6 membered heteroaryl optionally substituted with $C_1$-$C_4$ alkyl; or (d) amide-bond coupling a compound of Formula IVa-PG:

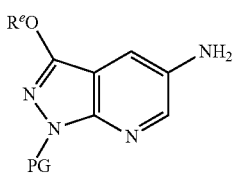

IVa-PG wherein PG is a protecting group and $R^e$ is as defined herein; with compound 4:

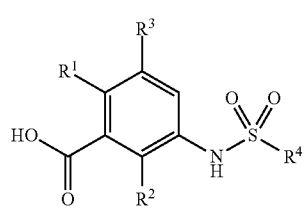

4 wherein $R^1$, $R^2$, $R^3$ and $R^4$ are as defined herein;

followed by deprotection to provide a compound of Formula Id:

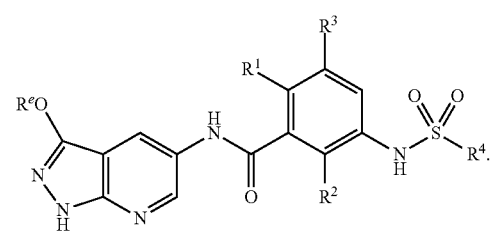

Id

Another embodiment of the present invention provides a process for preparing compounds of Formula I (or subsets of Formula I), comprising:

(a) reacting compound 30:

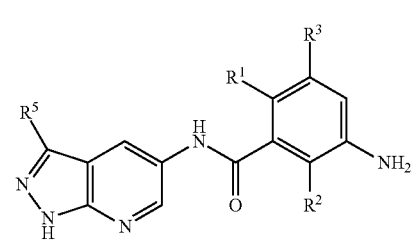

30 wherein $R^1$, $R^2$, $R^3$ and $R^5$ are as defined herein; with a sulfonyl chloride:

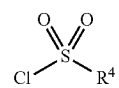

wherein $R^4$ is as defined herein, in the presence of a base and in an organic solvent to provide a compound of Formula I:

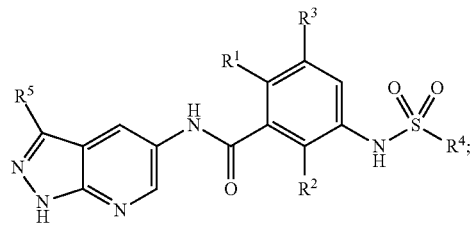

I (b) coupling an amine of Formula IVa:

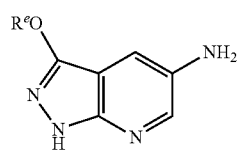

IVa wherein $R^e$ is as defined herein, with compound of Formula 4:

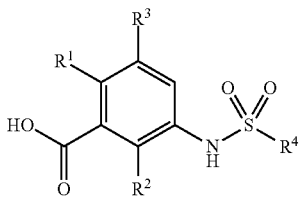
4 wherein $R^1$, $R^2$, $R^3$ and $R^4$ are as defined herein, to provide a compound of Formula Id:

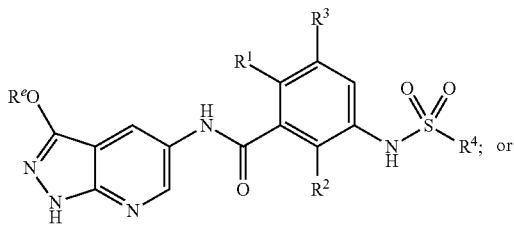
Id (c) coupling a compound of Formula IV:

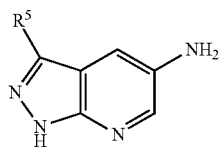
IV wherein $R^5$ is as defined herein, with compound 4a:

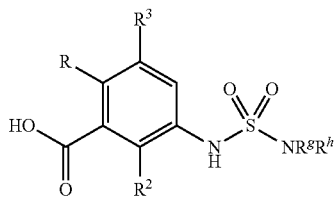
4a wherein $R^1$, $R^2$, $R^3$, $R^g$ and $R^h$ are as defined herein, to provide a compound of Formula If:

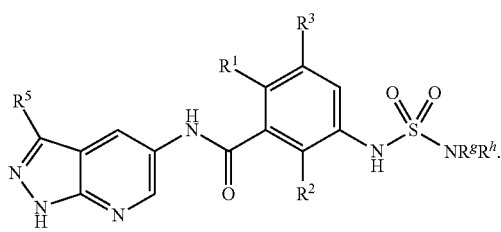
If

In certain embodiments of process (a), the base is pyridine. In certain embodiments or process (a), the solvent is dichloromethane.

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butyloxycarbonyl ("Boc"), benzyloxycarbonyl ("CBz") and 9-fluorenylmethyleneoxycarbonyl ("Fmoc"). The need for such protection is readily determined by one skilled in the art. For a general description of protecting groups and their use, see T. W. Greene, et al. *Greene's Protective Groups in Organic Synthesis*. New York: Wiley Interscience, 2006.

Methods of Separation

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H., et al. "Chromatographic resolution of enantiomers: Selective review." *J. Chromatogr.*, 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*. New York: Marcel Dekker, Inc., 1993.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. *Stereochemistry of Organic Compounds*. New York: John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III, Peyton. "Resolution of (±)-5-Bromonornicotine. Synthesis of (R)- and (S)-Nornicotine of High Enantiomeric Purity." *J. Org. Chem*. Vol. 47, No. 21 (1982): pp. 4165-4167), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111).

By method (3), a racemic mixture of two enantiomers can be separated by chromatography using a chiral stationary phase (Lough, W. J., Ed. *Chiral Liquid Chromatography*. New York: Chapman and Hall, 1989; Okamoto, Yoshio, et al. "Optical resolution of dihydropyridine enantiomers by high-performance liquid chromatography using phenylcarbamates of polysaccharides as a chiral stationary phase." *J. of Chromatogr*. Vol. 513 (1990): pp. 375-378). Enriched or purified enantiomers can be distinguished by methods used to distinguish other chiral molecules with asymmetric carbon atoms, such as optical rotation and circular dichroism.

Biological Evaluation

B-Raf mutant protein 447-717 (V600E) was co-expressed with the chaperone protein Cdc37, complexed with Hsp90 (Roe, S. Mark, et al. "The Mechanism of Hsp90 Regulation by the Protein Kinase-Specific Cochaperone p50$^{cdc37}$." *Cell*. Vol. 116 (2004): pp. 87-98; Stancato, L F, et al. "Raf exists in a native heterocomplex with Hsp90 and p50 that can be reconstituted in a cell free system." *J. Biol. Chem*. 268(29) (1993): pp. 21711-21716).

Determining the activity of Raf in the sample is possible by a number of direct and indirect detection methods (US 2004/0082014). Activity of human recombinant B-Raf protein may be assessed in vitro by assay of the incorporation of radio labeled phosphate to recombinant MAP kinase (MEK), a known physiological substrate of B-Raf, according to US 2004/0127496 and WO 03/022840. The activity/inhibition of V600E full-length B-Raf was estimated by measuring the incorporation of radio labeled phosphate from [γ-$^{33}$P]ATP into FSBA-modified wild-type MEK (see Example A).

Administration and Pharmaceutical Formulations

The compounds of the invention may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal.

The compounds may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drums Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

One embodiment of the present invention includes a pharmaceutical composition comprising a compound of Formula I, or a stereoisomer or pharmaceutically acceptable salt thereof. In a further embodiment, the present invention provides a pharmaceutical composition comprising a compound of Formula I, or a stereoisomer or pharmaceutically acceptable salt thereof, together with a pharmaceutically acceptable carrier or excipient.

Another embodiment of the present invention provides a pharmaceutical composition comprising a compound of Formula I for use in the treatment of a hyperproliferative disease.

Another embodiment of the present invention provides a pharmaceutical composition comprising a compound of Formula I for use in the treatment of cancer.

Methods of Treatment with Compounds of the Invention

The invention includes methods of treating or preventing disease or condition by administering one or more compounds of this invention, or a stereoisomer or pharmaceutically acceptable salt thereof. In one embodiment, a human patient is treated with a compound of Formula I, or a stereoisomer or pharmaceutically acceptable salt thereof, and a pharmaceutically acceptable carrier, adjuvant, or vehicle in an amount to detectably inhibit B-Raf activity.

In another embodiment, a human patient is treated with a compound of Formula I, or a stereoisomer, tautomer, prodrug or pharmaceutically acceptable salt thereof, and a pharmaceutically acceptable carrier, adjuvant, or vehicle in an amount to detectably inhibit B-Raf activity.

In another embodiment of the present invention, a method of treating a hyperproliferative disease in a mammal comprising administering a therapeutically effective amount of the compound of Formula I, or a stereoisomer, tautomer, prodrug or pharmaceutically acceptable salt thereof, to the mammal is provided.

In another embodiment of the present invention, a method of treating a hyperproliferative disease in a mammal comprising administering a therapeutically effective amount of the compound of Formula I, or a stereoisomer or pharmaceutically acceptable salt thereof, to the mammal is provided.

In another embodiment of the present invention, a method of treating kidney disease in a mammal comprising administering a therapeutically effective amount of the compound of Formula I, or a stereoisomer, tautomer, prodrug or pharmaceutically acceptable salt thereof, to the mammal is provided. In a further embodiment, the kidney disease is polycystic kidney disease.

In another embodiment, a method of treating or preventing cancer in a mammal in need of such treatment, wherein the method comprises administering to said mammal a therapeutically effective amount of a compound of Formula I, or a stereoisomer or pharmaceutically acceptable salt thereof. The cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, NSCLC, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia. Another embodiment of the present invention provides the use of a compound of Formula I, or a stereoisomer or pharmaceutically acceptable salt thereof, in the manufacture of a medicament for the treatment of cancer.

In another embodiment, a method of treating or preventing cancer in a mammal in need of such treatment, wherein the method comprises administering to said mammal a therapeutically effective amount of a compound of Formula I, or a stereoisomer, tautomer, prodrug or pharmaceutically acceptable salt thereof.

Another embodiment of the present invention provides the use of a compound of Formula I, or a stereoisomer, tautomer, prodrug or pharmaceutically acceptable salt thereof, in the manufacture of a medicament for the treatment of cancer.

Another embodiment of the present invention provides the use of a compound of Formula I, or a stereoisomer, tautomer, prodrug or pharmaceutically acceptable salt thereof, in the manufacture of a medicament for the treatment of kidney disease. In a further embodiment, the kidney disease is polycystic kidney disease.

In another embodiment, a method of preventing or treating cancer, comprising administering to a mammal in need of such treatment an effective amount of a compound of Formula I, or a stereoisomer, tautomer, prodrug or pharmaceutically acceptable salt thereof, alone or in combination with one or more additional compounds having anti-cancer properties.

In another embodiment, a method of preventing or treating cancer, comprising administering to a mammal in need of such treatment an effective amount of a compound of Formula I, or a stereoisomer or pharmaceutically acceptable salt thereof, alone or in combination with one or more additional compounds having anti-cancer properties.

In one further embodiment, the cancer is a sarcoma.

In another further embodiment, the cancer is a carcinoma. In one further embodiment, the carcinoma is squamous cell carcinoma. In another further embodiment, the carcinoma is an adenoma or adenocarcinoma.

In another embodiment, a method of treating or preventing a disease or disorder modulated by B-Raf, comprising administering to a mammal in need of such treatment an effective amount of a compound of Formula I, or a stereoisomer or pharmaceutically acceptable salt thereof. Examples of such diseases and disorders include, but are not limited to, cancer. The cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, NSCLC, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

In another embodiment, a method of treating or preventing a disease or disorder modulated by B-Raf, comprising administering to a mammal in need of such treatment an effective amount of a compound of Formula I, or a stereoisomer, tautomer, prodrug or pharmaceutically acceptable salt thereof.

In another embodiment of the present invention, a method of preventing or treating kidney disease, comprising administering to a mammal in need of such treatment an effective amount of Formula I, or a stereoisomer, prodrug or pharmaceutically acceptable salt thereof, alone or in combination with one or more additional compounds. In another embodiment of the present invention, a method of preventing or treating polycystic kidney disease, comprising administering to a mammal in need of such treatment an effective amount of a compound of Formula I, or a stereoisomer, prodrug or pharmaceutically acceptable salt thereof, alone or in combination with one or more additional compounds.

Another embodiment of the present invention provides the use of a compound of Formula I, or a stereoisomer or pharmaceutically acceptable salt thereof, in the manufacture of a medicament for the treatment of cancer. The cancer is selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, NSCLC, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia. In a further embodiment, the use of a compound of Formula I in the manufacture of a medicament, for use as a b-Raf inhibitor in the treatment of a patient undergoing cancer therapy.

Another embodiment of the present invention provides the use of a compound of Formula I, or a stereoisomer, tautomer, prodrug or pharmaceutically acceptable salt thereof, in the manufacture of a medicament for the treatment of cancer.

Another embodiment of the present invention provides the use of a compound of Formula I, or a stereoisomer, tautomer, prodrug or pharmaceutically acceptable salt thereof, in the manufacture of a medicament for the treatment of polycystic kidney disease. In a further embodiment, the kidney disease is polycystic kidney disease.

Another embodiment of the present invention provides the compounds of Formula I for use in therapy.

Another embodiment of the present invention provides the compounds of Formula I for use in the treatment of a hyperproliferative disease. In a further embodiment, the hyperproliferative disease is cancer (as further defined and may be individually selected from those above).

Another embodiment of the present invention provides the compounds of Formula I for use in the treatment of kidney disease. In a further embodiment, the kidney disease is polycystic kidney disease.

Combination Therapy

The compounds of this invention and stereoisomers and pharmaceutically acceptable salts thereof may be employed alone or in combination with other therapeutic agents for treatment. The compounds of the present invention can be used in combination with one or more additional drugs, for example an anti-hyperproliferative, anti-cancer, or chemotherapeutic agent. The second compound of the pharmaceutical combination formulation or dosing regimen preferably has complementary activities to the compound of this invention such that they do not adversely affect each other. Such agents are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

A "chemotherapeutic agent" is a chemical compound useful in the treatment of cancer, regardless of mechanism of action. Chemotherapeutic agents include compounds used in "targeted therapy" and conventional chemotherapy. A number of suitable chemotherapeutic agents to be used as combination therapeutics are contemplated for use in the methods of the present invention. The present invention contemplates, but is not limited to, administration of numerous anticancer agents, such as: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g., interferons [e.g., IFN-a, etc.] and interleukins [e.g., IL-2, etc.], etc.); adoptive immunotherapy agents; hematopoietic growth factors; agents that induce tumor cell differentiation (e.g., all-trans-retinoic acid, etc.); gene therapy reagents; antisense therapy reagents and nucleotides; tumor vaccines; inhibitors of angiogenesis, and the like.

Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sunitinib (SUTENT®, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (NEXAVAR®, Bayer), Irinotecan (CAMPTOSAR®, Pfizer) and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminol evulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhône-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the Raf inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

EXAMPLES

In order to illustrate the invention, the following Examples are included. However, it is to be understood that these Examples do not limit the invention and are only meant to suggest a method of practicing the invention. Persons skilled in the art will recognize that the chemical reactions described may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Sigma-Aldrich, Alfa Aesar, or TCI, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography purification was done on a Biotage system (Manufacturer: Dyax Corporation) having a silica gel column or on a silica SepPak cartridge (Waters) or on a Teledyne Isco Combiflash purification system using prepacked silica gel cartridges. $^1$H NMR spectra were recorded on a Varian instrument operating at 400 MHz. $^1$H-NMR spectra were obtained as $CDCl_3$, $CD_2Cl_2$, $CD_3OD$, $D_2O$, $d_6$-DMSO, $d_6$-acetone or $(CD_3)_2CO$ solutions (reported in ppm), using tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05; $(CD_3)_2CO$: 2.05) the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz).

Example A

B-Raf $IC_{50}$ Assay Protocol

Activity of human recombinant B-Raf protein may be assessed in vitro by assay of the incorporation of radio labeled phosphate to recombinant MAP kinase (MEK), a known physiologic substrate of B-Raf, according to US 2004/0127496 and WO 03/022840. Catalytically active human recombinant B-Raf protein is obtained by purification from sf9 insect cells infected with a human B-Raf recombinant baculovirus expression vector.

The activity/inhibition of V600E full-length B-Raf was estimated by measuring the incorporation of radio labeled phosphate from [$\gamma$-$^{33}$P]ATP into FSBA-modified wild-type MEK. The 30-1 µL assay mixtures contained 25 mM Na Pipes, pH 7.2, 100 mM KCl, 10 mM $MgCl_2$, 5 mM β-glycerophosphate, 100 µM Na Vanadate, 4 µM ATP, 500 nCi [$\gamma$-$^{33}$P]ATP, 1 µM FSBA-MEK and 20 nM V600E full-length B-Raf. Incubations were carried out at 22° C. in a Costar 3365 plate (Corning). Prior to the assay, the B-Raf and FSBA-MEK were preincubated together in assay buffer at 1.5×(20 µL of 30 nM and 1.5 µM, respectively) for 15 minutes, and the assay was initiated by the addition of 10 µL of 10 µM ATP. Following the 60-minute incubation, the assay mixtures were quenched by the addition of 100 µL of 25% TCA, the plate was mixed on a rotary shaker for 1 minute, and the product was captured on a Perkin-Elmer GF/B filter plate using a Tomtec Mach III Harvester. After sealing the bottom of the plate, 35 μL of Bio-Safe II (Research Products International) scintillation cocktail were added to each well and the plate was top-sealed and counted in a Topcount NXT (Packard).

The compounds of Examples 1-149 were tested in the above assay and found to have an $IC_{50}$ of less than 1 μM.

Example B

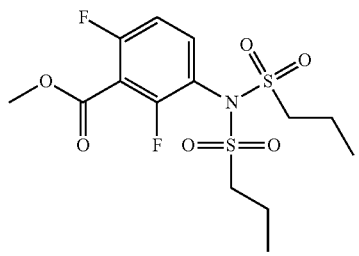 [SMILES: CCCS(=O)(=O)N(c1ccc(F)c(C(=O)OC)c1F)S(=O)(=O)CCC]

methyl 2,6-difluoro-3-(N-(propylsulfonyl)pronylsulfonamido)benzoate

Step A: A 1 L flask was charged with 2,6-difluoro-3-nitrobenzoic acid (17.0 g, 83.7 mmol) and MeOH (170 mL, 0.5M). The flask was placed in a cold water bath, and an addition funnel charged with a 2M solution of trimethylsilyl ("TMS") diazomethane in hexanes (209 mL, 419 mmol) was attached to the flask. The TMS diazomethane solution was added slowly to the reaction flask over the course of 2 hours. A large excess of reagent was required in order for the reaction to reach completion as determined by the ceased evolution of $N_2$ upon further addition of reagent. The volatiles were removed in vacuo to afford methyl 2,6-difluoro-3-nitrobenzoate as a solid (18.2 g, 99%). The material was taken directly onto Step B.

Step B: 10% (wt.) Pd on activated carbon (4.46 g, 4.19 mmol) was added to a 1 L flask charged with methyl 2,6-difluoro-3-nitrobenzoate (18.2 g, 83.8 mmol) under a nitrogen atmosphere. EtOH (350 mL, 0.25 M) was added, and then $H_2$ was passed through the reaction mixture for 15 minutes. The reaction mixture was stirred under two $H_2$ balloons overnight. The following day the reaction mixture was re-flushed with fresh $H_2$ balloons and stirred an additional 4 hours. Upon consumption of the starting material and intermediate hydroxylamine as determined by TLC, $N_2$ gas was flushed through the reaction mixture. The mixture was then filtered through glass microfibre filter ("GF/F") paper twice. The volatiles were removed to afford methyl 3-amino-2,6-difluorobenzoate as an oil (15.66 g, 99%). The material was taken directly onto the next step.

Step C: Propane-1-sulfonyl chloride (23.46 mL, 209.3 mmol) was slowly added to a solution of methyl 3-amino-2, 6-difluorobenzoate (15.66 g, 83.7 mmol) and triethylamine (35.00 mL, 251.1 mmol) in $CH_2Cl_2$ (175 mL, 0.5M) maintained in a cool water bath. The reaction mixture was stirred for 1 hour at room temperature. Water (300 mL) was added and the organic layer was separated, washed with water (2×300 mL) and brine (200 mL), then dried ($Na_2SO_4$), filtered and concentrated on an oil. The crude product was purified by column chromatography, eluting with 15% ethyl acetate ("EtOAc")/hexane. The isolated fractions were triturated with hexanes to afford methyl 2,6-difluoro-3-(N-(propylsulfonyl)propylsulfonamido)benzoate as a solid (24.4 g, 73% yield for 3 steps). $^1$H NMR (400 MHz, CDCl$_3$) δ 7.52-7.45 (m, 1H), 7.08-7.02 (m, 1H), 3.97 (s, 3H), 3.68-3.59 (m, 2H), 3.53-3.45 (m, 2H), 2.02-1.89 (m, 4H), 1.10 (t, J=7.4 Hz, 6H). m/z (APCI-neg) M-(SO$_2$Pr)=292.2.

Example C

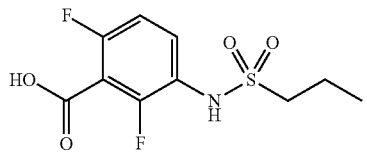 [SMILES: CCCS(=O)(=O)Nc1ccc(F)c(C(=O)O)c1F]

2,6-difluoro-3-(propylsulfonamido)benzoic acid

A 1N aqueous NaOH solution (150 mL, 150 mmol) was added to a solution of methyl 2,6-difluoro-3-(N-(propylsulfonyl)propylsulfonamido)benzoate (20.0 g, 50.1 mmol) in 4:1 THF/MeOH (250 mL, 0.2M). The reaction mixture was stirred at room temperature overnight. The majority of the organic solvents were then removed in vacuo (water bath temperature 35° C.). 1N HCl (150 mL) was slowly added to the mixture, and the resulting solid was filtered and rinsed with water (4×50 mL). The material was then washed with Et$_2$O (4×15 mL) to give 2,6-difluoro-3-(propylsulfonamido) benzoic acid as a solid (10.7 g, 77% yield). $^1$H NMR (400 MHz, d$_6$-DMSO) δ 9.74 (s, 1H), 7.57-7.50 (m, 1H), 7.23-7.17 (m, 1H), 3.11-3.06 (m, 2H), 1.79-1.69 (m, 2H), 0.98 (t, J=7.4 Hz, 3H). m/z (APCI-neg) M−1=278.0.

Example D

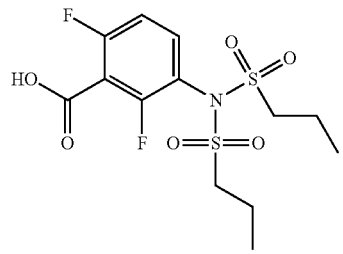 [SMILES: CCCS(=O)(=O)N(c1ccc(F)c(C(=O)O)c1F)S(=O)(=O)CCC]

2,6-difluoro-3-(N-(propylsulfonyl)propylsulfonamido)benzoic acid

Propane-1-sulfonyl chloride (1.225 mL, 10.92 mmol) was added to a mixture of 3-amino-2,6-difluorobenzoic acid (0.573 g, 3.310 mmol), triethylamine (2.030 mL, 14.56 mmol) and CH$_2$Cl$_2$ (17 mL, 0.2M) cooled to 0° C. The reaction mixture was allowed to warm to room temperature and stirred for 1 hour. The mixture was then partitioned between saturated NaHCO$_3$ (100 mL) and ethyl acetate (75 mL). The aqueous layer was washed with ethyl acetate (50 mL) and then acidified with concentrated HCl to a pH of about 1. The acidified aqueous layer was extracted with ethyl acetate (2×50 mL), and the combined ethyl acetate extracts were dried (Na$_2$SO$_4$), filtered and concentrated. The resulting residue was triturated with hexanes to afford 2,6-difluoro-3-(N-(propylsulfonyl)propyl-sulfonamido)benzoic acid as a solid (0.948 g, 74% yield). $^1$H NMR (400 MHz, d$_6$-DMSO) δ 7.90-7.84 (m, 1H), 7.39-7.34 (m, 1H), 3.73-3.58 (m, 4H), 1.88-1.74 (m, 4H), 1.01 (t, J=7.5 Hz, 6H). m/z (APCI-neg) M-(SO$_2$Pr)=278.1.

Example E

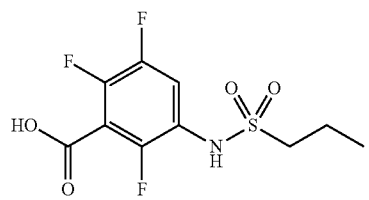 [SMILES: CCCS(=O)(=O)Nc1cc(F)c(F)c(C(=O)O)c1F]

2,3,6-trifluoro-5-(propylsulfonamido)benzoic acid 2,3,6-Trifluoro-5-(propylsulfonamido)benzoic acid (8.5%) was prepared according to the general procedure of Example D, substituting 3-amino-2,5,6-trifluorobenzoic acid for 3-amino-2,6-difluorobenzoic acid.

Example F

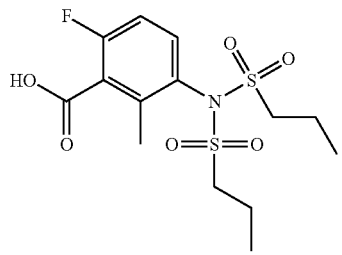 [SMILES: CCCS(=O)(=O)N(c1ccc(F)c(C(=O)O)c1C)S(=O)(=O)CCC]

6-fluoro-2-methyl-3-(N-(propylsulfonyl)propylsulfonamido)benzoic acid

6-Fluoro-2-methyl-3-(N-(propylsulfonyl)propylsulfonamido)benzoic acid (11%) was prepared according to the general procedure of Example D, substituting 3-amino-6-fluoro-2-methylbenzoic acid for 3-amino-2,6-difluorobenzoic acid.

Example G

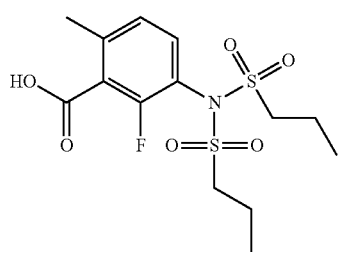 [SMILES: CCCS(=O)(=O)N(c1ccc(C)c(C(=O)O)c1F)S(=O)(=O)CCC]

2-fluoro-6-methyl-3-(N-(propylsulfonyl)propylsulfonamido)benzoic acid

2-Fluoro-6-methyl-3-(N-(propylsulfonyl)propylsulfonamido)benzoic acid (3%) was prepared according to the general procedure of Example D, substituting 3-amino-2-fluoro-6-methylbenzoic acid for 3-amino-2,6-difluorobenzoic acid.

Example H

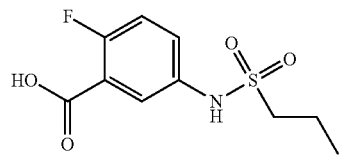 [SMILES: CCCS(=O)(=O)Nc1ccc(F)c(C(=O)O)c1]

2-fluoro-5-(propylsulfonamido)benzoic acid

Propane-1-sulfonyl chloride (0.0871 mL, 0.774 mmol) was dissolved in 10% Na$_2$CO$_3$ (1.65 mL, 1.55 mmol) at room temperature. 5-Amino-2-fluorobenzoic acid (0.100 g, 0.645 mmol) was added and heated to 60° C. overnight. Propane-1-sulfonyl chloride (0.0871 mL, 0.774 mmol) was added again, and the reaction mixture was heated at 60° C. for another hour. The reaction mixture was cooled to room temperature, diluted with water, taken to a pH of 10 with 10% Na$_2$CO$_3$ and extracted with DCM (2×). The reaction mixture was then taken to a pH of 2 with 1N HCl, extracted with DCM (3×) and concentrated to a solid, 2-fluoro-5-(propylsulfonamido)benzoic acid (29%).

Example I

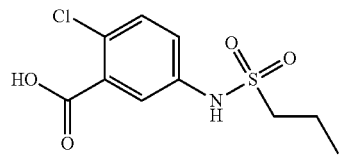 [SMILES: CCCS(=O)(=O)Nc1ccc(Cl)c(C(=O)O)c1]

2-chloro-5-(propylsulfonamido)benzoic acid

2-Chloro-5-(propylsulfonamido)benzoic acid (14%) was prepared according to the general procedure for Example H, substituting 5-amino-2-chlorobenzoic acid for 5-amino-2-fluorobenzoic acid.

Example J

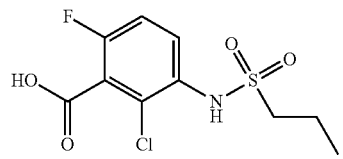

2-chloro-6-fluoro-3-(propylsulfonamido)benzoic acid

Step A: 2-Chloro-6-fluorobenzoic acid (2.00 g, 11.5 mmol) was dissolved in sulfuric acid (20 mL) and cooled to 0° C. Nitric acid (0.529 mL, 12.6 mmol) was added, and the reaction mixture was warmed to room temperature for one hour. The reaction mixture was diluted with water, and the aqueous portion was extracted with DCM (3×), dried over $Na_2SO_4$, concentrated to a solid, 2-chloro-6-fluoro-3-nitrobenzoic acid (97%), which was used directly in the next step without further purification.

Step B: 2-Chloro-6-fluoro-3-nitrobenzoic acid (0.100 g, 0.455 mmol) and Zn dust (0.298 g, 4.55 mmol) were taken up in THF (4 mL) and saturated aqueous $NH_4Cl$ (2 mL) and stirred at room temperature overnight. The reaction mixture was filtered through Celite, concentrated to a solid, and dissolved in water. The pH was adjusted to 2 with 1N HCl, and the aqueous portion was extracted with DCM (3×). The organic portion was dried over $Na_2SO_4$ and concentrated to a solid, 3-amino-2-chloro-6-fluorobenzoic acid (49%), which was used directly in the next step without further purification.

Step C: 2-Chloro-6-fluoro-3-(propylsulfonamido)benzoic acid (13%) was prepared according to the general procedure for Example H, substituting 3-amino-2-chloro-6-fluorobenzoic acid for 5-amino-2-fluorobenzoic acid.

Example K

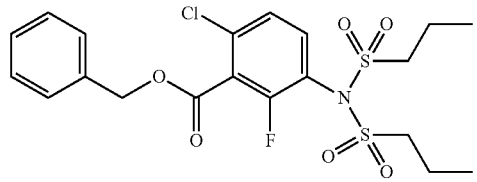 [SMILES: CCCS(=O)(=O)N(c1ccc(Cl)c(C(=O)OCc2ccccc2)c1F)S(=O)(=O)CCC]

benzyl 6-chloro-2-fluoro-3-(N-(propylsulfonyl)propylsulfonamido)benzoate

Step A: A flame dried flask equipped with a stir bar and rubber septum was charged with 4-chloro-2-fluoroaniline (5.00 g, 34.35 mmol) and dry THF (170 mL). This solution was chilled to −78° C., and n-BuLi (14.7 mL, 1.07 eq. of 2.5M solution in hexanes) was then added over a 15 minute period. This mixture was stirred at −78° C. for 20 minutes, and then a THF solution (25 mL) of 1,2-bis(chlorodimethylsilyl)ethane (7.76 g, 1.05 eq.) was added slowly (over a 10 minute period) to the reaction mixture. This was stirred for 1 hour, and then 2.5M n-BuLi in hexanes (15.11 mL, 1.1 eq.) was added slowly. After allowing the mixture to warm to room temperature for one hour, the mixture was chilled back to −78° C. A third allotment of n-BuLi (15.66 mL, 1.14 eq.) was added slowly, and the mixture was stirred at −78° C. for 75 minutes. Benzyl chloroformate (7.40 g, 1.2 eq.) was then added slowly, and the mixture was stirred at −78° C. for one hour. The cooling bath was then removed. The mixture was allowed to warm for 30 minutes and then quenched with water (70 mL) and concentrated HCl (25 mL). The mixture was allowed to continue to warm to room temperature. The mixture was then extracted with EtOAc. The extracts were washed twice with a saturated $Na_2HCO_3$ solution, once with water, dried over sodium sulfate and concentrated. The resulting residue was flashed on a 65 Biotage (30% ethyl acetate/hexane) to produce benzyl 3-amino-6-chloro-2-fluorobenzoate (4.3 g, 45%) as an oil. $^1$H NMR (DMSO-$d_6$, 400 MHz) δ 7.37-7.48 (m, 5H), 7.07 (dd, 1H, J=8, 2), 6.87 (t, 1H, J=8), 5.61 (br s, 2H), 5.40 (s, 2H).

Step B: Benzyl 3-amino-6-chloro-2-fluorobenzoate (4.3 g, 15.37 mmol) was dissolved in dry dichloromethane (270 mL) Triethylamine (5.36 mL, 2.5 eq.) was added, and the mixture was chilled to 0° C. Propane-1-sulfonyl chloride (3.63 mL, 32.3 mmol, 2.1 eq.) was then added via syringe, and a precipitate resulted. Once the addition was complete, the mixture was allowed to warm to room temperature, and the starting material was consumed as determined by TLC (3:1 hexane: ethyl acetate). The mixture was then diluted with dichloromethane (200 mL), washed with 2M aqueous HCl (2×100 mL), saturated $Na_2HCO_3$ solution, dried over sodium sulfate and concentrated. The resulting residue was purified on a 65 Biotage chromatography system (40% ethyl acetate/hexane) to produce benzyl 6-chloro-2-fluoro-3-(N-(propylsulfonyl)propylsulfonamido)benzoate (5.5 g, 72%) as an oil that slowly solidified upon standing. NMR (CDCl$_3$, 400 MHz) δ 7.28-7.45 (m, 7H), 5.42 (s, 2H), 3.58-3.66 (m, 2H), 3.43-3.52 (m, 2H), 1.08 (t, 6H, J=8).

Example L

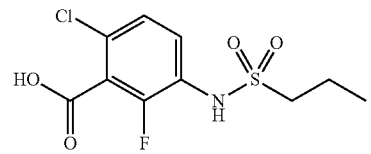 [SMILES: CCCS(=O)(=O)Nc1ccc(Cl)c(C(=O)O)c1F]

6-chloro-2-fluoro-3-(propylsulfonamido)benzoic acid

Benzyl 6-chloro-2-fluoro-3-(N-(propylsulfonyl)propylsulfonamido)benzoate (5.4 g, 10.98 mmol) was dissolved in THF (100 mL) and 1M aqueous KOH (100 mL). This mixture was refluxed for 16 hours and then allowed to cool to room temperature. The mixture was then acidified to a pH of 2 with 2M aqueous HCl and extracted with EtOAc (2 X). The extracts were washed with water, dried over sodium sulfate and concentrated to a solid that was triturated with hexanes/ether to give 6-chloro-2-fluoro-3-(propylsulfonamido)benzoic acid (2.2 g, 68%) as a solid. NMR (DMSO-$d_6$, 400 MHz) δ 9.93 (s, 1H), 7.49 (t, 1H, J=8), 7.38 (dd, 1H, J=8, 2), 3.11-3.16 (m, 2H), 1.68-1.78 (m, 2H), 0.97 (t, 3H, J=8).

Example M

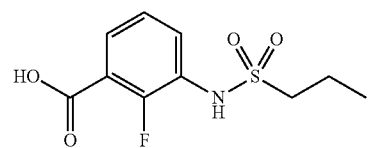 [SMILES: CCCS(=O)(=O)Nc1cccc(C(=O)O)c1F]

2-fluoro-3-(propylsulfonamido)benzoic acid

6-Chloro-2-fluoro-3-(propylsulfonamido)benzoic acid (0.5 g, 1.69 mmol) was dissolved in methanol (15 mL), and Pearlman's catalyst (one weight equivalent, 0.5 g, 20% Pd(OH)$_2$ on carbon, 50% by weight water) was added. This mixture was subjected to a balloon of hydrogen for 3 hours and then filtered through GF/F filter paper. The filtrate was concentrated to 2-fluoro-3-(propylsulfonamido)benzoic acid (396 mg, 90%) as a solid. MS (M−H+) 262. NMR (DMSO-d$_6$, 400 MHz) δ 13.36 (s, 1H), 9.76 (s, 1H), 7.58-7.70 (m, 2H), 7.26 (t, 1H, J=8), 3.10 (t, 2H, J=8), 1.69-1.80 (m, 2H), 0.98 (t, 3H, J=8).

Example N

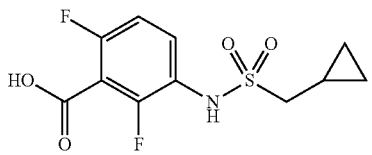 [SMILES: O=C(O)c1c(F)ccc(NS(=O)(=O)CC2CC2)c1F]

3-(cyclopropylmethylsulfonamido)-2,6-difluorobenzoic acid

Step A: Cyclopropylmethanesulfonyl chloride (1.27 g, 8.20 mmol) was added to a mixture of 3-amino-2,6-difluorobenzoic acid (0.430 g, 2.48 mmol), triethylamine (1.52 mL, 10.9 mmol) and CH$_2$Cl$_2$ (12 mL, 0.2M) cooled to 0° C. The reaction mixture was allowed to warm to room temperature and stirred for 1 hour. The mixture was then partitioned between saturated NaHCO$_3$ (75 mL) and ethyl acetate (50 mL). The aqueous layer was washed with ethyl acetate (50 mL) and then acidified to a pH of 1 with concentrated HCl. The acidified aqueous layer was extracted twice with ethyl acetate (2×50 mL), and the combined ethyl acetate extracts were dried (Na$_2$SO$_4$), filtered and concentrated to provide crude 3-(1-cyclopropyl-N-(cyclopropylmethylsulfonyl)methylsulfonamido)-2,6-difluorobenzoic acid (380 mg, 37%).

Step B: A solution of 1N NaOH (2.78 mL, 2.78 mmol) was added to a solution of crude 3-(1-cyclopropyl-N-(cyclopropylmethylsulfonyl)methylsulfonamido)-2,6-difluorobenzoic acid (380 mg, 0.928 mmol) in 4:1 THF/MeOH (5 mL, 0.2M). The reaction mixture was stirred at room temperature for 1 hour, after which most of the organic solvents were removed. 1N HCl (3 mL) was slowly added to the mixture to acidify to a pH of 1. The acidified aqueous layer was extracted with ethyl acetate (75 mL). The ethyl acetate extract was washed with water (2×20 mL), brine (20 mL), dried (Na$_2$SO$_4$), filtered and concentrated. Trituration of the residue with Et$_2$O afforded 3-(cyclopropylmethylsulfonamido)-2,6-difluorobenzoic acid as a solid (139 mg, 51%). $^1$H NMR (400 MHz, d$_6$-DMSO) δ 9.76 (s, 1H), 7.60-7.54 (m, 1H), 7.22-7.16 (m, 1H), 3.10 (d, J=7.0 Hz, 2H), 1.10-0.99 (m, 1H), 0.58-0.53 (m, 2H), 0.36-0.31 (m, 2H); m/z (APCI-neg) M-1=289.9.

Example O

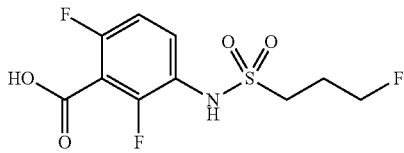 [SMILES: O=C(O)c1c(F)ccc(NS(=O)(=O)CCCF)c1F]

2,6-difluoro-3-(3-fluoropropylsulfonamido)benzoic acid

Methyl 2,6-difluoro-3-(N-(3-fluoropropylsulfonyl)-3-fluoropropylsulfonamido)benzoate was made according to the general procedure for Example B, substituting 3-fluoropropyl sulfonyl chloride for propane-1-sulfonyl chloride. $^1$H NMR (400 MHz, DMSO-d$_6$) δ 8.05-7.99 (m, 1H), 7.44 (t, 1H), 4.62 (t, 2H), 4.50 (t, 2H), 3.93 (s, 3H), 3.89-3.74 (m, 4H), 2.26-2.11 (m, 4H).

2,6-Difluoro-3-(3-fluoropropylsulfonamido)benzoic acid was prepared according to the general procedure for Example C, substituting methyl 2,6-difluoro-3-(N-(3-fluoropropylsulfonyl)-3-fluoropropylsulfonamido)benzoate for methyl 2,6-difluoro-3-(N-(propylsulfonyl)-propylsulfonamido)benzoate. $^1$H NMR (500 MHz, DMSO-d$_6$) δ 14.05 (br s, 1H), 9.71 (s, 1H), 7.56-7.50 (m, 1H), 7.20 (t, 1H), 3.12-3.08 (m, 2H), 1.73-1.66 (m, 2H), 1.39 (sx, 2H), 0.87 (t, 3H).

Example P

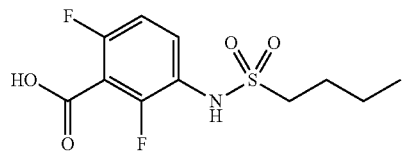 [SMILES: CCCCS(=O)(=O)Nc1ccc(F)c(C(=O)O)c1F]

3-(butylsulfonamido)-2,6-difluorobenzoic acid

Methyl 2,6-difluoro-3-(N-(butylsulfonyl)-butylsulfonamido)benzoate was made according to the general procedure for Example B, substituting butane-1-sulfonyl chloride for propane-1-sulfonyl chloride. $^1$H NMR (500 MHz, DMSO-d$_6$) δ 7.99-7.94 (m, 1H), 7.42 (t, 1H), 3.92 (s, 3H), 3.74-3.62 (m, 4H), 1.81-1.68 (m, 4H), 1.42 (sx, 4H), 0.89 (t, 6H).

3-(Butylsulfonamido)-2,6-difluorobenzoic acid was prepared according to the general procedure for Example C, substituting methyl 2,6-difluoro-3-(N-(butylsulfonyl)-butylsulfonamido)benzoate for methyl 2,6-difluoro-3-(N-(propylsulfonyl)-propylsulfonamido)benzoate. $^1$H NMR (400 MHz, DMSO-d$_6$) δ 14.05 (br s, 1H), 9.71 (s, 1H), 7.56-7.50 (m, 1H), 7.20 (t, 1H), 3.12-3.08 (m, 2H), 1.73-1.66 (m, 2H), 1.39 (sx, 2H), 0.87 (t, 3H).

Example Q

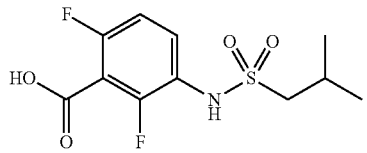 [SMILES: CC(C)CS(=O)(=O)Nc1ccc(F)c(C(=O)O)c1F]

2,6-difluoro-3-(2-methylpropylsulfonamido)benzoic acid

Methyl-2,6-difluoro-3-(N-(2-methylpropylsulfonyl)-2-methylpropyl-sulfonamido)benzoate was made according to the general procedure for Example B, substituting 2-methylpropyl sulfonyl chloride for propane-1-sulfonyl chloride. m/z (LC-MS) M+1=428.4.

2,6-Difluoro-3-(2-methylpropylsulfonamido)benzoic acid was prepared according to the general procedure for Example C, substituting methyl-2,6-difluoro-3-(N-(2-methylpropylsulfonyl)-2-methylpropylsulfonamido)benzoate for methyl 2,6-difluoro-3-(N-(propylsulfonyl)-propylsulfonamido)benzoate. ¹H NMR (400 MHz, DMSO-d₆) δ 14.01 (s, 1H), 9.71 (s, 1H), 7.56 (dd, 1H), 7.22 (dd, 1H), 3.02 (d, 2H), 2.18-2.15 (m, 1H), 1.03 (d, 6H); m/z (LC-MS) M+1=294.3.

Example R

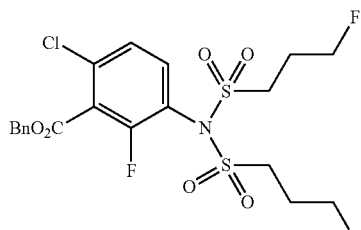

benzyl 6-chloro-2-fluoro-3-(3-fluoro-N-(3-fluoro-propylsulfonyl)propylsulfonamido)benzoate Benzyl 6-chloro-2-fluoro-3-(3-fluoro-N-(3-fluoropropyl-sulfonyl)propylsulfonamido)benzoate (92%) was prepared according to the general procedure for Example K, Step B substituting 3-fluoropropane-1-sulfonyl chloride for propane-1-sulfonyl chloride.

Example S

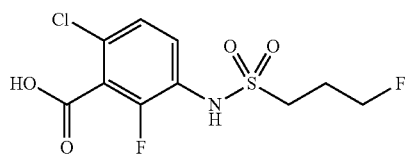

6-chloro-2-fluoro-3-(3-fluoropropylsulfonamido) benzoic acid

6-Chloro-2-fluoro-3-(3-fluoropropylsulfonamido)benzoic acid (71%) was prepared according to the general procedure for Example L substituting benzyl 6-chloro-2-fluoro-3-(3-fluoro-N-(3-fluoropropylsulfonyl)propylsulfonamido)benzoate for benzyl 6-chloro-2-fluoro-3-(N-(propylsulfonyl) propylsulfonamido)benzoate.

Example T

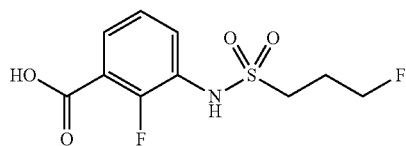 [SMILES: O=C(O)c1cccc(NS(=O)(=O)CCCF)c1F]

2-fluoro-3-(3-fluoropropylsulfonamido)benzoic acid

2-Fluoro-3-(3-fluoropropylsulfonamido)benzoic acid (81%) was prepared according to the general procedure for Example M substituting 6-chloro-2-fluoro-3-(3-fluoropropylsulfonamido)benzoic acid for 6-chloro-2-fluoro-3-(propylsulfonamido)benzoic acid.

Example U

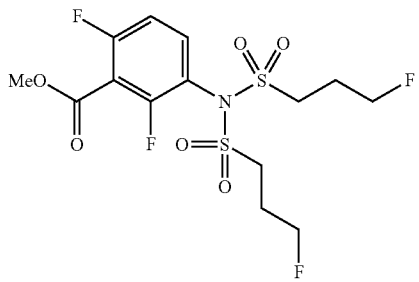 [SMILES: COC(=O)c1c(F)ccc(N(S(=O)(=O)CCCF)S(=O)(=O)CCCF)c1F]

methyl 2,6-difluoro-3-(3-fluoro-N-(3-fluoropropyl-sulfonyl)propylsulfonamido)benzoate 3-Fluoropropane-1-sulfonyl chloride (14.3 mL, 129 mmol) was slowly added to a solution of methyl 3-amino-2,6-difluorobenzoate (24.1 g, 129 mmol) and pyridine (31.2 mL, 386 mmol) in CH₂Cl₂ (360 mL). The reaction mixture was stirred for over two days at room temperature. The reaction mixture was diluted with methylene chloride. The reaction mixture was then washed with an aqueous solution of saturated sodium bicarbonate, 1N HCl, and brine, then dried (Na₂SO₄), filtered and concentrated to an oil to give methyl 2,6-difluoro-3-(3-fluoro-N-(3-fluoropropylsulfonyl)propyl-sulfonamido)benzoate (38.1 g). ¹H NMR (400 MHz, CDCl₃, ppm) 7.69 (dt, 1H), 7.00 (dt, 1H), 6.55 (s, 1H), 4.56 (dd, 2H), 3.28-3.17 (m, 2H), 2.32-2.15 (m, 2H).

Example V

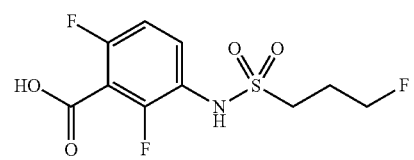

2,6-difluoro-3-(3-fluoropropylsulfonamido)benzoic acid 2,6-Difluoro-3-(N-(3-fluoropropylsulfonyl)propylsul-fonamido)benzoate (38 g, 120 mmol) was dissolved in 5:2 THF/MeOH (250 mL), and a solution of lithium hydroxide (8.77 g, 366 mmol) in water (50 mL) was added. The reaction mixture was stirred at room temperature for four hours. The majority of the organic solvents were then removed in vacuo. 2.5N HCl (500 mL) was slowly added to the mixture, and the resulting solid was filtered and rinsed with cold ether to give 2,6-difluoro-3-(3-fluoropropylsulfonamido)benzoic acid as a solid (29.3 g, 81% yield). ¹H NMR (400 MHz, CDCl₃ ppm)

9.85 (s, 1H), 7.54 (dt, 1H), 7.21 (dt, 1H), 4.54 (td, 2H), 2.20-2.00 (m, 2H), 3.24-3.18 (m, 2H).

Example W

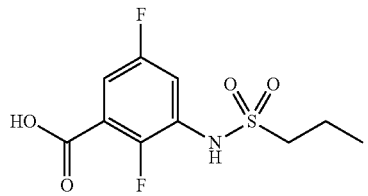 [SMILES: CCCS(=O)(=O)Nc1cc(F)cc(C(=O)O)c1F]

2,5-difluoro-3-(propylsulfonamido)benzoic acid

Step A: 2,5-Difluorobenzoic acid (2.01 g, 9.90 mmol, 31.3% yield) was dissolved in concentrated sulfuric acid (25 mL) and cooled to 0° C. Nitric Acid (1.46 mL, 34.8 mmol) was added, and the reaction mixture was stirred at room temperature for one hour. The solution was extracted with DCM (3×), and the combined organic layers were dried over sodium sulfate and concentrated. The residue was purified by column chromatography (1:1 hexanes:1% HCOOH/EtOAc) giving 2,5-difluoro-3-nitrobenzoic acid (2.01 g, 31.3%) as a solid.

Step B: 2,5-Difluoro-3-nitrobenzoic acid (2.00 g, 9.847 mmol) was dissolved in MeOH (60 mL). TMSCl (6.220 mL, 49.24 mmol) was added, and the reaction mixture was stirred at reflux for 4 hours. The reaction mixture was concentrated to about 20 mL, and the crystals produced were filtered and dried under high vacuum providing methyl 2,5-difluoro-3-nitrobenzoate (1.55 g, 72.4%) as a crystalline solid.

Step C: Methyl 3-amino-2,5-difluorobenzoate (96.5%) was prepared according to the general procedure for Example B, Step B, substituting methyl 2,5-difluoro-3-nitrobenzoate for methyl 2,6-difluoro-3-nitrobenzoate.

Step D: Methyl 2,5-difluoro-3-(N-(propylsulfonyl)propylsulfonamido) benzoate was prepared according to the general procedure for Example B, Step C, substituting methyl 3-amino-2,5-difluorobenzoate for methyl 3-amino-2,6-difluorobenzoate.

Step E: 2,5-Difluoro-3-(propylsulfonamido)benzoic acid (83.8%, two steps) was prepared according to the general procedure for Example C substituting methyl 2,5-difluoro-3-(N-(propylsulfonyl)propylsulfonamido)benzoate for methyl 2,6-difluoro-3-(N-(propylsulfonyl)propylsulfonamido)benzoate. $^1$H NMR (400 MHz, $d_6$-DMSO) δ 13.67 (br s, 1H), 10.07 (s, 1H), 7.46-7.50 (m, 1H), 7.38-7.42 (m, 1H), 3.17-3.21 (m, 2H), 1.70-1.76 (m, 2H), 0.95-0.99 (m, 3H); m/z (APCI-neg) M−1=278.1.

Example X

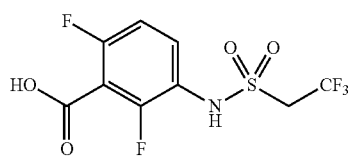 [SMILES: O=C(O)c1c(F)ccc(NS(=O)(=O)CC(F)(F)F)c1F]

2,6-difluoro-3-(2,2,2-trifluoroethylsulfonamido)benzoic acid

Step A: 2,2,2-Trifluoroethyl-sulfonyl chloride (459 mL, 4.15 mmol) was slowly added to a solution of methyl 3-amino-2,6-difluorobenzoate (311 g, 1.66 mmol) and pyridine (0.806 mL, 9.97 mmol) in dichloromethane (8.92 mL, 139 mmol), while applying external cooling using an acetone dry ice bath. The reaction mixture was stirred for 45 minutes, and the dry ice bath was removed. The reaction mixture was kept stirring for another hour. The mixture was diluted with EtOAc (100 mL), washed with water (2×25 mL) and brine (25 mL), dried (Na$_2$SO$_4$), filtered, and then concentrated to an oil. The crude product was purified by column chromatography, eluting with 15% EtOAc/hexane to afford methyl 2,6-difluoro-3-(2-trifluoroethylsulfonamido) benzoate as a solid (513 mg, 92.6% yield). $^1$H NMR (400 MHz, $d_6$-DMSO) δ 8.10-8.01 (m, 1H), 7.48 (t, 1H), 4.68 (s, 2H), 4.58 (s, 2H), 3.98 (s, 3H).

Step B: 2,6-Difluoro-3-(2-trifluoroethylsulfonamido)benzoic acid was prepared according to the general procedure for Example C, substituting methyl 2,6-difluoro-3-(2-trifluoroethylsulfonamido) benzoate for methyl 2,6-difluoro-3-(N-(propylsulfonyl)-propylsulfonamido)benzoate. $^1$H NMR (500 MHz, $d_6$-DMSO) δ 14.08 (br s, 1H), 9.75 (s, 1H), 7.58-7.52 (m, 1H), 7.25 (t, 1H), 3.15-3.11 (s, 2H).

Example Y

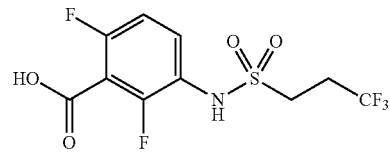 [SMILES: O=C(O)c1c(F)ccc(NS(=O)(=O)CCC(F)(F)F)c1F]

2,6-difluoro-3-(3,3,3-trifluoropropylsulfonamido)benzoic acid

Step A: Methyl 2,6-difluoro-3-(N-(3,3,3-trifluoropropylsulfonyl)-3,3,3-trifluoropropyl-sulfonamido) benzoate was made according to the general procedure for Example B, substituting 3,3,3-trifluoropropyl sulfonyl chloride for propane-1-sulfonyl chloride. $^1$H NMR (400 MHz, $d_6$-DMSO) δ 8.05-7.99 (m, 1H), 7.44 (t, 1H), 4.62 (t, 2H), 4.50 (t, 2H), 3.93 (s, 3H), 3.89-3.74 (m, 4H), 2.26-2.11 (m, 4H).

Step B: 2,6-Difluoro-3-(3,3,3-trifluoropropylsulfonamido)benzoic acid was prepared according to the general procedure for Example C, substituting methyl 2,6-difluoro-3-(N-(3,3,3-trifluoropropylsulfonyl)-3,3,3-trifluoropropylsulfonamido)benzoate for methyl 2,6-difluoro-3-(N-(propylsulfonyl)-propylsulfonamido)benzoate. $^1$H NMR (500 MHz, $d_6$-DMSO) δ 14.05 (br s, 1H), 9.71 (s, 1H), 7.56-7.50 (m, 1H), 7.20 (t, 1H), 3.12-3.08 (m, 2H), 1.73-1.66 (m, 2H).

Example Z

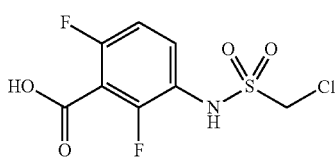 [SMILES: O=C(O)c1c(F)ccc(NS(=O)(=O)CCl)c1F]

2,6-difluoro-3-(2-chloromethylsulfonamido)benzoic acid

Step A: Methyl 2,6-difluoro-3-(N-(2-chloromethylsulfonyl)-2-chloromethyl-sulfonamido) benzoate was made according to the general procedure for Example B, substituting 2-chloromethyl sulfonyl chloride for propane-1-sulfonyl chloride. $^1$H NMR (400 MHz, d$_6$-DMSO) δ 8.08-7.97 (m, 1H), 7.45 (t, 1H), 4.65 (s, 2H), 4.55 (s, 2H), 4.02 (s, 3H).

Step B: 2,6-Difluoro-3-(2-chloromethylsulfonamido)benzoic acid was prepared according to the general procedure for Example C, substituting methyl 2,6-difluoro-3-(N-(2-chloromethylsulfonyl)-2-chloromethylsulfonamido)benzoate for methyl 2,6-difluoro-3-(N-(propylsulfonyl)-propylsulfonamido)benzoate. $^1$H NMR (500 MHz, d$_6$-DMSO) δ 14.10 (br s, 1H), 9.78 (s, 1H), 7.62-7.56 (m, 1H), 7.28 (t, 1H), 3.19-3.15 (s, 2H).

Example AB

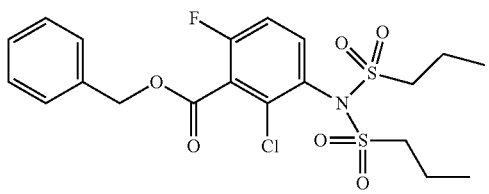 [SMILES: CCCS(=O)(=O)N(c1ccc(F)c(C(=O)OCc2ccccc2)c1Cl)S(=O)(=O)CCC]

benzyl 2-chloro-6-fluoro-3-(N-(propylsulfonyl)propylsulfonamido)benzoate

Step A: Benzyl 3-amino-2-chloro-6-fluorobenzoate (56%) was prepared according to the general procedure for Example K, substituting 2-chloro-4-fluoroaniline for 4-chloro-2-fluoroaniline. $^1$H NMR (400 MHz, d$_6$-DMSO) δ 7.48-7.32 (m, 5H), 7.11-7.05 (t, 1H), 6.94-6.89 (q, 1H), 5.53-5.49 (s, 2H), 5.41-5.39 (s, 2H).

Step B: Benzyl 3-amino-2-chloro-6-fluorobenzoate (330 mg, 1.2 mmol) was dissolved in dry dichloromethane (11.8 mL). Triethylamine (0.494 mL, 3.54 mmol) was added, and the mixture was chilled to 0° C. Propane-1-sulfonyl chloride (0.332 mL, 2.95 mmol) was then added via syringe. Once the addition was complete, the mixture was allowed to warm to ambient temperature and stir for 16 hours. The mixture was diluted with dichloromethane (11 mL) and washed with water (2×50 mL) and brine (25 mL), dried over sodium sulfate, and concentrated. The resulting residue was applied directly to a silica gel column and eluted with a gradient (5% to 40%) of ethyl acetate-hexanes to provide benzyl 2-chloro-6-fluoro-3-(N-(propylsulfonyl)propylsulfonamido)benzoate (413 mg, 0.840 mmol, 71.1% yield). $^1$H NMR (400 MHz, d$_6$-DMSO) δ 8.00-7.94 (q, 1H), 7.59-7.52 (t, 1H), 7.50-7.35 (m, 5H), 5.48-5.44 (s, 2H), 3.80-3.60 (m, 4H), 1.89-1.75 (m, 4H), 1.05-0.98 (t, 6H).

Example AC

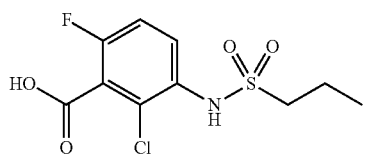 [SMILES: CCCS(=O)(=O)Nc1ccc(F)c(C(=O)O)c1Cl]

2-chloro-6-fluoro-3-(propylsulfonamido)benzoic acid

Step A: Benzyl 2-chloro-6-fluoro-3-(N-(propylsulfonyl)propylsulfonamido)benzoate (413.2 mg, 0.840 mmol) was dissolved in THF (8.4 mL) and 2.0M aqueous LiOH (1.26 mL). The mixture was refluxed for 16 hours and then allowed to cool to ambient temperature. The mixture was acidified to a pH of 0 with 1.0M HCl (5.0 mL) and then adjusted to a pH of 4 using saturated sodium bicarbonate. The mixture was extracted with EtOAc (2×). The extracts were washed with water (2×) and brine (1×), dried over sodium sulfate and concentrated to afford benzyl 2-chloro-6-fluoro-3-(propylsulfonamido)benzoate (174.5 mg, 0.4523 mmol, 53.9% yield). MS (APCI-neg) m/z=384.1 (M–H).

Step B: Benzyl 2-chloro-6-fluoro-3-(propylsulfonamido)benzoate (174.5 mg, 0.4523 mmol) was dissolved in 3:1 dioxane:water (7.5 mL) and treated with barium hydroxide (100.7 mg, 0.5879 mmol). The reaction mixture was heated to 80° C. for 16 hours and then allowed to cool to ambient temperature. The mixture was acidified to a pH of 0 with concentrated HCl. The reaction mixture was allowed to stir for 10 minutes, after which the pH was adjusted to a pH of 4 using saturated sodium bicarbonate. The mixture was extracted with EtOAc (2×). The extracts were washed with water (2×) and brine (1×), dried over sodium sulfate, and concentrated to afford 2-chloro-6-fluoro-3-(propylsulfonamido)benzoic acid (75.7 mg, 0.2560 mmol, 56.6% yield). MS (APCI-neg) m/z=293.9 (M–H).

Example AD

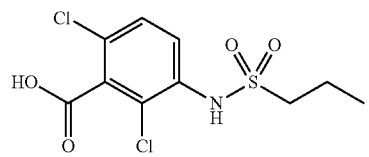 [SMILES: CCCS(=O)(=O)Nc1ccc(Cl)c(C(=O)O)c1Cl]

2,6-dichloro-3-(propylsulfonamido)benzoic acid

Step A: 2,6-Dichloro-3-nitrobenzoic acid (2.13 g, 9.03 mmol) was dissolved in 2:1 THF:saturated aqueous NH$_4$Cl and cooled to 0° C. The mixture was treated with zinc (11.8 g, 181 mmol). The reaction mixture was allowed to warm to ambient temperature and stir for 24 hours. The reaction mixture was filtered through GF/F paper while rinsing with THF. The mixture was acidified to a pH of 1 using 1.0M HCl and extracted with 15% 2-propanol:DCM (3×). The extracts were washed with water and brine, dried over sodium sulfate and concentrated to afford 3-amino-2,6-dichlorobenzoic acid (1.40 g, 6.82 mmol, 75.5% yield). MS (APCI-neg) m/z=203.6 (M−H).

Step B: 3-Amino-2,6-dichlorobenzoic acid (1.40 g, 6.82 mmol) was dissolved in dry dichloromethane (66.7 mL). Triethylamine (4.09 mL, 29.4 mmol) was added, and the mixture was chilled to 0° C. Propane-1-sulfonyl chloride (2.48 mL, 22 mmol) was then added via syringe. Once the addition was complete, the mixture was allowed to warm to ambient temperature and stir for 1 hour. The mixture was concentrated in vacuo and diluted with diethyl ether. The mixture was washed with 0.25M NaOH (80 mL), and the aqueous layer was acidified to a pH of 1 using 1.0M HCl. The aqueous layer was extracted with 15% 2-propanol:DCM (2×300 mL). The organic layer was collected, dried over sodium sulfate, and concentrated to afford 2,6-dichloro-3-(propylsulfonamido)benzoic acid (1.55 g, 4.96 mmol, 74.4% yield). $^1$H NMR (400 MHz, $d_6$-DMSO) δ 9.77-9.75 (s, 1H), 7.84-7.80 (d, 1H), 7.71-7.68 (d, 1H), 3.82-3.72 (m, 2H), 1.89-1.70 (m, 2H), 1.05-1.03 (m, 3H).

Example 1

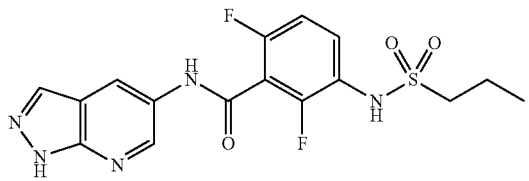 [SMILES: CCCS(=O)(=O)Nc1ccc(F)c(C(=O)Nc2cnc3[nH]ncc3c2)c1F]

2,6-difluoro-3-(propylsulfonamido)-N-(1H-pyrazolo[3,4-b]pyridin-5-yl)benzamide

Step A: 1H-Pyrazol-5-amine (5.3 g, 64 mmol) and 2-bromomalonaldehyde (9.9 g, 64 mmol) were suspended in acetic acid (100 mL). The reaction mixture was heated to reflux under $N_2$ for 6 hours. The reaction mixture was cooled to room temperature and concentrated to give a solid. The crude solids were suspended in MeOH (200 mL) and absorbed onto silica gel (200 g). The crude product was purified by column chromatography, eluting with hexanes/ethyl acetate (4:1), hexanes/ethyl acetate (2:1) to give 5-bromo-1H-pyrazolo[3,4-b]pyridine as a solid (3.1 g, 25%).

Step B: NaH (0.082 g, 2.06 mmol, 60% suspension in mineral oil) was added portionwise to a cold (0° C.) solution of 5-bromo-1H-pyrazolo[3,4-b]pyridine (0.204 g, 1.03 mmol) in dry THF (10 mL). The reaction mixture was stirred at 0° C. for 10 minutes before 2-(trimethylsilyl)ethoxymethyl chloride (0.31 mL, 0.292 mmol) was added dropwise via a syringe. The reaction mixture was left at room temperature overnight. The reaction mixture was diluted with ethyl acetate (50 mL) and carefully quenched with water (10 mL). The aqueous layer was separated and extracted with ethyl acetate (3×50 mL). The combined organic layers were dried, filtered and concentrated. The crude product was purified by column chromatography, eluting with hexanes/ethyl acetate (50:1) to give 5-bromo-1-((2-(trimethylsilyl)ethoxy)methyl)-1H-pyrazolo[3,4-b]pyridine (0.146 g, 43%) as an oil.

Step C: Pd$_2$(dibenzylidene acetone)$_3$ ("Pd$_2$dba$_3$"; 0.031 g, 0.033 mmol) was added to a suspension of 5-bromo-1-((2-(trimethylsilyl)ethoxy)methyl)-1H-pyrazolo[3,4-b]pyridine (0.110 g, 0.335 mmol), tert-butyl carbamate (0.118 g, 1.00 mmol), Xantphos (0.039 g, 0.067 mmol), Cs$_2$CO$_3$ (0.163 g, 0.503 mmol) in THF (10 mL). The reaction mixture was purged with argon for 10 minutes and heated to reflux under argon overnight. The reaction mixture was cooled to room temperature and concentrated. The crude product was purified by column chromatography, eluting with hexanes/ethyl acetate (9:1) to give tert-butyl 1-((2-(trimethylsilyl)ethoxy)methyl)-1H-pyrazolo[3,4-b]pyridin-5-ylcarbamate (0.100 g, 82%) as an oil.

Step D: tert-Butyl 1-((2-(trimethylsilyl)ethoxy)methyl)-1H-pyrazolo[3,4-b]pyridin-5-ylcarbamate (0.100 g, 0.274 mmol) was dissolved in 4N HCl in dioxane (8 mL), and the reaction mixture was left at room temperature overnight. The reaction mixture was concentrated. The resulting solids were suspended in DCM and neutralized with triethylamine. The crude product was purified by column chromatography, eluting with ethyl acetate to give 1H-pyrazolo[3,4-b]pyridin-5-amine (0.036 g, 95%) as an oil.

Step E: 1H-Pyrazolo[3,4-b]pyridin-5-amine (0.036 g, 0.027 mmol), 2,6-difluoro-3-(propylsulfonamido)benzoic acid (0.075 g, 0.27 mmol), EDCI (0.056 g, 0.30 mmol) and HOBt (0.040 g, 0.30 mmol) were dissolved in DMF (8 mL) and stirred at room temperature for 16 hours. The reaction mixture was diluted with ethyl acetate (200 mL), and the organic layers were washed with water (3×30 mL). The organic layers were dried, filtered and concentrated. The crude product was purified by column chromatography, eluting with hexanes/ethyl acetate (1:1) to give 2,6-difluoro-3-(propylsulfonamido)-N-(1H-pyrazolo[3,4-b]pyridin-5-yl)benzamide (0.064 g, 60%) as a solid. $^1$H NMR (400 MHz, CD$_3$OD) δ 8.7 (s, 1H), 8.6 (s, 1H), 8.1 (s, 1H), 7.7 (m, 1H), 7.1 (m, 1H), 3.1 (m, 2H), 1.9 (m, 2H), 1.1 (t, J=7.6 Hz, 3H); m/z (APCI-neg) M−1=394.2.

Example 2

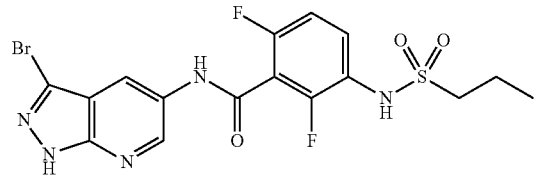 [SMILES: CCCS(=O)(=O)Nc1ccc(F)c(C(=O)Nc2cnc3[nH]nc(Br)c3c2)c1F]

N-(3-bromo-1H-pyrazolo[3,4-b]pyridin-5-yl)-2,6-difluoro-3-(propylsulfonamido)benzamide Step A: Bromine (1.91 mL, 37.1 mmol) was added dropwise to a solution of 1H-pyrazolo[3,4-b]pyridine (2.6 g, 21.8 mmol) in CHCl$_3$ (100 mL), and the reaction mixture was left at room temperature overnight. The reaction mixture was concentrated, and the resulting residue was taken up in ethyl acetate (200 mL) and saturated NaHCO$_3$ (50 mL) The aqueous layer was extracted with ethyl acetate (50 mL). The combined organic layers were dried, filtered and concentrated to give 3-bromo-1H-pyrazolo[3,4-b]pyridine (3.7 g, 86%) as a solid.

Step B: NaH (1.8 g, 44.9 mmol, 60% suspension in mineral oil) was added portionwise to a cold (0° C.) solution of 3-bromo-1H-pyrazolo[3,4-b]pyridine (3.7 g, 18.7 mmol) in dry THF (50 mL). After 10 minutes, 4-methylbenzene-1-sulfonyl chloride (5.3 g, 28.0 mmol) was added. The cold bath was removed, and the reaction mixture was left at room temperature overnight. The reaction mixture was placed in an ice bath, diluted with ethyl acetate (200 mL) and carefully quenched with water (20 mL). The aqueous layer was extracted with ethyl acetate (3×50 mL). The combined organic layers were dried, filtered and concentrated. The crude product was purified by column chromatography, eluting with hexanes/ethyl acetate (7:3) to give 3-bromo-1-tosyl-1H-pyrazolo[3,4-b]pyridine (4.6 g, 70%) as a solid.

Step C: Trifluoroacetic anhydride ("TFAA"; 7.3 mL, 52.2 mmol) was added dropwise over 20 minutes to an ice cold solution of tetrabutylammonium nitrate (16.4 g, 52.2 mmol) in DCM (200 mL). The resulting solution was stirred at 0° C. for 10 minutes and transferred to an ice cold solution of 3-bromo-1-tosyl-1H-pyrazolo[3,4-b]pyridine (4.6 g, 13.1 mmol) in DCM (20 mL) via cannula. The cold bath was removed, and the reaction mixture was left at room temperature overnight. The reaction mixture was quenched with water (100 mL), and the aqueous layer was extracted with DCM (50 mL). The combined organic layers were dried, filtered and concentrated. The crude product was purified by column chromatography, eluting with DCM/hexanes (2:1) to give 3-bromo-5-nitro-1-tosyl-1H-pyrazolo[3,4-b]pyridine (4.2 g, 81%) as a solid.

Step D: SnCl$_2$ dihydrate (0.85 g, 3.79 mmol) was added to a suspension of 3-bromo-5-nitro-1-tosyl-1H-indazole (0.300 g, 0.76 mmol) in ethyl acetate (25 mL), and the reaction mixture was heated to reflux overnight. The reaction mixture was cooled to room temperature and quenched with saturated NaHCO$_3$ (25 mL). The resulting suspension was filtered through a pad of celite, and the filter cake was washed with ethyl acetate (100 mL). The aqueous layer was extracted with ethyl acetate (3×50 mL). The combined organic layers were dried, filtered and concentrated. The crude product was purified by column chromatography, eluting with hexanes/ethyl acetate (1:1) to give 3-bromo-1-tosyl-1H-indazol-5-amine (0.256 g, 92%) as a solid.

Step E: K$_2$CO$_3$ (0.233 g, 1.68 mmol) was added to a solution of 3-bromo-1-tosyl-1H-pyrazolo[3,4-b]pyridin-5-amine (0.206 g, 0.56 mmol) in MeOH/H$_2$O (3:1, 8 mL), and the reaction mixture was stirred at room temperature overnight. The reaction mixture was concentrated. The resulting residue was taken up in water (10 mL), and the pH was adjusted to about 7 with acetic acid. The aqueous layer was extracted with ethyl acetate (3×50 mL) The combined organic layers were dried, filtered and concentrated. The crude product was purified by column chromatography, eluting with hexanes/ethyl acetate (1:4) to give 3-bromo-1H-pyrazolo[3,4-b]pyridin-5-amine (0.036 g, 30%) as a solid.

Step F: N-(3-bromo-1H-pyrazolo[3,4-b]pyridin-5-yl)-2,6-difluoro-3-(propylsulfonamido)benzamide was prepared according to Example 1, step E using 3-bromo-1H-pyrazolo[3,4-b]pyridin-5-amine (0.061 g, 76%). $^1$H NMR (400 MHz, CD$_3$OD) δ 8.7 (s, 1H), 8.5 (s, 1H), 7.7 (m, 1H), 7.1 (m, 1H), 3.1 (m, 2H), 1.9 (m, 2H), 1.1 (t, J=7.6 Hz, 3H); m/z (APCI-neg) M−1=472.2, 474.2.

Example 3

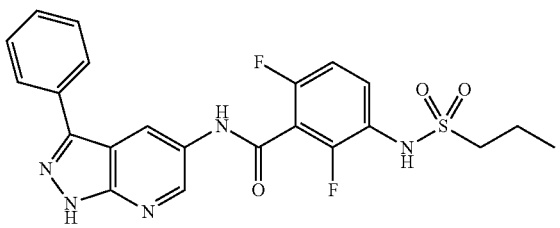 [SMILES: CCCS(=O)(=O)Nc1ccc(F)c(C(=O)Nc2cnc3[nH]nc(-c4ccccc4)c3c2)c1F]

2,6-difluoro-N-(3-phenyl-1H-pyrazolo[3,4-b]pyridin-5-yl)-3-(propylsulfonamido)benzamide Step A: N-Iodosuccinimide (8.1 g, 34.1 mmol) was added to a solution of 5-bromo-1H-pyrazolo[3,4-b]pyridine (4.5 g, 22.7 mmol) in dichloroethane (100 mL), and the reaction mixture was heated to reflux overnight. The reaction mixture was cooled to room temperature and diluted with THF (300 mL). The organic layers were washed with saturated Na$_2$S$_2$O$_3$ (100 mL) and brine (100 mL). The organic layers were dried, filtered and concentrated to a solid. The crude product was triturated with DCM and ethyl acetate to give 5-bromo-3-iodo-1H-pyrazolo[3,4-b]pyridine (5.5 g, 75%) as a solid.

Step B: NaH (1.31 g, 32.7 mmol, 60% suspension in mineral oil) was added portionwise to a cold (0° C.) solution of 5-bromo-3-iodo-1H-pyrazolo[3,4-b]pyridine (5.3 g, 16.4 mmol) in dry DMF (40 mL) The reaction mixture was stirred at 0° C. for 10 minutes before 2-(trimethylsilyl)ethoxymethyl chloride (4.91 mL, 27.8 mmol) was added dropwise via a syringe. The cold bath was removed, and the reaction mixture was stirred at room temperature for 1 hour. The reaction mixture was placed in an ice bath, diluted with ethyl acetate (400 mL) and carefully quenched with water (50 mL). The aqueous layer was separated and extracted with ethyl acetate (3×50 mL). The combined organic layers were dried, filtered and concentrated. The crude product was purified by column chromatography, eluting with hexanes/ethyl acetate (20:1) to give 5-bromo-3-iodo-1-((2-(trimethylsilyl)ethoxy)methyl)-1H-pyrazolo[3,4-b]pyridine (6.59 g, 89%) as a solid.

Step C: PdCl$_2$(dppf) dichloromethane adduct (0.017 g, 0.02 mmol) was added to a suspension of 5-bromo-3-iodo-1-((2-(trimethylsilyl)ethoxy)methyl)-1H-pyrazolo[3,4-b]pyridine (0.185 g, 0.41 mmol), phenylboronic acid (0.050 g, 0.41 mmol) and Na$_2$CO$_3$ (0.064 g, 0.61 mmol) in dimethylether ("DME")/EtOH/H$_2$O (5:2:1, 8 mL). The reaction mixture was purged with argon for 10 minutes and then heated to 90° C. under argon for 2 hours. The reaction mixture was cooled to room temperature and concentrated. The crude product was purified by column chromatography, eluting with hexanes/ethyl acetate (50:1) to give 5-bromo-3-phenyl-1-((2-(trimethylsilyl)ethoxy)methyl)-1H-pyrazolo[3,4-b]pyridine (0.080 g, 49%) as an oil.

Step D: 2,6-Difluoro-N-(3-phenyl-1H-pyrazolo[3,4-b]pyridin-5-yl)-3-(propylsulfonamido)benzamide was prepared according to Example 1, Steps C, D and E using 5-bromo-3-phenyl-1-((2-(trimethylsilyl)ethoxy)methyl)-1H-pyrazolo [3,4-b]pyridine. $^1$H NMR (400 MHz, CD$_3$OD) δ 9.0 (s, 1H), 8.7 (s, 1H), 8.0 (d, J=8.0 Hz, 2H), 7.7 (m, 1H), 7.5 (m, 2H), 7.4 (m, 1H), 7.1 (m, 1H), 3.1 (m, 2H), 1.9 (m, 2H), 1.1 (t, J=7.6 Hz, 3H); m/z (APCI-neg) M−1=470.3.

Example 4

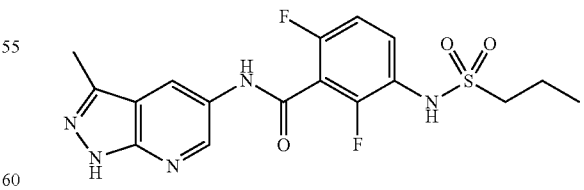

2,6-difluoro-N-(3-methyl-1H-pyrazolo[3,4-b]pyridin-5-yl)-3-(propylsulfonamido)benzamide Step A: A 5 mL reaction vessel was charged with 3-methyl-1H-pyrazol-5-amine (68 mg, 0.70 mmol), sodium nitromalonaldehyde monohydrate (121 mg, 0.77 mmol) and AcOH (2 mL). The flask was heated to 90° C. under a nitrogen atmosphere overnight. The following day the mixture was poured into water (10 mL), and the precipitate was filtered and rinsed with water (3×5 mL). The precipitate was triturated with minimal Et$_2$O to provide 3-methyl-5-nitro-1H-pyrazolo[3,4-b]pyridine as a solid (65 mg, 52% yield).

Step B: A 25 mL round bottom flask was charged with 3-methyl-5-nitro-1H-pyrazolo[3,4-b]pyridine (39 mg, 0.22 mmol) and 10% (wt.) Pd on activated carbon (12 mg, 0.011 mmol). EtOH (10 mL) was added, and then H$_2$ was passed through the reaction mixture for 15 minutes. The vessel was left to stir under an H$_2$ balloon for 4 hours, after which it was filtered through a 0.45 μm PVDF filter. The volatiles were removed to afford 3-methyl-1H-pyrazolo[3,4-b]pyridin-5-amine as a solid (30 mg, 92% yield).

Step C: 2,6-Difluoro-N-(3-methyl-1H-pyrazolo[3,4-b]pyridin-5-yl)-3-(propylsulfonamido)benzamide was prepared according to Example 1, Step E using 3-methyl-1H-pyrazolo[3,4-b]pyridin-5-amine (28 mg, 65% yield). $^1$H NMR (400 MHz, d$_6$-DMSO) δ 13.24 (s, 1H), 11.08 (s, 1H), 9.81 (s, 1H), 8.61-8.59 (m, 1H), 8.56-8.54 (m, 1H), 7.59-7.53 (m, 1H), 7.30-7.26 (m, 1H), 3.32 (s, 3H), 3.15-3.11 (m, 2H), 1.82-1.73 (m, 2H), 1.00 (t, J=7.5 Hz, 3H). m/z (APCI-pos) M+1=410.1.

Step C substituted 3-methyl-1H-pyrazolo[3,4-b]pyridin-5-amine for 1H-pyrazolo[3,4-b]pyridin-5-amine of Example 1, Step E.

Example 5

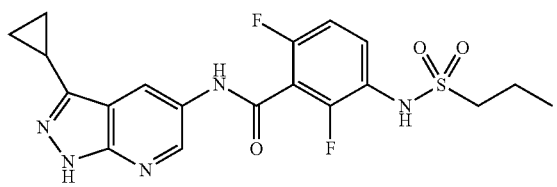 [SMILES: CCCS(=O)(=O)Nc1ccc(F)c(C(=O)Nc2cnc3[nH]nc(C4CC4)c3c2)c1F]

N-(3-cyclopropyl-1H-pyrazolo[3,4-b]pyridin-5-yl)-2,6-difluoro-3-(propylsulfonamido)benzamide Step A: 3-Cyclopropyl-5-nitro-1H-pyrazolo[3,4-b]pyridine was prepared according to Example 4, Step A, substituting 3-cyclopropyl-1H-pyrazol-5-amine for 3-methyl-1H-pyrazol-5-amine.

Yield of Step A: 9.67 g (83%)

Step B: 3-Cyclopropyl-1H-pyrazolo[3,4-b]pyridin-5-amine was prepared according to Example 4, Step B, substituting 3-cyclopropyl-5-nitro-1H-pyrazolo[3,4-b]pyridine for 3-methyl-5-nitro-1H-pyrazolo[3,4-b]pyridine.

Yield of Step B: 7.92 g (86%)

Step C: N-(3-Cyclopropyl-1H-pyrazolo[3,4-b]pyridin-5-yl)-2,6-difluoro-3-(propylsulfonamido)benzamide was prepared according to Example 4, Step C, substituting 3-cyclopropyl-1H-pyrazolo[3,4-b]pyridin-5-amine for 3-methyl-1H-pyrazolo[3,4-b]pyridin-5-amine. $^1$H NMR (400 MHz, d$_6$-DMSO) δ 13.19 (s, 1H), 11.08 (s, 1H), 9.81 (s, 1H), 8.65-8.63 (m, 1H), 8.57-8.55 (m, 1H), 7.59-7.53 (m, 1H), 7.30-7.26 (m, 1H), 3.15-3.11 (m, 2H), 2.32-2.26 (m, 1H), 1.82-1.73 (m, 2H), 1.03-0.93 (m, 7H). m/z (APCI-pos) M+1=436.1.

Yield of Step C, 5.22 g (52%)

Example 6

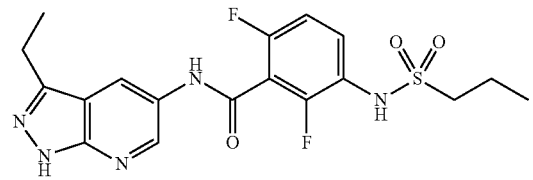 [SMILES: CCCS(=O)(=O)Nc1ccc(F)c(C(=O)Nc2cnc3[nH]nc(CC)c3c2)c1F]

N-(3-ethyl-1H-pyrazolo[3,4-b]pyridin-5-yl)-2,6-difluoro-3-(propylsulfonamido)benzamide Step A: 3-Ethyl-5-nitro-1H-pyrazolo[3,4-b]pyridine was prepared according to Example 4, Step A, substituting 3-ethyl-1H-pyrazol-5-amine for 3-methyl-1H-pyrazol-5-amine.

Step B: 3-Ethyl-1H-pyrazolo[3,4-b]pyridin-5-amine was prepared according to Example 4, Step B, substituting 3-ethyl-5-nitro-1H-pyrazolo[3,4-b]pyridine for 3-methyl-5-nitro-1H-pyrazolo[3,4-b]pyridine.

Step C: N-(3-Ethyl-1H-pyrazolo[3,4-b]pyridin-5-yl)-2,6-difluoro-3-(propylsulfonamido)benzamide was prepared according to Example 4, Step C, substituting 3-ethyl-1H-pyrazolo[3,4-b]pyridin-5-amine for 3-methyl-1H-pyrazolo[3,4-b]pyridin-5-amine. $^1$H NMR (400 MHz, d$_6$-DMSO) δ 13.25 (s, 1H), 11.08 (s, 1H), 9.81 (s, 1H), 8.63-8.61 (m, 1H), 8.57-8.55 (m, 1H), 7.59-7.53 (m, 1H), 7.30-7.26 (m, 1H), 3.15-3.11 (m, 2H), 2.94 (q, J=15.2, 7.6 Hz, 2H), 1.81-1.72 (m, 2H), 1.32 (t, J=8.0 Hz, 3H), 1.00 (t, J=7.4 Hz, 3H). m/z (APCI-pos) M+1=424.1.

Example 7

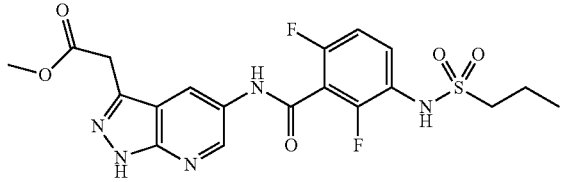 [SMILES: CCCS(=O)(=O)Nc1ccc(F)c(C(=O)Nc2cnc3[nH]nc(CC(=O)OC)c3c2)c1F]

methyl 2-(5-(2,6-difluoro-3-(propylsulfonamido)benzamido)-1H-pyrazolo[3,4-b]pyridin-3-yl)acetate Step A: 2-(5-Nitro-1H-pyrazolo[3,4-b]pyridin-3-yl)acetic acid was prepared according to Example 4, Step A, substituting 2-(5-amino-1H-pyrazol-3-yl)acetic acid for 3-methyl-1H-pyrazol-5-amine.

Step B: A conical reaction vial was charged with 2-(5-nitro-1H-pyrazolo[3,4-b]pyridin-3-yl)acetic acid (20.0 mg, 0.0900 mmol), MeOH (2 mL) and chlorotrimethylsilane (114 μl, 0.900 mmol). The reaction vessel was sealed and placed in a 65° C. heating block for 18 hours. The following day the volatiles were removed, and the residue was triturated with Et$_2$O. The resulting solid was removed by filtration. Concentration of the filtrate afforded methyl 2-(5-nitro-1H-pyrazolo[3,4-b]pyridin-3-yl) acetate, which was taken directly onto the next step.

Step C: Methyl 2-(5-amino-1H-pyrazolo[3,4-b]pyridin-3-yl)acetate was prepared according to Example 4, Step B, substituting methyl 2-(5-nitro-1H-pyrazolo[3,4-b]pyridin-3-yl)acetate for 3-methyl-5-nitro-1H-pyrazolo[3,4-b]pyridine.

Step D: Methyl 2-(5-(2,6-difluoro-3-(propylsulfonamido)benzamido)-1H-pyrazolo[3,4-b]pyridin-3-yl)acetate was prepared according to Example 4, Step C, substituting methyl 2-(5-amino-1H-pyrazolo[3,4-b]pyridin-3-yl)acetate for 3-methyl-1H-pyrazolo[3,4-b]pyridin-5-amine. $^1$H NMR (400 MHz, CD$_3$OD) δ 8.69-8.67 (m, 1H), 8.65-8.63 (m, 1H), 7.69-7.62 (m, 1H), 7.16-7.10 (m, 1H), 4.07 (s, 2H), 3.74 (s, 3H), 3.13-3.09 (m, 2H), 1.92-1.83 (m, 2H), 1.06 (t, J=7.4 Hz, 3H). m/z (APCI-pos) M+1=468.0.

Example 8

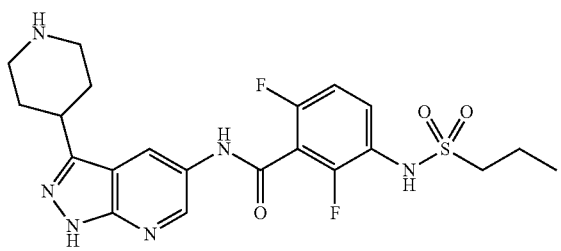 [SMILES: CCCS(=O)(=O)Nc1ccc(F)c(C(=O)Nc2cnc3[nH]nc(C4CCNCC4)c3c2)c1F]

2,6-difluoro-N-(3-(piperidin-4-yl)-1H-pyrazolo[3,4-b]pyridin-5-yl)-3-(propylsulfonamido)benzamide Step A: A 5 mL conical reaction vial was charged with tert-butyl 4-(2-cyanoacetyl)piperidine-1-carboxylate (348 mg, 1.379 mmol), hydrazine monohydrate (329.4 μL, 6.896 mmol) and EtOH (4 mL). The reaction vessel was sealed and heated to 80° C. for 20 hours. The volatiles were removed to afford tert-butyl 4-(5-amino-1H-pyrazol-3-yl)piperidine-1-carboxylate as a foam (367 mg, 99%).

Step B: Tert-butyl 4-(5-nitro-1H-pyrazolo[3,4-b]pyridin-3-yl)piperidine-1-carboxylate was prepared according to Example 4, Step A, substituting tert-butyl 4-(5-amino-1H-pyrazol-3-yl)piperidine-1-carboxylate for 3-methyl-1H-pyrazol-5-amine.

Step C: Tert-butyl 4-(5-amino-1H-pyrazolo[3,4-b]pyridin-3-yl)piperidine-1-carboxylate was prepared according to Example 4, Step B, substituting tert-butyl 4-(5-nitro-1H-pyrazolo[3,4-b]pyridin-3-yl)piperidine-1-carboxylate for 3-methyl-5-nitro-1H-pyrazolo[3,4-b]pyridine.

Step D: Tert-butyl 4-(5-(2,6-difluoro-3-(propylsulfonamido)benzamido)-1H-pyrazolo[3,4-b]pyridin-3-yl)piperidine-1-carboxylate was prepared according to Example 4, Step C, substituting tert-butyl 4-(5-amino-1H-pyrazolo[3,4-b]pyridin-3-yl)piperidine-1-carboxylate for 3-methyl-1H-pyrazolo[3,4-b]pyridin-5-amine.

Step E: tert-Butyl 4-(5-(2,6-difluoro-3-(propylsulfonamido)benzamido)-1H-pyrazolo[3,4-b]pyridin-3-yl)piperidine-1-carboxylate (7 mg, 0.01 mmol) was treated with a 0.5M solution of HCl in dioxane (0.5 mL, 2 mmol) at room temperature for 1 hour. The volatiles were removed in vacuo to afford 2,6-difluoro-N-(3-(piperidin-4-yl)-1H-pyrazolo[3,4-b]pyridin-5-yl)-3-(propylsulfonamido)benzamide hydrochloride as a solid (5 mg, 83%). $^1$H NMR (400 MHz, CD$_3$OD) δ 8.87-8.90 (m, 1H), 8.62-8.58 (m, 1H), 7.70-7.64 (m, 1H), 7.18-7.13 (m, 1H), 3.76-3.52 (m, 3H), 3.33-3.22 (m, 2H), 3.15-3.11 (m, 2H), 2.38-2.30 (m, 2H), 2.25-2.13 (m, 2H), 1.93-1.83 (m, 2H), 1.06 (t, J=7.4 Hz, 3H). m/z (APCI-pos) M+1=479.2.

Example 9

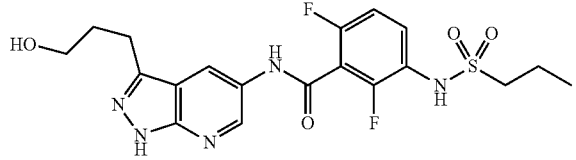 [SMILES: CCCS(=O)(=O)Nc1ccc(F)c(C(=O)Nc2cnc3[nH]nc(CCCO)c3c2)c1F]

2,6-difluoro-N-(3-(3-hydroxypropyl)-1H-pyrazolo[3,4-b]pyridin-5-yl)-3-(propylsulfonamido)benzamide Step A: 1N NaOH (15.9 mL, 15.9 mmol) was added to a solution of 3-iodo-1-tosyl-1H-indazol-5-amine (4.2 g, 10.6 mmol) in THF/MeOH (4:1, 100 mL), and the reaction mixture was stirred at room temperature for 1 hour. The pH was adjusted to about 7 with acetic acid, and the reaction mixture was concentrated. The resulting solids were taken up in water (100 mL) and ethyl acetate (100 mL). The aqueous layer was extracted with ethyl acetate (100 mL). The combined organic layers were dried, filtered and concentrated. The crude product was purified by column chromatography, eluting with hexanes/ethyl acetate (9:1), hexanes/ethyl acetate (4:1) to give 3-bromo-5-nitro-1H-pyrazolo[3,4-b]pyridine (1.9 g, 74%) as a solid.

Step B: Triethylamine (4 mL) was added to a solution of 3-bromo-5-nitro-1-tosyl-1H-pyrazolo[3,4-b]pyridine (0.825 g, 3.40 mmol), tert-butyldimethyl(prop-2-ynyloxy)silane (0.89 g, 5.09 mmol) in THF (20 mL) PdCl$_2$(PPh$_3$)$_2$ (0.119 g, 0.170 mmol) was added to the mixture, and the mixture was stirred at room temperature for 5 minutes before CuI (0.065 g, 0.34 mmol) was added. The reaction mixture was heated to reflux under argon for 40 hours. The reaction mixture was cooled to room temperature and concentrated. The crude product was purified by column chromatography, eluting with hexanes/ethyl acetate (4:1) to give 3-(3-(tert-butyldimethylsilyloxy)prop-1-ynyl)-5-nitro-1H-pyrazolo[3,4-b]pyridine (0.193 g, 17%) as a solid.

Step C: 10% (wt.) Pd on activated carbon (0.017 g, 0.016 mmol) was added to a solution of 3-(3-(tert-butyldimethylsilyloxy)prop-1-ynyl)-5-nitro-1H-pyrazolo[3,4-b]pyridine (0.053 g, 0.160 mmol) in a mixture of ethyl acetate/EtOH (1:1, 6 mL). The reaction mixture was purged with nitrogen for 5 minutes and then stirred under a hydrogen balloon overnight. The reaction mixture was filtered through GF/F paper. The filter cake was rinsed with ethyl acetate, and the filtrate was concentrated. The crude product was purified by column chromatography, eluting with hexanes/ethyl acetate (2:1), hexanes/ethyl acetate (1:1) to give 3-(3-(tert-butyldimethylsilyloxy)propyl)-1H-pyrazolo[3,4-b]pyridin-5-amine (0.028 g, 57%) as an oil.

Step D: N-(3-(3-(tert-butyldimethylsilyloxy)propyl)-1H-pyrazolo[3,4-b]pyridin-5-yl)-2,6-difluoro-3-(propylsulfonamido)benzamide (0.034 g, 66%) was prepared according to Example 1, Step E, using 3-(3-(tert-butyldimethylsilyloxy)propyl)-1H-pyrazolo[3,4-b]pyridin-5-amine.

Step E: Tetra-n-butylammonium fluoride ("TBAF"; 0.12 mL, 0.12 mmol, 1.0M in THF) was added to a solution of N-(3-(3-(tert-butyldimethylsilyloxy)propyl)-1H-pyrazolo[3,4-b]pyridin-5-yl)-2,6-difluoro-3-(propylsulfonamido)benzamide (0.034 g, 0.060 mmol) in THF (4.0 mL), and the reaction mixture was stirred at room temperature for 1 hour. The reaction mixture was concentrated, and the crude product was purified by column chromatography, eluting with ethyl acetate, ethyl acetate/MeOH (50:1) to give 2,6-difluoro-N-(3-(3-hydroxypropyl)-1H-pyrazolo[3,4-b]pyridin-5-yl)-3-(propylsulfonamido)benzamide (0.014 g, 52%) as a solid. $^1$H NMR (400 MHz, CD$_3$OD) δ 8.7 (s, 1H), 8.6 (s, 1H), 7.7 (m, 1H), 7.1 (m, 1H), 3.7 (t, J=7.0 Hz, 2H), 3.1-3.0 (m, 4H), 2.1 (m, 2H), 1.9 (m, 2H), 1.1 (t, J=7.6 Hz, 3H); m/z (APCI-neg) M−1=452.3.

Example 10

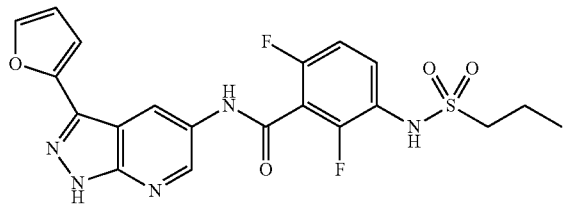 [SMILES: CCCS(=O)(=O)Nc1ccc(F)c(C(=O)Nc2cnc3[nH]nc(-c4ccco4)c3c2)c1F]

2,6-difluoro-N-(3-(furan-2-yl)-1H-pyrazolo[3,4-b]pyridin-5-yl)-3-(propylsulfonamido)benzamide Step A: 3-(Furan-2-yl)-5-nitro-1H-pyrazolo[3,4-b]pyridine was prepared according to Example 4, Step A, substituting 3-(furan-2-yl)-1H-pyrazol-5-amine for 3-methyl-1H-pyrazol-5-amine.

Step B: 3-(Furan-2-yl)-1H-pyrazolo[3,4-b]pyridin-5-amine was prepared according to Example 4, Step B, substituting 3-(furan-2-yl)-5-nitro-1H-pyrazolo[3,4-b]pyridine for 3-methyl-5-nitro-1H-pyrazolo[3,4-b]pyridine.

Step C: 2,6-Difluoro-N-(3-(furan-2-yl)-1H-pyrazolo[3,4-b]pyridin-5-yl)-3-(propylsulfonamido)benzamide was prepared according to Example 4, Step C, substituting 3-(furan-2-yl)-1H-pyrazolo[3,4-b]pyridin-5-amine for 3-methyl-1H-pyrazolo[3,4-b]pyridin-5-amine. $^1$H NMR (400 MHz, d$_6$-DMSO) δ 13.90 (s, 1H), 11.21 (s, 1H), 9.82 (s, 1H), 8.96-8.94 (m, 1H), 8.70-8.68 (m, 1H), 7.92-7.91 (m, 1H), 7.61-7.54 (m, 1H), 7.32-7.27 (m, 1H), 6.99-6.96 (m, 1H), 6.72-6.69 (m, 1H), 3.16-3.11 (m, 2H), 1.82-1.73 (m, 2H), 1.00 (t, J=7.4 Hz, 3H). m/z (APCI-pos) M+1=462.1.

Example 11

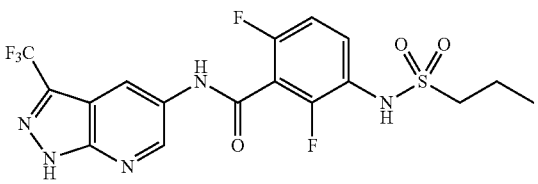 [SMILES: CCCS(=O)(=O)Nc1ccc(F)c(C(=O)Nc2cnc3[nH]nc(C(F)(F)F)c3c2)c1F]

2,6-difluoro-3-(propylsulfonamido)-N-(3-(trifluoromethyl)-1H-pyrazolo[3,4-b]pyridin-5-yl)benzamide Step A: Lithium diisopropylamide (8.2 mL, 14.8 mmol, 1.8M in heptane) was added to THF (20 mL) cooled to −78° C. in a dry ice/acetone bath. 2-Fluoropyridine (1.07 mL, 12.4 mmol) was added dropwise, and the resulting mixture stirred at −78° C. for 3 hours. Ethyl trifluoroacetate (2.06 mL, 17.2 mmol) was added to the suspension dropwise. The reaction mixture was allowed to slowly warm to room temperature. After 1 hour, the mixture was poured into 1M hydrochloric acid (35 mL) and extracted twice with ethyl acetate. The combined ethyl acetate extracts were washed with brine, dried over magnesium sulfate, filtered, and evaporated to yield the hydrate of 2,2,2-trifluoro-1-(2-fluoropyridin-3-yl)ethanone (1.9 g, 90%) as a semisolid.

Step B: Hydrazine hydrate (3.06 mL, 63.0 mmol) was added to 2,2,2-trifluoro-1-(2-fluoropyridin-3-yl)ethanone (1.9 g, 9.0 mmol) in absolute ethanol (50 mL), and the mixture was heated to reflux overnight. The cooled reaction mixture was evaporated to afford a solid, which was partitioned between water and ethyl acetate. The aqueous layer was extracted with another portion of ethyl acetate. The combined ethyl acetate extracts were washed twice with brine, dried over magnesium sulfate, filtered, and evaporated to yield 3-(trifluoromethyl)-1H-pyrazolo[3,4-b]pyridine (1.43 g, 85%) as a solid.

Step C: Trifluoroacetic anhydride (2.6 mL, 18.7 mmol) was added to a solution of tetrabutylammonium nitrate (5.7 g, 18.7 mmol) in dichloromethane (50 mL) cooled to 0° C. in an ice bath. After 5 minutes, 3-(trifluoromethyl)-1H-pyrazolo[3,4-b]pyridine (0.5 g, 2.67 mmol) was added portionwise. The resulting solution was stirred at room temperature overnight. The reaction mixture was treated with saturated aqueous sodium bicarbonate, and the layers were separated. The aqueous layer was extracted with dichloromethane. The combined organic layers were washed with saturated aqueous sodium bicarbonate, dried over magnesium sulfate, filtered, and evaporated to an oil. The crude product was purified by column chromatography, eluting with hexanes/ethyl acetate (2:1) to give 5-nitro-3-(trifluoromethyl)-1H-pyrazolo[3,4-b]pyridine (0.19 g, 31%) as a solid.

Step D: SnCl$_2$.2H$_2$O (1.3 g, 5.7 mmol) was added to 5-nitro-3-(trifluoromethyl)-1H-pyrazolo[3,4-b]pyridine (0.19 g, 0.82 mmol) in ethyl acetate (20 mL). The resulting solution was heated to reflux for 3 hours. The cooled yellow solution was treated with dilute aqueous sodium bicarbonate. The resulting slurry was filtered through celite, and the filter cake was washed with ethyl acetate. The layers were separated, and the organic layer was washed with brine, dried over magnesium sulfate, filtered, and evaporated to yield 3-(trifluoromethyl)-1H-pyrazolo[3,4-b]pyridine-5-amine (0.17 g, 99%) as a film.

Step E: 2,6-Difluoro-3-(propylsulfonamido)-N-(3-(trifluoromethyl)-1H-pyrazolo[3,4-b]pyridin-5-yl)benzamide was prepared according to Example 1, Step E, using 3-(trifluoromethyl)-1H-pyrazolo[3,4-b]pyridine-5-amine (0.0055 g, 1.3%). $^1$H NMR (400 MHz, CD$_3$OD) δ 8.77 (br s, 2H), 7.71-7.64 (m, 1H), 7.18-7.13 (m, 1H), 3.15-3.10 (m, 2H), 1.92-1.83 (m, 2H), 1.06 (t, 3H). m/z (APCI-pos) M−1=462.2.

Example 12

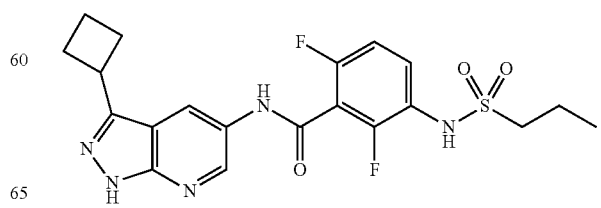

N-(3-cyclobutyl-1H-pyrazolo[3,4-b]pyridin-5-yl)-2,
6-difluoro-3-(propylsulfonamido)benzamide Step A: 3-Cyclobutyl-5-nitro-1H-pyrazolo[3,4-b]pyridine was prepared according to Example 4, Step A, substituting 3-cyclobutyl-1H-pyrazol-5-amine for 3-methyl-1H-pyrazol-5-amine.

Step B: 3-Cyclobutyl-1H-pyrazolo[3,4-b]pyridin-5-amine was prepared according to Example 4, Step B, substituting 3-cyclobutyl-5-nitro-1H-pyrazolo[3,4-b]pyridine for 3-methyl-5-nitro-1H-pyrazolo[3,4-b]pyridine.

Step C: N-(3-Cyclobutyl-1H-pyrazolo[3,4-b]pyridin-5-yl)-2,6-difluoro-3-(propylsulfonamido)benzamide was prepared according to Example 4, Step C, substituting 3-cyclobutyl-1H-pyrazolo[3,4-b]pyridin-5-amine for 3-methyl-1H-pyrazolo[3,4-b]pyridin-5-amine. $^1$H NMR (400 MHz, d$_6$-DMSO) δ 13.29 (s, 1H), 11.08 (s, 1H), 9.81 (s, 1H), 8.62-8.60 (m, 1H), 8.60-8.57 (m, 1H), 7.60-7.52 (m, 1H), 7.31-7.25 (m, 1H), 3.95-3.85 (m, 1H), 3.15-3.11 (m, 2H), 2.43-2.38 (m, 4H), 2.16-2.04 (m, 1H), 2.01-1.89 (m, 1H), 1.82-1.73 (m, 2H), 1.00 (t, J=7.4 Hz, 3H). m/z (APCI-pos) M+1=450.1.

Example 13

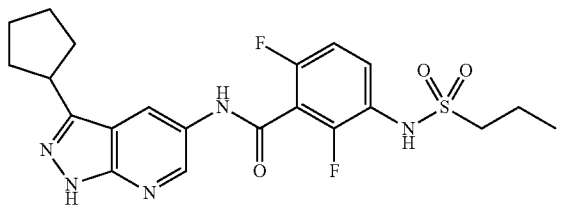 [SMILES: CCCS(=O)(=O)Nc1ccc(F)c(C(=O)Nc2cnc3[nH]nc(C4CCCC4)c3c2)c1F]

N-(3-cyclopentyl-1H-pyrazolo[3,4-b]pyridin-5-yl)-2,
6-difluoro-3-(propylsulfonamido)benzamide Step A: 3-Cyclopentyl-5-nitro-1H-pyrazolo[3,4-h]pyridine was prepared according to Example 4, Step A, substituting 3-cyclopentyl-1H-pyrazol-5-amine for 3-methyl-1H-pyrazol-5-amine.

Step B: 3-Cyclopentyl-1H-pyrazolo[3,4-b]pyridin-5-amine was prepared according to Example 4, Step B, substituting 3-cyclopentyl-5-nitro-1H-pyrazolo[3,4-b]pyridine for 3-methyl-5-nitro-1H-pyrazolo[3,4-b]pyridine.

Step C: N-(3-Cyclopentyl-1H-pyrazolo[3,4-b]pyridin-5-yl)-2,6-difluoro-3-(propylsulfonamido)benzamide was prepared according to Example 4, Step C, substituting 3-cyclopentyl-1H-pyrazolo[3,4-b]pyridin-5-amine for 3-methyl-1H-pyrazolo[3,4-b]pyridin-5-amine. $^1$H NMR (400 MHz, d$_6$-DMSO) δ 13.22 (s, 1H), 11.08 (s, 1H), 9.81 (s, 1H), 8.64-8.62 (m, 1H), 8.59-8.57 (m, 1H), 7.59-7.53 (m, 1H), 7.30-7.25 (m, 1H), 3.49-3.40 (m, 1H), 3.15-3.11 (m, 2H), 2.15-2.07 (m, 2H), 1.92-1.66 (m, 8H), 1.00 (t, J=7.4 Hz, 3H). m/z (APCI-pos) M+1=464.2.

Example 14

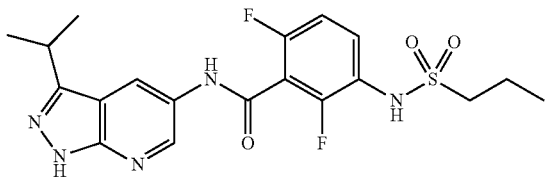 [SMILES: CCCS(=O)(=O)Nc1ccc(F)c(C(=O)Nc2cnc3[nH]nc(C(C)C)c3c2)c1F]

2,6-difluoro-N-(3-isopropyl-1H-pyrazolo[3,4-b]pyridin-5-yl)-3-(propylsulfonamido)benzamide Step A: 3-Isopropyl-5-nitro-1H-pyrazolo[3,4-b]pyridine was prepared according to Example 4, Step A, substituting 3-isopropyl-1H-pyrazol-5-amine for 3-methyl-1H-pyrazol-5-amine.

Step B: 3-Isopropyl-1H-pyrazolo[3,4-b]pyridin-5-amine was prepared according to Example 4, Step B, substituting 3-isopropyl-5-nitro-1H-pyrazolo[3,4-b]pyridine for 3-methyl-5-nitro-1H-pyrazolo[3,4-b]pyridine.

Step C: 2,6-Difluoro-N-(3-isopropyl-1H-pyrazolo[3,4-b]pyridin-5-yl)-3-(propylsulfonamido)benzamide was prepared according to Example 4, Step C, substituting 3-isopropyl-1H-pyrazolo[3,4-b]pyridin-5-amine for 3-methyl-1H-pyrazolo[3,4-b]pyridin-5-amine. $^1$H NMR (400 MHz, d$_6$-DMSO) δ 13.24 (s, 1H), 11.08 (s, 1H), 9.81 (s, 1H), 8.68-8.65 (m, 1H), 8.60-8.57 (m, 1H), 7.60-7.52 (m, 1H), 7.32-7.25 (m, 1H), 3.40-3.31 (m, 1H), 3.16-3.10 (m, 2H), 1.82-1.72 (m, 2H), 1.38 (d, J=7.2 Hz, 6H), 1.00 (t, J=7.5 Hz, 3H). m/z (APCI-pos) M+1=438.1.

Example 15

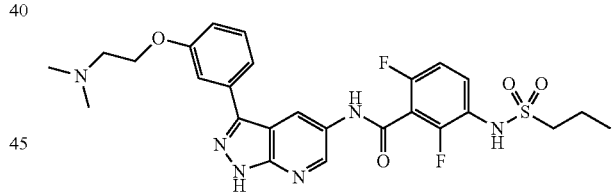

N-(3-(3-(2-(dimethylamino)ethoxy)phenyl)-1H-pyrazolo[3,4-b]pyridin-5-yl)-2,6-difluoro-3-propylsulfonamido)benzamide Step A: Diisopropyl diazene-1,2-dicarboxylate (1.56 g, 7.34 mmol) was added dropwise to a 0° C. solution of 3-bromophenol (1.155 g, 6.68 mmol), 2-(dimethylamino)ethanol (0.65 g, 7.34 mmol) and triphenylphosphine (1.93 g, 7.34 mmol) in THF (20 mL). The mixture was allowed to warm to room temperature over 16 hours, and then the volatiles were removed under reduced pressure. The resulting residue was partitioned between ethyl acetate (20 mL) and 1N HCl (20 mL), and the aqueous layer was collected and washed with ethyl acetate. The aqueous layer was neutralized with saturated NaHCO$_3$ (50 mL), extracted with ethyl acetate, and dried (MgSO$_4$). Purification via silica chromatography (eluting with 4% MeOH/DCM) afforded 2-(3-bromophenoxy)-N,N-dimethylethanamine (1.03 g, 63%) as an oil.

Step B: A mixture of 2-(3-bromophenoxy)-N,N-dimethylethanamine (500 mg, 2.05 mmol), 4,4,4',4',5,5,5',5'-octamethyl-2,2'-bi(1,3,2-dioxaborolane) (0.629 g, 2.48 mmol), KOAc (0.603 g, 6.14 mmol) and PdCl$_2$(dppf).DCM (0.050 g, 0.0614 mmol) was suspended in dioxane (6 mL) and degassed with argon for 10 minutes. The mixture was heated to 90° C. for 16 hours. The mixture was then cooled to room temperature and filtered through GF/F paper. The filtrate was washed with 5% aqueous NaCl (2×50 mL), dried (MgSO$_4$), and purified via silica gel chromatography (eluting with 8% MeOH/DCM) to afford N,N-dimethyl-2-(3-(4,4,5,5-tetramethyl-1,3,2-dioxaborolan-2-yl)phenoxy)ethanamine (111 mg, 19%) as an oil. $^1$H NMR (400 MHz, CDCl$_3$) δ 7.41-7.28 (m, 3H), 7.05-7.01 (m, 1H), 4.14-4.10 (m, 2H), 2.78-2.74 (m, 2H), 2.37 (s, 6H), 1.34 (s, 12H).

Step C: Pd(PPh$_3$)$_4$ (0.0075 g, 0.0065 mmol) was added to a suspension of N-(3-bromo-1H-pyrazolo[3,4-b]pyridin-5-yl)-2,6-difluoro-3-(propylsulfonamido)benzamide (0.031 g, 0.065 mmol), N,N-dimethyl-2-(3-(4,4,5,5-tetramethyl-1,3,2-dioxaborolan-2-yl)phenoxy)ethanamine (0.029 g, 0.098 mmol) and K$_2$CO$_3$ (0.072 g, 0.52 mmol) in MeCN/H$_2$O (4:1, 1 mL). The reaction mixture was heated to 160° C. in a microwave reactor for 30 minutes. The reaction mixture was cooled to room temperature, diluted with ethyl acetate and filtered through GF/F paper. The filter cake was rinsed with ethyl acetate (50 mL). The filtrate was transferred to a separation funnel, and the organic layers were washed with water (3×20 mL). The organic layers were dried, filtered and concentrated. The crude product was purified by column chromatography, eluting with DCM/MeOH (10:1), DCM/MeOH (10:1) containing 1% triethylamine to give N-(3-(3-(2-(dimethylamino)ethoxy)phenyl)-1H-pyrazolo[3,4-b]pyridin-5-yl)-2,6-difluoro-3-(propylsulfonamido)benzamide (0.010 g, 27%) as a solid. $^1$H NMR (400 MHz, CD$_3$OD) δ 9.0 (s, 1H), 8.7 (s, 1H), 7.7 (m, 1H), 7.6 (m, 2H), 7.5 (m, 1H), 7.2 (m, 1H), 7.1 (d, J=7.0 Hz, 1H), 4.3 (t, J=5.2 Hz, 2H), 3.1 (m, 2H), 3.0 (m, 2H), 2.5 (s, 6H), 1.9 (m, 2H), 1.1 (t, J=7.6 Hz, 3H); m/z (APCI-pos) M+1=559.1.

Example 16

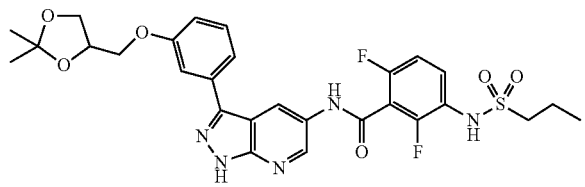 [SMILES: CCCS(=O)(=O)Nc1ccc(F)c(C(=O)Nc2cnc3[nH]nc(-c4cccc(OCC5COC(C)(C)O5)c4)c3c2)c1F]

N-(3-(3-((2,2-dimethyl-1,3-dioxolan-4-yl)methoxy)phenyl)-1H-pyrazolo[3,4-b]pyridin-5-yl)-2,6-difluoro-3-(propylsulfonamido)benzamide Step A: 4-((3-Bromophenoxy)methyl)-2,2-dimethyl-1,3-dioxolane (81% yield) was prepared following Example 15, Step A, substituting (2,2-dimethyl-1,3-dioxolan-4-yl)methanol for 2-(dimethylamino)ethanol.

Step B: 2-(3-((2,2-Dimethyl-1,3-dioxolan-4-yl)methoxy)phenyl)-4,4,5,5-tetramethyl-1,3,2-dioxaborolane (77% yield) was prepared following Example 15, Step B, substituting 4-((3-bromophenoxy)methyl)-2,2-dimethyl-1,3-dioxolane for 2-(3-bromophenoxy)-N,N-dimethylethanamine. $^1$H NMR (400 MHz, CDCl$_3$) δ 7.43-7.39 (m, 1H), 7.34-7.27 (m, 2H), 7.05-7.01 (m, 1H), 4.51-4.44 (m, 1H), 4.19-4.08 (m, 2H), 3.99-3.95 (m, 1H), 3.92-3.88 (m, 1H), 1.47 (s, 3H), 1.41 (s, 3H), 1.34 (s, 12H).

Step C: N-(3-(3-((2,2-Dimethyl-1,3-dioxolan-4-yl)methoxy)phenyl)-1H-pyrazolo[3,4-b]pyridin-5-yl)-2,6-difluoro-3-(propylsulfonamido)benzamide (71% yield) was prepared following Example 15, Step C, substituting 2-(3-((2,2-dimethyl-1,3-dioxolan-4-yl)methoxy)phenyl)-4,4,5,5-tetramethyl-1,3,2-dioxaborolane for N,N-dimethyl-2-(3-(4,4,5,5-tetramethyl-1,3,2-dioxaborolan-2-yl)phenoxy)ethanamine. $^1$H NMR (400 MHz, CD$_3$OD) δ 9.0 (s, 1H), 8.7 (s, 1H), 7.7 (m, 1H), 7.5 (m, 3H), 7.1 (m, 1H), 7.0 (m, 1H), 4.5 (m, 1H), 4.2-4.1 (m, 3H), 3.9 (m, 1H), 3.1 (m, 2H), 1.9 (m, 2H), 1.4 (s, 3H), 1.3 (s, 3H), 1.1 (t, J=7.6 Hz, 3H); m/z (APCI-neg) M−1=600.3.

Example 17

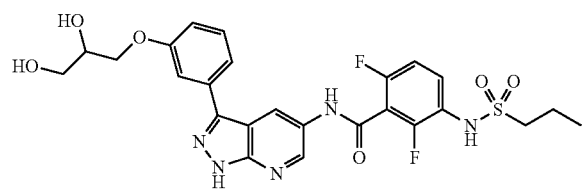 [SMILES: CCCS(=O)(=O)Nc1ccc(F)c(C(=O)Nc2cnc3[nH]nc(-c4cccc(OCC(O)CO)c4)c3c2)c1F]

N-(3-(3-(2,3-dihydroxypropoxy)phenyl)-1H-pyrazolo[3,4-b]pyridin-5-yl)-2,6-difluoro-3-(propylsulfonamido)benzamide 1N HCl (1.0 mL) was added to a solution of N-(3-(3-((2,2-dimethyl-1,3-dioxolan-4-yl)methoxy)phenyl)-1H-pyrazolo[3,4-b]pyridin-5-yl)-2,6-difluoro-3-(propylsulfonamido)benzamide (0.050 g, 0.083 mmol) in THF/MeOH (2:1, 3 mL), and the mixture was stirred at room temperature overnight. The reaction mixture was concentrated, and the residue was taken up in ethyl acetate (50 mL) and saturated NaHCO$_3$ (50 mL). The aqueous layer was extracted with ethyl acetate (3×50 mL). The combined organic layers were dried, filtered and concentrated. The crude product was purified by column chromatography, eluting with ethyl acetate to give N-(3-(3-(2,3-dihydroxypropoxy)phenyl)-1H-pyrazolo[3,4-b]pyridin-5-yl)-2,6-difluoro-3-(propylsulfonamido)benzamide (0.008 g, 17%) as a solid. $^1$H NMR (400 MHz, CD$_3$OD) δ 9.0 (s, 1H), 8.7 (s, 1H), 7.7 (m, 1H), 7.6-7.4 (m, 3H), 7.1 (m, 1H), 7.0 (m, 1H), 4.2 (m, 1H), 4.1-4.0 (m, 3H), 3.7 (m, 1H), 3.1 (m, 2H), 1.9 (m, 2H), 1.1 (t, J=7.6 Hz, 3H); m/z (APCI-neg) M−1=560.1.

Example 18

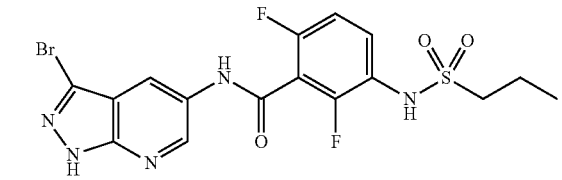 [SMILES: CCCS(=O)(=O)Nc1ccc(F)c(C(=O)Nc2cnc3[nH]nc(Br)c3c2)c1F]

N-(3-bromo-1H-pyrazolo[3,4-b]pyridin-5-yl)-2,6-difluoro-3-(propylsulfonamido)benzamide Step A: Trimethylaluminum (0.21 mL, 0.41 mmol, 2.0M solution in toluene) was added to a cold (0° C.) suspension of 3-bromo-1-tosyl-1H-pyrazolo[3,4-b]pyridin-5-amine (0.050 g, 0.136 mmol) in toluene (10 mL). The cold bath was removed, and the mixture was stirred at room temperature for 20 minutes. Methyl 2,6-difluoro-3-(N-(propylsulfonyl)propylsulfonamido)benzoate (0.060 g, 0.15 mmol) was added, and the reaction mixture was heated to 90° C. for 2 hours. The reaction mixture was cooled to room temperature and diluted with ethyl acetate (50 mL). 30% Aqueous potassium sodium tartrate solution (50 mL) was carefully added, and the resulting emulsion was stirred at room temperature for 30 minutes. The aqueous layer was extracted with ethyl acetate (2×50 mL). The combined organic layers were dried, filtered and concentrated. The crude product was used directly in the next step.

Step B: $K_2CO_3$ (0.151 g, 1.09 mmol) was added to a solution of N-(3-bromo-1-tosyl-1H-pyrazolo[3,4-b]pyridin-5-yl)-2,6-difluoro-3-(N-(propylsulfonyl)propylsulfonamido)benzamide (0.100 g, 0.136 mmol) in MeOH/$H_2O$ (4:1, 10 mL), and the reaction mixture was heated to 60° C. for 1 hour. The reaction mixture was cooled to room temperature and concentrated. The resulting residue was taken up in ethyl acetate (100 mL) and washed with water (50 mL). The crude product was purified by column chromatography, eluting with hexanes/ethyl acetate (2:1), hexanes/ethyl acetate (1:1) to give N-(3-bromo-1H-pyrazolo[3,4-b]pyridin-5-yl)-2,6-difluoro-3-(propylsulfonamido)benzamide (0.024 g, 37%, 2 steps) as a solid. $^1$H NMR (400 MHz, $CD_3OD$) δ 8.7 (s, 1H), 8.5 (s, 1H), 7.7 (m, 1H), 7.1 (m, 1H), 3.1 (m, 2H), 1.9 (m, 2H), 1.1 (t, J=7.6 Hz, 3H); m/z (APCI-neg) M−1=472.2, 474.2.

Example 19

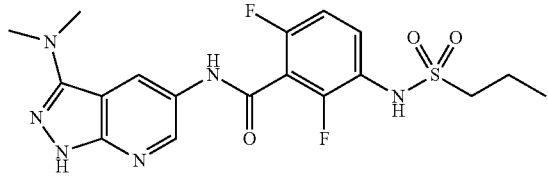 [SMILES: CCCS(=O)(=O)Nc1ccc(F)c(C(=O)Nc2cnc3[nH]nc(N(C)C)c3c2)c1F]

N-(3-(dimethylamino)-1H-pyrazolo[3,4-b]pyridin-5-yl)-2,6-difluoro-3-(propylsulfonamido)benzamide Step A: A suspension of 1H-pyrazol-5-amine (0.804 g, 9.48 mmol) and sodium nitromalonaldehyde monohydrate (1.56 g, 9.96 mmol) in acetic acid (12 mL) was heated to 90° C. overnight. The reaction mixture was cooled to room temperature and poured into water (50 mL). The resulting solids were collected by filtration. The solids were washed with water (3×20 mL) and dried in vacuo to give 5-nitro-1H-pyrazolo[3,4-b]pyridine (1.40 g, 84%) as a solid.

Step B: 4N NaOH (5.12 mL, 20.5 mmol) was added to a cold (0° C.) solution of 5-nitro-1H-pyrazolo[3,4-b]pyridine (0.84 g, 5.12 mmol) in dioxane (30 mL), followed by bromine (1.05 mL, 20.5 mmol). The cold bath was removed, and the reaction mixture was left at room temperature for 30 minutes. The reaction mixture was diluted with ethyl acetate (100 mL) and quenched with saturated $Na_2S_2O_3$ (50 mL) The aqueous layer was extracted with ethyl acetate (100 mL). The combined organic layers were dried, filtered and concentrated. The crude product was purified by column chromatography, eluting with hexanes/ethyl acetate (9:1) to give 3-bromo-5-nitro-1H-pyrazolo[3,4-b]pyridine (1.10 g, 88%) as a solid.

Step C: 40% Dimethyl amine in water (2.6 mL, 21 mmol) was added to a solution of 3-bromo-5-nitro-1H-pyrazolo[3,4-b]pyridine (0.063 g, 0.26 mmol) in DMF (6.0 mL), and the mixture was placed in a microwave reactor at 140° C. for 15 hours. The reaction mixture was diluted with ethyl acetate (100 mL), and the organic layer was washed with water (3×50 mL). The organic layers were dried, filtered and concentrated. The crude product was purified by column chromatography, eluting with hexanes/ethyl acetate (4:1) to give N,N-dimethyl-5-nitro-1H-pyrazolo[3,4-b]pyridin-3-amine (0.012 g, 22%) as a solid.

Step D: N3,N3-dimethyl-1H-pyrazolo[3,4-b]pyridine-3,5-diamine (0.008 g, 78%) was prepared according to Example 4, Step B, substituting N,N-dimethyl-5-nitro-1H-pyrazolo[3,4-b]pyridin-3-amine for 3-methyl-5-nitro-1H-pyrazolo[3,4-b]pyridine.

Step E: N-(3-(dimethylamino)-1H-pyrazolo[3,4-b]pyridin-5-yl)-2,6-difluoro-3-(propylsulfonamido)benzamide (0.007 g, 35%) was prepared according to Example 4, Step C, substituting N3,N3-dimethyl-1H-pyrazolo[3,4-b]pyridine-3,5-diamine for 3-methyl-1H-pyrazolo[3,4-b]pyridin-5-amine. $^1$H NMR (400 MHz, $CD_3OD$) δ 8.7 (s, 1H), 8.5 (s, 1H), 7.7 (m, 1H), 7.1 (m, 1H), 3.1 (m, 8H), 1.9 (m, 2H), 1.1 (t, J=7.6 Hz, 3H); m/z (APCI-pos) M+1=439.1.

Example 20

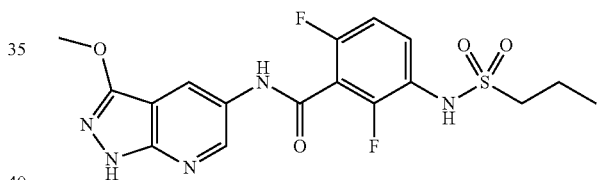

2,6-difluoro-N-(3-methoxy-1H-pyrazolo[3,4-b]pyridin-5-yl)-3-(propylsulfonamido)benzamide Step A: Methyl 5-bromo-2-chloronicotinate (10.04 g, 40.08 mmol) was dissolved in dry EtOH (400 mL) Hydrazine hydrate (8.97 mL, 120.3 mmol) was added, and the reaction mixture was heated to 80° C. for 8 hours. The precipitate was filtered and washed with 1:1 EtOH/$Et_2O$ to give 5-bromo-1H-pyrazolo[3,4-b]pyridin-3-ol (7.23 g, 84%) as a solid.

Step B: 5-Bromo-1H-pyrazolo[3,4-b]pyridin-3-ol (8.68 g, 40.56 mmol) and 1-(chloromethyl)-4-methoxybenzene (16.50 mL, 121.7 mmol) were dissolved in DMSO (250 mL). Powdered NaOH (2.433 g, 60.84 mmol) was added, and the reaction mixture was stirred at room temperature for 1 hour. The reaction mixture was partitioned between EtOAc and water and separated. The aqueous layer was extracted with EtOAc (3×). The combined organic layers were washed with water (3×), saturated aqueous $NaHCO_3$ (3×), brine, and dried over $Na_2SO_4$ and concentrated giving an oily solid. This solid was triturated with EtOAc and dried to provide 5-bromo-1-(4-methoxybenzyl)-1H-pyrazolo[3,4-b]pyridin-3-ol (7.0 g, 51.7%) as a solid.

Step C: 5-Bromo-1-(4-methoxybenzyl)-1H-pyrazolo[3,4-b]pyridin-3-ol (0.200 g, 0.599 mmol) was dissolved in DMF. Sodium hydride (0.0287 g, 0.718 mmol) was added and stirred for 10 minutes. Methyl iodide (0.0448 mL, 0.718 mmol) was added, and the reaction mixture was stirred overnight. The solution was partitioned between water and EtOAc. The organic layer was washed with water (3×), brine, dried over Na₂SO₄ and concentrated to an oil, which was purified by column chromatography (2:1 hexanes/EtOAc) to give 5-bromo-3-methoxy-1-(4-methoxybenzyl)-1H-pyrazolo[3,4-b]pyridine (0.11 g, 52.3%) as an oil.

Step D: 5-Bromo-3-methoxy-1-(4-methoxybenzyl)-1H-pyrazolo[3,4-b]pyridine (0.109 g, 0.313 mmol), tert-butyl carbamate (0.110 g, 0.939 mmol), Cs₂CO₃ (0.153 g, 0.470 mmol), Pd₂dba₃*CHCl₃ (0.0324 g, 0.0313 mmol) and 4,5-bis(diphenylphosphino)-9,9 dimethylxanthene (0.0362 g, 0.0626 mmol) were taken up in THF, degassed with argon for 15 minutes, and heated to reflux overnight. The solution was partitioned between water and EtOAc. The organic portion was washed with water (3×), brine, dried over Na₂SO₄ and concentrated to an oil which was purified by column chromatography (4:1 hexane/EtOAc) to give tert-butyl 3-methoxy-1-(4-methoxybenzyl)-1H-pyrazolo[3,4-b]pyridin-5-ylcarbamate (0.0298 g, 24.8%) as an oil.

Step E: tert-Butyl 3-methoxy-1-(4-methoxybenzyl)-1H-pyrazolo[3,4-b]pyridin-5-ylcarbamate (0.0159 g, 0.0414 mmol) was dissolved in trifluoroacetic acid (2.0 mL) and stirred at room temperature for 1 hour. The reaction mixture was concentrated to provide 3-methoxy-1 (4-methoxybenzyl)-1H-pyrazolo[3,4-b]pyridin-5-amine, which was used directly in the next step.

Step F: 3-Methoxy-1-(4-methoxybenzyl)-1H-pyrazolo[3,4-b]pyridin-5-amine (0.0118 g, 0.0414 mmol), 2,6-difluoro-3-(propylsulfonamido)benzoic acid (0.0127 g, 0.0455 mmol), EDCI (0.00873 g, 0.0455 mmol), and HOBt (0.00615 g, 0.0455 mmol) were dissolved in DMF (1.5 mL) and stirred overnight at room temperature. The solution was partitioned between water and EtOAc. The organic layer was washed with water (3×), brine, dried over Na₂SO₄ and concentrated to an oil, which was purified by column chromatography (4:1 to 3:2 hexane/EtOAc to give 2,6-difluoro-N-(3-methoxy-1-(4-methoxybenzyl)-1H-pyrazolo[3,4-b]pyridin-5-yl)-3-(propylsulfonamido)benzamide (0.003 g, 13.3%) as an oil.

Step G: 2,6-Difluoro-N-(3-methoxy-1-(4-methoxybenzyl)-1H-pyrazolo[3,4-b]pyridin-5-yl)-3-(propylsulfonamido)benzamide (0.0030 g, 0.0055 mmol) was taken up in TFA (2 mL) and heated to reflux for 8 hours. The reaction mixture was concentrated and purified by column chromatography (1:1 hexane/EtOAc) to provide 2,6-difluoro-N-(3-methoxy-1H-pyrazolo[3,4-b]pyridin-5-yl)-3-(propylsulfonamido)benzamide (0.0021 g, 90%) as a solid. ¹H NMR (400 MHz, (CD₃)₂CO) δ 8.65-8.66 (m, 2H), 7.65-7.71 (m, 1H), 7.15-7.20 (m, 1H), 4.07 (s, 3H), 3.16-3.19 (m, 2H), 1.84-1.90 (m, 2H), 1.03-1.07 (m, 3H); m/z (APCI-pos) M+1=426.1.

The following compounds in Table 1 were prepared following the above procedures.

TABLE 1

| Ex. # | Structure | Name | MS/NMR |
|---|---|---|---|
| 21 | 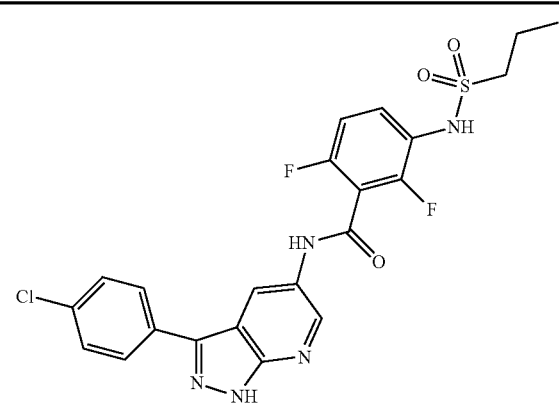 | N-(3-(4-chlorophenyl)-1H-pyrazolo[3,4-b]pyridin-5-yl)-2,6-difluoro-3-(propylsulfonamido)benzamide | ¹H NMR (400 MHz, CD₃OD) δ 9.0 (s, 1H), 8.7 (s, 1H), 8.0 (d, J = 8.8 Hz, 2H), 7.7 (m, 1H), 7.5 (d, J = 8.8 Hz, 2H), 7.1 (m, 2H), 3.1 (m, 2H), 1.9 (m, 2H), 1.1 (t, J = 7.6 Hz, 3H); m/z (APCI-neg) M − 1 = 504.2, 506.2 |
| 22 | 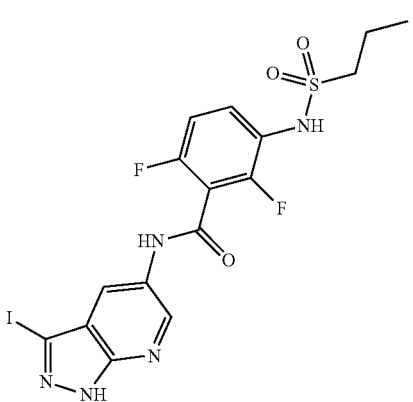 [SMILES: CCCS(=O)(=O)Nc1ccc(F)c(C(=O)Nc2cnc3[nH]nc(I)c3c2)c1F] | 2,6-difluoro-N-(3-iodo-1H-pyrazolo[3,4-b]pyridin-5-yl)-3-(propylsulfonamido)benzamide | ¹H NMR (400 MHz, CD₃OD) δ 8.7 (s, 1H), 8.4 (s, 1H), 7.7 (m, 1H), 7.1 (m, 1H), 3.1 (m, 2H), 1.9 (m, 2H), 1.1 (t, J = 7.6 Hz, 3H); m/z (APCI-neg) M − 1 = 520.1 |

TABLE 1-continued

| Ex. # | Structure | Name | MS/NMR |
|---|---|---|---|
| 23 | 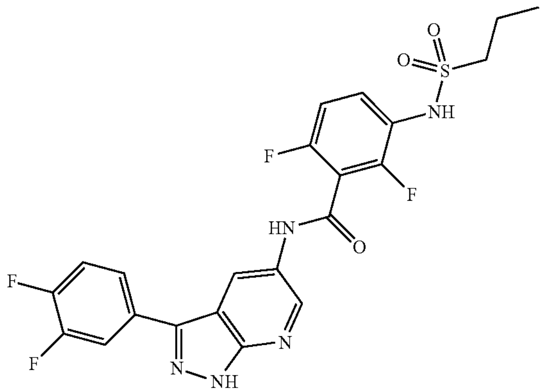 [SMILES: CCCS(=O)(=O)Nc1ccc(F)c(C(=O)Nc2cnc3[nH]nc(-c4ccc(F)c(F)c4)c3c2)c1F] | N-(3-(3,4-difluorophenyl)-1H-pyrazolo(3,4-b]pyridin-5-yl)-2,6-difluoro-3-(propylsulfonamido)benzamide | $^1$H NMR (400 MHz, CD$_3$OD) δ 9.0 (s, 1H), 8.7 (s, 1H), 7.9 (m, 1H), 7.8 (m, 1H), 7.7 (m, 1H), 7.4 (m, 1H), 7.1 (m, 1H), 3.1 (m, 2H), 1.9 (m, 2H), 1.1 (t, J = 7.6 Hz, 3H); m/z (APCI-neg) M − 1 = 506.3 |
| 24 | 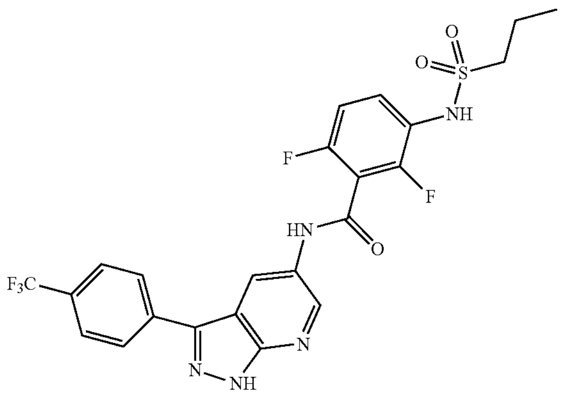 [SMILES: CCCS(=O)(=O)Nc1ccc(F)c(C(=O)Nc2cnc3[nH]nc(-c4ccc(C(F)(F)F)cc4)c3c2)c1F] | 2,6-difluoro-3-(propylsulfonamido)-N-(3-(4-(trifluoromethyl)phenyl)-1H-pyrazolo[3,4-b]pyridin-5-yl)benzamide | $^1$H NMR (400 MHz, CD$_3$OD) δ 9.0 (s, 1H), 8.7 (s, 1H), 8.2 (d, J = 8.8 Hz, 2H), 7.8 (d, J = 8.8 Hz, 2H), 7.7 (m, 1H), 7.1 (m, 2H), 3.1 (m, 2H), 1.9 (m, 2H), 1.1 (t, J = 7.6 Hz, 3H); m/z (APCI-neg) M − 1 = 538.2 |
| 25 | 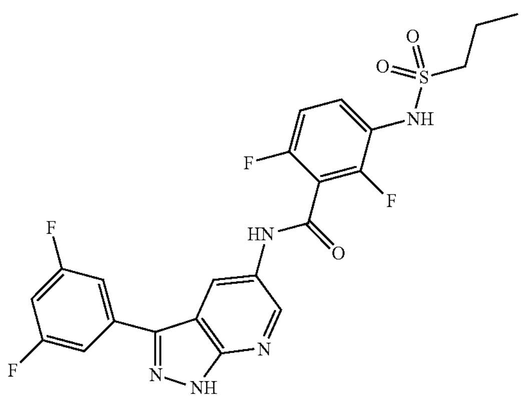 [SMILES: CCCS(=O)(=O)Nc1ccc(F)c(C(=O)Nc2cnc3[nH]nc(-c4cc(F)cc(F)c4)c3c2)c1F] | N-(3-(3,5-difluorophenyl)-1H-pyrazolo[3,4-b]pyridin-5-yl)-2,6-difluoro-3-(propylsulfonamido)benzamide | $^1$H NMR (400 MHz, CD$_3$OD) δ 9.0 (s, 1H), 8.7 (s, 1H), 7.7 (m, 1H), 7.6 (D, J = 6.4 Hz, 2H); 7.2 (m, 1H), 7.0 (m, 1H), 3.1 (m, 2H), 1.9 (m, 2H), 1.1 (t, J = 7.6 Hz, 3H); m/z (APCI-neg) M − 1 = 506.2 |
| 26 | 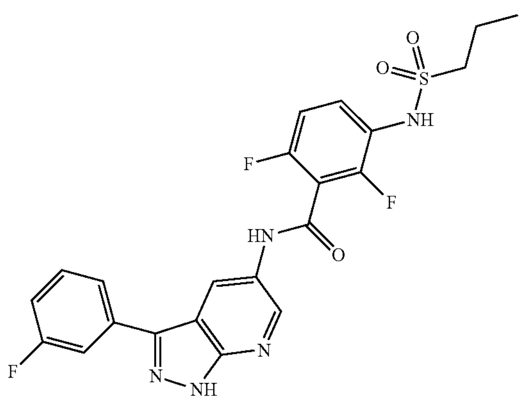 [SMILES: CCCS(=O)(=O)Nc1ccc(F)c(C(=O)Nc2cnc3[nH]nc(-c4cccc(F)c4)c3c2)c1F] | 2,6-difluoro-N-(3-(3-fluorophenyl)-1H-pyrazolo[3,4-b]pyridin-5-yl)-3-(propylsulfonamido)benzamide | $^1$H NMR (400 MHz, CD$_3$OD) δ 9.0 (s, 1H), 8.7 (s, 1H), 7.8 (d, J = 8.0 Hz, 1H), 7.7 (m, 2H), 7.5 (m, 1H), 7.2 (m, 2H), 3.1 (m, 2H), 1.9 (m, 2H), 1.1 (t, J = 7.6 Hz, 3H); m/z (APCI-neg) M − 1 = 488.2 |

TABLE 1-continued

| Ex. # | Structure | Name | MS/NMR |
|---|---|---|---|
| 27 | 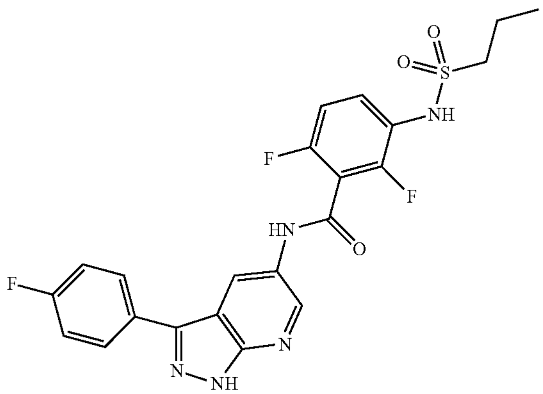 [SMILES: CCCS(=O)(=O)Nc1ccc(F)c(C(=O)Nc2cnc3[nH]nc(-c4ccc(F)cc4)c3c2)c1F] | 2,6-difluoro-N-(3-(4-fluorophenyl)-1H-pyrazolo[3,4-b]pyridin-5-yl)-3-(propylsulfonamido)benzamide | ¹H NMR (400 MHz, CD₃OD) δ 8.9 (s, 1H), 8.7 (s, 1H), 8.0 (m, 2H), 7.7 (m, 1H), 7.3 (m, 2H), 7.1 (m, 1H), 3.1 (m, 2H), 1.9 (m, 2H), 1.1 (t, J = 7.6 Hz, 3H); m/z (APCI-neg) M − 1 = 488.2 |
| 28 | 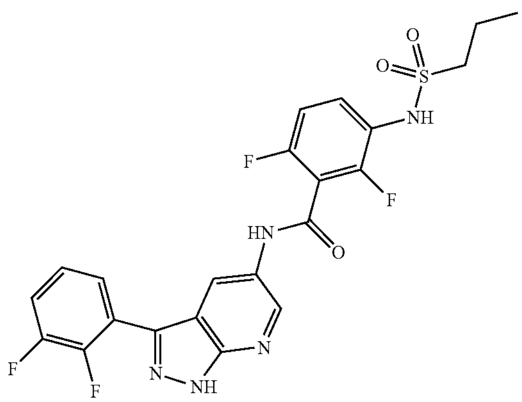 [SMILES: CCCS(=O)(=O)Nc1ccc(F)c(C(=O)Nc2cnc3[nH]nc(-c4cccc(F)c4F)c3c2)c1F] | N-(3-(2,3-difluorophenyl)-1H-pyrazolo[3,4-b]pyridin-5-yl)-2,6-difluoro-3-(propylsulfonamido)benzamide | ¹H NMR (400 MHz, CD₃OD) δ 8.7 (s, 2H), 7.6 (m, 2H), 7.3 (m, 2H), 7.1 (m, 1H), 3.1 (m, 2H), 1.9 (m, 2H), 1.1 (t, J = 7.6 Hz, 3H); m/z (APCI-neg) M − 1 = 506.3 |
| 29 | 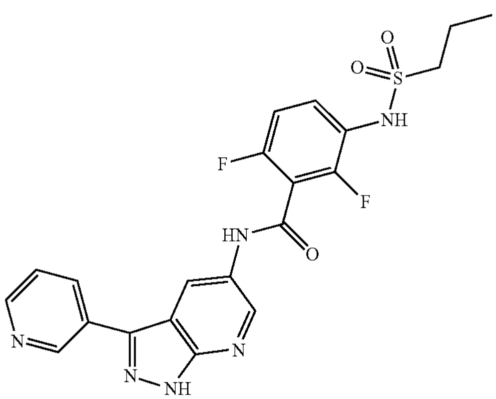 [SMILES: CCCS(=O)(=O)Nc1ccc(F)c(C(=O)Nc2cnc3[nH]nc(-c4cccnc4)c3c2)c1F] | 2,6-difluoro-3-(propylsulfonamido)-N-(3-(pyridin-3-yl)-1H-pyrazolo[3,4-b]pyridin-5-yl)benzamide | ¹H NMR (400 MHz, CD₃OD) δ 9.2 (br s, 1H), 9.0 (s, 1H), 8.7 (s, 1H), 8.6 (br s, 1H), 8.4 (d, J = 8.6 Hz, 1H), 7.7-7.6 (m, 2H), 7.1 (m, 1H), 3.1 (m, 2H), 1.9 (m, 2H), 1.1 (t, J = 7.6 Hz, 3H); m/z (APCI-neg) M − 1 = 471.2 |
| 30 | 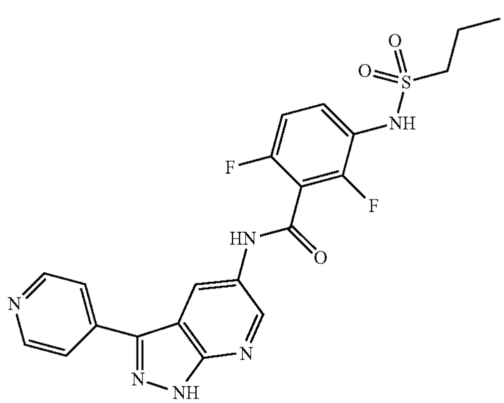 [SMILES: CCCS(=O)(=O)Nc1ccc(F)c(C(=O)Nc2cnc3[nH]nc(-c4ccncc4)c3c2)c1F] | 2,6-difluoro-3-(propylsulfonamido)-N-(3-(pyridin-4-yl)-1H-pyrazolo[3,4-b]pyridin-5-yl)benzamide | ¹H NMR (400 MHz, CD₃OD) δ 8.7 (s, 1H), 8.1 (s, 1H), 7.7-7.6 (m, 5H), 7.1 (m, 1H), 3.1 (m, 2H), 1.9 (m, 2H), 1.1 (t, J = 7.6 Hz, 3H); m/z (APCI-neg) M − 1 = 471.2 |

TABLE 1-continued

| Ex. # | Structure | Name | MS/NMR |
|---|---|---|---|
| 31 | 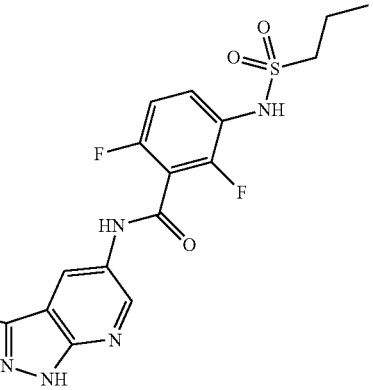 | N-(3-(3-chlorophenyl)-1H-pyrazolo[3,4-b]pyridin-5-yl)-2,6-difluoro-3-(propylsulfonamido)benzamide | $^1$H NMR (400 MHz, CD$_3$OD) δ 9.0 (s, 1H), 8.7 (s, 1H), 7.9 (d, J = 7.4 Hz, 1H), 7.7 (m, 1H), 7.5 (t, J = 7.6 Hz, 1H), 7.4 (d, J = 7.8 Hz, 1H), 7.2 (m, 2H), 3.1 (m, 2H), 1.9 (m, 2H), 1.1 (t, J = 7.6 Hz, 3H); m/z (APCI-neg) M − 1 = 504.2, 506.2 |
| 32 | 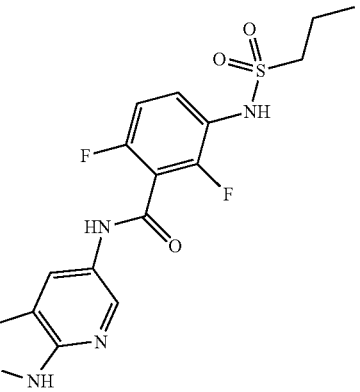 | 2,6-difluoro-N-(3-(1-methyl-1H-pyrazol-4-yl)-1H-pyrazolo[3,4-b]pyridin-5-yl)-3-(propylsulfonamido)benzamide | $^1$H NMR (400 MHz, CD$_3$OD) δ 8.9 (s, 1H), 8.6 (s, 1H), 8.2 (s, 1H), 8.0 (s, 1H), 7.7 (m, 1H), 7.1 (m, 1H), 3.1 (m, 2H), 1.9 (m, 2H), 1.1 (t, J = 7.6 Hz, 3H); m/z (APCI-neg) M − 1 = 474.2 |
| 33 | 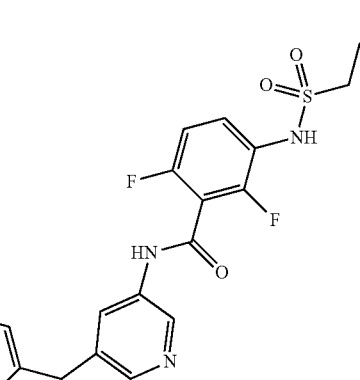 | N-(3-(4-(2-(dimethylamino)ethoxy)phenyl)-1H-pyrazolo[3,4-b]pyridin-5-yl)-2,6-difluoro-3-(propylsulfonamido)benzamide | $^1$H NMR (400 MHz, CD$_3$OD) δ 8.9 (s, 1H), 8.7 (s, 1H), 7.9 (d, J = 8.6 Hz, 2H), 7.6 (m, 1H), 7.1 (m, 3H), 4.2 (t, J = 5.4 Hz, 2H), 3.1 (m, 2H), 2.9 (t, J = 5.6 Hz, 2H), 2.4 (s, 6H), 1.9 (m, 2H), 1.1 (t, J = 7.6 Hz, 3H); m/z (APCI-pos) M + 1 = 559.1 |

TABLE 1-continued

| Ex. # | Structure | Name | MS/NMR |
|---|---|---|---|
| 34 | 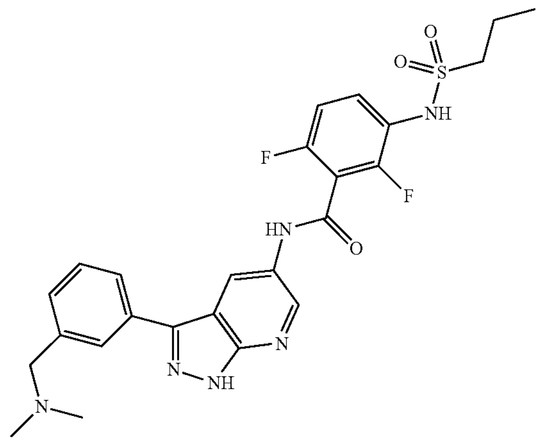 [SMILES: CCCS(=O)(=O)Nc1ccc(F)c(C(=O)Nc2cnc3[nH]nc(-c4cccc(CN(C)C)c4)c3c2)c1F] | N-(3-(3-((dimethylamino)methyl)phenyl)-1H-pyrazolo[3,4-b]pyridin-5-yl)-2,6-difluoro-3-(propylsulfonamido)benzamide | ¹H NMR (400 MHz, CD$_3$OD) δ 9.0 (s, 1H), 8.7 (s, 1H), 7.9 (m, 2H), 7.7 (m, 1H), 7.5 (m, 1H), 7.4 (d, J = 8.0 Hz, 2H), 7.1 (m, 1H), 3.7 (s, 2H), 3.1 (m, 2H), 2.4 (s, 6H), 1.9 (m, 2H), 1.1 (t, J = 7.6 Hz, 3H); m/z (APCI-pos) M + 1 = 529.1 |
| 35 | 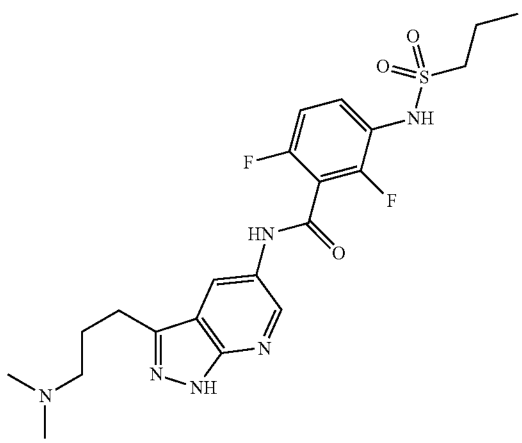 [SMILES: CCCS(=O)(=O)Nc1ccc(F)c(C(=O)Nc2cnc3[nH]nc(CCCN(C)C)c3c2)c1F] | N-(3-(3-(dimethylamino)propyl)-1H-pyrazolo[3,4-b]pyridin-5-yl)-2,6-difluoro-3-(propylsulfonamido)benzamide | ¹H NMR (400 MHz, CD$_3$OD) δ 8.7 (s, 1H), 8.6 (s, 1H), 7.6 (m, 1H), 7.1 (m, 1H), 3.1 (m, 2H), 3.0 (m, 2H), 2.6 (m, 2H), 2.4 (s, 6H), 2.1 (m, 2H), 1.9 (m, 2H), 1.1 (t, J = 7.6 Hz, 3H); m/z (APCI-pos) M + 1 = 481.1 |
| 36 | 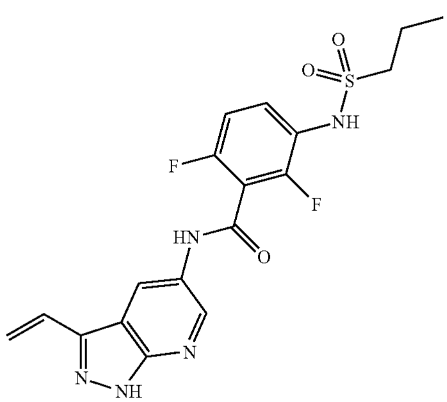 [SMILES: C=Cc1n[nH]c2ncc(NC(=O)c3c(F)ccc(NS(=O)(=O)CCC)c3F)cc12] | 2,6-difluoro-3-(propylsulfonamido)-N-(3-vinyl-1H-pyrazolo[3,4-b]pyridin-5-yl)benzamide | ¹H NMR (400 MHz, CD$_3$OD) δ 8.9 (s, 1H), 8.7 (s, 1H), 7.7 (m, 1H), 7.1 (m, 1H), 7.0 (m, 1H), 6.1 (m, 1H), 5.6 (m, 1H), 3.1 (m, 2H), 1.9 (m, 2H), 1.1 (t, J = 7.6 Hz, 3H); m/z (APCI-neg) M − 1 = 420.2 |

TABLE 1-continued

| Ex. # | Structure | Name | MS/NMR |
|---|---|---|---|
| 37 | 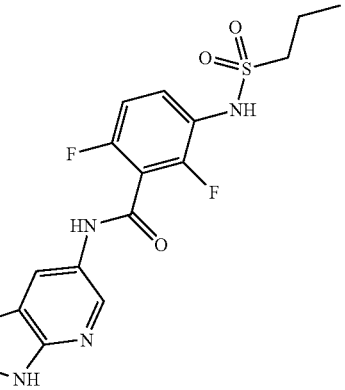 | 2,6-difluoro-N-(3-isobutyl-1H-pyrazolo[3,4-b]pyridin-5-yl)-3-(propylsulfonamido)benzamide | $^1$H NMR (400 MHz, CD$_3$OD) δ 8.7 (s, 1H), 8.6 (s, 1H), 7.7 (m, 1H), 7.1 (m, 1H), 3.1 (m, 2H), 2.8 (d, J = 7.2 Hz, 2H), 2.1 (m, 1H), 1.9 (m, 2H), 1.1 (t, J = 7.6 Hz, 3H), 1.0 (d, J = 6.0 Hz, 6H); m/z (APCI-pos) M + 1 = 452.1 |
| 38 | 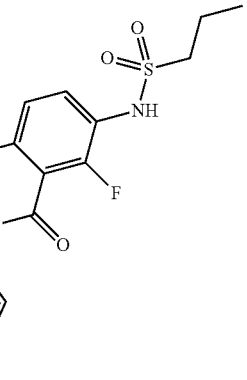 | 2,6-difluoro-N-(3-propyl-1H-pyrazolo[3,4-b]pyridin-5-yl)-3-(propylsulfonamido)benzamide | $^1$H NMR (400 MHz, CD$_3$OD) δ 8.7 (s, 1H), 8.6 (s, 1H), 7.7 (m, 1H), 7.1 (m, 1H), 3.1 (m, 2H), 3.0 (m, 2H), 1.9-1.8 (m, 4H), 1.1-1.0 (m, 6H); m/z (APCI-pos) M + 1 = 438.1 |
| 39 | 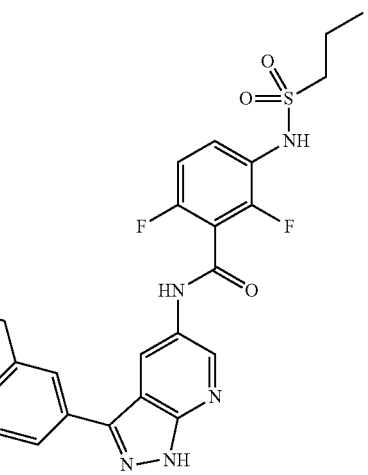 | 2,6-difluoro-N-(3-(3-(morpholinomethyl)phenyl)-1H-pyrazolo[3,4-b]pyridin-5-yl)-3-(propylsulfonamido)benzamide | $^1$H NMR (400 MHz, CD$_3$OD) δ 9.0 (s, 1H), 8.7 (s, 1H), 8.0 (s, 1H), 7.9 (m, 1H), 7.7 (m, 1H), 7.5 (m, 1H), 7.4 (m, 1H), 7.1 (m, 1H), 3.7 (m, 4H), 3.6 (s, 2H), 3.1 (m, 2H), 2.5 (m, 4H), 1.9 (m, 2H), 1.1 (t, J = 7.6 Hz, 3H); m/z (APCI-pos) M + 1 = 571.1 |

TABLE 1-continued

| Ex. # | Structure | Name | MS/NMR |
|---|---|---|---|
| 40 | 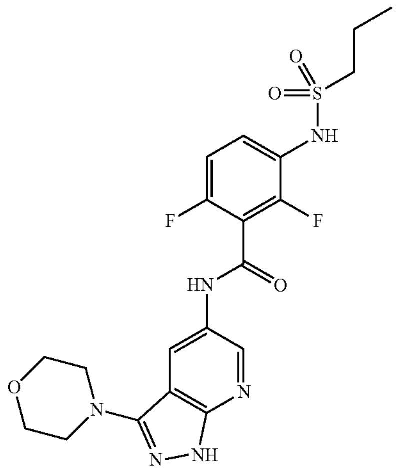 [SMILES: CCCS(=O)(=O)Nc1ccc(F)c(C(=O)Nc2cnc3[nH]nc(N4CCOCC4)c3c2)c1F] | 2,6-difluoro-N-(3-morpholino-1H-pyrazolo[3,4-b]pyridin-5-yl)-3-(propylsulfonamido)benzamide | $^1$H NMR (400 MHz, CD$_3$OD) δ 8.7 (s, 1H), 8.5 (s, 1H), 7.6 (m, 1H), 7.1 (m, 1H), 3.9 (m, 4H), 3.4 (m, 4H), 3.1 (m, 2H), 1.9 (m, 2H), 1.1 (t, J = 7.6 Hz, 3H); m/z (APCI-pos) M + 1 = 481.1 |
| 41 | 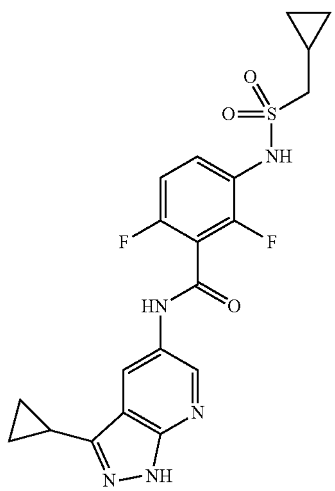 [SMILES: O=C(Nc1cnc2[nH]nc(C3CC3)c2c1)c1c(F)ccc(NS(=O)(=O)CC2CC2)c1F] | N-(3-cyclopropyl-1H-pyrazolo[3,4-b]pyridin-5-yl)-3-(cyclopropylmethylsulfonamido)-2,6-difluorobenzamide | $^1$H NMR (400 MHz, d$_6$-DMSO) δ 13.19 (s, 1H), 11.07 (s, 1H), 9.84 (s, 1H), 8.65-8.63 (m, 1H), 8.57-8.55 (m, 1H), 7.62-7.55 (m, 1H), 7.29-7.23 (m, 1H), 3.13 (d, J = 7.1 Hz, 2H), 2.34-2.25 (m, 1H), 1.12-1.04 (m, 1H), 1.03-0.97 (m, 2H), 0.98-0.92 (m, 2H), 0.61-0.56 (m, 2H), 0.39-0.34 (m, 2H); m/z (APCI-pos) M + 1 = 448.1 |
| 42 | 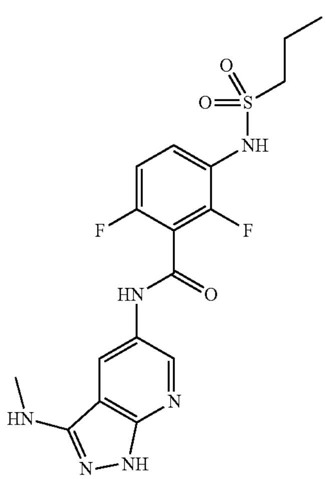 [SMILES: CCCS(=O)(=O)Nc1ccc(F)c(C(=O)Nc2cnc3[nH]nc(NC)c3c2)c1F] | 2,6-difluoro-N-(3-(methylamino)-1H-pyrazolo[3,4-b]pyridin-5-yl)-3-(propylsulfonamido)benzamide | $^1$H NMR (400 MHz, CD$_3$OD) δ 8.6 (s, 1H), 8.4 (s, 1H), 7.6 (m, 1H), 7.1 (m, 1H), 3.1 (m, 2H), 3.0 (s, 3H), 1.9 (m, 2H), 1.1 (t, J = 7.6 Hz, 3H); m/z (APCI-pos) M + 1 = 425.1 |

Example 43

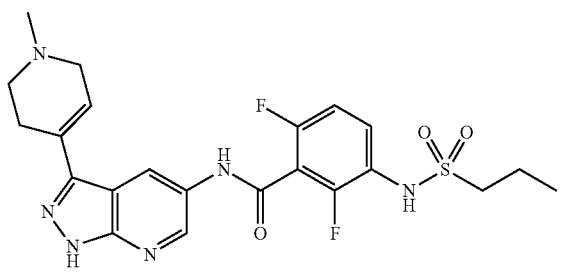 [SMILES: CCCS(=O)(=O)Nc1ccc(F)c(C(=O)Nc2cnc3[nH]nc(C4=CCN(C)CC4)c3c2)c1F]

2,6-difluoro-N-(3-(1-methyl-1,2,3,6-tetrahydropyridin-4-yl)-1H-pyrazolo yl)-3-(propylsulfonamido)benzamide Step A: tert-Butyl 4-(5-(2,6-difluoro-3-(propylsulfonamido)benzamido)-1H-pyrazolo[3,4-b]pyridin-3-yl)-5,6-dihydropyridine-1-(2H)-carboxylate (30%) was prepared according to the general procedure for Example 15, Step C, substituting tert-butyl 4-(4,4,5,5-tetramethyl-1,3,2-dioxaborolan-2-yl)-5,6-dihydropyridine-1-(2H)-carboxylate (Eastwood, Paul R. "A versatile synthesis of 4-aryl tetrahydropyridines via palladium mediated Suzuki cross-coupling with cyclic vinyl boronates" *Tetrahedron Lett.* 41(19) (2000): pp. 3705-3708) for N,N-dimethyl-2-(3-(4,4,5,5-tetramethyl-1,3,2-dioxaborolan-2-yl)phenoxy)ethanamine.

Step B: A solution of tert-butyl 4-(5-(2,6-difluoro-3-(propylsulfonamido)benzamido)-1H-pyrazolo[3,4-b]pyridin-3-yl)-5,6-dihydropyridine-1(2H)-carboxylate (27 mg, 0.47 mmol) in $CH_2Cl_2$ (5 mL) was treated with trifluoroacetic acid (3 mL). After 2 hours, the volatiles were removed under reduced pressure, leaving the trifluoroacetic acid salt of 2,6-difluoro-3-(propylsulfonamido)-N-(3-(1,2,3,6-tetrahydropyridin-4-yl)-1H-pyrazolo[3,4-b]pyridin-5-yl)benzamide (22 mg, quantitative yield).

Step C: 37% Aqueous formaldehyde (100 μL) was added to a solution of 2,6-difluoro-3-(propylsulfonamido)-N-(3-(1,2,3,6-tetrahydropyridin-4-yl)-1H-pyrazolo[3,4-b]pyridin-5-yl)benzamide (22 mg, 0.046 mmol) in 5:1 $CH_2Cl_2$/MeOH (6 mL), followed by a drop of AcOH. After 5 minutes, sodium triacetoxyborohydride (49 mg, 5 equiv) was added, and the reaction mixture was stirred for 2 hours at ambient temperature. The reaction mixture was quenched with MeOH, concentrated, and purified by silica gel chromatography (10:90:1 MeOH/$CHCl_3$/$NH_4OH$) to afford 2,6-difluoro-N-(3-(1-methyl-1,2,3,6-tetrahydropyridin-4-yl)-1H-pyrazolo[3,4-b]pyridin-5-yl)-3-(propylsulfonamido)benzamide as a white solid (14 mg, 62%). $^1$H NMR (400 MHz, $CD_3OD$) δ 8.90-8.88 (m, 1H), 8.62-8.60 (m, 1H), 7.70-7.63 (m, 1H), 7.17-7.11 (m, 1H), 6.57-6.53 (m, 1H), 3.35-3.31 (m, 2H), 3.14-3.09 (m, 2H), 2.90-2.83 (m, 4H), 2.49 (s, 3H), 1.92-1.82 (m, 2H), 1.08-1.04 (m, 3H); m/z (APCI-pos) M+1=491.0.

Example 44

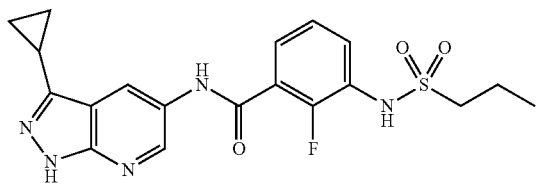 [SMILES: CCCS(=O)(=O)Nc1cccc(C(=O)Nc2cnc3[nH]nc(C4CC4)c3c2)c1F]

N-(3-cyclopropyl-1H-pyrazolo[3,4-b]pyridin-5-yl)-2-fluoro-3-(propylsulfonamido)benzamide N-(3-Cyclopropyl-1H-pyrazolo[3,4-b]pyridin-5-yl)-2-fluoro-3-(propylsulfonamido)benzamide (84%) was prepared according to the general procedure for Example 1, Step E substituting 3-cyclopropyl-1H-pyrazolo[3,4-b]pyridin-5-amine for 1H-pyrazolo[3,4-b]pyridin-5-amine and substituting 2-fluoro-3-(propylsulfonamido)benzoic acid for 2,6-difluoro-3-(propylsulfonamido)benzoic acid. $^1$H NMR (400 MHz, $d_6$-DMSO) δ 13.15 (s, 1H), 10.67 (s, 1H), 9.84 (s, 1H), 8.63-8.61 (m, 2H), 7.60-7.50 (m, 2H), 7.35-7.30 (m, 1H), 3.19-3.14 (m, 2H), 2.31-2.23 (m, 1H), 1.83-1.73 (m, 2H), 1.03-0.94 (m, 7H); m/z (APCI-neg) M−1=416.3.

Example 45

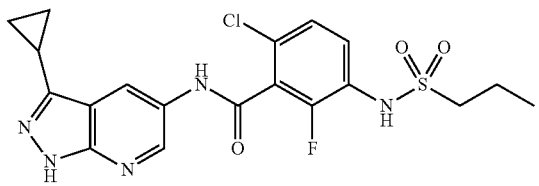 [SMILES: CCCS(=O)(=O)Nc1ccc(Cl)c(C(=O)Nc2cnc3[nH]nc(C4CC4)c3c2)c1F]

6-chloro-N-(3-cyclopropyl-1H-pyrazolo[3,4-b]pyridin-5-yl)-2-fluoro-3-(propylsulfonamido)benzamide 6-Chloro-N-(3-cyclopropyl-1H-pyrazolo[3,4-b]pyridin-5-yl)-2-fluoro-3-(propylsulfonamido)benzamide (85%) was prepared according to the general procedure for Example 1, Step E substituting 3-cyclopropyl-1H-pyrazolo[3,4-b]pyridin-5-amine for 1H-pyrazolo[3,4-b]pyridin-5-amine and substituting 6-chloro-2-fluoro-3-(propylsulfonamido)benzoic acid for 2,6-difluoro-3-(propylsulfonamido)benzoic acid. $^1$H NMR (400 MHz, $d_6$-DMSO) δ 13.19 (s, 1H), 11.06 (s, 1H), 9.99 (br s, 1H), 8.65-8.64 (m, 1H), 8.56-8.54 (m, 1H), 7.57-7.52 (m, 1H), 7.47-7.43 (m, 1H), 3.19-3.14 (m, 2H), 2.35-2.26 (m, 1H), 1.81-1.72 (m, 2H), 1.03-0.92 (m, 7H); m/z (APCI-pos) M+1=452.1.

Example 46

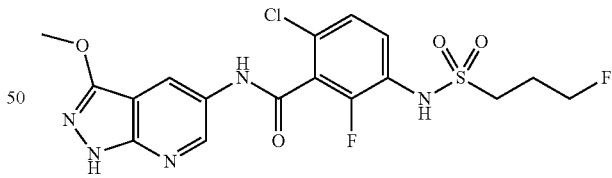

6-chloro-2-fluoro-3-(3-fluoropropylsulfonamido)-N-(3-methoxy-1H-pyrazolo[3,4-b]pyridin-5-yl)benzamide 6-Chloro-2-fluoro-3-(3-fluoropropylsulfonamido)-N-(3-methoxy-1H-pyrazolo[3,4-b]pyridin-5-yl)benzamide (42% over two steps) was prepared according to the general procedure for Example 20, Steps F and G, substituting 6-chloro-2-fluoro-3-(3-fluoropropylsulfonamido)benzoic acid for 2,6-difluoro-3-(propylsulfonamido)benzoic acid. $^1$H NMR (400 MHz, $d_6$-DMSO) δ 12.61 (s, 1H), 11.08 (s, 1H), 10.12 (s, 1H), 8.59-8.57 (s, 1H), 8.48-8.46 (m, 1H), 7.58-7.52 (m, 1H), 7.48-7.45 (m, 1H), 4.64-4.60 (m, 1H), 4.52-4.48 (m, 1H), 4.02 (s, 3H), 3.31-3.26 (m, 2H), 2.20-2.06 (m, 2H); m/z (APCI-pos) M+1=460.0.

Example 47

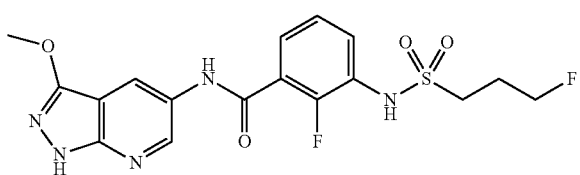 [SMILES: COc1n[nH]c2ncc(NC(=O)c3cccc(NS(=O)(=O)CCCF)c3F)cc12]

2-fluoro-3-(3-fluoropropylsulfonamido)-N-(3-methoxy-1H-pyrazolo[3,4-b]pyridin-5-yl)benzamide 2-Fluoro-3-(3-fluoropropylsulfonamido)-N-(3-methoxy-1H-pyrazolo[3,4-b]pyridin-5-yl)benzamide (47% over two steps) was prepared according to the general procedure for Example 20, Steps F and G, substituting 2-fluoro-3-(3-fluoropropylsulfonamido)benzoic acid for 2,6-difluoro-3-(propylsulfonamido)benzoic acid. $^1$H NMR (400 MHz, d$_6$-DMSO) δ 12.56 (s, 1H), 10.69 (s, 1H), 9.97 (s, 1H), 8.65-8.63 (s, 1H), 8.48-8.46 (m, 1H), 7.61-7.51 (m, 2H), 7.35-7.30 (m, 1H), 4.64-4.60 (m, 1H), 4.53-4.49 (m, 1H), 4.02 (s, 3H), 3.31-3.26 (m, 2H), 2.21-2.07 (m, 2H); m/z (APCI-pos) M+1=426.1.

Example 48

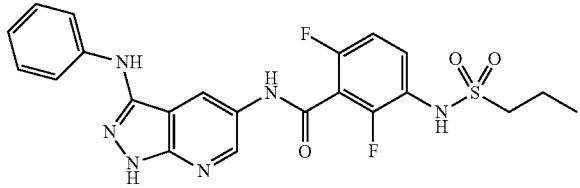 [SMILES: CCCS(=O)(=O)Nc1ccc(F)c(C(=O)Nc2cnc3[nH]nc(Nc4ccccc4)c3c2)c1F]

2,6-difluoro-N-(3-(phenylamino)-1H-pyrazolo[3,4-b]pyridin-5-yl)-3-(propylsulfonamido)benzamide Step A: NaH (0.165 g, 4.11 mmol, 60% suspension in mineral oil) was added portionwise to a cold (0° C.) solution of 3-bromo-5-nitro-1H-pyrazolo[3,4-b]pyridine (0.5 g, 2.06 mmol) in dry DMF (20 mL). The reaction mixture was stirred at 0° C. for 10 minutes, and 2-(trimethylsilyl)ethoxymethyl chloride (0.617 mL, 3.50 mmol) was added dropwise via a syringe. The cold bath was removed, and the reaction mixture was stirred at room temperature for 1 hour. The reaction mixture was placed in an ice bath, diluted with ethyl acetate (400 mL) and carefully quenched with water (50 mL). The aqueous layer was separated and extracted with ethyl acetate (3×50 mL). The combined organic layers were dried, filtered and concentrated. The crude product was purified by column chromatography, eluting with hexanes/ethyl acetate (20:1) to give 3-bromo-5-nitro-1-((2-(trimethylsilyl)ethoxy)methyl)-1H-pyrazolo[3,4-b]pyridine (0.636 g, 83%) as a solid.

Step B: Aniline (0.035 mL, 0.386 mmol), Pd$_2$dba$_3$ (0.024 g, 0.0257 mmol), Xantphos (0.030 g, 0.0714 mmol), K$_3$PO$_4$ (0.120 g, 0.566 mmol) was added to a suspension of 3-bromo-5-nitro-1-((2-(trimethylsilyl)ethoxy)methyl)-1H-pyrazolo[3,4-b]pyridine (0.096 g, 0.257 mmol) in toluene (10 mL), and the mixture was heated to reflux overnight. The reaction mixture was cooled to room temperature and filtered through celite. The filter cake was washed with ethyl acetate. The combined filtrate was concentrated to give the crude product 5-nitro-N-phenyl-1-(2-(trimethylsilyl)ethoxy)methyl)-1H-pyrazolo[3,4-b]pyridin-3-amine. This material was used without purification in the next step.

Step C: SnCl$_2$ dihydrate (0.243 g, 1.28 mmol) was added to a suspension of 5-nitro-N-phenyl-1-((2-(trimethylsilyl)ethoxy)methyl)-1H-pyrazolo[3,4-b]pyridin-3-amine (0.099 g, 0.257 mmol) in ethyl acetate (25 mL), and the reaction mixture was heated to reflux overnight. The reaction mixture was cooled to room temperature and quenched with saturated aqueous NaHCO$_3$ (25 mL). The resulting suspension was filtered through a pad of celite, and the filter cake was washed with ethyl acetate (100 mL). The aqueous layer was extracted with ethyl acetate (3×50 mL). The combined organic layers were dried, filtered and concentrated. The crude product was purified by column chromatography, eluting with hexanes/ethyl acetate (1:1), hexanes/ethyl acetate (1:2) to give N3-phenyl-1H-pyrazolo[3,4-b]pyridine-3,5-diamine (0.012 g, 21% over 3 steps) as solids.

Step D: 2,6-Difluoro-N-(3-(phenylamino)-1H-pyrazolo[3,4-b]pyridin-5-yl)-3-(propylsulfonamido)benzamide was prepared according to Example 1, Step E using N3-phenyl-1H-pyrazolo[3,4-b]pyridine-3,5-diamine (10 mg, 39% yield). $^1$H NMR (400 MHz, CD$_3$OD) δ 8.8 (s, 1H), 8.5 (s, 1H), 7.7 (m, 1H), 7.6 (m, 2H), 7.3 (m, 2H), 7.1 (m, 1H), 6.9 (m, 1H), 3.1 (m, 2H), 1.9 (m, 2H), 1.1 (t, J=7.6 Hz, 3H); m/z (APCI-pos) M+1=487.1.

Example 49

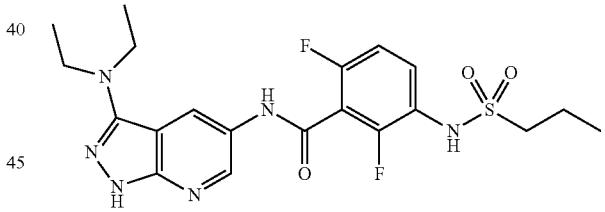

N-(3-(diethylamino)-1H-pyrazolo[3,4-b]pyridin-5-yl)-2,6-difluoro-3-(propylsulfonamido)benzamide Step A: N-(5-Nitro-1H-pyrazolo[3,4-b]pyridin-3-yl)acetamide (930 mg, 74% yield) was prepared according to Example 4, Step A, substituting 1H-pyrazole-3,5-diamine for 3-methyl-1H-pyrazol-5-amine.

Step B: A mixture of N-(5-nitro-1H-pyrazolo[3,4-b]pyridin-3-yl)acetamide (530 mg, 2.40 mmol), EtOH (2.4 mL, 1M) and concentrated HCl (37%) (2.5 mL, 68.6 mmol) was heated to 85° C. for 3 hours. The volatiles were removed to afford 5-nitro-1H-pyrazolo[3,4-b]pyridin-3-amine hydrochloride (500 mg, 97% yield) as a solid.

Step C: 5-Nitro-1H-pyrazolo[3,4-b]pyridin-3-amine hydrochloride was suspended in EtOAc (300 mL) and water (100 mL). The mixture was treated with a 2M solution of NaOH (1027 μL, 2.05 mmol). The organic layer was separated, washed with water (2×50 mL) and brine (50 mL), dried (Na$_2$SO$_4$), filtered and concentrated to afford 5-nitro-1H-pyrazolo[3,4-b]pyridin-3-amine (275 mg, 75% yield) as a solid.

Step D: Acetaldehyde (0.258 g, 5.86 mmol) and a drop of acetic acid were added to a solution of 5-nitro-1H-pyrazolo[3,4-b]pyridin-3-amine (0.105 g, 0.586 mmol) in THF/dichloroethane ("DCE") (12 mL, 1:1). NaBH(OAc)$_3$ (1.24 g, 5.86 mmol) was added, and the mixture was left at room temperature for 60 hours. The reaction mixture was diluted with ethyl acetate (50 mL) and quenched with water (10 mL). The aqueous layer was extracted with ethyl acetate (2×50 mL). The combined organic layers were dried, filtered and concentrated. The crude product was purified by column chromatography, eluting with hexanes/ethyl acetate (9:1), hexanes/ethyl acetate (4:1) to give N,N-diethyl-5-nitro-1H-pyrazolo[3,4-b]pyridin-3-amine (22 mg, 16% yield) as a solid.

Step E: N3,N3-Diethyl-1H-pyrazolo[3,4-b]pyridine-3,5-diamine (10 mg, 52% yield) was prepared according to Example 2, Step D substituting N,N-diethyl-5-nitro-1H-pyrazolo[3,4-b]pyridin-3-amine for 3-bromo-5-nitro-1-tosyl-1H-pyrazolo[3,4-b]pyridine.

Step F: N-(3-(Diethylamino)-1H-pyrazolo[3,4-b]pyridin-5-yl)-2,6-difluoro-3-(propylsulfonamido)benzamide (13 mg, 57% yield) was prepared according to Example 1, Step E, substituting N3,N3-diethyl-1H-pyrazolo[3,4-b]pyridine-3,5-diamine for 1H-pyrazolo[3,4-b]pyridin-5-amine. $^1$H NMR (400 MHz, CD$_3$OD) δ 8.7 (s, 1H), 8.5 (s, 1H), 7.7 (m, 1H), 7.1 (m, 1H), 3.5 (m, 4H), 3.1 (m, 2H), 1.9 (m, 2H), 1.2 (m, 6H), 1.1 (t, J=7.6 Hz, 3H); m/z (APCI-pos) M+1=467.1.

Example 50

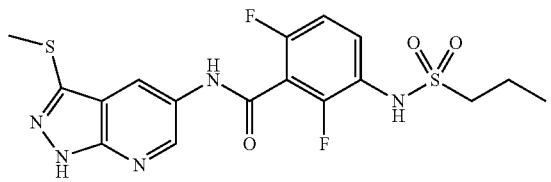

2,6-difluoro-N-(3-(methylthio)-1H-pyrazolo[3,4-b]pyridin-5-yl)-3-(propylsulfonamido)benzamide Step A: Ethyl 2-cyanoacetate (2.00 mL, 18.7 mmol) was added dropwise to a cold suspension (0° C.) of NaH (1.50 g, 37.5 mmol, 60% in mineral oil) in benzene (20 mL), followed by the addition of CS$_2$ (1.7 mL, 28.1 mmol). DMF (4 mL) was added slowly. The mixture was stirred for 30 minutes before MeI (3.52 mL, 56.2 mmol) was added. The resulting mixture was stirred at room temperature overnight. Benzene (50 mL) was added, and the yellow slurry was quenched with ice-water. The organic layer was separated, dried, filtered and concentrated. The crude product was purified by column chromatography, eluting with hexanes/ethyl acetate (4:1) to give ethyl 2-cyano-3,3-bis(methylthio)acrylate (2.2 g, 54%) as a solid.

Step B: A solution of ethyl 2-cyano-3,3-bis(methylthio)acrylate (2.2 g, 10.1 mmol) and hydrazine (0.325 mL, 10.1 mmol) in 2-propanol (20 mL) was heated at reflux overnight. The reaction mixture was cooled to room temperature and concentrated. The crude product was purified by column chromatography, eluting with hexanes/ethyl acetate (1:1) to give ethyl 5-amino-3-(methylthio)-1H-pyrazole-4-carboxylate (1.2 g, 59%) as a solid. m/z (APCI-pos) M+1=202.0.

Step C: Ethyl 5-amino-3-(methylthio)-1H-pyrazole-4-carboxylate (1.2 g, 5.96 mmol) was dissolved in a solution of LiOH (1.14 g, 47.7 mmol) in MeOH/H$_2$O (40 mL, 9:1). The resulting solution was heated at reflux for 72 hours. The reaction mixture was cooled to room temperature and concentrated. The residue was diluted with water, and the insoluble material was removed by filtration. The filtrate was extracted with ethyl acetate (4×100 mL), and the combined organic layers were dried, filtered and concentrated to give 3-(methylthio)-1H-pyrazol-5-amine (0.61 g, 79%) as a solid. m/z (APCI-pos) M+1=130.0.

Step D: 3-(Methylthio)-5-nitro-1H-pyrazolo[3,4-b]pyridine was prepared according to Example 4, Step A using 3-(methylthio)-1H-pyrazol-5-amine (0.600 g, 83%). m/z (APCI-nega) M−1=209.2.

Step E: 3-(Methylthio)-1H-pyrazolo[3,4-b]pyridin-5-amine was prepared according to Example 4, Step B using 3-(methylthio)-5-nitro-1H-pyrazolo[3,4-b]pyridine (0.500 g, 97%). m/z (APCI-pos) M+1=181.1.

Step F: 2,6-Difluoro-N-(3-(methylthio)-1H-pyrazolo[3,4-b]pyridin-5-yl)-3-(propylsulfonamido)benzamide was prepared according to Example 1, Step E using 3-(methylthio)-1H-pyrazolo[3,4-b]pyridin-5-amine (0.075 g, 61%). $^1$H NMR (400 MHz, CD$_3$OD) δ 8.7 (s, 1H), 8.6 (s, 1H), 7.7 (m, 1H), 7.1 (m, 1H), 3.1 (m, 2H), 2.6 (s, 3H), 1.9 (m, 2H), 1.1 (t, J=7.6 Hz, 3H); m/z (APCI-pos) M+1=442.0.

Example 51

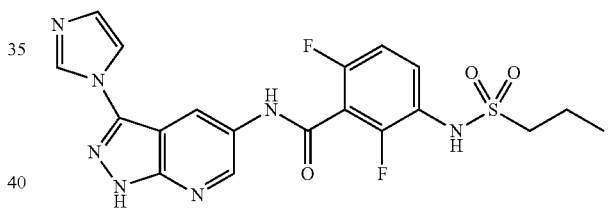

N-(3-(1H-imidazol-1-yl)-1H-pyrazolo[3,4-b]pyridin-5-yl)-2,6-difluoro-3-(propylsulfonamido)benzamide Step A: Imidazole (280 mg, 4.1 mmol), potassium carbonate (1.40 g, 10 mmol), L-proline (95 mg, 0.82 mmol), and cuprous iodide (78 mg, 0.41 mmol) were added to 3-bromo-5-nitro-pyrazolopyridine (500 mg, 2.1 mmol) in DMSO (5 mL). The resulting mixture was heated in a sealed vial at 110° C. overnight. The reaction mixture was diluted with water and 10% isopropyl alcohol ("IPA")/DCM. The resulting slurry was filtered through celite, and the layers were separated. The aqueous layer was extracted with another portion of 10% IPA/DCM. The combined organic layers were washed twice with brine, dried over magnesium sulfate, filtered, and evaporated to yield 3-(1H-imidazol-1-yl)-5-nitro-1H-pyrazolo[3,4-b]pyridine (220 mg, 46% yield) as a solid.

Step B: SnCl$_2$.2H$_2$O (1.03 g, 4.56 mmol) was added to 3-(1H-imidazol-1-yl)-5-nitro-1H-pyrazolo[3,4-b]pyridine (210 mg, 0.912 mmol) in ethyl acetate (100 mL). The mixture was heated to reflux for 1 hour. The cooled reaction mixture was diluted with ethyl acetate and treated dropwise with saturated aqueous sodium bicarbonate. The slurry was stirred for 30 minutes and then filtered through celite. The filtrate was washed with saturated aqueous sodium bicarbonate, brine, dried over magnesium sulfate, filtered, and evaporated to yield 3-(1H-imidazol-1-yl)-1H-pyrazolo[3,4-b]pyridin-5-amine (90 mg, 49% yield) as a solid.

Step C: 2,6-Difluoro-3-(propylsulfonamido)benzoic acid (140 mg, 0.495 mmol), HOBt.H₂O (89 mg, 0.584 mmol), and EDCI (120 mg, 0.674 mmol) was added to 3-(1H-imidazol-1-yl)-1H-pyrazolo[3,4-b]pyridin-5-amine (90 mg, 0.450 mmol) in DMF (10 mL). The mixture was stirred at ambient temperature overnight. The reaction mixture was evaporated, and the residue partitioned between ethyl acetate and water. The ethyl acetate was washed with brine, dried over magnesium sulfate, filtered, and concentrated to an oil. The crude product was purified by column chromatography (10:1 DCM:MeOH), which was followed by trituration with DCM to afford N-(3-(1H-imidazol-1-yl)-1H-pyrazolo[3,4-b]pyridin-5-yl)-2,6-difluoro-3-(propylsulfonamido)benzamide (57.7 mg, 28% yield) as a solid. $^1$H NMR (400 MHz, CD$_3$OD) δ 8.80 (d, 1H), 8.74 (d, 1H), 8.36 (s, 1H), 7.80 (s, 1H), 7.70-7.64 (m, 1H), 7.27 (s, 1H), 7.17-7.12 (m, 1H), 3.14-3.09 (m, 2H), 1.92-1.82 (m, 2H), 1.06 (t, 3H); m/z (ESI-pos) M+1 462.2.

Example 52

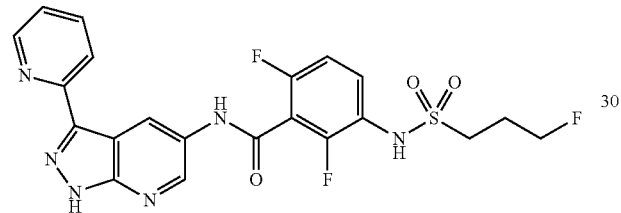

2,6-difluoro-3-(3-fluoropropylsulfonamido)-N-(3-(pyridin-2-yl)-1H-pyrazolo[3,4-b]pyridin-5-yl)benzamide Step A: 3-(2-Pyridyl)-3-oxopropanenitrile (3.0 g, 0.37 mol) was dissolved in ethanol (22 mL) and treated with hydrazine (1.9 mL, 0.062 mol) at reflux for 24 hours. The reaction mixture was concentrated, diluted with brine and extracted into ethyl acetate (2×50 mL). The combined organic layers were dried (MgSO$_4$), concentrated and purified by silica gel chromatography eluting with 2-20% methanol in methylene chloride to afford 3-(pyridin-2-yl)-1H-pyrazol-5-amine (3.0 g, 91% yield).

Step B: A 50 mL reaction vessel was charged with 3-(pyridin-2-yl)-1H-pyrazol-5-amine (1.5 g, 9.4 mmol), sodium nitromalonaldehyde monohydrate (1.54 g, 9.8 mmol) and water (9 mL). The flask was heated to 100° C. overnight, and the cooled reaction mixture was extracted with ethyl acetate (3×25 mL). The combined organic layers were dried (MgSO$_4$), to provide crude 3-(pyridin-2-yl)-5-nitro-1H-pyrazolo[3,4-b]pyridine (2.0 g, 88% yield) as a solid.

Step C: A 50 ml round bottom flask was charged with 3-(pyridin-2-yl)-5-nitro-1H-pyrazolo[3,4-b]pyridine (0.10 g, 0.41 mmol) and tin dichloride (1.0 g, 5.2 mmol) in ethyl acetate (10 mL) and methanol (10 mL) and was heated to reflux for 3 hours. The reaction mixture was cooled and poured into saturated aqueous sodium bicarbonate and filtered through celite. The organic layer was separated, dried (MgSO$_4$), and concentrated. The residue was purified by silica gel chromatography eluting with 10-60% methanol in methylene chloride to afford 3-(pyridin-2-yl)-1H-pyrazolo[3,4-b]pyridin-5-amine (52 mg, 59% yield) as a solid.

Step D: 2,6-Difluoro-N-(3-(pyridin-2-yl)-1H-pyrazolo[3,4-b]pyridin-5-yl)-3-(propylsulfonamido)benzamide was prepared according to Example 1, Step E using 3-(pyridin-2-yl)-1H-pyrazolo[3,4-b]pyridin-5-amine (52 mg, 45% yield). $^1$H NMR (400 MHz, d$_6$-DMSO) δ 13.98 (s, 1H), 11.16 (s, 1H), 9.79 (s, 1H), 9.29 (d, J=2.3, 1H), 8.77 (d, J=2.3, 1H), 8.74 (d, J=3.5, 1H), 8.19 (d, J=8.0, 1H), 7.93 (t, J=7.8, 1H), 7.62-7.53 (m, 1H), 7.43-7.38 (m, 1H), 7.32-7.25 (m, 1H), 3.18-3.10 (m, 2H), 1.84-1.72 (m, 2H), 1.00 (t, J=7.4, 3H); m/z (APCI-pos) M+1=473.1.

Example 53

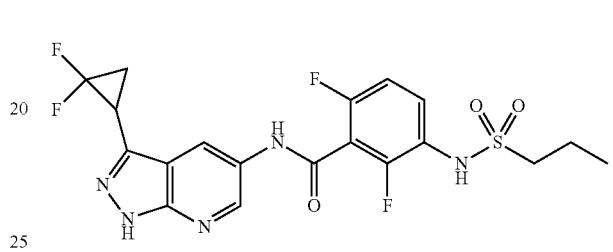

N-3-(2,2-difluorocyclopropyl)-1H-pyrazolo[3,4-b]pyridin-5-yl)-2,6-difluoro-3-(propylsulfonamido)benzamide Step A: A solution of acetonitrile (0.97 mL, 18.5 mmol) in tetrahydrofuran (50 mL) was cooled to −78° C. and treated with n-butyllithium in hexanes (11.7 mL, 19.0 mmol) over 5 minutes. The reaction mixture was stirred for 30 minutes, and then n-butyl 2,2-difluorocyclopropane carboxylate (3.0 g, 16.8 mmol) was added. The reaction mixture was allowed to warm to room temperature over 2 hours. The reaction mixture was poured into water (25 mL) and acidified by addition of 10% aqueous hydrochloric acid. The organic layers were extracted into diethyl ether (3×30 mL), dried (MgSO$_4$) and concentrated to afford crude 3-(2,2-difluorocyclopropyl)-3-oxo-propionitrile (2 g).

Step B: Crude 3-(2,2-difluorocyclopropyl)-3-oxo-propionitrile (2 g) was dissolved in ethanol (18 mL) and treated with hydrazine (2.5 mL, 0.050 mol) at reflux for 24 hours. The reaction mixture was concentrated, diluted with brine and extracted into ethyl acetate (2×50 mL). The combined organic layers were dried (MgSO$_4$), concentrated and purified by silica gel chromatography eluting with 1-15% methanol in methylene chloride to afford 3-(2,2-difluorocyclopropyl)-1H-pyrazol-5-amine (1.8 g, 54% yield).

Step C: 3-(2,2-Difluorocyclopropane)-5-nitro-1H-pyrazolo[3,4-b]pyridine was prepared according to Example 4, Step A, substituting 3-(2,2-difluorocyclopropane)-1H-pyrazol-5-amine for 3-methyl-1H-pyrazol-5-amine.

Step D: 3-(2,2-Difluorocyclopropane)-1H-pyrazolo[3,4-b]pyridin-5-amine was prepared according to Example 4, Step B, substituting 3-(2,2-difluorocyclopropane)-5-nitro-1H-pyrazolo[3,4-b]pyridine for 3-methyl-5-nitro-1H-pyrazolo[3,4-b]pyridine.

Step E: 2,6-Difluoro-N-(3-(2,2-difluorocyclopropane)-1H-pyrazolo[3,4-b]pyridin-5-yl)-3-(propylsulfonamido)benzamide was prepared according to Example 1, Step C, substituting 3-(2,2-difluorocyclopropane)-1H-pyrazolo[3,4-b]pyridin-5-amine for 3-methyl-1H-pyrazolo[3,4-b]pyridin-5-amine. The final product was purified by reverse phase chromatography to afford racemic 2,6-difluoro-N-(3-(2,2-difluorocyclopropyl)-1H-pyrazolo[3,4-b]pyridin-5-yl)-3-(propylsulfonamido)benzamide. $^1$H NMR (400 MHz, d$_6$-DMSO) δ 13.60 (s, 1H), 11.08 (s, 1H), 10.06-9.31 (m, 1H), 8.70 (d, J=2.2, 1H), 8.62 (d, J=2.2, 1H), 7.54 (dd, J=9.1, 15.0, 1H), 7.24 (t, J=8.7, 1H), 3.50-3.30 (m, 2H), 3.13-3.04 (m, 1H), 2.60-2.51 (m, 2H), 2.30-2.05 (m, 1H), 1.82-1.70 (m, 1H), 1.03-0.95 (m, 3H); m/z (APCI-pos) M+1=472.1.

Racemic 2,6-difluoro-N-(3-(2,2-difluorocyclopropyl)-1H-pyrazolo[3,4-b]pyridin-5-yl)-3-(propylsulfonamido) benzamide was purified using chiral HPLC to afford the pure enantiomers:

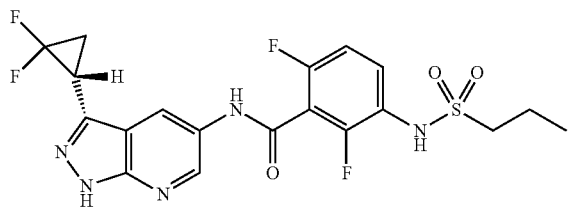

(R)—N-(3-(2,2-difluorocyclopropyl)-1H-pyrazolo[3,4-b]pyridin-5-yl)-2,6-difluoro-3-(propylsulfonamido)benzamide: $^1$H NMR (400 MHz, d$_6$-DMSO) δ 13.60 (s, 1H), 11.09 (s, 1H), 10.03-9.30 (m, 1H), 8.70 (d, J=2.2, 1H), 8.60 (d, J=2.2, 1H), 7.54 (dd, J=9.1, 15.0, 1H), 7.22 (t, J=8.7, 1H), 3.50-3.30 (m, 2H), 3.13-3.04 (m, 1H), 2.60-2.50 (m, 2H), 2.32-2.05 (m, 1H), 1.84-1.70 (m, 1H), 1.03-0.95 (m, 3H); m/z (APCI-pos) M+1=472.1.

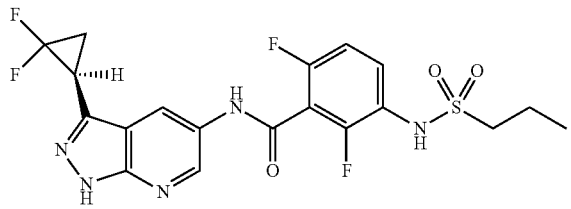 [SMILES: CCCS(=O)(=O)Nc1ccc(F)c(C(=O)Nc2cnc3[nH]nc([C@@H]4CC4(F)F)c3c2)c1F]

(S)—N-(3-(2,2-difluorocyclopropyl)-1H-pyrazolo[3,4-b]pyridin-5-yl)-2,6-difluoro-3-(propylsulfonamido)benzamide: $^1$H NMR (400 MHz, d$_6$-DMSO) δ 13.60 (s, 1H), 11.10 (s, 1H), 10.10-9.27 (m, 1H), 8.69 (d, J=2.2, 1H), 8.62 (d, J=2.3, 1H), 7.54 (dd, J=9.1, 15.0, 1H), 7.23 (t, J=8.6, 1H), 3.48-3.35 (m, 2H), 3.12-3.05 (m, 1H), 2.60-2.52 (m, 2H), 2.25-2.05 (m, 1H), 1.82-1.70 (m, 1H), 1.08-0.85 (m, 3H); m/z (APCI-pos) M+1=472.1.

Example 54

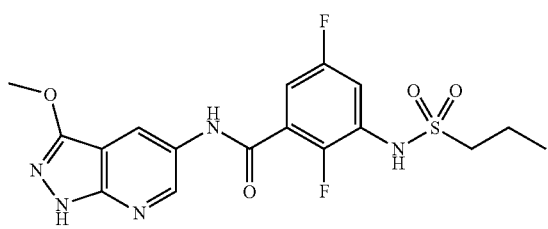 [SMILES: CCCS(=O)(=O)Nc1cc(F)cc(C(=O)Nc2cnc3[nH]nc(OC)c3c2)c1F]

2,5-difluoro-N-(3-methoxy-1H-pyrazolo[3,4-b]pyridin-5-yl)-3-(propylsulfonamido)benzamide Step A: 2,5-Difluoro-N-(3-methoxy-1-(4-methoxybenzyl)-1H-pyrazolo[3,4-b]pyridin-5-yl)-3-(propylsulfonamido)benzamide was prepared according to the general procedure for Example 20, Step F, substituting 2,5-difluoro-3-(propylsulfonamido)benzoic acid for 2,6-difluoro-3-(propylsulfonamido)benzoic acid.

Step B: 2,5-Difluoro-N-(3-methoxy-1H-pyrazolo[3,4-b]pyridin-5-yl)-3-(propylsulfonamido)benzamide (57%, 2 steps) was prepared according to the general procedure for Example 20, Step G, substituting 2,5-difluoro-N-(3-methoxy-1-(4-methoxybenzyl)-1H-pyrazolo[3,4-b]pyridin-5-yl)-3-(propylsulfonamido)benzamide for 2,6-difluoro-N-(3-methoxy-1-(4-methoxybenzyl)-1H-pyrazolo[3,4-b]pyridin-5-yl)-3-(propylsulfonamido)benzamide. $^1$H NMR (400 MHz, d$_6$-DMSO) δ 12.58 (s, 1H), 10.75 (s, 1H), 10.14 (br s, 1H), 7.36-7.46 (m, 2H), 4.02 (s, 3H), 3.21-3.25 (m, 2H), 1.73-1.79 (m, 2H), 0.98-1.01 (m, 3H); m/z (APCI-pos) M+1=426.1.

Example 55

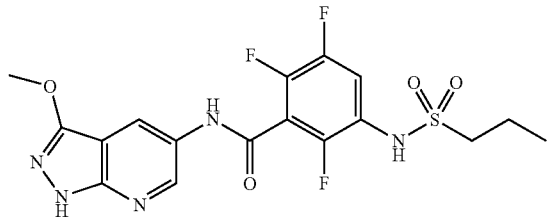 [SMILES: CCCS(=O)(=O)Nc1cc(F)c(F)c(C(=O)Nc2cnc3[nH]nc(OC)c3c2)c1F]

2,3,6-trifluoro-N-(3-methoxy-1H-pyrazolo[3,4-b]pyridin-5-yl)-5-(propylsulfonamido)benzamide Step A: 2,3,6-Trifluoro-N-(3-methoxy-1-(4-methoxybenzyl)-1H-pyrazolo[3,4-b]pyridin-5-yl)-3-(propylsulfonamido)benzamide was prepared according to the general procedure for Example 20, Step F, substituting 2,3,6-trifluoro-3-(propylsulfonamido)benzoic acid for 2,6-difluoro-3-(propylsulfonamido)benzoic acid.

Step B: 2,3,6-Trifluoro-N-(3-methoxy-1H-pyrazolo[3,4-b]pyridin-5-yl)-3-(propylsulfonamido)benzamide (66%, 2 steps) was prepared according to the general procedure for Example 20, Step G, substituting 2,3,6-difluoro-N-(3-methoxy-1-(4-methoxybenzyl)-1H-pyrazolo[3,4-b]pyridin-5-yl)-3-(propylsulfonamido)benzamide for 2,6-difluoro-N-(3-methoxy-1-(4-methoxybenzyl)-1H-pyrazolo[3,4-b]pyridin-5-yl)-3-(propylsulfonamido)benzamide. $^1$H NMR (400 MHz, d$_6$-DMSO) δ 12.63 (s, 1H), 11.19 (s, 1H), 10.08 (s, 1H), 8.57 (s, 1H), 8.48 (s, 1H), 7.63-7.70 (m, 1H), 4.02 (s, 3H), 3.18-3.22 (m, 2H), 1.73-1.79 (m, 2H), 0.98-1.01 (m, 3H); m/z (APCI-pos) M+1=442.2.

Example 56

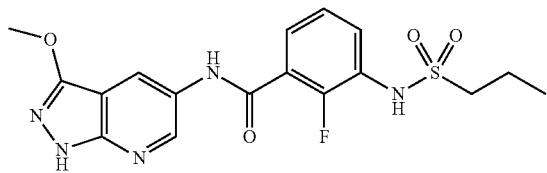 [SMILES: CCCS(=O)(=O)Nc1cccc(C(=O)Nc2cnc3[nH]nc(OC)c3c2)c1F]

2-fluoro-N-(3-methoxy-1H-pyrazolo[3,4-b]pyridin-5-yl)-3-(propylsulfonamido)benzamide Step A: 2-Fluoro-N-(3-methoxy-1-(4-methoxybenzyl)-1H-pyrazolo[3,4-b]pyridin-5-yl)-3-(propylsulfonamido) benzamide was prepared according to the general procedure for Example 20, Step F, substituting 2-fluoro-3-(propylsulfonamido)benzoic acid for 2,6-difluoro-3-(propylsulfonamido)benzoic acid.

Step B: 2-Fluoro-N-(3-methoxy-1H-pyrazolo[3,4-b]pyridin-5-yl)-3-(propylsulfonamido)benzamide (74%, 2 steps) was prepared according to the general procedure for Example 20, Step G, substituting 2-fluoro-N-(3-methoxy-1-(4-methoxybenzyl)-1H-pyrazolo[3,4-b]pyridin-5-yl)-3-(propylsulfonamido)benzamide for 2,6-difluoro-N-(3-methoxy-1-(4-methoxybenzyl)-1H-pyrazolo[3,4-b]pyridin-5-yl)-3-(propylsulfonamido)benzamide. $^1$H NMR (400 MHz, $d_6$-DMSO) δ 12.57 (s, 1H), 10.70 (s, 1H), 9.83 (br s, 1H), 8.64 (s, 1H), 8.48 (s, 1H), 7.57 (br s, 1H), 7.51 (br s, 1H), 7.30-7.32 (m, 1H), 4.01 (s, 3H), 3.13-3.17 (m, 2H), 1.76-1.78 (m, 2H), 0.97-1.00 (m, 3H); m/z (APCI-pos) M+1=408.1.

Example 57

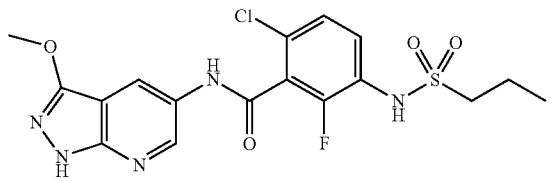 [SMILES: CCCS(=O)(=O)Nc1ccc(Cl)c(C(=O)Nc2cnc3[nH]nc(OC)c3c2)c1F]

6-chloro-2-fluoro-N-(3-methoxy-1H-pyrazolo[3,4-b]pyridin-5-yl)-3-(propylsulfonamido)benzamide Step A: 6-Chloro-2-fluoro-N-(3-methoxy-1-(4-methoxybenzyl)-1H-pyrazolo[3,4-b]pyridin-5-yl)-3-(propylsulfonamido)benzamide was prepared according to the general procedure for Example 20, Step F, substituting 6-chloro-2-fluoro-3-(propylsulfonamido)benzoic acid for 2,6-difluoro-3-(propylsulfonamido)benzoic acid.

Step B: 6-Chloro-2-fluoro-N-(3-methoxy-1H-pyrazolo[3,4-b]pyridin-5-yl)-3-(propylsulfonamido)benzamide (77%, 2 steps) was prepared according to the general procedure for Example 20, Step G, substituting 6-chloro-2-fluoro-N-(3-methoxy-1-(4-methoxybenzyl)-1H-pyrazolo[3,4-b]pyridin-5-yl)-3-(propylsulfonamido)benzamide for 2,6-difluoro-N-(3-methoxy-1-(4-methoxybenzyl)-1H-pyrazolo[3,4-b]pyridin-5-yl)-3-(propylsulfonamido)benzamide. $^1$H NMR (400 MHz, $d_6$-DMSO) δ 12.60 (s, 1H), 11.07 (s, 1H), 9.97 (br s, 1H), 8.58 (s, 1H), 8.48 (s, 1H), 7.52-7.57 (m, 1H), 7.44-7.46 (m, 1H), 4.02 (s, 3H), 3.15-3.19 (m, 2H), 1.73-1.79 (m, 2H), 0.97-1.01 (m, 3H); m/z (APCI-pos) M+1=442.1, 444.0.

Example 58

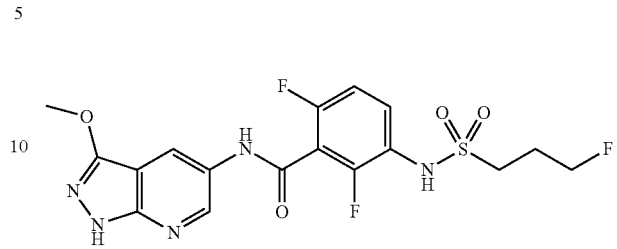

2,6-difluoro-3-(3-fluoropropylsulfonamido)-N-(3-methoxy-1H-pyrazolo[3,4-b]pyridin-5-yl)benzamide Step A: 2,6-Difluoro-3-(3-fluoropropylsulfonamido)-N-(3-methoxy-1-(4-methoxybenzyl)-1H-pyrazolo[3,4-b]pyridin-5-yl)benzamide was prepared according to the general procedure for Example 20, Step F, substituting 2,6-difluoro-3-(3-fluoropropylsulfonamido)benzoic acid for 2,6-difluoro-3-(propylsulfonamido)benzoic acid.

Step B: 2,6-Difluoro-3-(3-fluoropropylsulfonamido)-N-(3-methoxy-1H-pyrazolo[3,4-b]pyridin-5-yl)benzamide (64%, 2 steps) was prepared according to the general procedure for Example 20, Step G, substituting 2,6-difluoro-3-(3-fluoropropylsulfonamido)-N-(3-methoxy-1-(4-methoxybenzyl)-1H-pyrazolo[3,4-b]pyridin-5-yl)benzamide for 2,6-difluoro-N-(3-methoxy-1-(4-methoxybenzyl)-1H-pyrazolo[3,4-b]pyridin-5-yl)-3-(propylsulfonamido)benzamide. $^1$H NMR (400 MHz, $d_6$-DMSO) δ 12.60 (s, 1H), 11.10 (s, 1H), 9.94 (br s, 1H), 8.59 (s, 1H), 8.49 (s, 1H), 7.54-7.60 (m, 1H), 7.27-7.31 (m, 1H), 4.64-4.61 (m, 1H), 4.49-4.52 (m, 1H), 4.02 (s, 3H), 3.24-3.28 (m, 2H), 2.07-2.21 (m, 2H); m/z (APCI-pos) M+1=444.1.

Example 59

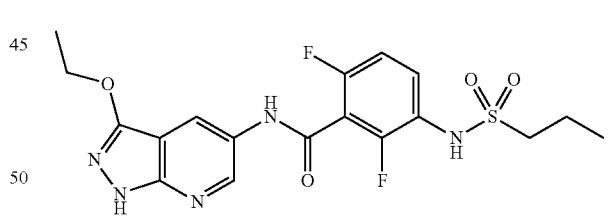

N-(3-ethoxy-1H-pyrazolo[3,4-b]pyridin-5-yl)-2,6-difluoro-3-(propylsulfonamido)benzamide Step A: 5-Bromo-3-ethoxy-1-(4-methoxybenzyl)-1H-pyrazolo[3,4-b]pyridine (62%) was prepared according to the general procedure for Example 20, Step C, substituting ethyl iodide for methyl iodide.

Step B: tert-Butyl 3-ethoxy-1-(4-methoxybenzyl)-1H-pyrazolo[3,4-b]pyridin-5-ylcarbamate (33%) was prepared according to the general procedure for Example 20, Step D, substituting 5-bromo-3-ethoxy-1-(4-methoxybenzyl)-1H-pyrazolo[3,4-b]pyridine for 5-bromo-3-methoxy-1-(4-methoxybenzyl)-1H-pyrazolo[3,4-b]pyridine.

Step C: 3-Ethoxy-1-(4-methoxybenzyl)-1H-pyrazolo[3,4-b]pyridin-5-amine (56%) was prepared according to the general procedure for Example 20, Step E, substituting tert-butyl 3-ethoxy-1-(4-methoxybenzyl)-1H-pyrazolo[3,4-b]pyridin-5-ylcarbamate for tert-butyl 3-methoxy-1-(4-methoxybenzyl)-1H-pyrazolo[3,4-b]pyridin-5-ylcarbamate.

Step D: N-(3-Ethoxy-1-(4-methoxybenzyl)-1H-pyrazolo[3,4-b]pyridin-5-yl)-2,6-difluoro-3-(propylsulfonamido)benzamide was prepared according to the general procedure for Example 20, Step F, substituting 3-ethoxy-1-(4-methoxybenzyl)-1H-pyrazolo[3,4-b]pyridin-5-amine for 3-methoxy-1-(4-methoxybenzyl)-1H-pyrazolo[3,4-b]pyridin-5-amine.

Step E: N-(3-Ethoxy-1H-pyrazolo[3,4-b]pyridin-5-yl)-2,6-difluoro-3-(propylsulfonamido)benzamide (83%, 2 steps) was prepared according to the general procedure for Example 20, Step G, substituting N-(3-ethoxy-1-(4-methoxybenzyl)-1H-pyrazolo[3,4-b]pyridin-5-yl)-2,6-difluoro-3-(propylsulfonamido)benzamide for 2,6-difluoro-N-(3-methoxy-1-(4-methoxybenzyl)-1H-pyrazolo[3,4-b]pyridin-5-yl)-3-(propylsulfonamido)benzamide. $^1$H NMR (400 MHz, d$_6$-DMSO) δ 12.60 (s, 1H), 11.07 (s, 1H), 9.97 (br s, 1H), 8.58 (s, 1H), 8.48 (s, 1H), 7.52-7.57 (m, 1H), 7.44-7.46 (m, 1H), 4.02 (s, 3H), 3.15-3.19 (m, 2H), 1.73-1.79 (m, 2H), 0.97-1.01 (m, 3H); m/z (APCI-pos) M+1=442.1, 444.0.

Example 60

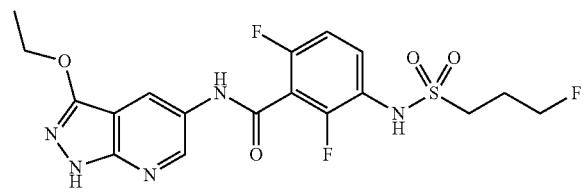 [SMILES: CCOc1n[nH]c2ncc(NC(=O)c3c(F)ccc(NS(=O)(=O)CCCF)c3F)cc12]

N-(3-ethoxy-1H-pyrazolo[3,4-b]pyridin-5-yl)-2,6-difluoro-3-(3-fluoropropylsulfonamido)benzamide Step A: N-(3-Ethoxy-1-(4-methoxybenzyl)-1H-pyrazolo[3,4-b]pyridin-5-yl)-2,6-difluoro-3-(3-fluoropropylsulfonamido)benzamide was prepared according to the general procedure for Example, Step F, substituting 3-ethoxy-1-(4-methoxybenzyl)-1H-pyrazolo[3,4-b]pyridin-5-amine for 3-methoxy-1-(4-methoxybenzyl)-1H-pyrazolo[3,4-b]pyridin-5-amine and substituting 2,6-difluoro-3-(3-fluoropropylsulfonamido)benzoic acid for 2,6-difluoro-3-(propylsulfonamido)benzoic acid.

Step B: N-(3-Ethoxy-1H-pyrazolo[3,4-b]pyridin-5-yl)-2,6-difluoro-3-fluoropropylsulfonamido)benzamide (82%, 2 steps) was prepared according to the general procedure for Example 20, Step G, substituting N-(3-ethoxy-1-(4-methoxybenzyl)-1H-pyrazolo[3,4-b]pyridin-5-yl)-2,6-difluoro-3-(3-fluoropropylsulfonamido)benzamide for 2,6-difluoro-N-(3-methoxy-1-(4-methoxybenzyl)-1H-pyrazolo[3,4-b]pyridin-5-yl)-3-(propylsulfonamido)benzamide $^1$H NMR (400 MHz, d$_6$-DMSO) δ 12.57 (s, 1H), 11.10 (s, 1H), 9.94 (br s, 1H), 8.55 (s, 1H), 8.51 (s, 1H), 7.56-7.60 (m, 1H), 7.27-7.32 (m, 1H), 4.61-4.64 (m, 1H), 4.49-4.52 (m, 1H), 4.36-4.42 (m, 2H), 3.24-3.28 (m, 2H), 2.08-2.20, 1.40-1.43 (m, 3H); m/z (APCI-pos) M+1=458.1.

Example 61

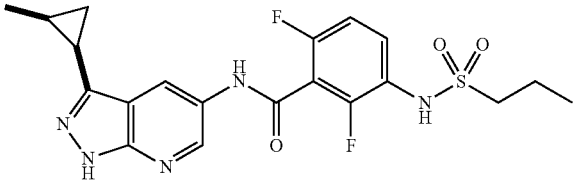

2,6-difluoro-N-(3-(cis-2-methylcyclopropyl)-1H-pyrazolo[3,4-b]pyridin-5-yl)-3-(propylsulfonamido)benzamide Step A: Acetonitrile (0.102 mL, 1.95 mmol) was dissolved in THF. Potassium 2,2-dimethylpropan-1-olate (3.44 mL, 5.85 mmol) was added, followed by addition of ethyl-2-methylcyclopropanecarboxylate (1.0 g, 7.80 mmol). After five minutes, the reaction mixture was quenched with 1N HCl and then partitioned with EtOAc. The organic layer was washed with water (3×), brine, dried over Na$_2$SO$_4$ and concentrated to give 3-(2-methylcyclopropyl)-3-oxopropanenitrile as an oil, which was used in the next step without further purification.

Step B: 3-(2-Methylcyclopropyl)-3-oxopropanenitrile (0.240 g, 1.95 mmol) was dissolved in dry ethanol (3 mL). Hydrazine monohydrate (0.728 mL, 9.75 mmol) was added, and the reaction mixture was heated to 80° C. for 20 minutes. The reaction mixture was then cooled to room temperature and concentrated. Silica gel chromatography (5% MeOH/DCM) provided a mixture of cis and trans isomers which were separated by chiral HPLC providing 3-(cis-2-methylcyclopropyl)-1H-pyrazol-5-amine (74 mg, 28% for two steps) as an oil.

Step C: 3-(cis-2-Methylcyclopropyl)-1H-pyrazol-5-amine (0.0742 g, 0.541 mmol) and sodium nitromalonaldehyde hydrate (0.0892 g, 0.568 mmol) were heated in AcOH at 90° C. overnight. Water was added, and the precipitate was collected by filtration. This solid was taken up in water as a slurry and heated to reflux for two days. The solution was cooled to room temperature, and the resulting crystals were collected by filtration. The mother liquor was extracted with DCM (3×), dried over Na$_2$SO$_4$ and concentrated to a solid, which was combined with the crystals to provide 3-(cis-2-methylcyclopropyl)-5-nitro-1H-pyrazolo[3,4-b]pyridine (42 mg, 65%) as a solid.

Step D: 3-(cis-2-Methylcyclopropyl)-5-nitro-1H-pyrazolo[3,4-b]pyridine (0.0462 g, 0.212 mmol) and Pd/C were taken up in MeOH. Hydrogen gas was passed through for 10 minutes, and the reaction mixture was stirred under a hydrogen atmosphere for 20 minutes. The solution was filtered through celite and concentrated to provide 3-(cis-2-methylcyclopropyl)-1H-pyrazolo[3,4-b]pyridin-5-amine as an oil, which was used without further purification.

Step E: 3-(cis-2-Methylcyclopropyl)-1H-pyrazolo[3,4-b]pyridin-5-amine (0.0399 g, 0.212 mmol), 2,6-difluoro-3-(propylsulfonamido)benzoic acid (0.0651 g, 0.233 mmol), EDCI (0.0488 g, 0.254 mmol), and HOBt (0.0344 g, 0.254 mmol) were dissolved in DMF and stirred overnight at room temperature. The solution was partitioned between water and EtOAc. The organic layer was washed with water (3×), brine, dried over Na$_2$SO$_4$ and concentrated to an oil, which was purified by column chromatography (1:2 hexanes/EtOAc) to give 2,6-difluoro-N-(3-((1R,2S)-2-methylcyclopropyl)-1H- pyrazolo[3,4-b]pyridin-5-yl)-3-(propylsulfonamido)benzamide (66 mg, 69%) as a solid. $^1$H NMR (400 MHz, d$_6$-DMSO) 13.16 (s, 1H), 11.07 (s, 1H), 9.81 (s, 1H), 8.63 (s, 1H), 8.55 (s, 1H), 7.53-7.59 (m, 1H), 7.26-7.31 (m, 1H), 3.11-3.15 (m, 2H), 1.99-2.03 (m, 1H), 1.75-1.80 (m, 2H), 1.32-1.34 (m, 1H), 1.14-1.22 (m, 3H) 0.99-1.02 (m, 3H), 0.78-0.83 (m, 3H); m/z (APCI-pos) M+1=450.1.

Example 62

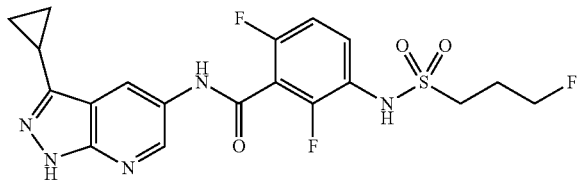 [SMILES: O=C(Nc1cnc2[nH]nc(C3CC3)c2c1)c1c(F)ccc(NS(=O)(=O)CCCF)c1F]

N-(3-cyclopropyl-1H-pyrazolo[3,4-b]pyridin-5-yl)-2,6-difluoro-3-(3-fluoropropylsulfonamido)benzamide 3-Cyclopropyl-1H-pyrazolo[3,4-b]pyridin-5-amine (0.024 g, 0.138 mmol), 2,6-difluoro-3-(3-fluoropropylsulfonamido)benzoic acid (0.045 g, 0.151 mmol), EDCI (0.029 g, 0.151 mmol) and HOBt (0.019 g, 0.138 mmol) were dissolved in DMF (0.52 mL) and stirred at room temperature for 16 hours. The reaction mixture was purified by reverse phase HPLC to give N-(3-cyclopropyl-1H-pyrazolo[3,4-b]pyridin-5-yl)-2,6-difluoro-3-(3-fluoropropylsulfonamido)benzamide (0.031 g, 50%) as a solid. $^1$H NMR (400 MHz, d$_6$-DMSO) δ 13.17 (s, 1H), 11.06 (s, 1H), 9.92 (br s, 1H), 8.63 (s, 1H), 8.56 (s, 1H), 7.60-7.54 (m, 1H), 7.28 (t, 1H), 4.62 (t, 1H), 4.51 (t, 1H), 3.29-3.23 (m, 3H), 2.33-2.26 (m, 1H), 2.19-2.09 (m, 2H), 1.01-0.93 (m, 3H); m/z (ES-MS) 454.2 (100.0%) [M+1].

Example 63

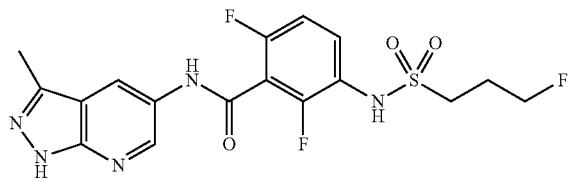 [SMILES: Cc1n[nH]c2ncc(NC(=O)c3c(F)ccc(NS(=O)(=O)CCCF)c3F)cc12]

2,6-difluoro-3-(3-fluoropropylsulfonamido)-N-(3-methyl-1H-pyrazolo[3,4-b]pyridin-5-yl)benzamide 3-Methyl-1H-pyrazolo[3,4-b]pyridin-5-amine (0.100 g, 0.675 mmol, Example 4, Step B), 2,6-difluoro-3-(3-fluoropropylsulfonamido)benzoic acid (0.211 g, 0.709 mmol), EDCI (0.136 g, 0.709 mmol) and HOBt (0.091 g, 0.675 mmol) were dissolved in DMF (1.9 mL) and stirred at room temperature for 16 hours. The reaction mixture was purified by reverse phase HPLC to give 2,6-difluoro-3-(3-fluoropropylsulfonamido)-N-(3-methyl-1H-pyrazolo[3,4-b]pyridin-5-yl)benzamide (0.085 g, 29%) as a solid. $^1$H NMR (400 MHz, d$_6$-DMSO) δ 13.22 (s, 1H), 11.05 (s, 1H), 9.93 (br s, 1H), 8.60-8.59 (m, 1H), 8.55-8.54 (m, 1H), 7.59-7.53 (m, 1H), 7.30-7.25 (m, 1H), 4.62 (t, 1H), 4.50 (t, 1H), 3.26-3.23 (m, 2H), 2.20-2.07 (m, 2H); m/z (ES-MS) 428.1 (100.0%) [M+1].

Example 64

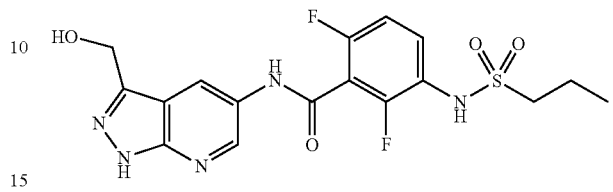

2,6-difluoro-N-(3-(hydroxymethyl)-1H-pyrazolo[3,4-b]pyridin-5-yl)-3-(propylsulfonamido)benzamide Step A: A round-bottom flask was charged with 3-(benzyloxymethyl)-1H-pyrazol-5-amine (1.74 g, 8.56 mmol, Honma, T. et al. "A Novel Approach for the Development of Selective Cdk4 Inhibitors: Library Design Based on Locations of Cdk4 Specific Amino Acid Residues." *J. Med. Chem.* Vol. 44, No. 26 (2001): 4628-4640), sodium nitromalonaldehyde monohydrate (1.46 g, 9.42 mmol) and acetic acid (8.7 mL). The reaction mixture was heated at 100° C. for 24 hours. The reaction mixture was poured into water and then extracted with ethyl acetate (2×). The combined organic layers were dried with sodium sulfate, filtered and concentrated in vacuo. The crude product was purified by flash chromatography to afford 3-(benzyloxymethyl)-5-nitro-1H-pyrazolo[3,4-b]pyridine (1.37 g, 56%) as a solid.

Step B: BBr$_3$ (7.4 mL, 7.4 mmol, 1M in heptane) was added to a solution of 3-(benzyloxymethyl)-5-nitro-1H-pyrazolo[3,4-b]pyridine (0.70 g, 2.46 mmol) in dichloromethane (25 mL) at −78° C., and the reaction mixture was stirred at this temperature for 1 hour. Saturated aqueous NaHCO$_3$ was added, followed by addition of ethyl acetate. The layers were separated, and the aqueous layer extracted with ethyl acetate (2×). The combined organic layers were dried with sodium sulfate, filtered and concentrated in vacuo. The crude product was purified by flash chromatography to afford (5-nitro-1H-pyrazolo[3,4-b]pyridin-3-yl)methanol (417 mg, 87%), as a solid.

Step C: A sealed microwave vial was charged with (5-nitro-1H-pyrazolo[3,4-b]pyridin-3-yl)methanol (0.10 g, 0.515 mmol), iron (0.345 g, 6.18 mmol), ammonium chloride (0.110 g, 2.06 mmol) and ethanol:water (2.25 mL, 4:1). The mixture was heated in a microwave reactor at 110° C. for 20 minutes. The reaction mixture was filtered through a pad of celite. The filtrate was diluted with ethyl acetate and washed with saturated aqueous NaHCO$_3$. The aqueous layer was extracted with ethyl acetate (2×). The combined organic layers were dried with sodium sulfate, filtered and concentrated in vacuo to afford crude (5-amino-1H-pyrazolo[3,4-b]pyridin-3-yl)methanol that was used into the next step without further purification.

Step D: (5-Amino-1H-pyrazolo[3,4-b]pyridin-3-yl)methanol (0.040 g, 0.675 mmol), 2,6-difluoro-3-(propylsulfonamido)benzoic acid (0.071 g, 0.256 mmol), EDCI (0.049 g, 0.256 mmol) and HOBt (0.033 g, 0.244 mmol) were dissolved in DMF (0.53 mL) and stirred at room temperature for 16 hours. The reaction mixture was directly purified by reverse phase HPLC to give 2,6-difluoro-N-(3-(hydroxymethyl)-1H-pyrazolo[3,4-b]pyridin-5-yl)-3-(propylsulfonamido)benzamide (0.051 g, 49%) as a solid. $^1$H NMR (400

MHz, d$_6$-DMSO) δ 13.37 (s, 1H), 11.05 (s, 1H), 9.93 (br s, 1H), 8.74 (d, 1H), 8.58 (d, 1H), 7.58-7.52 (m, 1H), 7.26 (t, 1H), 5.36 (t, 1H), 4.78 (d, 2H), 3.12 (m, 2H), 1.77 (m, 2H), 1.00 (t, 3H); m/z (ES-MS) 426.1 (98.0%) [M+1].

Example 65

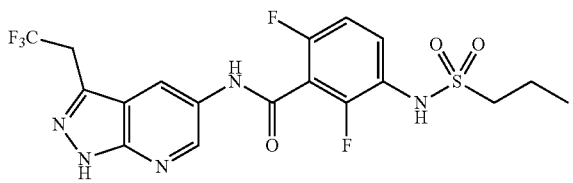 [SMILES: CCCS(=O)(=O)Nc1ccc(F)c(C(=O)Nc2cnc3[nH]nc(CC(F)(F)F)c3c2)c1F]

2,6-difluoro-3-(propylsulfonamido)-N-(3-(2,2,2-trifluoroethyl)-1H-pyrazolo[3,4-b]pyridin-5-yl)benzamide Step A: A round-bottom flask was charged with 3-(2,2,2-trifluoroethyl)-1H-pyrazol-5-amine (0.145 g, 0.878 mmol, WO 2008/005956), sodium nitromalonaldehyde monohydrate (0.150 g, 0.966 mmol) and water (3.5 mL). The reaction mixture was heated at 85° C. for 16 hours. The reaction mixture was poured into water and subsequently extracted with ethyl acetate (2×). The combined organic layers were dried with sodium sulfate, filtered and concentrated in vacuo. The crude product was purified by flash chromatography to afford 5-nitro-3-(2,2,2-trifluoroethyl)-1H-pyrazolo[3,4-b]pyridine (0.078 g, 36%).

Step B: 3-(2,2,2-Trifluoroethyl)-1H-pyrazolo[3,4-b]pyridin-5-amine was prepared according to Example 64, Step C, substituting 5-nitro-3-(2,2,2-trifluoroethyl)-1H-pyrazolo[3,4-b]pyridine for (5-nitro-1H-pyrazolo[3,4-b]pyridin-3-yl)methanol.

Step C: 2,6-Difluoro-3-(propylsulfonamido)-N-(3-(2,2,2-trifluoroethyl)-1H-pyrazolo[3,4-b]pyridin-5-yl)benzamide was prepared according to Example 64, Step D, substituting 3-(2,2,2-trifluoroethyl)-1H-pyrazolo[3,4-b]pyridin-5-amine for (5-amino-1H-pyrazolo[3,4-b]pyridin-3-yl)methanol. $^1$H NMR (400 MHz, d$_6$-DMSO) δ 13.77 (s, 1H), 11.13 (s, 1H), 9.79 (br s, 1H), 8.72-8.71 (m, 1H), 8.64-8.63 (m, 1H), 7.59-7.53 (m, 1H), 7.27 (t, 1H), 4.10 (q, 2H), 3.14-3.10 (m, 2H), 1.77 (m, 2H), 1.00 (t, 3H); m/z (ES-MS) 478.1 (100.0%) [M+1].

Example 66

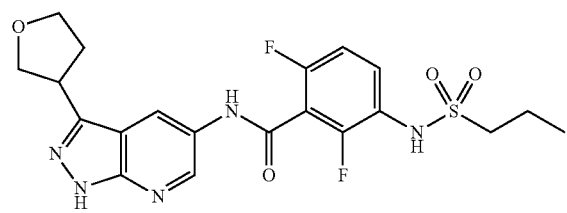 [SMILES: CCCS(=O)(=O)Nc1ccc(F)c(C(=O)Nc2cnc3[nH]nc(C4CCOC4)c3c2)c1F]

2,6-difluoro-3-(propylsulfonamido)-N-(3-(tetrahydrofuran-3-yl)-1H-pyrazolo[3,4-b]pyridin-5-yl)benzamide Step A: A solution of KOt-Amyl (1.7M in toluene, 7.47 mL, 12.7 mmol) was added slowly to a solution of acetonitrile (276 μL 5.28 mmol) in THF (14 mL, 0.3M). Methyl tetrahydrofuran-3-carboxylate (550 mg, 4.23 mmol) was added dropwise, and the reaction mixture was stirred at room temperature for 2 hours. The mixture was then quenched with 0.5M HCl (30 mL) and extracted with EtOAc (100 mL). The organic layer was washed with water (3×25 mL) and brine (25 mL), dried (Na$_2$SO$_4$), filtered, and concentrated. The crude product 3-oxo-3-(tetrahydrofuran-3-yl)propanenitrile was taken directly on to Step B.

Step B: 3-(Tetrahydrofuran-3-yl)-1H-pyrazol-5-amine (195 mg, 30% yield for Steps A and B) was prepared according to Example 8, Step A, substituting 3-oxo-3-(tetrahydrofuran-3-yl)propanenitrile for tert-butyl 4-(2-cyanoacetyl)piperidine-1-carboxylate.

Step C: 5-Nitro-3-(tetrahydrofuran-3-yl)-1H-pyrazolo[3,4-b]pyridine (185 mg, 80% yield) was prepared according to Example 4, Step A, substituting 3-(tetrahydrofuran-3-yl)-1H-pyrazol-5-amine for 3-methyl-1H-pyrazol-5-amine.

Step D: 3-(Tetrahydrofuran-3-yl)-1H-pyrazolo[3,4-b]pyridin-5-amine (125 mg, 95% yield) was prepared according to Example 4, Step B, substituting 5-nitro-3-(tetrahydrofuran-3-yl)-1H-pyrazolo[3, 4-1)]pyridine for 3-methyl-5-nitro-1H-pyrazolo[3,4-b]pyridine.

Step E: 2,6-Difluoro-3-(propylsulfonamido)-N-(3-(tetrahydrofuran-3-yl)-1H-pyrazolo[3,4-b]pyridin-5-yl)benzamide was prepared according to Example 1, Step E, substituting 3-(tetrahydrofuran-3-yl)-1H-pyrazolo[3,4-b]pyridin-5-amine for 1H-pyrazolo[3,4-b]pyridin-5-amine (130 mg, 57% yield). $^1$H NMR (400 MHz, d$_6$-DMSO) 13.39 (s, 1H), 11.11 (s, 1H), 9.83 (s, 1H), 8.65-8.62 (m, 2H), 7.60-7.53 (m, 1H), 7.33-7.25 (m, 1H), 4.14-4.09 (m, 1H), 4.00-3.93 (m, 1H), 3.92-3.80 (m, 3H), 3.16-3.10 (m, 2H), 2.45-2.35 (m, 1H), 2.24-2.14 (m, 1H), 1.82-1.72 (m, 1H), 1.00 (t, J=7.4 Hz, 3H). m/z (APCI-pos) M+1=466.1.

Example 67

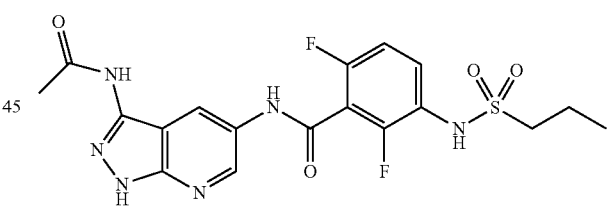

N-(3-acetamido-1H-pyrazolo[3,4-b]pyridin-5-yl)-2,6-difluoro-3-(propylsulfonamido)benzamide Step A: N-(5-Amino-1H-pyrazolo[3,4-b]pyridin-3-yl)acetamide (82 mg, 96% yield) was prepared according to Example 4, Step B, substituting N-(5-nitro-1H-pyrazolo[3,4-b]pyridin-3-yl)acetamide for 3-methyl-5-nitro-1H-pyrazolo[3,4-b]pyridine.

Step B: N-(3-Acetamido-1H-pyrazolo[3,4-b]pyridin-5-yl)-2,6-difluoro-3-(propylsulfonamido)benzamide (51 mg, 51% yield) was prepared according to Example 1, Step E, substituting N-(5-amino-1H-pyrazolo[3,4-b]pyridin-3-yl)acetamide for 1H-pyrazolo[3,4-b]pyridin-5-amine. $^1$H NMR (400 MHz, d$_6$-DMSO) δ 13.23 (s, 1H), 11.05 (s, 1H), 10.65 (s, 1H), 9.81 (s, 1H), 8.73-8.71 (m, 1H), 8.65-8.63 (m, 1H), 7.59-7.52 (m, 1H), 7.30-7.24 (m, 1H), 3.15-3.10 (m, 2H), 2.12 (s, 3H), 1.82-1.72 (m, 2H), 1.00 (t, J=7.5 Hz, 3H); m/z (APCI-pos) M+1=453.1.

Example 68

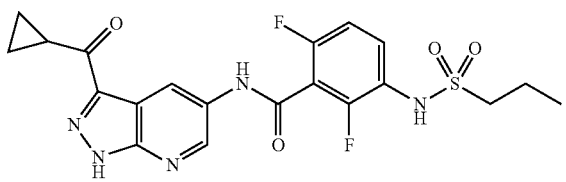 [SMILES: CCCS(=O)(=O)Nc1ccc(F)c(C(=O)Nc2cnc3[nH]nc(C(=O)C4CC4)c3c2)c1F]

N-3-cyclopropanecarbonyl)-1H-pyrazolo[3,4-b]pyridin-5-yl)-2,6-difluoro-3-(propylsulfonamido)benzamide Step A: i-PrMgCl (0.32 mL, 0.64 mmol) was added to 3-iodo-1H-pyrazolo[3,4-b]pyridine (3.1 mL, 0.61 mmol) in THF (3 mL) at 0° C. After 10 minutes, another portion of i-PrMgCl (0.32 mL, 0.64 mmol) was added. After 10 minutes, neat cyclopropanecarbaldehyde (0.074 mL, 0.98 mmol) was added dropwise and stirred at 0° C. for 1 hour. The mixture was diluted with EtOAc (5 mL) and aqueous ammonium chloride, and extracted with EtOAc (2×5 mL). The resulting residue was purified via flash chromatography eluting with EtOAc to afford cyclopropyl(1H-pyrazolo[3,4-b]pyridin-3-yl)methanol (0.052 g, 0.28 mmol, 44.9% yield).

Step B: Cyclopropyl(1H-pyrazolo[3,4-b]pyridin-3-yl)methanol (200 mg, 1.06 mmol) was taken up in DCM (8 mL). Dess-Martin (0.448 g, 1.06 mmol) was added to this solution, which was stirred at room temperature for 10 minutes. A solution of 10% sodium thiosulfate in saturated aqueous bicarbonate was added and resulted in a biphasic solution, which was vigorously stirred for 30 minutes. The organic layers were extracted with DCM (3×10 mL), dried over sodium sulfate and concentrated. Chromatography (EtOAc) afforded cyclopropyl(1H-pyrazolo[3,4-b]pyridin-3-yl)methanone (100 mg, 50.5%) as an oil, which crystallized upon standing.

Step C: NaH (0.030 g, 0.75 mmol) was added to cyclopropyl(1H-pyrazolo[3,4-b]pyridin-3-yl)methanone (100 mg, 0.534 mmol) in DMF (2 mL) at 0° C. After 10 minutes, tosyl chloride (0.13 g, 0.69 mmol) was added, and the reaction mixture was allowed to warm to room temperature. The reaction mixture was stirred at room temperature for 16 hours and then quenched with ice and water. The mixture was extracted with EtOAc (3×10 mL) and dried over sodium sulfate. Column chromatography afforded cyclopropyl(1-tosyl-1H-pyrazolo[3,4-b]pyridin-3-yl)methanone (127 mg, 70%) as an oil, which crystallized upon standing.

Step D: TFAA (0.083 mL, 0.60 mmol) was added dropwise over 20 minutes to an ice cold solution of tetrabutylammonium nitrate (181 mg, 595 mmol) in DCM (2 mL). The resulting solution was stirred at 0° C. for 10 minutes and transferred to an ice cold solution of cyclopropyl(1-tosyl-1H-pyrazolo[3,4-b]pyridin-3-yl)methanone (0.13 g, 0.37 mmol) in DCM (2 mL) via cannula. The cold bath was removed, and the reaction mixture was left at room temperature overnight. The reaction mixture was quenched with water (4 mL) and extracted with DCM (3×3 mL). The combined organic layers were dried, filtered and concentrated. The crude product was purified by column chromatography, eluting with DCM/hexanes (2:1) to give cyclopropyl(5-nitro-1-tosyl-1H-pyrazolo[3,4-b]pyridin-3-yl)methanone (0.076 g, 0.197 mmol, 52.9% yield).

Step E: NaOH (0.39 mL, 0.39 mmol) was added to cyclopropyl(5-nitro-1-tosyl-1H-pyrazolo[3,4-b]pyridin-3-yl)methanone (0.076 g, 0.20 mmol) in THF:MeOH (1 ml, 4:1). After the compound dissolved in about 5 minutes, the reaction was complete. The reaction mixture was diluted with aqueous ammonium chloride (8 mL) and extracted with EtOAc (3×4 mL). The combined organic layers were dried over sodium sulfate, decanted, and concentrated to provide cyclopropyl(5-nitro-1H-pyrazolo[3,4-b]pyridin-3-yl)methanone (0.040 g, 0.17 mmol, 88% yield).

Step F: SnCl$_2$ dihydrate (0.24 g, 1.1 mmol) was added to cyclopropyl(5-nitro-1H-pyrazolo[3,4-b]pyridin-3-yl)methanone (0.050 g, 0.22 mmol) in EtOAc (1 mL). The reaction mixture was heated to reflux for 6 hours. The mixture was then cooled, diluted with EtOAc (5 mL), aqueous bicarbonate (5 mL) and filtered through celite. The organic layers were extracted with EtOAc (3×5 mL), dried over sodium sulfate, and concentrated to provide (5-amino-1H-pyrazolo[3,4-b]pyridin-3-yl)(cyclopropyl)methanone (0.035 g, 0.17 mmol, 80% yield).

Step G: N-(3-(Cyclopropanecarbonyl)-1H-pyrazolo[3,4-b]pyridin-5-yl)-2,6-difluoro-3-(propylsulfonamido)benzamide (0.002 mg, 70%) was prepared according to Example 1, Step E using (5-amino-1H-pyrazolo[3,4-b]pyridin-3-yl)(cyclopropyl)methanone. $^1$H NMR (400 MHz, CD$_3$OD) δ 8.99-9.02 (m, 1H), 8.79-8.82 (m, 1H), 7.62-7.72 (m, 1H), 7.12-7.18 (m, 1H), 3.09-3.15 (m, 2H), 2.70 (s, 1H), 1.82-1.93 (m, 2H), 1.27-1.31 (m, 1H), 1.19-1.24 (m, 2H), 1.08-1.14 (m, 2H), 1.03-1.09 (m, 3H); m/z (APCI-neg) M−1=462.2.

Example 69

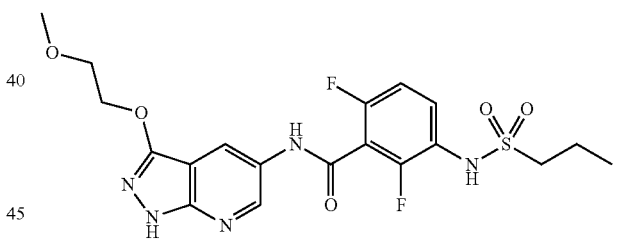

2,6-difluoro-N-(3-(2-methoxyethoxy)-1H-pyrazolo[3,4-b]pyridin-5-yl)-3-(propyl sulfonamido)benzamide Step A: Cesium carbonate (25.3 g, 77.6 mmol) was added to 3-iodo-5-nitro-1H-pyrazolo[3,4-b]pyridine (15 g, 52 mmol) in DMF (500 mL). Then 1-(chloromethyl)-4-methoxybenzene (10.57 mL, 77.58 mmol) was added, which was stirred at room temperature for 16 hours. Water (1 L) was then added to the reaction mixture, which resulted in a precipitate. The solids were collected by filtration and transferred into a flask with the aid of i-PrOH. The concentrate was triturated with EtOAc/Et$_2$O (3:1 EtOAc/Et$_2$O, 750 mL) to give 3-iodo-1-(4-methoxybenzyl)-5-nitro-1H-pyrazolo[3,4-b]pyridine (12.1 g, 29.5 mmol, 56.9%) as a solid.

Step B: 3-Iodo-1-(4-methoxybenzyl)-5-nitro-1H-pyrazolo[3,4-b]pyridine (2.0 g, 4.88 mmol), 1,10-phenanthroline (0.879 g, 4.88 mmol), copper (I) iodide (0.929 g, 4.88 mmol), potassium fluoride (4.96 g, 34.1 mmol), and 2-methoxyethanol (11.1 g, 146 mmol) were suspended in toluene (65 mL) and stirred at reflux for 20 hours. The mixture was cooled, diluted with EtOAc, filtered through a plug of silica, and concentrated. The crude product was purified via column chromatography eluting with 6:4 EtOAc-hexanes to afford 1-(4-methoxybenzyl)-3-(2-methoxyethoxy)-5-nitro-1H-pyrazolo[3,4-b]pyridine (400 mg, 1.12 mmol, 22.9%).

Step C: Fe (0) (0.251 g, 4.49 mmol) and ammonium chloride (0.600 g, 11.2 mmol) were added to 1-(4-methoxybenzyl)-3-(2-methoxyethoxy)-5-nitro-1H-pyrazolo[3,4-b]pyridine (402 mg, 1.12 mmol) in EtOH (8 mL) and water (3.7 mL). The mixture was stirred at 85° C. for 5 hours. The mixture was diluted with EtOAc-water and filtered through GF/F paper. The filtrate was diluted with aqueous bicarbonate and extracted with EtOAc (3×12 mL), dried over sodium sulfate, decanted and concentrated to provide 1-(4-methoxybenzyl)-3-(2-methoxyethoxy)-1H-pyrazolo[3,4-b]pyridin-5-amine (338 mg, 92%).

Step D: 2,6-Difluoro-N-(1-(4-methoxybenzyl)-3-(2-methoxyethoxy)-1H-pyrazolo[3,4-b]pyridin-5-yl)-3-(propylsulfonamido)benzamide (125 mg, 77.6%) was prepared according to Example 1, Step E using 1-(4-methoxybenzyl)-3-(2-methoxyethoxy)-1H-pyrazolo[3,4-b]pyridin-5-amine (89.7 mg).

Step E: 2,6-Difluoro-N-(3-(2-methoxyethoxy)-1H-pyrazolo[3,4-b]pyridin-5-yl)-3-(propylsulfonamido)benzamide (83 mg, 83.4%) was prepared according to Example 20, Step G using 2,6-difluoro-N-(1-(4-methoxybenzyl)-3-(2-methoxyethoxy)-1H-pyrazolo[3,4-b]pyridin-5-yl)-3-(propylsulfonamido)benzamide (125 mg). $^1$H NMR (400 MHz, CD$_3$OD) δ 8.60-8.61 (m, 1H), 8.54-8.55 (m, 1H), 7.61-7.69 (m, 1H), 7.09-7.15 (m, 1H), 4.50-4.54 (m, 2H), 3.82-3.85 (m, 2H), 3.34 (s, 3H), 3.08-3.13 (m, 2H), 1.82-1.92 (m, 2H), 1.03-1.08 (m, 3H); m/z (APCI-pos) M+1=491.1.

Example 70

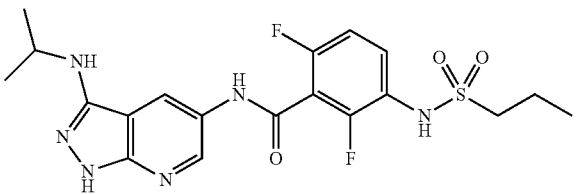 [SMILES: CCCS(=O)(=O)Nc1ccc(F)c(C(=O)Nc2cnc3[nH]nc(NC(C)C)c3c2)c1F]

2,6-difluoro-N-(3-(isopropylamino)-1H-pyrazolo[3,4-b]pyridin-5-yl)-3-(propylsulfonamido)benzamide Step A: A solution of NaOH (40 g, 999 mmol) in H$_2$O (40 mL) was slowly added via an addition funnel such that the internal temperature did not exceed 10° C. to a cold (0° C.) solution of ethyl 2-cyanoacetate (53.3 mL, 499.5 mmol) and carbon disulfide (30.2 mL, 499.5 mmol) in absolute EtOH (600 mL) Once the addition was complete, the reaction mixture was allowed to stir at room temperature for 10 minutes. The reaction mixture was then cooled to 5° C. The resulting solids were isolated by filtration and washed with EtOH (100 mL), ether (500 mL) and dried in vacuo to give sodium 2-cyano-3-ethoxy-3-oxoprop-1-ene-1,1-bis(thiolate) (110.0 g, 97%) as a solid.

Step B: 2-Cyano-3-ethoxy-3-oxoprop-1-ene-1,1-bis(thiolate) (110.0 g, 490 mmol) was introduced to a solution of NaOH (32.8 g, 819.4 mmol) dissolved in water (230 mL). The mixture was heated to 40° C. for 5 hours and then cooled to room temperature. The solution was diluted with EtOH (410 mL). The layers were separated, and the low layer was diluted with water to a total volume of 770 mL. The solution was cooled to 5° C., and dimethyl sulfate (77.5 mL, 819.4 mmol) was added at a rate such that the internal temperature was maintained below 15° C. Once the addition was complete, the temperature was held at 15° C. for 20 minutes and then between 28-30° C. for 20 minutes. The solution was cooled to 15° C. and filtered. The filtrate was acidified with 4N HCl to a pH of about 2. The resulting solids were collected by filtration and dried under vacuum to give 2-cyano-3,3-bis(methylthio)acrylic acid (35.1 g, 34%) as a solid.

Step C: Propan-2-amine (0.9 mL, 10.6 mmol) was added dropwise to a cold (0° C.) solution of 2-cyano-3,3-bis(methylthio)acrylic acid (0.500 g, 2.64 mmol) in MeOH (6 mL), and the mixture was stirred at room temperature overnight. The next morning, the reaction mixture was concentrated on a rotovap taking care not to heat the water bath (bath temperature about 20° C.). The crude product (Z)-3-(isopropylamino)-3-(methylthio)acrylonitrile was used directly in Step D.

Step D: A mixture of (Z)-3-(isopropylamino)-3-(methylthio)acrylonitrile (0.413 g, 2.64 mmol) and hydrazine monohydrate (0.38 mL, 7.93 mmol) in EtOH (6 mL) was heated to reflux for 16 hours. After cooling to room temperature, the reaction mixture was concentrated. The residue was purified by column chromatography, eluting with ethyl acetate, DCM/MeOH (9:1) to give N3-isopropyl-1H-pyrazole-3,5-diamine (0.231 g, 62% over 2 steps) as an oil.

Step E: A solution of N3-isopropyl-1H-pyrazole-3,5-diamine (0.231 g, 1.85 mmol) and sodium nitromalonaldehyde monohydrate (0.307 g, 1.95 mmol) in water (20 mL) was heated to 100° C. overnight. The reaction mixture was cooled to room temperature, and the pH was adjusted to about 6 with acetic acid. The resulting solids were collected by filtration, washed with water and dried in vacuo to give N-isopropyl-5-nitro-1H-pyrazolo[3,4-b]pyridin-3-amine (0.243 g, 59%). m/z (APCI-neg) M−1=220.3.

Step F: N3-Isopropyl-1H-pyrazolo[3,4-b]pyridine-3,5-diamine (0.200 g, 97%) was prepared according to Example 4, Step B using N-isopropyl-5-nitro-1H-pyrazolo[3,4-b]pyridin-3-amine. m/z (APCI-pos) M+1=192.2.

Step G: 2,6-Difluoro-N-(3-(isopropylamino)-1H-pyrazolo[3,4-b]pyridin-5-yl)-3-(propylsulfonamido)benzamide (0.100 g, 90%) was prepared according to Example 1, Step E using N3-isopropyl-1H-pyrazolo[3,4-b]pyridine-3,5-diamine. $^1$H NMR (400 MHz, CD$_3$OD) δ 8.6 (s, 1H), 8.5 (s, 1H), 7.7 (m, 1H), 7.1 (m, 1H), 3.9 (m, 1H), 3.1 (m, 2H), 1.9 (m, 2H), 1.3 (d, J=6.2 Hz, 6H), 1.1 (t, J=7.6 Hz, 3H); m/z (APCI-pos) M+1=453.1.

Example 71

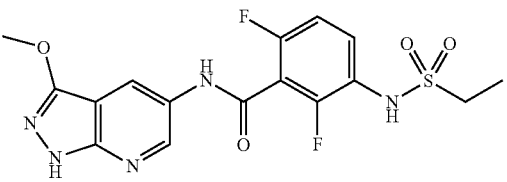 [SMILES: CCS(=O)(=O)Nc1ccc(F)c(C(=O)Nc2cnc3[nH]nc(OC)c3c2)c1F]

3-(ethylsulfonamido)-2,6-difluoro-N-(3-methoxy-1H-pyrazolo[3,4-b]pyridin-5-yl)benzamide 3-(Ethylsulfonamido)-2,6-difluoro-N-(3-methoxy-1H-pyrazolo[3,4-b]pyridin-5-yl)benzamide was prepared according to the general procedure for Example 20, Step F, substituting 3-(ethylsulfonamido)-2,6-difluorobenzoic acid for 2,6-difluoro-3-(propylsulfonamido)benzoic acid. $^1$H NMR (400 MHz, d$_6$-DMSO) δ 12.62-12-65 (s, 1H), 11.12-11.14 (s, 1H), 9.83-9.87 (s, 1H), 8.58-8.60 (m, 1H), 8.49-8.51 (m, 1H), 7.53-7.60 (m, 1H), 7.25-7.31 (m, 1H), 4.02 (3, 3H), 3.11-3.18 (m, 2H), 1.26-1.31 (m, 3H); m/z (APCI-neg) M−1=410.1.

Example 72

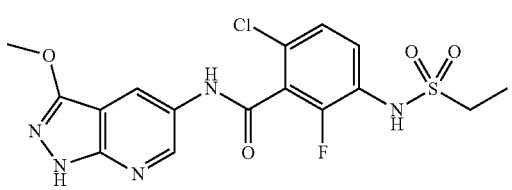

6-chloro-3-(ethylsulfonamido)-2-fluoro-N-(3-methoxy-1H-pyrazolo[3,4-b]pyridin-5-yl)benzamide 6-Chloro-3-(ethylsulfonamido)-2-fluoro-N-(3-methoxy-1H-pyrazolo[3,4-b]pyridin-5-yl)benzamide was prepared according to the general procedure for Example 20, Step F, substituting 6-chloro-3-(ethylsulfonamido)-2-fluorobenzoic acid for 2,6-difluoro-3-(propylsulfonamido)benzoic acid. m/z (APCI-neg) M−1=426.1.

Example 73

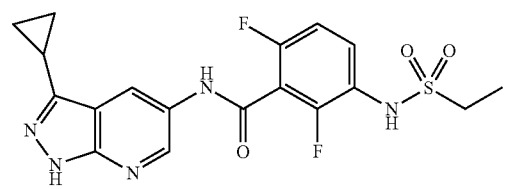 [SMILES: CCS(=O)(=O)Nc1ccc(F)c(C(=O)Nc2cnc3[nH]nc(C4CC4)c3c2)c1F]

N-(3-cyclopropyl-1H-pyrazolo[3,4-b]pyridin-5-yl)-3-(ethylsulfonamido)-2,6-difluorobenzamide N-(3-Cyclopropyl-1H-pyrazolo[3,4-b]pyridin-5-yl)-3-(ethylsulfonamido)-2,6-difluorobenzamide was prepared according to the general procedure for Example 5, substituting 3-(ethylsulfonamido)-2,6-difluorobenzoic acid for 3-(ethylsulfonamido)-2,6-difluorobenzoic acid. $^1$H NMR (400 MHz, d$_6$-DMSO) δ 13.21-13.23 (s, 1H), 11.11-11.13 (s, 1H), 9.83-9.87 (s, 1H), 8.64-8.66 (m, 1H), 8.55-57 (m, 1H), 7.53-7.61 (m, 1H), 7.26-7.32 (m, 1H), 3.13-3.19 (m, 2H), 2.25-2.35 (m, 1H), 1.26-1.32 (m, 3H), 0.92-1.04 (m, 4H); m/z (APCI-neg) M−1=420.2.

Example 74

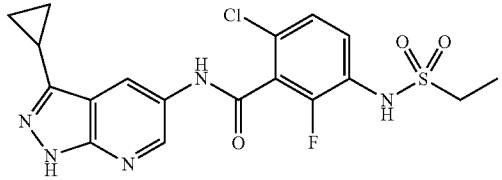 [SMILES: CCS(=O)(=O)Nc1ccc(Cl)c(C(=O)Nc2cnc3[nH]nc(C4CC4)c3c2)c1F]

6-chloro-N-(3-cyclopropyl-1H-pyrazolo[3,4-b]pyridin-5-yl)-3-(ethylsulfonamido)-2-fluorobenzamide 6-Chloro-N-(3-cyclopropyl-1H-pyrazolo[3,4-b]pyridin-5-yl)-3-(ethylsulfonamido)-2-fluorobenzamide benzamide was prepared according to the general procedure for Example 5, substituting 6-chloro-3-(ethylsulfonamido)-2-fluorobenzoic acid for 2,6-difluoro-3-(propylsulfonamido)benzoic acid. $^1$H NMR (400 MHz, CDCl$_3$) δ 8.66-8.68 (br s, 1H), 8.46-8.47 (br s, 1H), 8.09-8.14 (m, 1H), 7.89-7.92 (m, 1H), 7.64-7.74 (m, 1H), 7.27-7.30 (m, 1H), 3.15-3.22 (m, 2H), 2.17-2.26 (m, 1H), 1.38-1.44 (m, 3H), 1.05-1.12 (m, 4H); m/z (APCI-neg) M−1=436.1.

Example 75

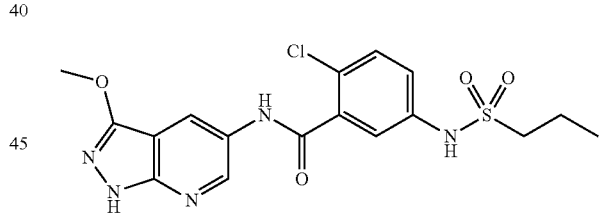

2-chloro-N-(3-methoxy-1H-pyrazolo[3,4-b]pyridin-5-yl)-5-(propylsulfonamido)benzamide 2-Chloro-N-(3-methoxy-1H-pyrazolo[3,4-b]pyridin-5-yl)-5-(propylsulfonamido)benzamide was prepared according to the general procedure for Example 20, Step F, substituting 2-chloro-5-(propylsulfonamido)benzoic acid for 2,6-difluoro-3-(propylsulfonamido)benzoic acid. $^1$H NMR (400 MHz, CD$_3$OD) δ 8.59-8.63 (m, 1H), 8.47-8.51 (m, 1H), 7.43-7.50 (m, 1H), 7.32-7.39 (m, 1H), 4.09 (s, 3H), 3.09-3.17 (m, 2H), 2.76-2.87 (m, 2H), 0.99-1.07 (m, 3H); m/z (APCI-neg) M−1=422.8.

Example 76

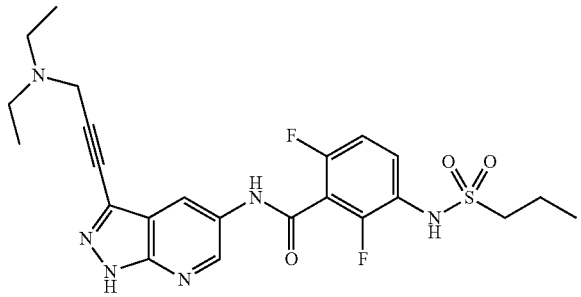 [SMILES: CCCS(=O)(=O)Nc1ccc(F)c(C(=O)Nc2cnc3[nH]nc(C#CCN(CC)CC)c3c2)c1F]

N-(3-(3-(diethylamino)prop-1-ynyl)-1H-pyrazolo[3,4-b]pyridin-5-yl)-2,6-difluoro-3-propylsulfonamido)benzamide Step A: 3-Iodo-1-(4-methoxybenzyl)-5-nitro-1H-pyrazolo[3,4-b]pyridine (3.5 g, 8.5 mmol), EtOH (70 mL), water (30 mL), Fe (0) (1.9 g, 34 mmol), and NH₄Cl (4.6 g, 85 mmol) were charged to a 250 mL round-bottomed flask. This mixture was warmed to 80° C. for 4 hours, and then allowed to cool to room temperature. The mixture was filtered through GF/F filter paper and concentrated to remove EtOH. The organic layers were extracted with EtOAc (2×100 mL), dried over Na₂SO₄, and concentrated to get 3-iodo-1-(4-methoxybenzyl)-1H-pyrazolo[3,4-b]pyridin-5-amine (2.7 g, 74%) of crude product as an oil.

Step B: 2,6-Difluoro-N-(3-(3-hydroxyprop-1-ynyl)-1H-pyrrolo[2,3-b]pyridin-5-yl)-3-(propylsulfonamido)benzamide (76%) was prepared according to the general procedure for Example 1 step E, substituting 3-iodo-1-(4-methoxybenzyl)-1H-pyrazolo[3, 4-1)]pyridin-5-amine for 1H-pyrazolo[3,4-b]pyridin-5-amine.

Step C: 2,6-Difluoro-N-(3-iodo-1-(4-methoxybenzyl)-1H-pyrazolo[3,4-b]pyridin-5-yl)-3-(propylsulfonamido)benzamide (100 mg, 0.156 mmol), N,N-diethylprop-2-yn-1-amine (19.1 mg, 0.172 mmol), triethylamine (212.6 µL 1.56 mmol), copper(I) iodide (1.19 mg, 0.00624 mmol) and THF (10 mL) were added to a 100 mL round-bottomed flask. Next, Pd(PPh₃)₄ (7.21 mg, 0.00624 mmol) was added under nitrogen. The mixture was heated to 50° C. for 24 hours. The mixture was cooled to room temperature and diluted with brine (50 mL). The mixture was extracted with EtOAc (50 mL), dried with sodium sulfate, filtered and concentrated to get N-(3-(3-(diethylamino)prop-1-ynyl)-1-(4-methoxybenzyl)-1H-pyrazolo[3, 4-1)]pyridin-5-yl)-2,6-difluoro-3-(propylsulfonamido)benzamide (115 mg, 88%) as a solid.

Step D: 2,6-Difluoro-N-(3-(3-hydroxyprop-1-ynyl)-1H-pyrrolo[2,3-b]pyridin-5-yl)-3-(propylsulfonamido)benzamide (12%) was prepared according to the general procedure for Example 20, Step G, substituting N-(3-(3-(diethylamino)prop-1-ynyl)-1-(4-methoxybenzyl)-1H-pyrazolo[3,4-b]pyridin-5-yl)-2,6-difluoro-3-(propylsulfonamido) benzamide for 2,6-difluoro-N-(3-methoxy-1-(4-methoxybenzyl)-1H-pyrazolo[3,4-b]pyridin-5-yl)-3-(propylsulfonamido)benzamide. ¹H NMR (CDCl₃) δ 9.45 (br s, 1H), 8.64 (m, 1H), 8.55 (m, 1H), 7.56 (m, 1H), 6.86 (m, 1H), 3.69 (m, 2H), 3.04 (m, 2H), 2.70 (m, 5H), 1.82 (m, 3H), 1.11 (t, J=7.2 Hz, 6H), 0.96 (t, J=7.4 Hz, 3H). ¹⁹F NMR (CDCl₃) δ −124.7 (1F), −115.5 (1F). m/z (APCI-pos) M+1=505.1.

Example 77

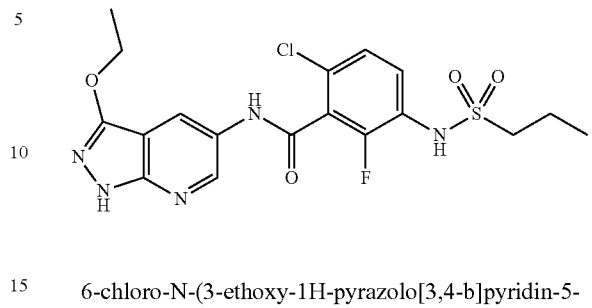

6-chloro-N-(3-ethoxy-1H-pyrazolo[3,4-b]pyridin-5-yl)-2-fluoro-3-(propylsulfonamido)benzamide Step A: A mixture of 5-nitro-1H-pyrazolo[3,4-b]pyridin-3-ol (0.4 g, 2.2 mmol), DMAP (0.027 g, 0.22 mmol), and di-tert-butyl dicarbonate (0.53 g, 2.4 mmol) was stirred under nitrogen at room temperature for 3 days. The reaction mixture was treated with EtOAc (200 mL), washed with saturated aqueous NH₄Cl, saturated aqueous NaHCO₃, and brine. The organic layer was dried over MgSO₄ and concentrated under reduced pressure to give the crude material. The crude material was purified by silica gel flash column chromatography (5:1=hexane:EtOAc) to afford tert-butyl 3-hydroxy-5-nitro-1H-pyrazolo[3,4-b]pyridine-1-carboxylate (0.35 g, 56% yield). LRMS (ACPI neg) m/e 279.0 (M−1).

Step B: A solution of DIAD in THF (10 mL) was added slowly via a syringe pump under N₂ at room temperature for 1 hour to a solution of tert-butyl 3-hydroxy-5-nitro-1H-pyrazolo[3,4-b]pyridine-1-carboxylate (0.35 g, 1.2 mmol), EtOH (0.069 g, 1.5 mmol), and PPh₃ (0.49 g, 1.9 mmol). The reaction mixture was poured onto water (20 mL) and extracted with EtOAc. The combined organic layers were washed with brine, dried over MgSO₄, and concentrated under reduced pressure to give the crude material. The crude material was treated with MeOH to give tert-butyl 3-ethoxy-5-nitro-1H-pyrazolo[3,4-b]pyridine-1-carboxylate as a precipitate. The filtrate was concentrated and treated with a solution (10:1 hexane:EtOAc) to precipitate triphenylphosphineoxide. Then, the filtrate was concentrated and flash chromatographed (SiO₂, 10:1=hexane:EtOAc) to afford tert-butyl 3-ethoxy-5-nitro-1H-pyrazolo[3,4-b]pyridine-1-carboxylate (total 0.237 g, 62% yield). LRMS (ACPI pos) m/e 209.0 ((M-Boc)+1).

Step C: A mixture of tert-butyl 3-ethoxy-5-nitro-1H-pyrazolo[3,4-b]pyridine-1-carboxylate (0.237 g, 0.769 mmol) and Pd/C (0.082 g, 0.0769 mmol, 10% Wt) in THF-EtOH solution (2:1 ratio, 15 mL) was stirred at room temperature. Hydrogen gas was then introduced with a balloon to the reaction mixture. After 2 hours, the mixture was filtered with MeOH to remove Pd/C and concentrated to give the desired product. The crude material was purified by silica gel flash column chromatography (SiO₂, 5:1=Hexane:EtOAc) to afford tert-butyl 5-amino-3-ethoxy-1H-pyrazolo[3,4-b]pyridine-1-carboxylate (0.21 g, 98% yield). LRMS (ACPI pos) m/e 179.1 ((M-Boc)+1).

Step D: A mixture of 6-chloro-2-fluoro-3-(propylsulfonamido)benzoic acid (0.446 g, 1.51 mmol), EDCI (0.723 g, 3.77 mmol), and HOBt (0.578 g, 3.77 mmol) in DMF (6 mL) was stirred at room temperature for 25 minutes. tert-Butyl 5-amino-3-ethoxy-1H-pyrazolo[3,4-b]pyridine-1-carboxylate (0.21 g, 0.755 mmol) was added to the reaction mixture, followed by the addition of Et₃N (0.53 mL, 3.77 mmol). After stirring for 4 hours, the reaction mixture was diluted with EtOAc, washed with saturated aqueous NH$_4$Cl, saturated aqueous NaHCO$_3$ and brine. The organic layer was dried over MgSO$_4$ and concentrated under reduced pressure to give the crude material. The crude material was purified by silica gel flash column chromatography (10% MeOH in CH$_2$Cl$_2$) to afford tert-butyl 5-(6-chloro-2-fluoro-3-(propylsulfonamido)benzamido)-3-ethoxy-1H-pyrazolo[3,4-b]pyridine-1-carboxylate (90 mg, 22% yield).

Step E: A mixture of tert-butyl 5-(6-chloro-2-fluoro-3-(propylsulfonamido)benzamido)-3-ethoxy-1H-pyrazolo[3,4-b]pyridine-1-carboxylate (0.090 g, 0.162 mmol) and TFA (3.12 mL, 40.5 mmol) in CH$_2$Cl$_2$ (5 mL) was stirred at room temperature for 30 minutes. The reaction mixture was concentrated under reduced pressure using toluene to azeotrope. The crude material was purified by silica gel flash column chromatography (5% 7N NH$_3$-MeOH in CH$_2$Cl$_2$) to afford 6-chloro-N-(3-ethoxy-1H-pyrazolo[3,4-b]pyridin-5-yl)-2-fluoro-3-(propylsulfonamido)benzamide (40 mg, 54% yield). LRMS (ACPI pos) m/e 456.1 (M+1). $^1$H NMR (400 MHz, d$_6$-DMSO) δ 12.57 (s, 1H), 11.08 (s, 1H), 9.98 (br s, 1H), 8.55 (d, 1H), 8.50 (d, 1H), 7.55 (t, 1H), 7.46 (d, 1H), 4.40 (q, 2H), 3.16 (t, 2H), 1.75 (m, 2H), 1.42 (t, 3H), 0.99 (t, 3H); $^{19}$F NMR (376 MHz, DMSO) δ –124.0.

Example 78

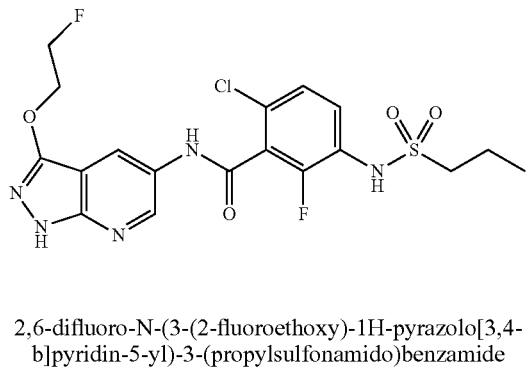

2,6-difluoro-N-(3-(2-fluoroethoxy)-1H-pyrazolo[3,4-b]pyridin-5-yl)-3-(propylsulfonamido)benzamide Step A: 3-(2-Fluoroethoxy)-5-nitro-1-tosyl-1H-pyrazolo[3,4-b]pyridine was prepared from 5-nitro-1-tosyl-1H-pyrazolo[3,4-b]pyridin-3-ol (0.24 g, 0.718 mmol) according to the procedure of Example 77, Step B, substituting 2-fluoroethanol for ethanol. The crude material was treated in next step without further purification. LRMS (ACPI pos) m/e 381.0 (M+1).

Step B: A mixture of 3-(2-fluoroethoxy)-5-nitro-1-tosyl-1H-pyrazolo[3,4-b]pyridine (0.273 g, 0.718 mmol) and aqueous K$_2$CO$_3$ (1.8 mL, 2M) in MeOH (14 mL) was heated at 55° C. for 1 hour. After cooling to room temperature, the mixture was diluted with 10% aqueous citric acid, extracted with EtOAc, washed with saturated aqueous NaHCO$_3$ and brine, dried over MgSO$_4$, and concentrated to give 3-(2-fluoroethoxy)-5-nitro-1H-pyrazolo[3,4-b]pyridine. The material was purified by silica gel flash column chromatography (1% MeOH in CH$_2$Cl$_2$) to afford 3-(2-fluoroethoxy)-5-nitro-1H-pyrazolo[3,4-b]pyridine along with a byproduct. LRMS (ESI pos) m/e 207.0 (M–F).

Step C: 3-(2-Fluoroethoxy)-1H-pyrazolo[3,4-b]pyridin-5-amine was prepared from 3-(2-fluoroethoxy)-5-nitro-1H-pyrazolo[3,4-b]pyridine according to the procedure of Example 77, Step C. The product was purified by silica gel flash column chromatography (SiO$_2$, 2% 7N NH$_3$-MeOH in CH$_2$Cl$_2$) to provide the product as a solid (64 mg, 46% yield, 3 step process). LRMS (APCI pos) m/e 197.0 (M+1). $^1$H-NMR (400 MHz, d$_6$-DMSO) δ 12.0 (s, 1H), 8.02 (s, 1H), 7.08 (s, 1H), 4.98 (s, 2H), 4.85 (m, 1H), 4.73 (m, 1H), 4.54 (m, 1H), 4.46 (m, 1H); $^{19}$F NMR (376 MHz, DMSO) δ –223.0.

Step D: A mixture of 3-(2-fluoroethoxy)-1H-pyrazolo[3,4-b]pyridin-5-amine (0.020 g, 0.10 mmol), 2,6-difluoro-3-(propylsulfonamido)benzoic acid (0.031 g, 0.11 mmol), EDCI (0.021 g, 0.11 mmol), and HOBt (0.017 g, 0.11 mmol) in DMF (6 mL) was stirred at room temperature for 1 hour. The reaction mixture was diluted with EtOAc and washed with saturated aqueous NH$_4$Cl, saturated aqueous NaHCO$_3$ and brine. The organic layer was dried over MgSO$_4$ and concentrated under reduced pressure to give 2,6-difluoro-N-(3-(2-fluoroethoxy)-1H-pyrazolo[3,4-b]pyridin-5-yl)-3-(propylsulfonamido)benzamide. The crude material was purified by silica gel flash column chromatography (5% 7N NH$_3$-MeOH in CH$_2$Cl$_2$) to afford 2,6-difluoro-N-(3-(2-fluoroethoxy)-1H-pyrazolo[3,4-b]pyridin-5-yl)-3-(propylsulfonamido)benzamide (41 mg, 88% yield). LRMS (ACPI pos) m/e 458.1 (M+1). $^1$H-NMR (400 MHz, d$_6$-DMSO) δ 12.68 (s, 1H), 11.12 (s, 1H), 9.73 (br s, 1H), 8.58 (d, 1H), 8.54 (d, 1H), 7.55 (q, 1H), 7.27 (t, 1H), 4.90 (m, 1H), 4.78 (m, 1H), 4.63 (m, 1H), 4.55 (m, 1H), 3.12 (t, 2H), 1.76 (m, 2H), 0.99 (t, 3H); $^{19}$F NMR (376 MHz, DMSO) δ –117.3, –122.6, –223.1.

Example 79

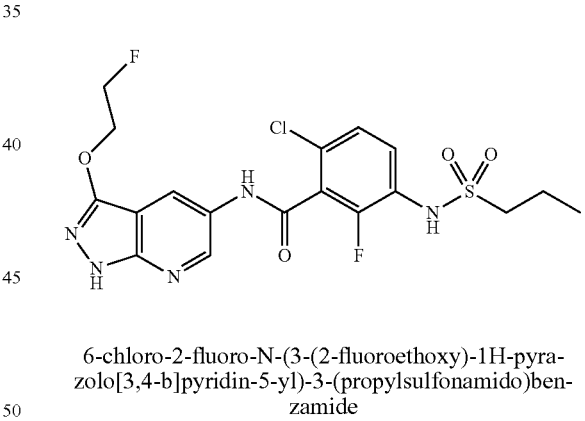

6-chloro-2-fluoro-N-(3-(2-fluoroethoxy)-1H-pyrazolo[3,4-b]pyridin-5-yl)-3-(propylsulfonamido)benzamide 6-Chloro-2-fluoro-N-(3-(2-fluoroethoxy)-1H-pyrazolo[3,4-b]pyridin-5-yl)-3-(propylsulfonamido)benzamide was prepared according to the general procedure of Example 78, Step D, using 3-(2-fluoroethoxy)-1H-pyrazolo[3,4-b]pyridin-5-amine (0.035 g, 0.18 mmol) and 6-chloro-2-fluoro-3-(propylsulfonamido)benzoic acid (0.058 g, 0.20 mmol). The crude material was purified by silica gel flash column chromatography (5 to 7% 7N NH$_3$-MeOH in CH$_2$Cl$_2$) to afford the desired product which was triturated with Et$_2$O (51 mg, 60% yield). LRMS (ACPI pos) m/e 474.0 (M+1). $^1$H NMR (400 MHz, d$_6$-DMSO) δ 12.68 (s, 1H), 11.10 (s, 1H), 9.99 (br s, 1H), 8.58 (d, 1H), 8.54 (d, 1H), 7.55 (t, 1H), 7.46 (d, 1H), 4.91 (m, 1H), 4.78 (m, 1H), 4.63 (m, 1H), 4.55 (m, 1H), 3.16 (t, 2H), 1.75 (m, 2H), 0.99 (t, 3H); $^{19}$F NMR (376 MHz, DMSO) δ –124.0, –223.1.

Example 80

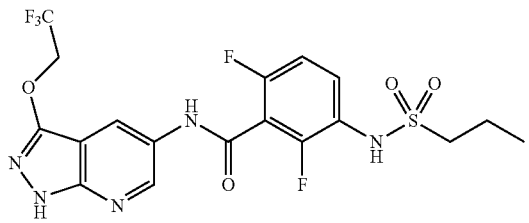 [SMILES: CCCS(=O)(=O)Nc1ccc(F)c(C(=O)Nc2cnc3[nH]nc(OCC(F)(F)F)c3c2)c1F]

2,6-difluoro-3-(propylsulfonamido)-N-(3-(2,2,2-trifluoroethoxy)-1H-pyrazolo[3,4-b]pyridin-5-yl)benzamide 2,6-Difluoro-3-(propylsulfonamido)-N-(3-(2,2,2-trifluoroethoxy)-1H-pyrazolo[3,4-b]pyridin-5-yl)benzamide was prepared according to the general procedure in Example 78, substituting trifluoroethanol for ethanol. The crude material was purified by silica gel flash column chromatography (5% 7N NH$_3$-MeOH in CH$_2$Cl$_2$) to afford the desired product which was rinsed with Et$_2$O (67 mg, 67% yield). LRMS (ACPI pos) m/e 494.1 (M+1). $^1$H-NMR (400 MHz, d$_6$-DMSO) δ 12.92 (s, 1H), 11.16 (s, 1H), 9.81 (br s, 1H), 8.61 (d, 1H), 8.57 (d, 1H), 7.57 (m, 1H), 7.28 (t, 1H), 5.07 (q, 2H), 3.12 (m, 2H), 1.77 (m, 2H), 0.99 (t, 3H); $^{19}$F NMR (376 MHz, DMSO) δ −73.1, −117.1, −122.5.

Example 81

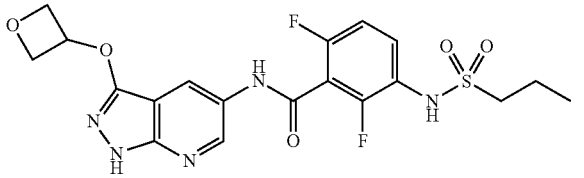 [SMILES: CCCS(=O)(=O)Nc1ccc(F)c(C(=O)Nc2cnc3[nH]nc(OC4COC4)c3c2)c1F]

2,6-difluoro-N-(3-(oxetan-3-yloxy)-1H-pyrazolo[3,4-b]pyridin-5-yl)-3-(propylsulfonamido)benzamide Step A: A stirred mixture of 5-nitro-1H-pyrazolo[3,4-b]pyridin-3-ol (0.2 g, 1.1 mmol), 4-dimethylaminopyridine ("DMAP"; 0.014 g, 0.11 mmol), triethylamine ("TEA"; 155 µL, 1.1 mmol) and di-tert-butyl dicarbonate (0.24 g, 1.0 mmol) was stirred in THF (10 mL) under N$_2$ at room temperature for 5 hours. The reaction mixture was then concentrated, washed with Et$_2$O, and filtered to afford tert-butyl 3-hydroxy-5-nitro-1H-pyrazolo[3,4-b]pyridine-1-carboxylate (0.15 g, 47% yield). LRMS (ACPI neg) m/e 278.9 (M−1).

Step B: tert-Butyl 5-nitro-3-(oxetan-3-yloxy)-1H-pyrazolo[3,4-b]pyridine-1-carboxylate was prepared from tert-butyl 3-hydroxy-5-nitro-1H-pyrazolo[3,4-b]pyridine-1-carboxylate (0.20 g, 0.71 mmol) according to the general procedure from Example 77, Step B, substituting oxetan-3-ol for ethanol. The crude material was purified by silica gel flash column chromatography (SiO$_2$, CH$_2$Cl$_2$) to provide the product as a solid (194 mg, 80.7% yield). LRMS (ACPI neg) m/e 235.0 ((M-Boc)-1).

Step C: tert-Butyl 5-amino-3-(oxetan-3-yloxy)-1H-pyrazolo[3,4-b]pyridine-1-carboxylate was prepared according to the general procedure for Example 77, Step C. The crude product was purified by silica gel flash column chromatography (8% 7N NH$_3$-MeOH in CH$_2$Cl$_2$) to afford the desired product (0.17 g, 84% yield). LRMS (ACPI pos) m/e 207.0 ((M-Boc)+1).

Step D: 3-(Oxetan-3-yloxy)-1H-pyrazolo[3,4-b]pyridin-5-amine was prepared according to the general procedure for Example 77, Step E. The crude product was purified by silica gel flash column chromatography (8% 7N NH$_3$-MeOH in CH$_2$Cl$_2$) to afford the desired product (84 mg, 69.5% yield). LRMS (ACPI pos) m/e 207.0 (M+1).

Step E: 3-(Oxetan-3-yloxy)-1H-pyrazolo[3,4-b]pyridin-5-amine was prepared according to the general procedure for Example 78, Step D. The crude product was purified by silica gel flash column chromatography (8% 7N NH$_3$-MeOH in CH$_2$Cl$_2$) to afford the desired product, which was triturated with Et$_2$O (22 mg, 12% yield). LRMS (ACPI pos) m/e 468.1 (M+1). $^1$H-NMR (400 MHz, d$_6$-DMSO) δ 12.68 (s, 1H), 11.12 (s, 1H), 9.73 (br s, 1H), 8.58 (d, 1H), 8.54 (d, 1H), 7.55 (q, 1H), 7.27 (t, 1H), 5.60 (m, 1H), 4.93 (t, 2H), 4.70 (t, 2H), 3.12 (t, 2H), 1.76 (m, 2H), 0.99 (t, 3H); $^{19}$F NMR (376 MHz, DMSO) δ−117.3, −122.6.

Example 82

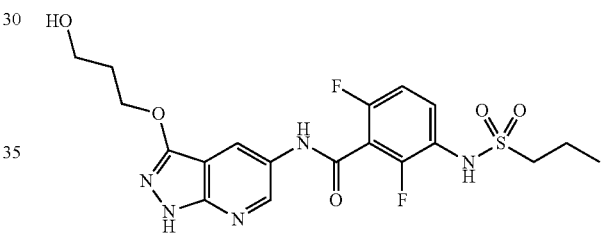

2,6-difluoro-N-(3-(3-hydroxypropoxy)-1H-pyrazolo[3,4-b]pyridin-5-yl)-3-(propylsulfonamido)benzamide Step A: tert-Butyl 3-(3-(tert-butyldimethylsilyloxy)propoxy)-5-nitro-1H-pyrazolo[3,4-b]pyridine-1-carboxylate was prepared according to the general procedure for Example 77, Step B, substituting 3-(tert-butyldimethylsilyloxy)propan-1-ol for ethanol. The crude product was purified by silica gel flash column chromatography (SiO$_2$, 10% EtOAc in hexanes) to provide the product (375 mg, 93% yield). LRMS (APCI neg) m/e 452.1 (M−1).

Step B: tert-Butyl 5-amino-3-(3-(tert-butyldimethylsilyloxy)propoxy)-1H-pyrazolo[3,4-b]pyridine-1-carboxylate was prepared according to the general procedure for Example 77, Step C. The crude product was purified by silica gel flash column chromatography (SiO$_2$, 5% 7N NH$_3$-MeOH, in DCM) to afford the desired product (0.31 g, 87% yield). LRMS (ACPI pos) m/e 323.0 ((M-Boc)+1).

Step C: 3-(5-Amino-1H-pyrazolo[3,4-b]pyridin-3-yloxy)propan-1-ol was prepared according to the general procedure for Example 77, Step E. The crude product was purified by silica gel flash column chromatography (8% 7N NH$_3$-MeOH in CH$_2$Cl$_2$) to provide the product (0.15 g, 41% yield). LRMS (APCI pos) m/e 209.1 (M+1).

Step D: 2,6-Difluoro-N-(3-(3-hydroxypropoxy)-1H-pyrazolo[3,4-b]pyridin-5-yl)-3-(propylsulfonamido)benzamide was prepared according to the general procedure for Example 78, Step D. The crude material was purified by silica gel flash column chromatography (8% 7N NH$_3$-MeOH in CH$_2$Cl$_2$) to afford the desired product, which was triturated with Et$_2$O (38.7 mg, 24% yield). LRMS (ACPI pos) m/e 470.1 (M+1). $^1$H-NMR (400 MHz, d$_6$-DMSO) δ 12.92 (s, 1H), 11.16 (s, 1H), 9.81 (br s, 1H), 8.61 (d, 1H), 8.57 (d, 1H), 7.57 (m, 1H), 7.28 (t, 1H), 4.57 (7, 1H), 4.41 (m, 2H), 3.60 (m, 2H), 1.95 (m, 2H), 1.77 (m, 2H), 0.99 (t, 3H); $^{19}$F NMR (376 MHz, DMSO) δ −117.1, −122.5.

Example 83

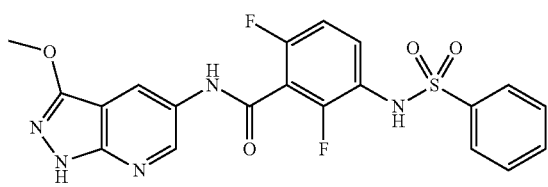 [SMILES: COc1n[nH]c2ncc(NC(=O)c3c(F)ccc(NS(=O)(=O)c4ccccc4)c3F)cc12]

2,6-difluoro-N-(3-methoxy-1H-pyrazolo[3,4-b]pyridin-5-yl)-3-(phenylsulfonamido)benzamide Step A: 3-Methoxy-1H-pyrazolo[3,4-b]pyridin-5-amine (563 mg, 3.43 mmol) in N,N-dimethylformamide (17.1 mL) was sequentially treated with 2,6-difluoro-3-nitrobenzoic acid (766.2 mg, 3.772 mmol), 1-(3-dimethylaminopropyl)-3-ethylcarbodiimide hydrochloride (723.2 mg, 3.772 mmol), and 1-hydroxybenzotriazole (509.7 mg, 3.772 mmol) at ambient temperature. After 24 hours, the reaction mixture was diluted with ethyl acetate, washed with water (4×), sodium bicarbonate (2×), and brine (1×), dried over sodium sulfate, and concentrated. The crude product was triturated with dichloromethane to provide 2,6-difluoro-N-(3-methoxy-1H-pyrazolo[3,4-b]pyridin-5-yl)-3-nitrobenzamide (820.6 mg, 2.350 mmol, 68.5% yield) as a solid. MS (APCI-neg) m/z=347.8 (M−H).

Step B: 2,6-Difluoro-N-(3-methoxy-1H-pyrazolo[3,4-b]pyridin-5-yl)-3-nitrobenzamide (762.3 mg, 2.183 mmol) was dissolved in ethyl acetate (21.8 mL) and treated with tin (II) chloride dehydrate (2463 mg, 10.91 mmol). The reaction mixture was heated to reflux for 2 hours and then allowed to cool to ambient temperature. The reaction mixture was quenched with saturated sodium carbonate and filtered. The filtrate was washed with water (2×), sodium bicarbonate (2×), and brine (1×), dried over sodium sulfate, and concentrated to afford 3-amino-2,6-difluoro-N-(3-methoxy-1H-pyrazolo[3,4-b]pyridin-5-yl)benzamide (588.2 mg, 1.842 mmol, 84.4% yield) as a solid. $^1$H NMR (400 MHz, d$_6$-DMSO) δ 12.629-12.519 (s, 1H), 10.980-10.883 (s, 1H), 8.675-8.583 (s, 1H), 8.544-8.458 (s, 1H), 6.993-6.811 (m, 2H), 5.297-5.188 (s, 2H), 4.093-3.973 (s, 3H); MS (APCI-pos) m/z=320.3 (M+H).

Step C: 3-Amino-2,6-difluoro-N-(3-methoxy-1H-pyrazolo[3,4-b]pyridin-5-yl)benzamide (0.005 g, 0.0157 mmol) was taken up as a slurry in CHCl$_3$ (1.0 mL). Three drops of pyridine were added, followed by the addition of benzenesulfonyl chloride (0.00600 mL, 0.0470 mmol). The slurry was stirred overnight at room temperature. The reaction mixture was concentrated and purified by silica gel chromatography to provide 2,6-difluoro-N-(3-methoxy-1H-pyrazolo[3,4-b]pyridin-5-yl)-3-(phenylsulfonamido)benzamide (5.7 mg, 79%) as a solid. $^1$H NMR (400 MHz, d$_6$-DMSO) δ 12.59 (s, 1H), 11.01 (s, 1H), 10.39 (br s, 1H), 8.55 (s, 1H), 8.44 (s, 1H), 7.76-7.78 (m, 2H), 7.64-7.68 (m, 1H), 7.57-7.61 (m, 1H), 7.31-7.37 (m, 1H), 7.17-7.21 (m, 1H), 4.01 (s, 3H); m/z (APCI-neg) M−1=458.2.

Example 84

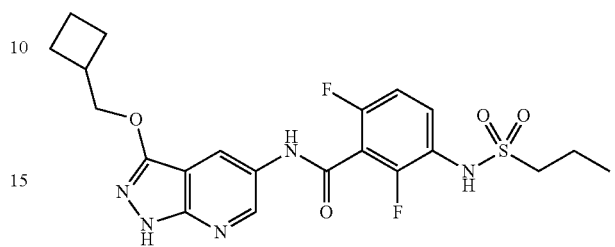

N-(3-(cyclobutylmethoxy)-1H-pyrazolo[3,4-b]pyridin-5-yl)-2,6-difluoro-3-(propylsulfonamido)benzamide Step A: 3-Iodo-5-nitro-1H-pyrazolo[3,4-b]pyridine (1.00 g, 3.45 mmol) and cesium carbonate (1.69 g, 5.17 mmol) were combined in dry DMF (35 mL). p-Methoxybenzyl chloride (0.702 mL, 5.17 mmol) was added to this mixture, and the mixture was stirred at room temperature for 22 hours. Water (200 mL) was then added to the reaction mixture, resulting in a precipitate, which was collected by filtration. The solids were triturated with 3:1 EtOAc/Et$_2$O (50 mL) to give 3-iodo-1-(4-methoxybenzyl)-5-nitro-1H-pyrazolo[3,4-b]pyridine (1 g, 71%) as a solid.

Step B: 3-Iodo-1-(4-methoxybenzyl)-5-nitro-1H-pyrazolo[3,4-b]pyridine (0.100 g, 0.244 mmol), cyclobutylmethanol (1.05 mL, 12.19 mmol), 1,10-phenanthroline (0.044 g, 0.244 mmol), copper (I) iodide (0.046 g, 0.244 mmol), and 40% KF/Al$_2$O$_3$ (0.248 g, 1.71 mmol) were combined in a reaction vial and heated to 115° C. for 24 hours. After cooling to room temperature, the mixture was diluted with EtOAc (20 mL) and filtered through GF/F filter paper. The filtrate was then concentrated and passed through a 10 g SepPak cartridge, eluting with DCM. The fractions were collected and then purified by preparative TLC (2×0.5 mm plates, 15% EtOAc/hexanes) to give 3-(cyclobutylmethoxy)-1-(4-methoxybenzyl)-5-nitro-1H-pyrazolo[3,4-b]pyridine (22 mg, 24.5%) as a solid.

Step C: 3-(Cyclobutylmethoxy)-1-(4-methoxybenzyl)-1H-pyrazolo[3,4-b]pyridin-5-amine (67%) was prepared according to Example 2, Step D, substituting 3-(cyclobutylmethoxy)-1-(4-methoxybenzyl)-5-nitro-1H-pyrazolo[3,4-b]pyridine for 3-bromo-5-nitro-1-tosyl-1H-indazole. (APCI-pos) M+1=339.1.

Step D: N-(3-(Cyclobutylmethoxy)-1-(4-methoxybenzyl)-1H-pyrazolo[3,4-b]pyridin-5-yl)-2,6-difluoro-3-(propylsulfonamido)benzamide was prepared according to Example 1, Step E, substituting 3-(cyclobutylmethoxy)-1-(4-methoxybenzyl)-5-nitro-1H-pyrazolo[3,4-b]pyridine for 1H-pyrazolo[3,4-b]pyridin-5-amine. m/z (APCI-pos) M+1=600.0.

Step E: N-(3-(Cyclobutylmethoxy)-1-(4-methoxybenzyl)-1H-pyrazolo[3,4-b]pyridin-5-yl)-2,6-difluoro-3-(propylsulfonamido)benzamide (0.017 g, 0.028 mmol) was dissolved in TFA (3 mL) and warmed to 50° C. for 16 hours. The mixture was then heated to 70° C. for 3 hours. The reaction mixture was then concentrated under reduced pressure, and the resulting residue was dissolved in DCM (10 mL), washed with saturated sodium bicarbonate solution (2×), dried over sodium sulfate and concentrated under reduced pressure. Preparative TLC (2×0.5 mm plates, 7% MeOH/DCM) afforded N-(3-(cyclobutylmethoxy)-1H-pyrazolo[3,4-b]pyridin-5-yl)-2,6-difluoro-3-(propylsulfonamido)benzamide (3 mg, 22%) as a solid. $^1$H NMR (400 MHz, $d_6$-DMSO) δ 8.67-8.62 (m, 1H), 8.56-8.52 (m, 1H), 7.68-7.62 (m, 1H), 7.17-7.10 (m, 1H), 4.39-4.33 (m, 2H), 3.15-3.08 (m, 2H), 2.93-2.82 (m, 1H), 2.22-2.13 (m, 2H), 2.04-1.82 (m, 6H), 1.10-1.02 (m, 3H); m/z (APCI-pos) M+1=480.1.

Example 85

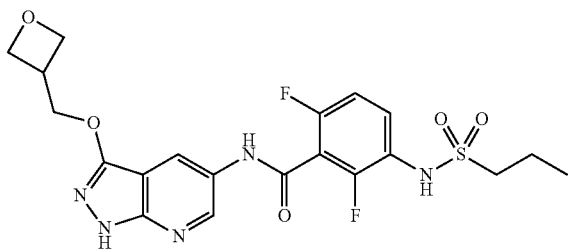 [SMILES: CCCS(=O)(=O)Nc1ccc(F)c(C(=O)Nc2cnc3[nH]nc(OCC4COC4)c3c2)c1F]

2,6-difluoro-N-(3-(oxetan-3-ylmethoxy)-1H-pyrazolo[3,4-b]pyridin-5-yl)-3-(propylsulfonamido)benzamide Step A: Nitromalonaldehyde sodium salt monohydrate (3.57 g, 22.7 mmol) was added to suspension of 5-amino-1-tosyl-1H-pyrazol-3-ol (5.00 g, 19.7 mmol; see Elgemeie, Galal H., et al. "Novel Synthesis of 5-Amino-1-arylsulfonyl-4-pyrazolin-3-ones as a New Class of N-Sulfonylated Pyrazoles." *J. Chem. Res.* (*S*). Issue 6 (1999): pp. 384-385) in acetic acid (30 mL). The mixture was heated at 50° C. for 4 hours. The partial suspension was allowed to cool and diluted with water. The resulting solid was collected by vacuum filtration and dried under high vacuum to afford 5-nitro-1-tosyl-1H-pyrazolo[3,4-b]pyridin-3-ol (4.21 g, 12.6 mmol, 63.8% yield) as a solid.

Step B: 5-Nitro-1-tosyl-1H-pyrazolo[3,4-b]pyridin-3-ol (0.05 g, 0.150 mmol) was dissolved in DMF (1.5 mL). Cesium carbonate (0.146 g, 0.450 mmole) was added, and then 3-(iodomethyl)oxetane (0.030 g, 0.150 mmol; prepared according to US 2008/0021032) was added to the mixture. The mixture was stirred at room temperature for 16 hours. The mixture was then diluted with water and extracted with EtOAc (2×50 mL), and the extracts were washed with brine (1×), dried over sodium sulfate and concentrated under reduced pressure. Preparative TLC (0.5 mm plate, 1:1 ethyl acetate/hexanes) afforded 5-nitro-3-(oxetan-3-ylmethoxy)-1-tosyl-1H-pyrazolo[3,4-b]pyridine (15 mg, 19%) as a solid. $^1$H NMR (400 MHz, CDCl$_3$) δ 9.54-9.52 (m, 1H), 8.83-8.81 (m, 1H), 8.05-7.99 (m, 2H), 7.34-7.28 (m, 2H), 4.93-4.86 (m, 2H), 4.78-4.72 (m, 2H), 4.62-4.55 (m, 2H), 3.57-3.48 (m, 1H), 2.40 (s, 3H).

Step C: 5-Nitro-3-(oxetan-3-ylmethoxy)-1-tosyl-1H-pyrazolo[3,4-b]pyridine (0.015 g, 0.0371 mmol) was dissolved in methanol (0.5 mL). Aqueous potassium carbonate (0.093 mL, 2M in water) was added, and the mixture was warmed to 60° C. for 1 hour. The mixture was then diluted with water (20 mL) and extracted with EtOAc (2×20 mL), and the extracts were dried over sodium sulfate and concentrated to 5-nitro-3-(oxetan-3-ylmethoxy)-1H-pyrazolo[3,4-b]pyridine (5 mg, 54%). This material was used without further purification. m/z (APCI-pos) M+1=251.2.

Step D: 5-Nitro-3-(oxetan-3-ylmethoxy)-1H-pyrazolo[3,4-b]pyridine (0.005 g, 0.020 mmol) was dissolved in ethanol (1 mL) and saturated ammonium chloride solution (0.5 mL) Iron powder (0.0044 g, 0.080 mmol) was added, and the mixture was warmed to 70° C. for 1.5 hours. The mixture was then filtered through GF/F filter paper. The filtrate was then extracted with 5% MeOH/EtOAc (2×), and the extracts were dried over sodium sulfate and concentrated under reduced pressure to 3-(oxetan-3-ylmethoxy)-1H-pyrazolo[3,4-b]pyridin-5-amine (3 mg, 68%). m/z (APCI-pos) M+1=221.2. This material was used without further purification.

Step E: 2,6-Difluoro-N-(3-(oxetan-3-ylmethoxy)-1H-pyrazolo[3,4-b]pyridin-5-yl)-3-(propylsulfonamido)benzamide was prepared according to Example 1, Step E, substituting 3-(oxetan-3-ylmethoxy)-1H-pyrazolo[3,4-b]pyridin-5-amine for 1H-pyrazolo[3,4-b]pyridin-5-amine. $^1$H NMR (400 MHz, CD$_3$OD) δ 8.60-8.58 (m, 1H), 8.55-8.53 (m, 1H), 7.71-7.62 (m, 1H), 7.18-7.10 (m, 1H), 4.94-4.88 (m, 2H), 4.69-4.60 (m, 4H), 3.61-3.53 (m, 1H), 3.15-3.07 (m, 2H), 1.91-1.81 (m, 2H), 1.09-1.01 (m, 3H); m/z (APCI-pos) M+1=482.2.

Example 86

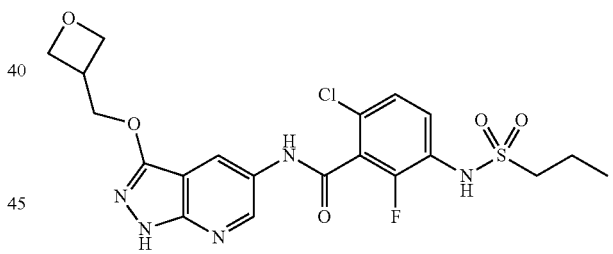

6-chloro-2-fluoro-N-(3-(oxetan-3-ylmethoxy)-1H-pyrazolo[3,4-b]pyridin-5-yl)-3-(propylsulfonamido)benzamide 6-Chloro-2-fluoro-N-(3-(oxetan-3-ylmethoxy)-1H-pyrazolo[3,4-b]pyridin-5-yl)-3-(propylsulfonamido)benzamide was prepared according to Example 1, Step E, substituting 3-(oxetan-3-ylmethoxy)-1H-pyrazolo[3,4-b]pyridin-5-amine for 1H-pyrazolo[3,4-b]pyridin-5-amine and 6-chloro-2-fluoro-3-(propylsulfonamido)benzoic acid for 2,6-difluoro-3-(propylsulfonamido)benzoic acid. $^1$H NMR (400 MHz, CD$_3$OD) δ 8.60-8.57 (m, 1H), 8.54-8.51 (m, 1H), 7.67-7.62 (m, 1H), 7.38-7.34 (m, 1H), 4.94-4.88 (m, 2H), 4.69-4.60 (m, 4H), 3.61-3.51 (m, 1H), 3.17-3.09 (m, 2H), 1.91-1.81 (m, 2H), 1.09-1.01 (m, 3H); m/z (APCI-pos) M+1=498.2, 500.2.

Example 87

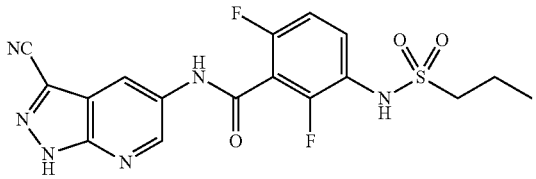 [SMILES: CCCS(=O)(=O)Nc1ccc(F)c(C(=O)Nc2cnc3[nH]nc(C#N)c3c2)c1F]

N-(3-cyano-1H-pyrazolo[3,4-b]pyridin-5-yl)-2,6-difluoro-3-(propylsulfonamido)benzamide N-(3-Bromo-1H-pyrazolo[3,4-b]pyridin-5-yl)-2,6-difluoro-3-(propylsulfonamido)benzamide (0.14 g, 0.285 mmol), zinc cyanide (0.047 g, 0.399 mmol), $Pd_2(dba)_3$ (0.021 g, 0.023 mmol), 1,1'-bis(diphenylphosphino)ferrocene (0.025 g, 0.046 mmol) and zinc (0.009 g, 0.142 mmol) were combined with N,N'-dimethylacetamide (1.5 mL) in a microwave vessel and heated in a microwave reactor to 150° C. for 40 minutes. The reaction mixture was filtered, and the filtrate was concentrated. The crude mixture was directly purified by reverse phase HPLC to afford N-(3-cyano-1H-pyrazolo[3,4-b]pyridin-5-yl)-2,6-difluoro-3-(propylsulfonamido)benzamide (0.038 g, 32%). $^1H$ NMR (400 MHz, $d_6$-DMSO) δ 11.39 (s, 1H), 9.74 (br s, 1H), 8.81 (d, 1H), 8.77 (d, 1H), 7.59 (td, 1H), 7.30 (t, 1H), 3.20-3.06 (m, 2H), 1.87-1.68 (m, 2H), 1.00 (t, 3H); m/z (ES-MS) 421.1 (98.9%) [M+1].

Example 88

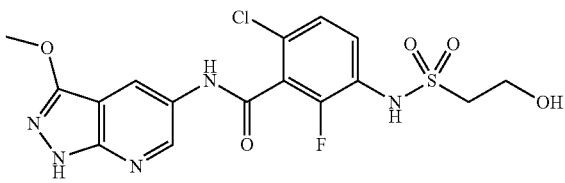 [SMILES: COc1n[nH]c2ncc(NC(=O)c3c(Cl)ccc(NS(=O)(=O)CCO)c3F)cc12]

6-chloro-2-fluoro-3-(3-hydroxypropylsulfonamido)-N-(3-methoxy-1H-pyrazolo[3,4-b]pyridin-5-yl)benzamide Step A: A 100 mL, round-bottomed flask was charged with benzyl 3-amino-6-chloro-2-fluorobenzoate (1.0 g, 3.58 mmol), 3-(4-methoxyphenoxy)propane-1-sulfonyl chloride (2.84 g, 10.7 mmol), N-ethyl-N-isopropylpropan-2-amine (1.91 mL, 10.7 mmol) and DCM (15 mL). The reaction mixture was stirred at −78° C. until LC-MS showed that the starting material had been consumed (about 12 hours). Then the reaction mixture was cooled to room temperature and partitioned between EtOAc (500 mL) and water (200 mL). The phases were separated, and the aqueous phase was extracted with EtOAc (3×200 mL). The combined organic layers were dried ($Na_2SO_4$), filtered and concentrated to yield crude benzyl 6-chloro-2-fluoro-3-(3-(4-methoxyphenoxy)-N-(3-(4-methoxyphenoxy)propylsulfonyl)propylsulfonamido)benzoate. The crude product was used in the next step.

Step B: A 100 mL, round-bottomed flask was charged with benzyl 6-chloro-2-fluoro-3-(3-(4-methoxyphenoxy)-N-(3-(4-methoxyphenoxy)propylsulfonyl)propylsulfonamido) benzoate (1.08 g, 1.47 mmol), potassium hydroxide (4.40 mL, 4.40 mmol) and MeOH (10 mL). The reaction mixture was stirred at room temperature until TLC showed that the starting material had been consumed (about 12 hours). HCl (5 mL, 1N) was added. Then the reaction mixture was partitioned between EtOAc (500 mL) and water (100 mL). The phases were separated, and the aqueous phase was extracted with EtOAc (3×200 mL). The combined organic layers were dried ($Na_2SO_4$), filtered and concentrated to yield crude 6-chloro-2-fluoro-3-(3-(4-methoxyphenoxy)propylsulfonamido)benzoic acid. The crude product was purified by silica gel chromatography (EtOAc/hexane from 1/4 to 1/0, v/v) to afford 6-chloro-2-fluoro-3-(3-(4-methoxyphenoxy)propylsulfonamido)benzoic acid (0.58 g, 95.1%). $^1H$ NMR (400 MHz, $CDCl_3$) δ 10.02 (s, 1H), 7.39-7.53 (m, 2H), 6.81 (m, 4H), 4.01 (t, 2H), 3.64 (s, 3H), 3.34 (t, 2H), 2.11 (m, 2H).

Step C: A 100 mL, round-bottomed flask was charged with 3-methoxy-1-(4-methoxybenzyl)-1H-pyrazolo[3,4-b]pyridin-5-amine (123.0 mg, 0.43 mmol), 6-chloro-2-fluoro-3-(3-(4-methoxyphenoxy)propylsulfonamido)benzoic acid (271.1 mg, 0.65 mmol), N1-((ethylimino)methylene)-N3,N3-dimethylpropane-1,3-diamine hydrochloride (124.4 mg, 0.65 mmol), 1H-benzo[d][1,2,3]triazol-1-ol hydrate (99.4 mg, 0.65 mmol), N-ethyl-N-isopropylpropan-2-amine (83.9 mg, 0.65 mmol) and DCM (1.5 mL). The reaction mixture was stirred at room temperature until LC-MS showed that the starting material had been consumed (about 12 hours). Then the reaction mixture was partitioned between EtOAc (300 mL) and water (150 mL). The phases were separated, and the aqueous phase was extracted with EtOAc (3×150 mL). The combined organic layers were dried ($Na_2SO_4$), filtered and concentrated to yield a crude product. The crude product was purified by silica gel chromatography (EtOAc/hexane from 1/4 to 1/0, v/v) to afford 6-chloro-2-fluoro-N-(3-methoxy-1-(4-methoxybenzyl)-1H-pyrazolo[3,4-b]pyridin-5-yl)-3-(3-(4-methoxyphenoxy)propylsulfonamido)benzamide (228.3 mg, 77.14%). LRMS (APCI pos): >95% purity, 254 nm, m/e 684.1 and 686.2 (M+1).

Step D: A 100 mL, round-bottomed flask was charged with 6-chloro-2-fluoro-N-(3-methoxy-1-(4-methoxybenzyl)-1H-pyrazolo[3,4-b]pyridin-5-yl)-3-(3-(4-methoxyphenoxy)propylsulfonamido)benzamide (228.3 mg, 0.33 mmol) and TFA (0.5 mL). The reaction mixture was stirred at 80° C. until LC-MS showed that the starting material had been consumed (overnight). Then the $CF_3COOH$ was removed under reduced pressure. The residue was purified by silica gel chromatography (EtOAc/hexane from 1/4 to 1/0, v/v) to afford 6-chloro-2-fluoro-N-(3-methoxy-1H-pyrazolo[3,4-b]pyridin-5-yl)-3-(3-(4-methoxyphenoxy)propylsulfonamido)benzamide (181.4 mg, 96.38%). LRMS (APCI pos): >95% purity, 254 nm, m/e 564.1 and 566.1 (M+1).

Step E: A 100 mL, round-bottomed flask was charged with 6-chloro-2-fluoro-N-(3-methoxy-1H-pyrazolo[3,4-b]pyridin-5-yl)-3-(3-(4-methoxyphenoxy) propylsulfonamido) benzamide (30.0 mg, 0.053 mmol), $Ce(NH_4)_2(NO_2)_6$ (72.9 mg, 0.13 mmol) and $CH_3CN$ (0.5 mL) The reaction mixture was stirred at room temperature until LC-MS showed that the starting material had been consumed (overnight). Then the reaction mixture was partitioned between EtOAc (200 mL) and water (100 mL). The phases were separated, and the aqueous phase was extracted with EtOAc (3×100 mL) The combined organic layers were dried ($Na_2SO_4$), filtered and concentrated to yield a crude product. The crude product was purified by silica gel chromatography (EtOAc/hexane from 1/2 to 1/0, v/v) to afford impure 6-chloro-2-fluoro-3-(3-hydroxypropylsulfonamido)-N-(3-methoxy-1H-pyrazolo[3,4-b]pyridin-5-yl)benzamide (20.3 mg). Further purification by preparation HPLC afforded pure product (2.1 mg, 8.6%). LRMS (APCI pos): >95% purity, 254 nm, m/e 458.2 (M+1). $^1$H NMR (400 MHz, CDCl$_3$) δ 8.59 (d, 1H), 8.50 (d, 1H), 7.65 (m, 1H), 7.36 (d, 1H), 4.01 (s, 3H), 3.65 (t, 2H), 3.25 (t, 2H), 2.03 (m, 2H).

Example 89

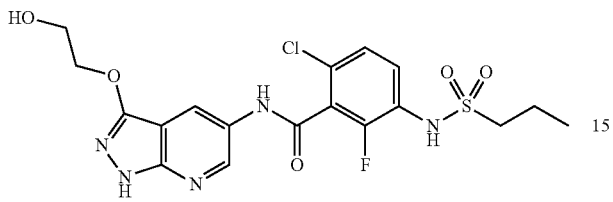

6-chloro-2-fluoro-N-(3-(2-hydroxyethoxy)-1H-pyrazolo[3,4-b]pyridin-5-yl)-3-(propylsulfonamido)benzamide Step A: 1M NaOH (46.5 mL, 46.5 mmol) was added to a solution of ethyl 5-amino-3-(2-hydroxyethoxy)-1H-pyrazole-4-carboxylate (2.00 g, 9.29 mmol, prepared as described in Neidlein, Richard, et al. "Heterocyclic Compounds from 2-(Alkoxycarbonylcyanomethylene)-1,3-dioxolanes." J. Het. Chem. Vol. 26 (1989): pp. 1335-1340) in ethanol (30 mL), and the mixture was refluxed overnight. The solution was washed with DCM with 25% IPA, then acidified to a pH of 3 with concentrated HCl. Gas evolution was observed. The solution was washed with DCM with 25% IPA, and the aqueous layer was evaporated. The residue was treated with methanol, filtered, and the filtrate was evaporated to yield crude 2-(5-amino-1H-pyrazol-3-yloxy)ethanol (3.28 g) along with inorganic salts.

Step B: Nitromalonaldehyde sodium salt monohydrate (1.46 g, 9.29 mmol) was added to crude 2-(5-amino-1H-pyrazol-3-yloxy)ethanol (3.28 g) with salts (1.33 g, 9.29 mmol theoretical) in acetic acid (10 mL). This was heated at 90° C. for 2 hours. The cooled reaction mixture was diluted with water, and the mixture was extracted twice with DCM containing 25% IPA. The organic extracts were dried over magnesium sulfate, filtered, and evaporated to yield regioisomer 2-(6-nitropyrazolo[1,5-a]pyrimidin-2-yloxy)ethanol (0.77 g, 3.43 mmol) as a solid. The 2-(6-nitropyrazolo[1,5-a]pyrimidin-2-yloxy)ethanol (460 mg, 2.9 mmol) was suspended in water (40 mL), treated with saturated aqueous sodium bicarbonate (2 mL), and the mixture was refluxed for 2 hours. The cooled reaction mixture was extracted three times with DCM containing 25% IPA. The organic extracts were dried over magnesium sulfate, filtered, and evaporated to an oil. The crude material was purified by column chromatography with ethyl acetate to provide 2-(5-nitro-1H-pyrazolo[3,4-b]pyridin-3-yloxy)ethanol (60 mg, 0.27 mmol, 2.9% yield) as a solid.

Step C: Iron powder (0.075 g 1.34 mmol) and ammonium chloride (0.14 g, 2.68 mmol) were added to 2-(5-nitro-1H-pyrazolo[3,4-b]pyridin-3-yloxy)ethanol (60 mg, 0.27 mmol) in ethanol:water (5 mL, 2:1). The mixture was heated at 85° C. in a sealed vial. After 5 hours, the reaction mixture was filtered and evaporated to afford crude product as a solid. The crude was absorbed on silica gel and chromatographed on a silica gel plug with 10:1 ethyl acetate:methanol. Fractions 2-5 contained 2-(5-amino-1H-pyrazolo[3,4-b]pyridin-3-yloxy) ethanol (21.8 mg, 0.112 mmol, 42% yield) as a solid.

Step D: 6-Chloro-2-fluoro-N-(3-(2-hydroxyethoxy)-1H-pyrazolo[3,4-b]pyridin-5-yl)-3-(propylsulfonamido)benzamide (30.2 mg, 57%) was prepared according to the general procedure for Example 1, Step E, substituting 6-chloro-3-(propylsulfonamido)-2-fluorobenzoic acid for 3-(propylsulfonamido)-2,6-difluorobenzoic acid and 2-(5-amino-1H-pyrazolo[3,4-b]pyridin-3-yloxy)ethanol for 1H-pyrazolo[3,4-b]pyridin-5-amine. $^1$H NMR (400 MHz, CD$_3$OD) δ 8.58 (br s, 2H), 7.64 (t, 1H), 7.38-7.35 (m, 1H), 4.46 (t, 2H), 3.96 (t, 2H) 3.16-3.12 (m, 2H), 1.91-1.81 (m, 1H), 1.05 (t, 3H); m/z (ESI-pos) M+1=472.1.

Example 90

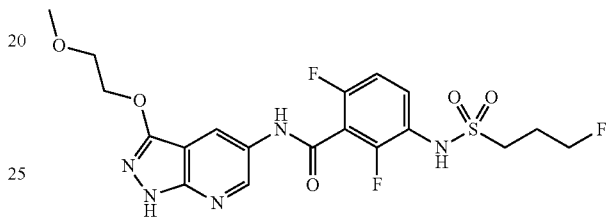

2,6-difluoro-3-(3-fluoropropylsulfonamido)-N-(3-(2-methoxyethoxy)-1H-pyrazolo[3,4-b]pyridin-5-yl) benzamide 2,6-Difluoro-3-(3-fluoropropylsulfonamido)-N-(3-(2-methoxyethoxy)-1H-pyrazolo[3,4-b]pyridin-5-yl)benzamide was prepared according to the general procedure for Example 1, Step E, substituting 2,6-difluoro-3-(3-fluoropropylsulfonamido)benzoic acid for 2,6-difluoro-3-(propylsulfonamido)benzoic acid and 3-(2-methoxyethoxy)-1H-pyrazolo[3,4-b]pyridin-5-amine for 1H-pyrazolo[3,4-b]pyridin-5-amine. $^1$H NMR (400 MHz, CD$_3$OD) δ 8.59-8.61 (m, 1H), 8.53-8.55 (m, 1H), 7.62-7.70 (m, 1H), 7.11-7.18 (m, 1H), 4.59-4.63 (m, 1H), 4.47-4.54 (m, 3H), 3.82-3.85 (m, 2H), 3.45 (s, 3H), 3.24-3.29 (m, 2H), 2.15-2.29 (m, 2H); m/z (APCI-pos) M−1=488.1.

Example 91

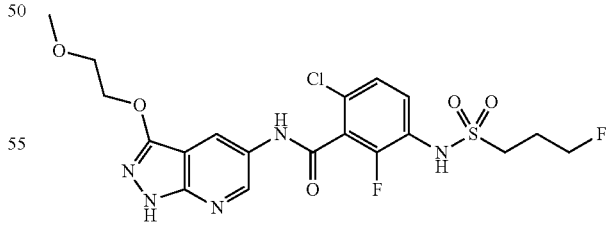

6-chloro-2-fluoro-3-(3-fluoropropylsulfonamido)-N-(3-(2-methoxyethoxy)-1H-pyrazolo[3,4-b]pyridin-5-yl)benzamide 6-Chloro-2-fluoro-3-(3-fluoropropylsulfonamido)-N-(3-(2-methoxyethoxy)-1H-pyrazolo[3,4-b]pyridin-5-yl)benzamide was prepared according to the general procedure for Example 1, Step E, substituting 6-chloro-2-fluoro-3-(3-fluoropropylsulfonamido)benzoic acid for 2,6-difluoro-3-(propylsulfonamido)benzoic acid and 3-(2-methoxyethoxy)-1H-pyrazolo[3,4-b]pyridin-5-amine for 1H-pyrazolo[3,4-b]pyridin-5-amine. $^1$H NMR (400 MHz, CD$_3$OD) δ 8.61-8.62 (m, 1H), 8.52-8.54 (m, 1H), 7.60-7.66 (m, 1H), 7.33-7.37 (m, 1H), 4.58-4.62 (m, 1H), 4.46-4.54 (m, 3H), 3.81-3.85 (m, 2H), 3.45 (s, 3H), 3.24-3.29 (m, 2H), 2.14-2.29 (m, 2H); m/z (APCI-neg) M−1=502.2.

Example 92

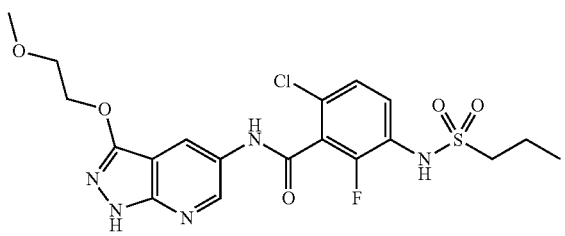

6-chloro-2-fluoro-N-(3-(2-methoxyethoxy)-1H-pyrazolo[3,4-b]pyridin-5-yl)-3-(propylsulfonamido)benzamide 6-Chloro-2-fluoro-N-(3-(2-methoxyethoxy)-1H-pyrazolo[3,4-b]pyridin-5-yl)-3-(propylsulfonamido)benzamide was prepared according to the general procedure for Example 1, Step E, substituting 6-chloro-2-fluoro-3-(propylsulfonamido)benzoic acid for 2,6-difluoro-3-(propylsulfonamido)benzoic acid and 3-(2-methoxyethoxy)-1H-pyrazolo[3,4-b]pyridin-5-amine for 1H-Pyrazolo[3,4-b]pyridin-5-amine. $^1$H NMR (400 MHz, CD$_3$OD) δ 8.59-8.61 (m, 1H), 8.52-8.54 (m, 1H), 7.61-7.66 (m, 1H), 7.33-7.37 (m, 1H), 4.50-4.54 (m, 2H), 3.82-3.85 (m, 2H), 3.45 (s, 3H), 3.11-3.17 (m, 2H), 1.81-1.91 (m, 2H), 1.03-1.08 (m, 3H); m/z (APCI-neg) M−1=486.1.

Example 93

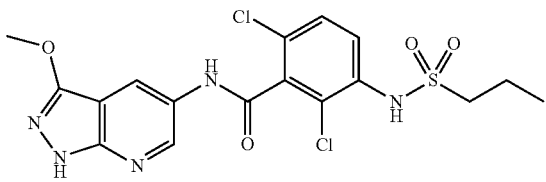

2,6-dichloro-N-(3-methoxy-1H-pyrazolo[3,4-b]pyridin-5-yl)-3-(propylsulfonamido)benzamide 3-Methoxy-1H-pyrazolo[3,4-b]pyridin-5-amine (50 mg, 0.305 mmol) in N,N-dimethylformamide (3.0 mL) was sequentially treated with 2,6-dichloro-3-(propylsulfonamido)benzoic acid (356 mg, 1.14 mmol), EDCI (117 mg, 0.609 mmol), and HOBt (82.3 mg, 0.609 mmol) and heated to 60° C. After 72 hours, the reaction mixture was allowed to cool to ambient temperature. The mixture was diluted with ethyl acetate, washed with water (4×), sodium bicarbonate (2×), and brine (1×), dried over sodium sulfate, and concentrated. The crude product was applied directly to a silica gel column and eluted with a gradient (30% to 100%) of ethyl acetate-hexanes to provide 2,6-dichloro-N-(3-methoxy-1H-pyrazolo[3,4-b]pyridin-5-yl)-3-(propylsulfonamido)benzamide (67.8 mg, 0.0524 mmol, 35.4% yield) as a solid. $^1$H NMR (400 MHz, d$_6$-DMSO) δ 12.63-12.59 (s, 1H), 11.04-11.00 (s, 1H), 9.83-9.79 (s, 1H), 8.59-8.570 (d, 1H), 8.47-8.45 (d, 1H), 7.60-7.57 (m, 2H), 4.03-4.01 (s, 3H), 3.21-3.13 (m, 2H), 1.83-1.73 (m, 2H), 1.02-0.97 (t, 3H); MS (APCI-neg) m/z=456.1 (M−H).

Example 94

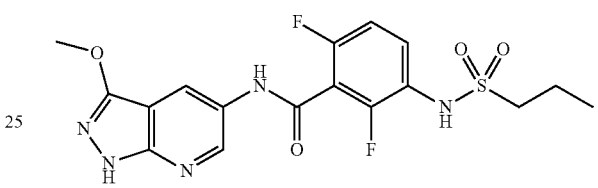

2,6-difluoro-N-(3-methoxy-1H-pyrazolo[3,4-b]pyridin-5-yl)-3-(propylsulfonamido)benzamide Step A: 3-Methoxy-5-nitro-1H-pyrazolo[3,4-b]pyridine (38%) was prepared according to Example 4, Step A, substituting 3-methoxy-1H-pyrazol-5-amine (prepared as described in JP 01013072) for 3-methyl-1H-pyrazol-5-amine.

Step B: 3-Methoxy-1H-pyrazolo[3,4-b]pyridin-5-amine (99%) was prepared according to Example 4, Step B, substituting 3-methoxy-5-nitro-1H-pyrazolo[3,4-b]pyridine for 3-methyl-5-nitro-1H-pyrazolo[3,4-b]pyridine.

Step C: 2,6-Difluoro-N-(3-methoxy-1H-pyrazolo[3,4-b]pyridin-5-yl)-3-(propylsulfonamido)benzamide (55%) was prepared according to Example 1, Step E, substituting 3-methoxy-1H-pyrazolo[3,4-b]pyridin-5-amine for 1H-pyrazolo[3,4-b]pyridin-5-amine.

Step D: 2,6-Difluoro-N-(3-methoxy-1H-pyrazolo[3,4-b]pyridin-5-yl)-3-(propylsulfonamido)benzamide (0.963 g, 2.26 mmol) was taken up in ethanol (23 mL) as a slurry. 24% Potassium ethanolate (0.888 mL, 2.26 mmol) was added, and the slurry was heated to 50° C. and sonicated for 10 minutes until the solids went into solution. The solution was cooled, filtered through celite and concentrated to an oil. The oil was taken up in Et$_2$O, which precipitated a solid. The homogeneous suspension was concentrated and dried under vacuum to provide potassium (2,6-difluoro-3-(3-methoxy-1H-pyrazolo[3,4-b]pyridin-5-ylcarbamoyl)phenyl)(propylsulfonyl)amide (1.05 g, 100%) as a solid. $^1$H NMR (400 MHz, d$_6$-DMSO) δ 12.56 (s, 1H), 10.87 (s, 1H), 8.64 (s, 1H), 8.51 (s, 1H), 7.30-7.36 (m, 1H), 6.78-6.80 (m, 1H), 4.01 (s, 3H), 2.61-2.65 (m, 2H), 1.59-1.65 (m, 2H), 0.88-0.92 (t, 3H).

Example 95

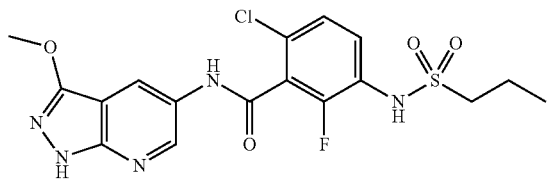 [SMILES: CCCS(=O)(=O)Nc1ccc(F)c(C(=O)Nc2cnc3[nH]nc(OC)c3c2)c1F]

6-chloro-2-fluoro-N-(3-methoxy-1H-pyrazolo[3,4-b]pyridin-5-yl)-3-(propylsulfonamido)benzamide Step A: 3-Methoxy-1-(4-methoxybenzyl)-1H-pyrazolo[3,4-b]pyridin-5-amine (0.020 g, 0.070 mmol), 6-chloro-2-fluoro-3-(propylsulfonamido)benzoic acid (0.023 g, 0.077 mmol), EDCI (0.015 g, 0.077 mmol), and HOBt (0.010 g, 0.077 mmol) were dissolved in DMF (1.0 mL) and stirred for two days at room temperature. The solution was partitioned between water and EtOAc. The organic layers were washed with water (3×), brine, dried over $Na_2SO_4$ and concentrated to an oil. The residue was purified by column chromatography (2:1 hexanes/EtOAc) giving 6-chloro-2-fluoro-N-(3-methoxy-1-(4-methoxybenzyl)-1H-pyrazolo[3,4-b]pyridin-5-yl)-3-(propylsulfonamido)benzamide (0.027 g, 68%) as a solid.

Step B: 6-Chloro-2-fluoro-N-(3-methoxy-1-(4-methoxybenzyl)-1H-pyrazolo[3,4-b]pyridin-5-yl)-3-(propylsulfonamido)benzamide (0.027 g, 0.0480 mmol) was heated to reflux in TFA overnight. The reaction mixture was cooled to room temperature and was concentrated to an oil. DCM was added to the oil resulting in a precipitate, which was collected by filtration giving 6-chloro-2-fluoro-N-(3-methoxy-1H-pyrazolo[3,4-b]pyridin-5-yl)-3-(propylsulfonamido)benzamide (0.0175 g, 82%) as a solid. $^1$H NMR (400 MHz, $d_6$-DMSO) δ 12.60 (s, 1H), 11.07 (1H, s), 9.99 (br s, 1H), 8.58 (s, 1H), 8.49 (s, 1H), 7.52-7.57 (m, 1H), 7.44-7.46 (m, 1H), 4.02 (s, 3H), 3.15-3.19 (m, 2H), 1.73-1.79 (m, 2H), 0.97-1.01 (m, 3H); m/z (APCI-pos) M+1=442.1.

Example 96

2,6-difluoro-N-(3-methoxy-1H-pyrazolo[3,4-b]pyridin-5-yl)-3-(N-propylsulfamoylamino)benzamide Step A: Propylsulfamoyl chloride (0.379 mL, 2.40 mmol) was added to methyl 3-amino-2,6-difluorobenzoate (0.150 mL, 0.802 mmol), TEA (0.335 mL, 2.40 mmol) in DCM (1.5 mL) at 0° C. The solution was warmed to room temperature overnight. The solids were filtered, and the supernate was concentrated to provide crude methyl 2,6-difluoro-3-(N-propylsulfamoylamino)benzoate, which was used directly in next step.

Step B: NaOH (1M, 3.20 mL, 3.20 mmol) was added to methyl 2,6-difluoro-3-(N-propylsulfamoylamino)benzoate (0.24 g, 0.80 mmol) in 2:1 THF:MeOH (3 mL). The solution was stirred at room temperature for 16 hours, and then the solution was stirred at 70° C. for 16 hours. The solution was concentrated under reduced pressure to about half volume and then washed with EtOAc. The pH was adjusted to about 5, and the mixture was extracted with EtOAc (3×5 mL). The organic layers were dried over sodium sulfate, decanted and concentrated to provide 2,6-difluoro-3-(N-propylsulfamoylamino)benzoic acid.

Step C: 2,6-Difluoro-3-(N-propylsulfamoylamino)benzoic acid (0.095 g, 0.32 mmol), 3-methoxy-1H-pyrazolo[3,4-b]pyridin-5-amine (0.053 g, 0.32 mmol), HOBt (0.044 g, 0.32 mmol), and EDCI (0.062 g, 0.32 mmol) were dissolved in DMF (1.6 mL) and stirred at room temperature for 16 hours. The mixture was diluted with EtOAc (30 mL) and washed with a mixture of 1:1:1 water:bicarbonate:brine (3×20 mL). The organic layers were dried over sodium sulfate and concentrated under reduced pressure. The residue was purified via column chromatography eluting with 1:1 then 8:2 EtOAc:hexanes to provide 2,6-difluoro-N-(3-methoxy-1H-pyrazolo[3,4-b]pyridin-5-yl)-3-(N-propylsulfamoylamino)benzamide (0.090 g, 0.20 mmol, 63% yield). $^1$H NMR (400 MHz, $CD_3OD$) δ 8.57-8.60 (m, 1H), 8.47-8.49 (m, 1H), 7.63-7.70 (m, 1H), 7.04-7.11 (m, 1H), 4.07 (s, 3H), 2.94-3.30 (m, 2H), 1.45-1.56 (m, 2H), 0.85-0.90 (m, 3H); m/z (APCI-pos) M+1=441.1.

Example 97

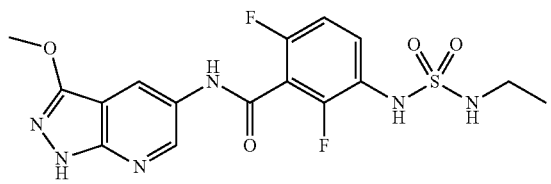 [SMILES: CCNS(=O)(=O)Nc1ccc(F)c(C(=O)Nc2cnc3[nH]nc(OC)c3c2)c1F]

3-(N-ethylsulfamoylamino)-2,6-difluoro-N-(3-methoxy-1H-pyrazolo[3,4-b]pyridin-5-yl)benzamide 3-(N-Ethylsulfamoylamino)-2,6-difluoro-N-(3-methoxy-1H-pyrazolo[3,4-b]pyridin-5-yl)benzamide was prepared following Example 96, substituting ethylsulfamoyl chloride for propylsulfamoyl chloride in Step A. $^1$H NMR (400 MHz, $CD_3OD$) δ 8.56-8.62 (m, 1H), 8.47-8.52 (m, 1H), 7.62-7.71 (m, 1H), 7.04-7.13 (m, 1H), 4.08 (s, 3H), 3.01-3.11 (m, 2H), 1.07-1.16 (m, 3H); m/z (APCI-pos) M+1=427.1.

Example 98

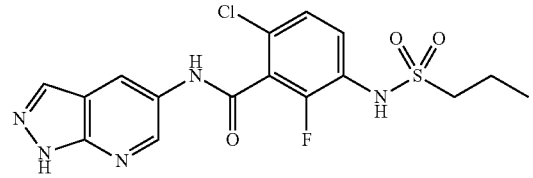 [SMILES: CCCS(=O)(=O)Nc1ccc(Cl)c(C(=O)Nc2cnc3[nH]ncc3c2)c1F]

6-chloro-2-fluoro-3-(propylsulfonamido)-N-(1H-pyrazolo[3,4-b]pyridin-5-yl)benzamide 1H-Pyrazolo[3,4-b]pyridin-5-amine (1.55 g, 11.6 mmol), 6-chloro-2-fluoro-3-(propylsulfonamido)benzoic acid (3.59 g, 12.1 mmol), EDCI (2.44 g, 12.7 mmol), and HOBt (0.25 g, 0.16 mmol) were dissolved in DMF (30 mL) and stirred at room temperature for 16 hours. The reaction mixture was concentrated. The residue was diluted with ethyl acetate (500 mL), and the organic layers were washed with water (3×50 mL). The organic layers were dried, filtered and concentrated. The crude solids were washed with DCM (3×50 mL) to give 6-chloro-2-fluoro-3-(propylsulfonamido)-N-(1H-pyrazolo[3,4-b]pyridin-5-yl)benzamide (2.7 g, 58%) as a solid. $^1$H NMR (400 MHz, CD$_3$OD) δ 8.7 (s, 1H), 8.6 (s, 1H), 8.1 (s, 1H), 7.7 (m, 1H), 7.4 (m, 1H), 3.1 (m, 2H), 1.9 (m, 2H), 1.1 (t, J=7.6 Hz, 3H); m/z (APCI-neg) M−1=410.2, 412.2.

Example 99

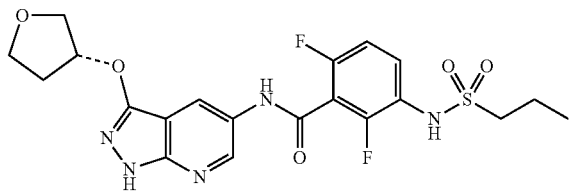

(R)-2,6-difluoro-3-(propylsulfonamido)-N-(3-(tetrahydrofuran-3-yloxy)-1H-pyrazolo[3,4-b]pyridin-5-yl)benzamide The title compound (20% yield over 4 steps) was prepared according to the general procedure for Example 78, Steps A through D, substituting (S)-tetrahydrofuran-3-ol for 2-fluoroethanol. LRMS (APCI-pos) m/e 482.1 (M+1). $^1$H NMR (400 MHz, CD$_3$OD) δ 8.60-8.58 (m, 1H), 8.52-8.50 (m, 1H), 7.69-7.62 (m, 1H), 7.17-7.11 (m, 1H), 5.50-5.45 (m, 1H), 4.10-3.99 (m, 4H), 3.94-3.88 (m, 1H), 3.14-3.08 (m, 2H), 2.39-2.24 (m, 2H), 1.92-1.81 (m, 2H), 1.08-1.03 (m, 3H).

Example 100

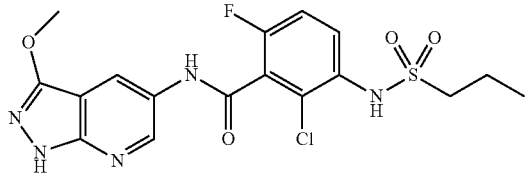 [SMILES: CCCS(=O)(=O)Nc1ccc(F)c(C(=O)Nc2cnc3[nH]nc(OC)c3c2)c1Cl]

2-chloro-6-fluoro-N-(3-methoxy-1H-pyrazolo[3,4-b]pyridin-5-yl)-3-(propylsulfonamido)benzamide 2-Chloro-6-fluoro-3-(propylsulfonamido)benzoic acid (75.7 mg, 0.256 mmol) in N,N-dimethylformamide (2.5 mL) was sequentially treated with 3-methoxy-1H-pyrazolo[3,4-b]pyridin-5-amine (46.2 mg, 0.282 mmol), EDCI (54.0 mg, 0.282 mmol), and HOBt (38.0 mg, 0.282 mmol). The reaction mixture was allowed to stir at ambient temperature for 24 hours. The mixture was then diluted with ethyl acetate and washed with water (4×), sodium bicarbonate (2×), and brine, dried over sodium sulfate and concentrated. The crude product was triturated with DCM to afford 2-chloro-6-fluoro-N-(3-methoxy-1H-pyrazolo[3,4-b]pyridin-5-yl)-3-(propylsulfonamido)benzamide (18.0 mg, 0.0407 mmol, 15.9% yield) as a solid. $^1$H NMR (400 MHz, d$_6$-DMSO) δ 12.62-12.56 (s, 1H), 11.08-11.03 (s, 1H), 9.78-9.65 (s, 1H), 8.61-8.56 (s, 1H), 8.50-8.45 (s, 1H), 7.63-7.55 (m, 1H), 7.44-7.35 (m, 1H), 4.03-3.99 (s, 3H), 3.14-3.07 (m, 2H), 1.83-1.73 (m, 2H), 1.04-0.95 (t, 3H); MS (APCI-neg) m/z=440.1 (M−H).

Example 101

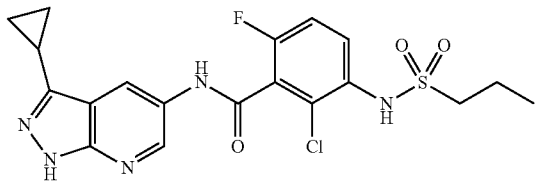 [SMILES: CCCS(=O)(=O)Nc1ccc(F)c(C(=O)Nc2cnc3[nH]nc(C4CC4)c3c2)c1Cl]

2-chloro-N-(3-cyclopropyl-1H-pyrazolo[3,4-b]pyridin-5-yl)-6-fluoro-3-(propyl sulfonamido)benzamide 3-Cyclopropyl-1H-pyrazolo[3,4-b]pyridin-5-amine (0.0744 g, 0.427 mmol), 2-chloro-6-fluoro-3-(propylsulfonamido)benzoic acid (0.139 g, 0.470 mmol), EDCI (0.0901 g, 0.470 mmol), and HOBt (0.0635 g, 0.470 mmol) were dissolved in DMF (2 mL) and stirred for 24 hours. The reaction mixture was diluted with ethyl acetate and washed with water (4 X), saturated aqueous sodium bicarbonate solution (2×), and brine, dried over sodium sulfate and concentrated. The crude product was triturated with 1:1 DCM/Et$_2$O to afford 2-chloro-N-(3-cyclopropyl-1H-pyrazolo[3,4-b]pyridin-5-yl)-6-fluoro-3-(propylsulfonamido)benzamide (128 mg, 66% yield) as a solid. $^1$H NMR (400 MHz, d$_6$-DMSO) δ 13.21 (s, 1H), 11.08 (s, 1H), 9.74 (s, 1H), 8.66 (s, 1H), 8.55 (s, 1H), 7.59-7.63 (m, 1H), 7.40-7.46 (m, 1H), 3.11-3.15 (m, 2H), 2.29-2.31 (m, 1H), 1.79-1.80 (m, 2H), 0.95-1.00 (m, 7H); MS (APCI-neg) m/z=452.2, 454.1 (M+H).

Example 102

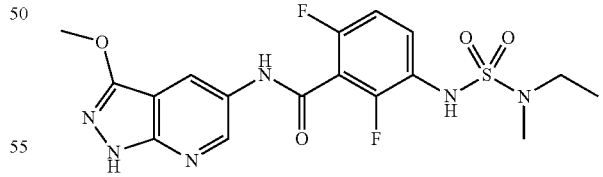

3-(N-ethyl-N-methylsulfamoylamino)-2,6-difluoro-N-(3-methoxy-1H-pyrazolo[3,4-b]pyridin-5-yl)benzamide Step A: A solution of triethylamine (0.260 mL, 1.85 mmol) and methyl 3-amino-2,6-difluorobenzoate (0.257 mL, 1.85 mmol) was added dropwise to sulfuryl dichloride (0.156 mL, 1.85 mmol) in DCM (3 mL) at −78° C. After 2 hours, N-methylethanamine (0.304 mL, 3.70 mmol) was added and then let warm to room temperature overnight. The solvent was concentrated under reduced pressure, and the residue was taken up in NaOH (2 mL, 1M) and washed with EtOAc. The aqueous pH was lowered to below 3 and, the mixture was extracted with EtOAc (3×5 mL). The combined organic layers were dried over sodium sulfate, decanted and concentrated under reduced pressure. The residue was purified via silica gel chromatography eluting with 7:3 hexane:EtOAc to afford impure methyl 3-(N-ethyl-N-methylsulfamoylamino)-2,6-difluorobenzoate (0.280 g, 49.0% yield).

Step B: NaOH (0.908 mL, 1.82 mmol) was added to methyl 3-(N-ethyl-N-methylsulfamoylamino)-2,6-difluorobenzoate (0.280 g, 0.908 mmol) in THF:MeOH (3:2; 5 mL). The mixture was warmed to 60° C. for 16 hours. The cooled mixture was concentrated under reduced pressure, and the residue was taken up in 1M NaOH (4 mL) and washed with EtOAc. The aqueous pH was lowered to below 3, and the mixture was extracted with EtOAc (3×6 mL) to provide crude 3-(N-ethyl-N-methylsulfamoylamino)-2,6-difluorobenzoic acid (222 mg, 83% yield).

Step C: HOBt (0.017 g, 0.13 mmol), EDCI (0.054 g, 0.28 mmol), and 3-methoxy-1H-pyrazolo[3,4-b]pyridin-5-amine (0.046 g, 0.28 mmol) was added to 3-(N-ethyl-N-methylsulfamoylamino)-2,6-difluorobenzoic acid (0.075 g, 0.25 mmol) in DMF (1 mL). The reaction mixture was stirred at room temperature for 16 hours. The mixture was diluted with EtOAc (6 mL) and washed with brine (3×5 mL). The organic layers were dried over sodium sulfate, decanted, and concentrated under reduced pressure. The residue was purified via silica gel chromatography eluting with 5% MeOH:DCM to afford 3-(N-ethyl-N-methylsulfamoylamino)-2,6-difluoro-N-(3-methoxy-1H-pyrazolo[3,4-b]pyridin-5-yl)benzamide (0.055 g, 0.12 mmol, 49% yield). $^1$H NMR (400 MHz, CD$_3$OD) δ 8.60-8.63 (m, 1H), 8.50-8.52 (m, 1H), 7.63-7.70 (m, 1H), 7.09-7.15 (m, 1H), 4.09 (s, 3H), 3.18-3.25 (m, 2H), 2.83 (s, 3H), 1.09-1.14 (m, 3H); m/z (APCI-neg) M−1=439.0.

The following compounds in Table 2 were prepared following the above procedures.

TABLE 2

| Ex. # | Structure | Name | MS/NMR |
|---|---|---|---|
| 103 | 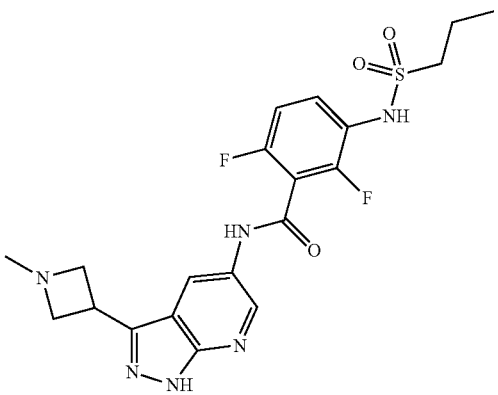 [SMILES: CCCS(=O)(=O)Nc1ccc(F)c(C(=O)Nc2cnc3[nH]nc(C4CN(C)C4)c3c2)c1F] | 2,6-difluoro-N-(3-(1-methylazetidin-3-yl)-1H-pyrazolo[3,4-b]pyridin-5-yl)-3-(propylsulfonamido)benzamide | $^1$H NMR (400 MHz, d$_6$-DMSO) δ 13.40 (s, 1H), 11.07 (s, 1H), 8.73 (dd, J = 2.1, 60.0, 3H), 7.52 (d, J = 9.1, 15.1, 1H), 7.19 (t, J = 8.7, 2H), 4.98-1.33 (m, 95H), 0.98 (t, J = 7.4, 5H); m/z (LC-MS) M + 1 = 465.5 |
| 104 | 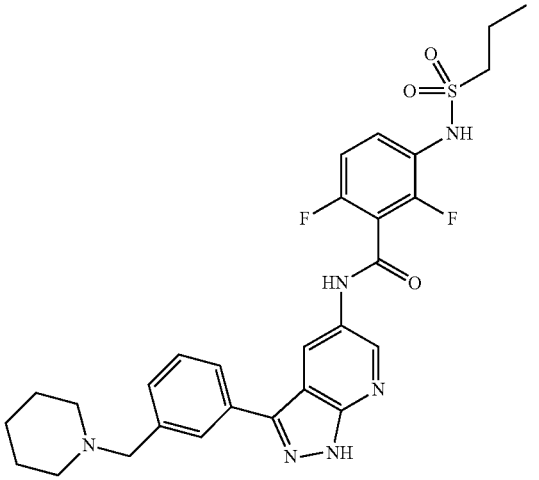 [SMILES: CCCS(=O)(=O)Nc1ccc(F)c(C(=O)Nc2cnc3[nH]nc(-c4cccc(CN5CCCCC5)c4)c3c2)c1F] | 2,6-difluoro-N-(3-(3-(piperidin-1-ylmethyl)phenyl)-1H-pyrazolo[3,4-b]pyridin-5-yl)-3-(propylsulfonamido)benzamide | $^1$H NMR (400 MHz, CD$_3$OD) δ 9.0 (s, 1H), 8.7 (s, 1H), 8.0 (s, 1H), 7.9 (m, 1H), 7.6 (m, 1H), 7.5 (m, 1H), 7.4 (m, 1H), 7.1 (m, 1H), 3.7 (s, 2H), 3.1 (m, 2H), 2.6 (m, 4H), 1.9 (m, 2H), 1.6 (m, 4H), 1.5 (m, 2H), 1.1 (t, J = 7.6 Hz, 3H); m/z (APCI-pos) M + 1 = 569.1 |

| Ex. # | Structure | Name | MS/NMR |
|---|---|---|---|
| 105 | 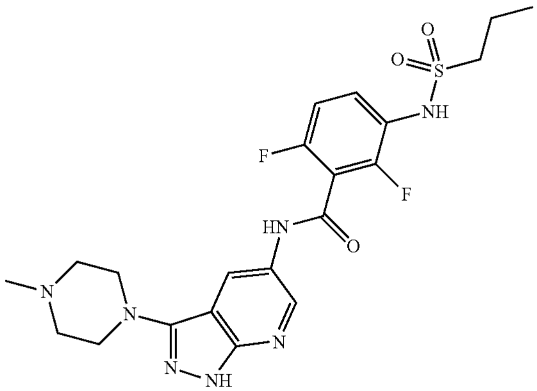 [SMILES: CCCS(=O)(=O)Nc1ccc(F)c(C(=O)Nc2cnc3[nH]nc(N4CCN(C)CC4)c3c2)c1F] | 2,6-difluoro-N-(3-(4-methylpiperazin-1-yl)-1H-pyrazolo[3,4-b]pyridin-5-yl)-3-(propylsulfonamido)benzamide | $^1$H NMR (400 MHz, CD$_3$OD) δ 8.7 (s, 1H), 8.5 (s, 1H), 7.6 (m, 1H), 7.1 (m, 1H), 3.5 (m, 4H), 3.1 (m, 2H), 2.7 (m, 4H), 2.4 (s, 3H), 1.9 (m, 2H), 1.1 (t, J = 7.6 Hz, 3H); m/z (APCI-pos) M + 1 = 494.2 |
| 106 | 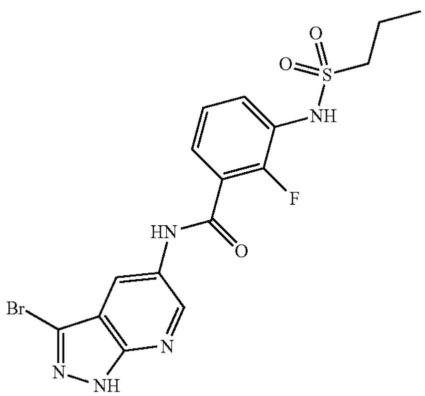 [SMILES: CCCS(=O)(=O)Nc1cccc(C(=O)Nc2cnc3[nH]nc(Br)c3c2)c1F] | N-(3-bromo-1H-pyrazolo[3,4-b]pyridin-5-yl)-2-fluoro-3-(propylsulfonamido)benzamide | $^1$H NMR (400 MHz, CD$_3$OD) δ 8.7 (s, 1H), 8.5 (s, 1H), 7.7 (m, 1H), 7.5 (m, 1H), 7.3 (m, 1H), 3.1 (m, 2H), 1.9 (m, 2H), 1.1 (t, J = 7.6 Hz, 3H); m/z (APCI-neg) M − 1 = 454.1, 456.1 |
| 107 | 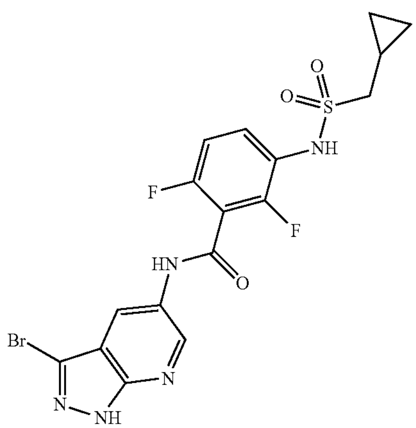 [SMILES: O=C(Nc1cnc2[nH]nc(Br)c2c1)c1c(F)ccc(NS(=O)(=O)CC2CC2)c1F] | N-(3-bromo-1H-pyrazolo[3,4-b]pyridin-5-yl)-3-(cyclopropylmethylsulfonamido)-2,6-difluorobenzamide | $^1$H NMR (400 MHz, CD$_3$OD) δ 8.7 (s, 1H), 8.6 (s, 1H), 7.7 (m, 1H), 7.1 (m, 1H), 3.1 (m, 2H), 1.1 (m, 1H), 0.6 (m, 2H), 0.4 (m, 2H); m/z (APCI-neg) M − 1 = 484.1, 486.1 |
| 108 | 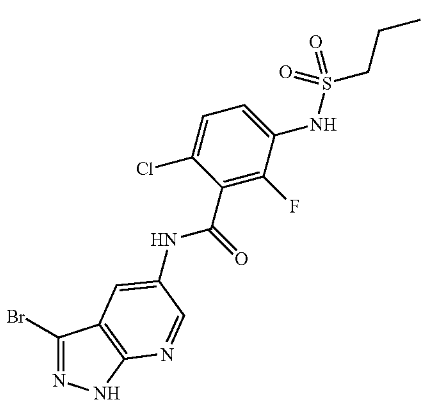 [SMILES: CCCS(=O)(=O)Nc1ccc(Cl)c(C(=O)Nc2cnc3[nH]nc(Br)c3c2)c1F] | N-(3-bromo-1H-pyrazolo[3,4-b]pyridin-5-yl)-6-chloro-2-fluoro-3-(propylsulfonamido)benzamide | $^1$H NMR (400 MHz, CD$_3$OD) δ 8.7 (s, 1H), 8.6 (s, 1H), 7.7 (m, 1H), 7.4 (m, 1H), 3.1 (m, 2H), 1.9 (m, 2H), 1.1 (t, J = 7.6 Hz, 3H); m/z (APCI-neg) M − 1 = 488.1, 490.1 |

TABLE 2-continued

| Ex. # | Structure | Name | MS/NMR |
|---|---|---|---|
| 109 | 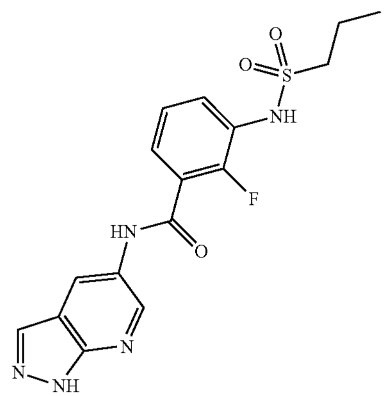 [SMILES: CCCS(=O)(=O)Nc1cccc(C(=O)Nc2cnc3[nH]ncc3c2)c1F] | 2-fluoro-3-(propylsulfonamido)-N-(1H-pyrazolo[3,4-b]pyridin-5-yl)benzamide | $^1$H NMR (400 MHz, CD$_3$OD) δ 8.7 (m, 2H), 8.1 (s, 1H), 7.7 (m, 1H), 7.5 (m, 1H), 7.3 (m, 1H), 3.1 (m, 2H), 1.9 (m, 2H), 1.1 (t, J = 7.6 Hz, 3H); m/z (APCI-neg) M − 1 = 376.3 |
| 110 | 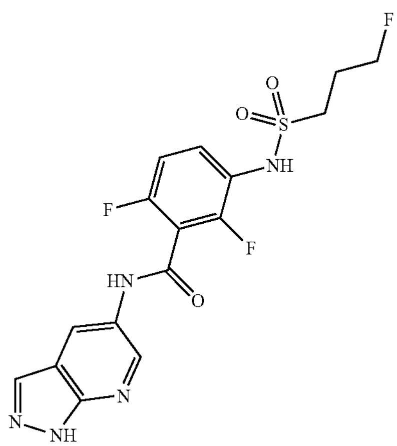 [SMILES: O=C(Nc1cnc2[nH]ncc2c1)c1c(F)ccc(NS(=O)(=O)CCCF)c1F] | 2,6-difluoro-3-(3-fluoropropyl-sulfonamido)-N-(1H-pyrazolo[3,4-b]pyridin-5-yl)benzamide | $^1$H NMR (400 MHz, CD$_3$OD) δ 8.7 (s, 1H), 8.6 (s, 1H), 8.1 (s, 1H), 7.7 (m, 1H), 7.1 (m, 1H), 4.6 (m, 1H), 4.5 (m, 1H), 3.2 (m, 2H), 2.3-2.1 (m, 2H); m/z (APCI-neg) M − 1 = 412.1 |
| 111 | 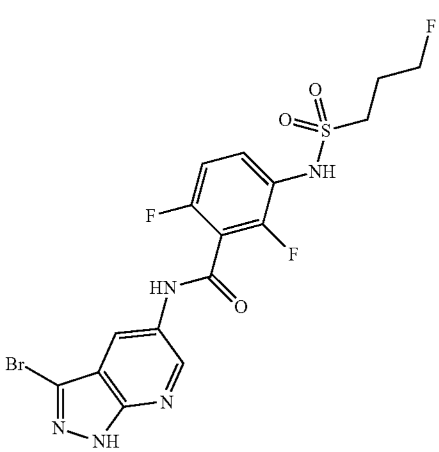 [SMILES: O=C(Nc1cnc2[nH]nc(Br)c2c1)c1c(F)ccc(NS(=O)(=O)CCCF)c1F] | N-(3-bromo-1H-pyrazolo[3,4-b]pyridin-5-yl)-2,6-difluoro-3-(3-fluoropropylsulfonamido)benzamide | $^1$H NMR (400 MHz, CD$_3$OD) δ 8.7 (s, 1H), 8.6 (s, 1H), 7.7 (m, 1H), 7.2 (m, 1H), 4.6 (m, 1H), 4.5 (m, 1H), 3.2 (m, 2H), 2.3-2.1 (m, 2H); m/z (APCI-neg) M − 1 = 490.1, 492.1 |

| Ex. # | Structure | Name | MS/NMR |
|---|---|---|---|
| 112 | 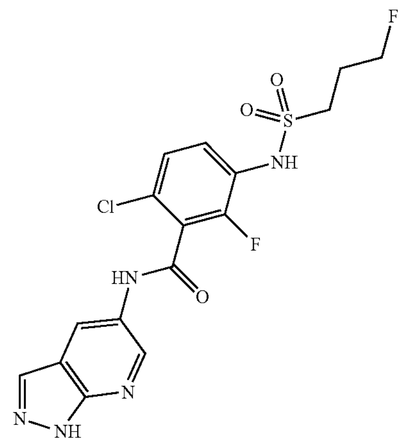 [SMILES: O=C(Nc1cnc2[nH]ncc2c1)c1c(Cl)ccc(NS(=O)(=O)CCCF)c1F] | 6-chloro-2-fluoro-3-(3-fluoropropylsulfonamido)-N-(1H-pyrazolo[3,4-b]pyridin-5-yl)benzamide | $^1$H NMR (400 MHz, CD$_3$OD) δ 8.7 (s, 1H), 8.6 (s, 1H), 8.1 (s, 1H), 7.7 (m, 1H), 7.4 (m, 1H), 4.6 (m, 1H), 4.5 (m, 1H), 3.2 (m, 2H), 2.3-2.1 (m, 2H); m/z (APCI-pos) M + 1 = 430.1, 432.1 |
| 113 | 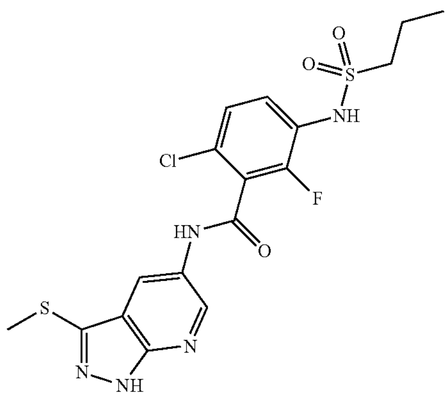 [SMILES: CCCS(=O)(=O)Nc1ccc(Cl)c(C(=O)Nc2cnc3[nH]nc(SC)c3c2)c1F] | 6-chloro-2-fluoro-N-(3-(methylthio)-1H-pyrazolo[3,4-b]pyridin-5-yl)-3-(propylsulfonamido)benzamide | $^1$H NMR (400 MHz, CD$_3$OD) δ 8.7 (s, 1H), 8.6 (s, 1H), 7.6 (m, 1H), 7.4 (m, 1H), 3.1 (m, 2H), 2.6 (s, 3H), 1.9 (m, 2H), 1.1 (t, J = 7.6 Hz, 3H); m/z (APCI-pos) M + 1 = 458.0, 460.0 |
| 114 | 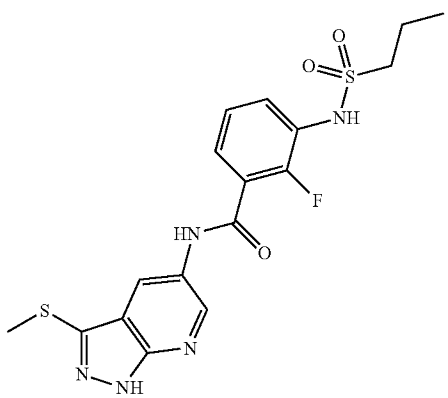 [SMILES: CCCS(=O)(=O)Nc1cccc(C(=O)Nc2cnc3[nH]nc(SC)c3c2)c1F] | 2-fluoro-N-(3-(methylthio)-1H-pyrazolo[3,4-b]pyridin-5-yl)-3-(propylsulfonamido)benzamide | $^1$H NMR (400 MHz, CD$_3$OD) δ 8.7 (s, 1H), 8.6 (s, 1H), 7.7 (m, 1H), 7.5 (m, 1H), 7.3 (m, 1H), 3.2 (m, 2H), 2.6 (s, 3H), 1.9 (m, 2H), 1.1 (t, J = 7.6 Hz, 3H); m/z (APCI-pos) M + 1 = 424.1 |
| 115 | 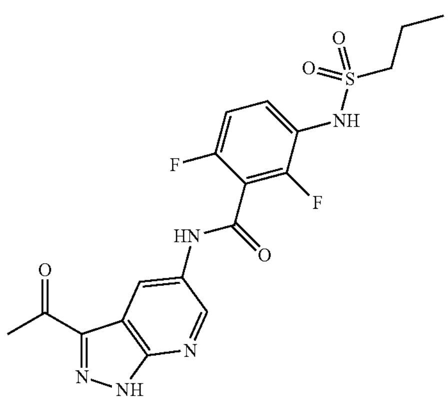 [SMILES: CCCS(=O)(=O)Nc1ccc(F)c(C(=O)Nc2cnc3[nH]nc(C(C)=O)c3c2)c1F] | N-(3-acetyl-1H-pyrazolo[3,4-b]pyridin-5-yl)-2,6-difluoro-3-(propylsulfonamido)benzamide | $^1$H NMR (400 MHz, CD$_3$OD) δ 9.01-9.03 (m, 1H), 8.78-8.80 (m, 1H), 7.63-7.71 (m, 1H), 7.11-7.18 (m, 1H), 3.09-3.15 (m, 2H), 2.70 (s, 1H), 1.82-1.93 (m, 2H), 1.04-1.09 (m, 3H); m/z (APCI-neg) M − 1 = 436.2 |

TABLE 2-continued

| Ex. # | Structure | Name | MS/NMR |
|---|---|---|---|
| 116 | 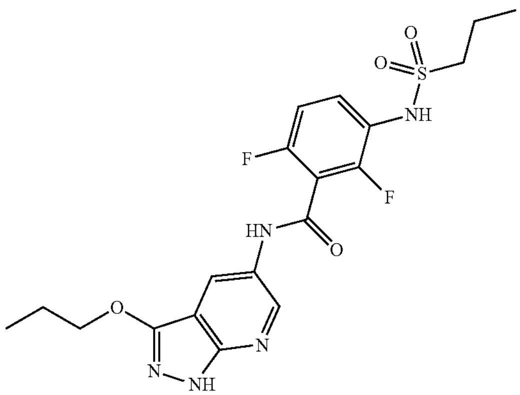 [SMILES: CCCOc1n[nH]c2ncc(NC(=O)c3c(F)ccc(NS(=O)(=O)CCC)c3F)cc12] | 2,6-difluoro-N-(3-propoxy-1H-pyrazolo[3,4-b]pyridin-5-yl)-3-(propylsulfonamido)benzamide | ¹H NMR (400 MHz, CD₃OD) δ 8.58-8.60 (m, 1H), 8.51-8.53 (m, 1H), 7.62-7.69 (m, 1H), 7.11-7.17 (m, 1H), 4.32-4.37 (m, 2H), 3.09-3.14 (m, 2H), 1.82-1.96 (m, 4H), 1.03-1.11 (m, 6H); m/z (APCI-pos) M + 1 = 454.1 |
| 117 | 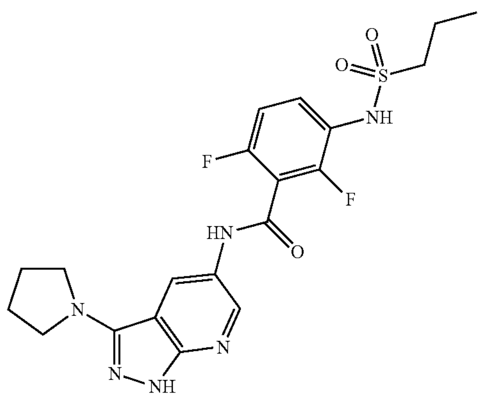 [SMILES: CCCS(=O)(=O)Nc1ccc(F)c(C(=O)Nc2cnc3[nH]nc(N4CCCC4)c3c2)c1F] | 2,6-difluoro-3-(propylsulfonamido)-N-(3-(pyrrolidin-1-yl)-1H-pyrazolo[3,4-b]pyridin-5-yl)benzamide | ¹H NMR (400 MHz, CD₃OD) δ 8.7 (s, 1H), 8.5 (s, 1H), 7.7 (m, 1H), 7.1 (m, 1H), 3.6 (m, 4H), 3.1 (m, 2H), 2.1 (m, 4H), 1.9 (m, 2H), 1.1 (t, J = 7.6 Hz, 3H); m/z (APCI-pos) M + 1 = 465.2 |
| 118 | 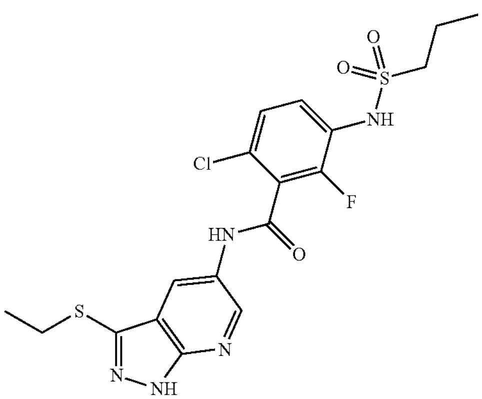 [SMILES: CCCS(=O)(=O)Nc1ccc(Cl)c(C(=O)Nc2cnc3[nH]nc(SCC)c3c2)c1F] | 6-chloro-N-(3-(ethylthio)-1H-pyrazolo[3,4-b]pyridin-5-yl)-2-fluoro-3-(propylsulfonamido)benzamide | ¹H NMR (400 MHz, CD₃OD) δ 8.7 (s, 1H), 8.6 (s, 1H), 7.7 (m, 1H), 7.4 (m, 1H), 3.2-3.1 (m, 4H), 1.9 (m, 2H), 1.3 (t, J = 7.0 Hz, 3H), 1.1 (t, J = 7.6 Hz, 3H); m/z (APCI-pos) M + 1 = 472.1, 474.1 |
| 119 | 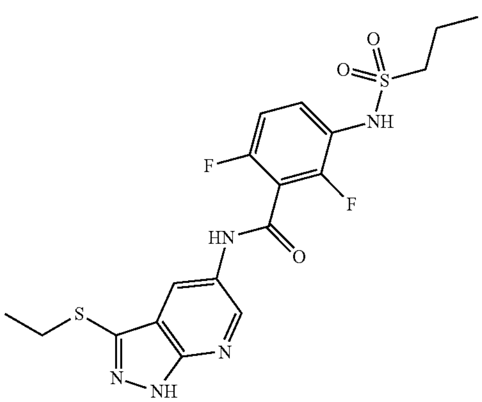 [SMILES: CCCS(=O)(=O)Nc1ccc(F)c(C(=O)Nc2cnc3[nH]nc(SCC)c3c2)c1F] | N-(3-(ethylthio)-1H-pyrazolo[3,4-b]pyridin-5-yl)-2,6-difluoro-3-(propylsulfonamido)benzamide | ¹H NMR (400 MHz, CD₃OD) δ 8.7 (s, 1H), 8.6 (s, 1H), 7.7 (m, 1H), 7.1 (m, 1H), 3.2-3.1 (m, 4H), 1.9 (m, 2H), 1.3 (t, J = 7.0 Hz, 3H), 1.1 (t, J = 7.6 Hz, 3H); m/z (APCI-pos) M + 1 = 456.1 |

TABLE 2-continued

| Ex. # | Structure | Name | MS/NMR |
|---|---|---|---|
| 120 | 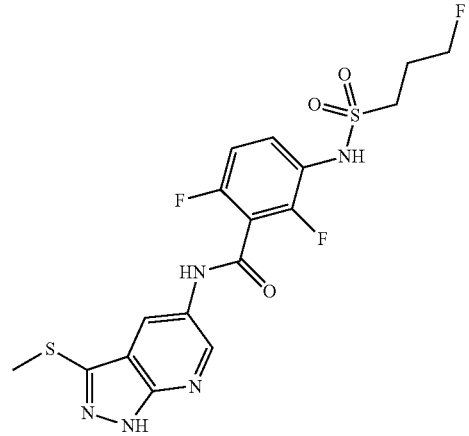 [SMILES: CSc1n[nH]c2ncc(NC(=O)c3c(F)ccc(NS(=O)(=O)CCCF)c3F)cc12] | 2,6-difluoro-3-(3-fluoropropylsulfonamido)-N-(3-(methylthio)-1H-pyrazolo[3,4-b]pyridin-5-yl)benzamide | $^1$H NMR (400 MHz, CD$_3$OD) δ 8.7 (s, 1H), 8.6 (s, 1H), 7.7 (m, 1H), 7.2 (m, 1H), 4.6 (m, 1H), 4.5 (m, 1H), 3.3 (m, 2H), 2.6 (s, 3H), 2.3-2.1 (m, 2H); m/z (APCI-pos) M + 1 = 460.1 |
| 121 | 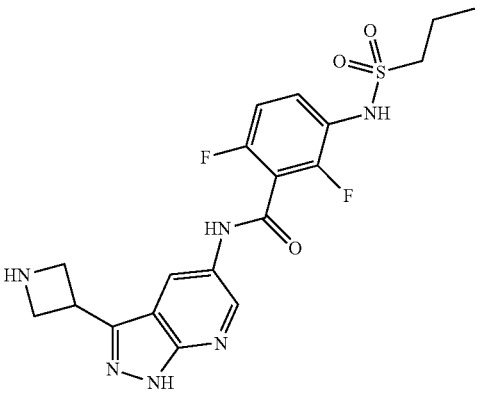 [SMILES: CCCS(=O)(=O)Nc1ccc(F)c(C(=O)Nc2cnc3[nH]nc(C4CNC4)c3c2)c1F] | N-(3-(azetidin-3-yl)-1H-pyrazolo[3,4-b]pyridin-5-yl)-2,6-difluoro-3-(propylsulfonamido)benzamide | $^1$H NMR (400 MHz, d$_6$-DMSO) δ 14.23-13.08 (m, 1H), 11.36-10.93 (m, 1H), 8.67 (d, J = 57.3, 2H), 7.70-7.36 (m, 1H), 7.36-6.96 (m, 1H), 5.59-1.83 (m, 83H), 1.71 (s, 2H), 0.96 (t, J = 7.4, 3H); m/z (LC-MS) M + 1 = 451.5 |
| 122 | 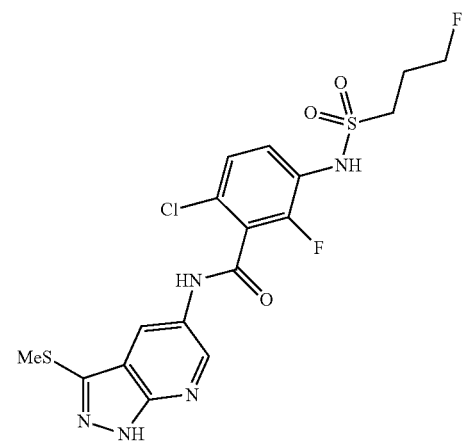 [SMILES: CSc1n[nH]c2ncc(NC(=O)c3c(Cl)ccc(NS(=O)(=O)CCCF)c3F)cc12] | 6-chloro-2-fluoro-3-(3-fluoropropylsulfonamido)-N-(3-(methylthio)-1H-pyrazolo[3,4-b]pyridin-5-yl)benzamide | $^1$H NMR (400 MHz, CD$_3$OD) δ 8.7 (s, 1H), 8.6 (s, 1H), 7.7 (m, 1H), 7.4 (m, 1H), 4.6 (m, 1H), 4.5 (m, 1H), 3.3 (m, 2H), 2.6 (s, 3H), 2.3-2.1 (m, 2H); m/z (APCI-pos) M + 1 = 476.1, 478.1 |

| Ex. # | Structure | Name | MS/NMR |
|---|---|---|---|
| 123 | 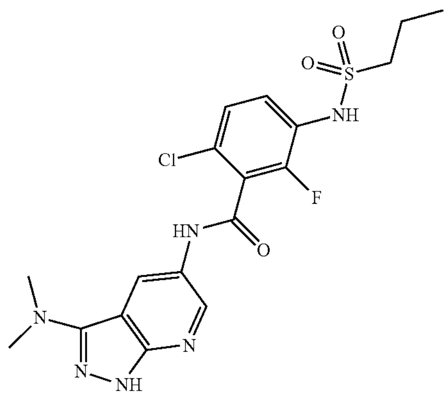 [SMILES: CCCS(=O)(=O)Nc1ccc(Cl)c(C(=O)Nc2cnc3[nH]nc(N(C)C)c3c2)c1F] | 6-chloro-N-(3-(dimethylamino)-1H-pyrazolo[3,4-b]pyridin-5-yl)-2-fluoro-3-(propylsulfonamido)benzamide | $^1$H NMR (400 MHz, CD$_3$OD) δ 8.7 (s, 1H), 8.5 (s, 1H), 7.6 (m, 1H), 7.4 (m, 1H), 3.3 (m, 8H), 1.9 (m, 2H), 1.1 (t, J = 7.6 Hz, 3H); m/z (APCI-pos) M + 1 = 455.1, 457.1 |
| 124 | 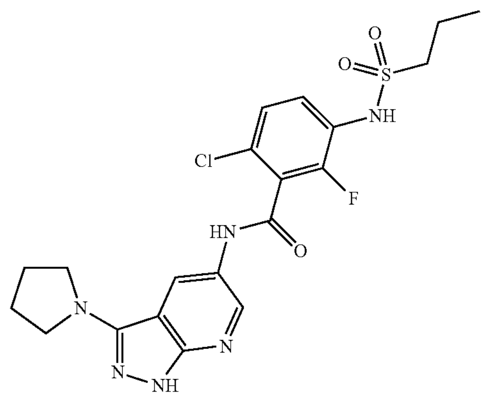 [SMILES: CCCS(=O)(=O)Nc1ccc(Cl)c(C(=O)Nc2cnc3[nH]nc(N4CCCC4)c3c2)c1F] | 6-chloro-2-fluoro-3-(propylsulfonamido)-N-(3-(pyrrolidin-1-yl)-1H-pyrazolo[3,4-b]pyridin-5-yl)benzamide | $^1$H NMR (400 MHz, CD$_3$OD) δ 8.7 (s, 1H), 8.5 (s, 1H), 7.6 (m, 1H), 7.4 (m, 1H), 3.6 (m, 4H), 3.1 (m, 2H), 2.1 (m, 4H), 1.9 (m, 2H), 1.1 (t, J = 7.6 Hz, 3H); m/z (APCI-pos) M + 1 = 481.1, 483.1 |
| 125 | 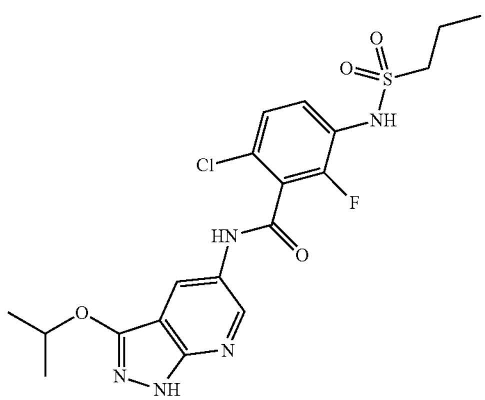 [SMILES: CCCS(=O)(=O)Nc1ccc(Cl)c(C(=O)Nc2cnc3[nH]nc(OC(C)C)c3c2)c1F] | 6-chloro-2-fluoro-N-(3-isopropoxy-1H-pyrazolo[3,4-b]pyridin-5-yl)-3-(propylsulfonamido)benzamide | $^1$H NMR (500 MHz, d$_6$-DMSO) δ 12.51 (s, 1H), 11.00 (s, 1H), 8.50 (d, J = 25.8, 2H), 7.52 (d, J = 8.7, 1H), 7.40 (s, 1H), 5.20-4.92 (m, 1H), 3.12 (s, 2H), 1.75 (d, J = 7.7, 2H), 1.39 (d, J = 6.1, 5H), 0.99 (t, J = 7.4, 3H); m/z (LC-MS) M + 1 = 470.9 |
| 126 | 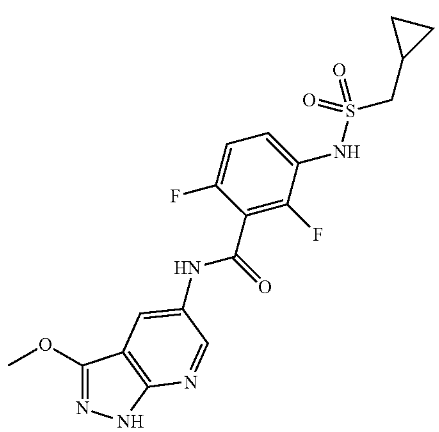 [SMILES: COc1n[nH]c2ncc(NC(=O)c3c(F)ccc(NS(=O)(=O)CC4CC4)c3F)cc12] | 3-(cyclopropylmethylsulfonamido)-2,6-difluoro-N-(3-methoxy-1H-pyrazolo[3,4-b]pyridin-5-yl)benzamide | $^1$H NMR (400 MHz, d$_6$-DMSO) δ 12.58 (s, 1H), 11.05 (s, 1H), 9.80 (s, 1H), 8.59 (d, J = 2.4, 1H), 8.47 (d, J = 2.2, 1H), 7.58 (dd, J = 9.1, 15.0, 1H), 7.24 (t, J = 8.8, 1H), 4.02 (s, 3H), 3.11 (d, J = 7.1, 2H), 1.08 (s, 1H), 0.72-0.47 (m, 2H), 0.36 (q, J = 4.6, 2H); m/z (LC-MS) M + 1 = 438.4 |

TABLE 2-continued

| Ex. # | Structure | Name | MS/NMR |
|---|---|---|---|
| 127 | 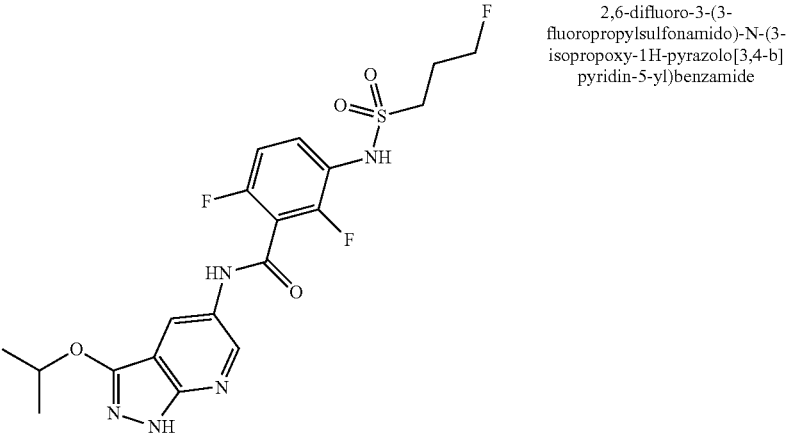 | 2,6-difluoro-3-(3-fluoropropylsulfonamido)-N-(3-isopropoxy-1H-pyrazolo[3,4-b]pyridin-5-yl)benzamide | $^1$H NMR (400 MHz, d$_6$-DMSO) δ 12.53 (s, 1H), 11.05 (s, 1H), 10.20-9.72 (m, 1H), 8.51 (dd, J = 2.3, 20.7, 2H), 7.56 (dd, J = 9.0, 14.9, 1H), 7.26 (t, J = 8.7, 1H), 5.21-4.90 (m, 1H), 4.62 (t, J = 6.0, 1H), 4.50 (t, J = 6.0, 1H), 2.31-1.95 (m, 3H), 1.39 (d, J = 6.1, 7H); m/z (LC-MS) M + 1 = 472.4 |
| 128 | 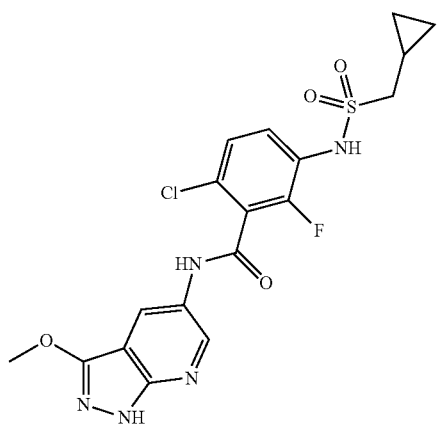 [SMILES: COc1n[nH]c2ncc(NC(=O)c3c(Cl)ccc(NS(=O)(=O)CC4CC4)c3F)cc12] | 6-chloro-3-(cyclopropylmethylsulfonamido)-2-fluoro-N-(3-methoxy-1H-pyrazolo[3,4-b]pyridin-5-yl)benzamide | $^1$H NMR (400 MHz, d$_6$-DMSO) δ 12.58 (s, 1H), 11.02 (s, 1H), 10.36-9.76 (m, 1H), 8.59 (d, J = 2.4, 1H), 8.47 (d, J = 2.2, 1H), 7.56 (t, J = 8.7, 1H), 7.39 (d, J = 9.1, 1H), 3.98 (d, 3H), 1.06 (s, 1H), 0.72-0.45 (m, 2H), 0.34 (q, J = 4.6, 2H); m/z (LC-MS) M+1 = 454.8 |
| 129 | 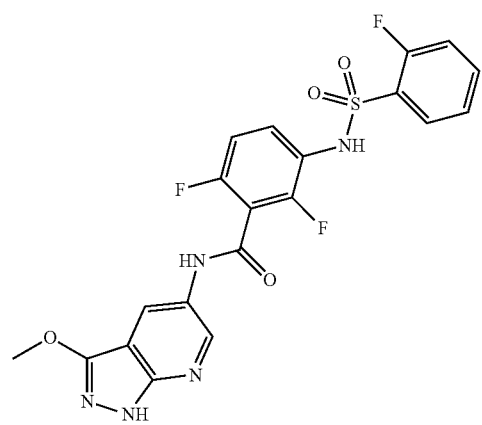 [SMILES: COc1n[nH]c2ncc(NC(=O)c3c(F)ccc(NS(=O)(=O)c4ccccc4F)c3F)cc12] | 2,6-difluoro-3-(2-fluorophenylsulfonamido)-N-(3-methoxy-1H-pyrazolo[3,4-b]pyridin-5-yl)benzamide | $^1$H NMR (400 MHz, d$_6$-DMSO) δ 12.59 (s, 1H), 11.04 (s. 1H), 10.66 (s, 1H), 8.55 (d, 1H), 8.44 (d, 1H), 7.75 (m, 2H), 7.48 (m, 1H), 7.37 (m, 2H), 7.23 (t, 1H), 4.01 (s, 3H); MS (APCI-neg) m/z = 476.1 (M − H) |

TABLE 2-continued

| Ex. # | Structure | Name | MS/NMR |
|---|---|---|---|
| 130 | 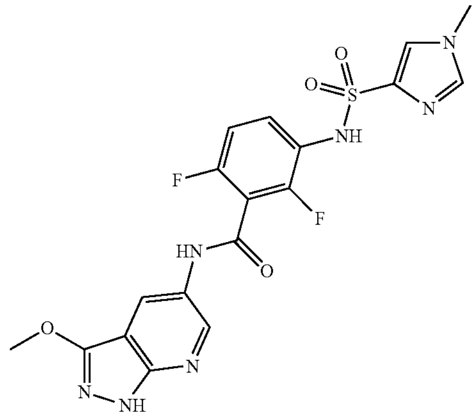 | 2,6-difluoro-N-(3-methoxy-1H-pyrazolo[3,4-b]pyridin-5-yl)-3-(1-methyl-1H-imidazole-4-sulfonamido)benzamide | $^1$H NMR (400 MHz, d$_6$-DMSO) δ 12.63-12.56 (s, 1H), 11.01-11.02 (s, 1H), 10.22-10.21 (s, 1H), 8.62-8.55 (m, 1H), 8.50-8.44 (m, 1H), 7.85-7.80 (m, 1H), 7.78-7.73 (m, 1H), 7.54-7.46 (m, 1H), 7.25-7.14 (m, 1H), 4.05-3.99 (s, 3H), 3.73-3.64 (s, 3H); MS (APCI-pos) m/z = 464.1 (M + H) |
| 131 | 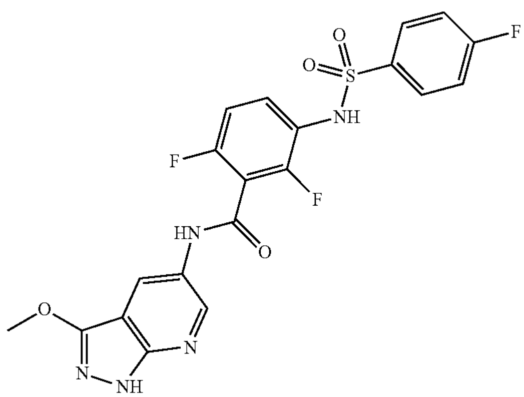 [SMILES: COc1n[nH]c2ncc(NC(=O)c3c(F)ccc(NS(=O)(=O)c4ccc(F)cc4)c3F)cc12] | 2,6-difluoro-3-(4-fluorophenylsulfonamido)-N-(3-methoxy-1H-pyrazolo[3,4-b]pyridin-5-yl)benzamide | $^1$H NMR (400 MHz, d$_6$-DMSO) δ 12.64-12.58 (s, 1H), 11.06-11.00 (s, 1H), 10.47-10.37 (s, 1H), 8.60-8.54 (m, 1H), 8.49-8.42 (m, 1H), 7.88-7.78 (m, 2H), 7.50-7.42 (m, 2H), 7.39-7.31 (m, 1H), 7.27-7.18 (m, 1H), 4.06-3.99 (s, 3H); MS (APCI-pos) m/z = 478.1 (M + H) |
| 132 | 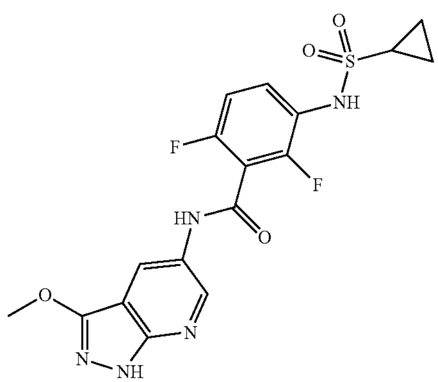 [SMILES: COc1n[nH]c2ncc(NC(=O)c3c(F)ccc(NS(=O)(=O)C4CC4)c3F)cc12] | 3-(cyclopropanesulfonamido)-2,6-difluoro-N-(3-methoxy-1H-pyrazolo[3,4-b]pyridin-5-yl)benzamide | $^1$H NMR (400 MHz, d$_6$-DMSO) δ 12.63-12.56 (s, 1H), 11.12-11.06 (s, 1H), 9.84-9.71 (s, 1H), 8.62-8.56 (m, 1H), 8.50-8.45 (m, 1H), 7.62-7.50 (m, 1H), 7.30-7.19 (m, 1H), 4.03-3.97 (s, 3H), 2.72-2.61 (m, 1H), 1.03-0.92 (m, 2H), 0.92-0.84 (m, 2H); MS (APCI-pos) m/z = 424.2 (M + H) |
| 133 | 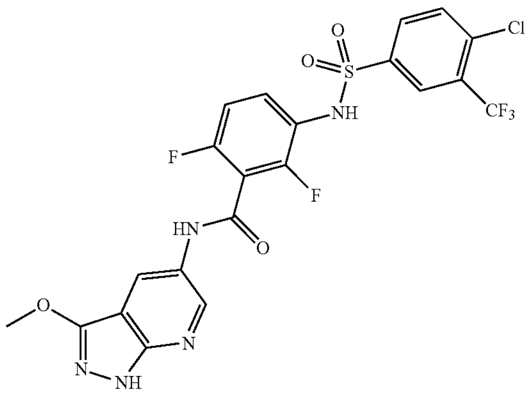 [SMILES: COc1n[nH]c2ncc(NC(=O)c3c(F)ccc(NS(=O)(=O)c4ccc(Cl)c(C(F)(F)F)c4)c3F)cc12] | 3-(4-chloro-3-(trifluoromethyl)phenylsulfonamido)-2,6-difluoro-N-(3-methoxy-1H-pyrazolo[3,4-b]pyridin-5-yl)benzamide | $^1$H NMR (400 MHz, CD$_3$OD) δ 8.57-8.53 (m, 1H), 8.46-8.43 (m, 1H), 8.20-8.17 (m, 1H), 8.01-7.95 (d, 1H), 7.81-7.76 (d, 1H), 7.59-7.51 (m, 1H), 7.10-7.03 (t, 1H), 4.10-4.06 (s, 3H); MS (APCI-pos) m/z = 562.1 (M + H) |

TABLE 2-continued

| Ex. # | Structure | Name | MS/NMR |
|---|---|---|---|
| 134 | 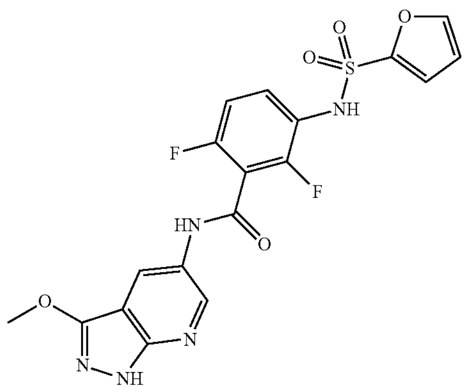 [SMILES: COc1n[nH]c2ncc(NC(=O)c3c(F)ccc(NS(=O)(=O)c4ccco4)c3F)cc12] | 2,6-difluoro-3-(furan-2-sulfonamido)-N-(3-methoxy-1H-pyrazolo[3,4-b]pyridin-5-yl)benzamide | $^1$H NMR (400 MHz, CD$_3$OD) δ 8.59-8.54 (m, 1H), 8.49-8.45 (m, 1H), 7.75-7.72 (m, 1H), 7.58-7.49 (m, 1H), 7.12-7.03 (m, 1H), 7.00-6.96 (m, 1H), 6.57-6.53 (m, 1H), 4.10-4.06 (s, 3H); MS (APCI-pos) m/z = 450.1 (M + H) |
| 135 | 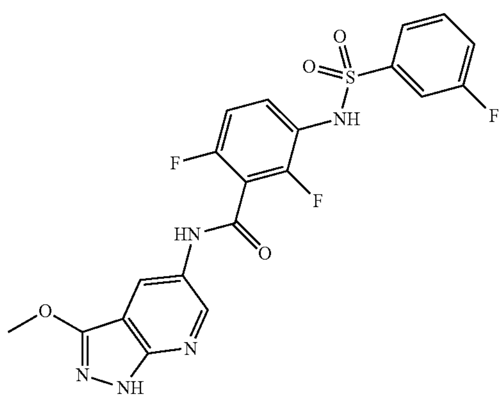 [SMILES: COc1n[nH]c2ncc(NC(=O)c3c(F)ccc(NS(=O)(=O)c4cccc(F)c4)c3F)cc12] | 2,6-difluoro-3-(3-fluorophenylsulfonamido)-N-(3-methoxy-1H-pyrazolo[3,4-b]pyridin-5-yl)benzamide | $^1$H NMR (400 MHz, d$_6$-DMSO) δ 12.61-12.56 (s, 1H), 11.04-10.99 (s, 1H), 10.56-10.45 (s, 1H), 8.59-8.54 (m, 1H), 7.72-7.65 (m, 1H), 7.64-7.52 (m, 3H), 7.42-7.31 (m, 1H), 7.28-7.19 (m, 1H), 4.04-4.00 (s, 3H); MS (APCI-neg) m/z = 476.1 (M − H) |
| 136 | 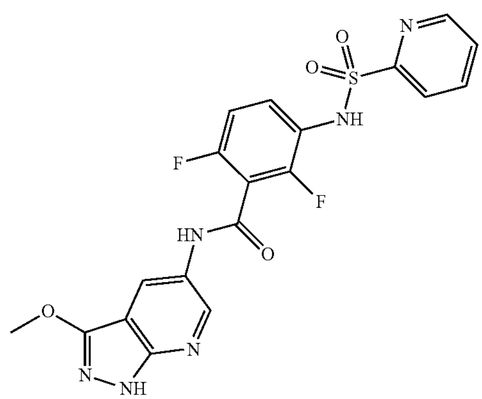 [SMILES: COc1n[nH]c2ncc(NC(=O)c3c(F)ccc(NS(=O)(=O)c4ccccn4)c3F)cc12] | 2,6-difluoro-N-(3-methoxy-1H-pyrazolo[3,4-b]pyridin-5-yl)-3-(pyridine-2-sulfonamido)benzamide | $^1$H NMR (400 MHz, CD$_3$OD) δ 8.69-8.64 (m, 1H), 8.58-8.54 (m, 1H), 8.48-8.45 (m, 1H), 8.04-7.96 (m, 1H), 7.67-7.56 (m, 2H), 7.05-6.99 (m, 1H), 4.12-4.06 (s, 3H); MS (APCI-pos) m/z = 461.1 (M + H) |
| 137 | 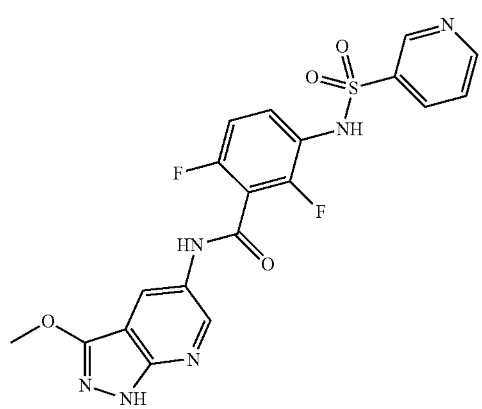 [SMILES: COc1n[nH]c2ncc(NC(=O)c3c(F)ccc(NS(=O)(=O)c4cccnc4)c3F)cc12] | 2,6-difluoro-N-(3-methoxy-1H-pyrazolo[3,4-b]pyridin-5-yl)-3-(pyridine-3-sulfonamido)benzamide | $^1$H NMR (400 MHz, d$_6$-DMSO) δ 12.60-12.56 (s, 1H), 11.03-10.99 (s, 1H), 10.65-10.60 (s, 1H), 8.94-8.89 (m, 1H), 8.88-8.83 (m, 1H), 8.58-8.53 (m, 1H), 8.46-8.42 (m, 1H), 8.18-8.11 (m, 1H), 7.70-7.63 (m, 1H), 7.46-7.36 (m, 1H), 7.29-7.21 (m, 1H), 4.04-4.00 (s, 3H); MS (APCI-pos) m/z = 461.1 (M + H) |

TABLE 2-continued

| Ex. # | Structure | Name | MS/NMR |
|---|---|---|---|
| 138 | 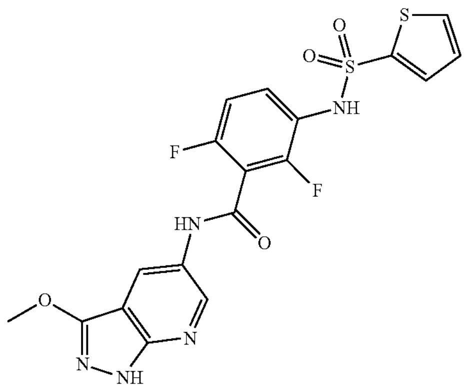 [SMILES: COc1n[nH]c2ncc(NC(=O)c3c(F)ccc(NS(=O)(=O)c4cccs4)c3F)cc12] | 2,6-difluoro-N-(3-methoxy-1H-pyrazolo[3,4-b]pyridin-5-yl)-3-(thiophene-2-sulfonamido)benzamide | $^1$H NMR (400 MHz, d$_6$-DMSO) δ 12.61-12.55 (s, 1H), 11.04-11.01 (s, 1H), 10.57-10.48 (s, 1H), 8.60-8.56 (m, 1H), 8.48-8.43 (m, 1H), 8.00-7.94 (m, 1H), 7.58-7.52 (m, 1H), 7.45-7.35 (m, 1H), 7.28-7.21 (m, 1H), 7.21-7.15 (m, 1H), 4.05-3.99 (s, 3H); MS (APCI-pos) m/z = 466.1 (M + H) |
| 139 | 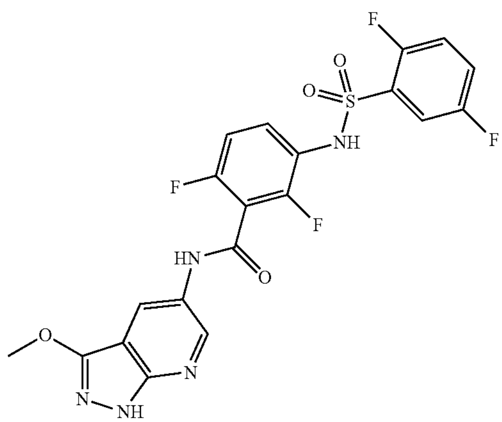 [SMILES: COc1n[nH]c2ncc(NC(=O)c3c(F)ccc(NS(=O)(=O)c4cc(F)ccc4F)c3F)cc12] | 3-(2,5-difluorophenylsulfonamido)-2,6-difluoro-N-(3-methoxy-1H-pyrazolo[3,4-b]pyridin-5-yl)benzamide | $^1$H NMR (400 MHz, d$_6$-DMSO) δ 12.60-12.55 (s, 1H), 11.04-11.00 (s, 1H), 10.85-10.77 (s, 1H), 8.59-8.55 (m, 1H), 8.47-8.43 (m, 1H), 7.65-7.51 (m, 3H), 7.45-7.36 (m, 1H), 7.27-7.16 (m, 1H), 4.05-3.99 (s, 3H); MS (APCI-neg) m/z = 494.2 (M − H) |
| 140 | 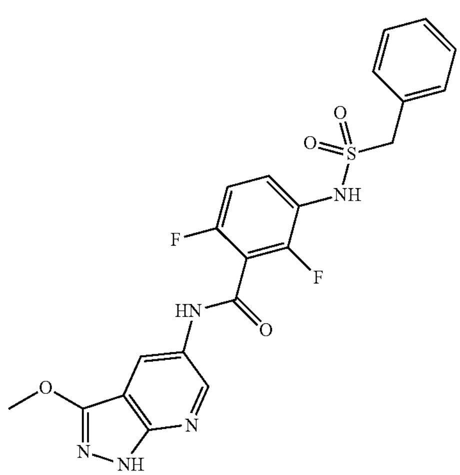 [SMILES: COc1n[nH]c2ncc(NC(=O)c3c(F)ccc(NS(=O)(=O)Cc4ccccc4)c3F)cc12] | 2,6-difluoro-N-(3-methoxy-1H-pyrazolo[3,4-b]pyridin-5-yl)-3-(phenylmethylsulfonamido)benzamide | $^1$H NMR (400 MHz, d$_6$-DMSO) δ 12.60-12.56 (s, 1H), 11.07-11.04 (s, 1H), 9.90-9.69 (s, 1H), 8.63-8.59 (m, 1H), 8.51-8.47 (m, 1H), 7.46-7.34 (m, 6H), 7.24-7.16 (t, 1H), 4.53-4.48 (s, 2H), 4.04-4.01 (s, 3H); MS (APCI-pos) m/z = 474.1 (M + H) |

TABLE 2-continued

| Ex. # | Structure | Name | MS/NMR |
|---|---|---|---|
| 141 | 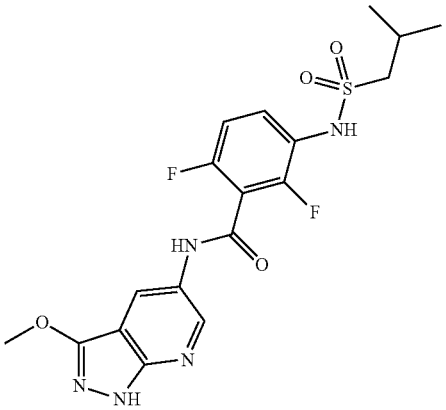 [SMILES: COc1n[nH]c2ncc(NC(=O)c3c(F)ccc(NS(=O)(=O)CC(C)C)c3F)cc12] | 2,6-difluoro-N-(3-methoxy-1H-pyrazolo[3,4-b]pyridin-5-yl)-3-(2-methylpropylsulfonamido)benzamide | $^1$H NMR (400 MHz, d$_6$-DMSO) δ 12.60 (s, 1H), 11.08 (s, 1H), 9.80 (s, 1H), 8.59 (d, J = 2.3, 1H), 8.48 (d, J = 2.2, 1H), 7.56 (td, J = 5.9, 9.0, 1H), 7.27 (t, J = 8.8, 1H), 4.02 (s, 3H), 3.05 (d, J = 6.4, 2H), 2.20 (dt, J = 6.6, 13.3, 1H), 1.04 (d, J = 6.7, 6H); m/z (LC-MS) M + 1 = 440.4 |
| 142 | 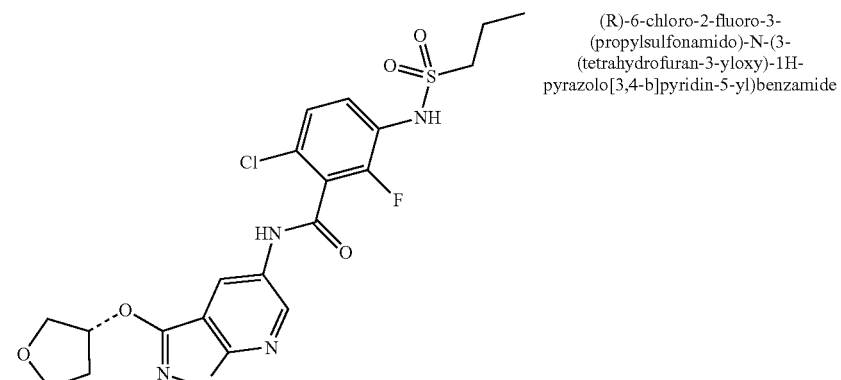 | (R)-6-chloro-2-fluoro-3-(propylsulfonamido)-N-(3-(tetrahydrofuran-3-yloxy)-1H-pyrazolo[3,4-b]pyridin-5-yl)benzamide | $^1$H NMR (400 MHz, CD$_3$OD) δ 8.60-8.58 (m, 1H), 8.51-8.49 (m, 1H), 7.67-7.62 (m, 1H), 7.38-7.34 (m, 1H), 5.50-5.46 (m, 1H), 4.10-4.00 (m, 4H), 3.95-3.88 (m, 1H), 3.17-3.12 (m, 2H), 2.39-2.25 (m, 2H), 1.91-1.81 (m, 2H), 1.08-1.03 (m, 3H); LRMS (APCI-pos) m/e 498.0 (M + 1) |
| 143 | 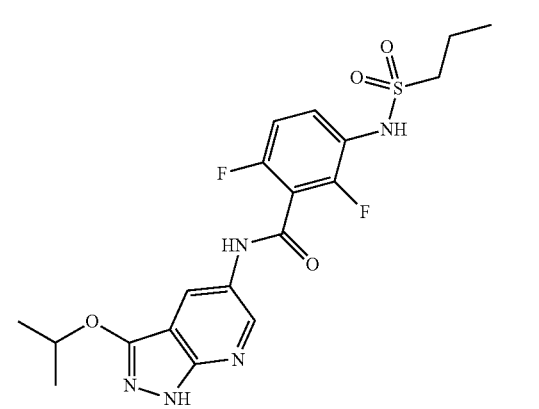 [SMILES: CCCS(=O)(=O)Nc1ccc(F)c(C(=O)Nc2cnc3[nH]nc(OC(C)C)c3c2)c1F] | 2,6-difluoro-N-(3-isopropoxy-1H-pyrazolo[3,4-b]pyridin-5-yl)-3-(propylsulfonamido)benzamide | $^1$H NMR (400 MHz, CD$_3$OD) δ 8.59-8.57 (m, 1H), 8.49-8.48 (m, 1H), 7.69-7.63 (m, 1H), 7.16-7.11 (m, 1H), 5.15-5.08 (m, 1H), 3.14-3.09 (m, 2H), 1.92-1.82 (m, 2H), 1.44 (d, J = 6.3 Hz, 6H), 1.06 (t, J = 7.4 Hz, 3H); m/z (APCI-pos) M + 1 = 454.1 |
| 144 | 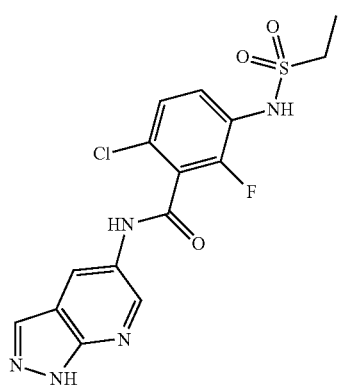 [SMILES: CCS(=O)(=O)Nc1ccc(Cl)c(C(=O)Nc2cnc3[nH]ncc3c2)c1F] | 6-chloro-3-(ethylsulfonamido)-2-fluoro-N-(1H-pyrazolo[3,4-b]pyridin-5-yl)benzamide | $^1$H NMR (400 MHz, d$_6$-DMSO) δ 13.68 (s, 1H), 11.10 (s, 1H), 10.00 (s, 1H), 8.67-8.65 (m, 1H), 8.63-8.61 (m, 1H), 8.17 (s, 1H), 7.57-7.53 (m, 1H), 7.47-7.44 (m, 1H), 3.22-3.16 (m, 2H), 1.28 (t, J = 7.3 Hz, 3H); m/z (APCI-pos) M + 1 = 398.1 |

TABLE 2-continued

| Ex. # | Structure | Name | MS/NMR |
|---|---|---|---|
| 145 | 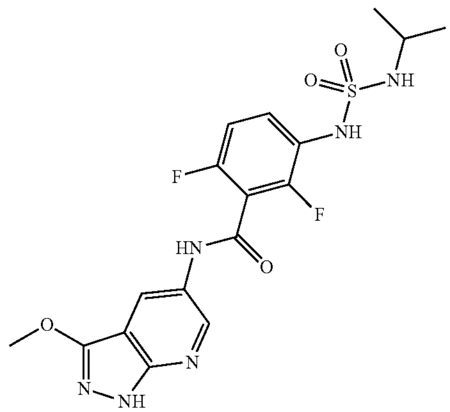 [SMILES: COc1n[nH]c2ncc(NC(=O)c3c(F)ccc(NS(=O)(=O)NC(C)C)c3F)cc12] | 2,6-difluoro-3-(N-isopropylsulfamoylamino)-N-(3-methoxy-1H-pyrazolo[3,4-b]pyridin-5-yl)benzamide | $^1$H NMR (400 MHz, CD$_3$OD) δ 8.59-8.60 (m, 1H), 8.50-8.52 (m, 1H), 7.65-7.72 (m, 1H), 7.07-7.13 (m, 1H), 4.09 (s, 3H), 3.49-3.56 (m, 1H), 1.12-1.15 (m, 6H); m/z (APCI-neg) M − 1 = 439.0 |
| 146 | 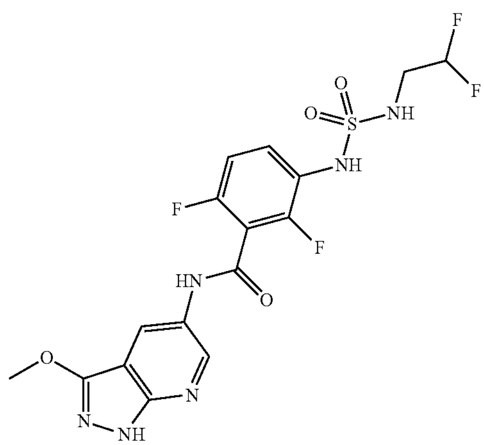 [SMILES: COc1n[nH]c2ncc(NC(=O)c3c(F)ccc(NS(=O)(=O)NCC(F)F)c3F)cc12] | 3-(N-(2,2-difluoroethyl)sulfamoylamino)-2,6-difluoro-N-(3-methoxy-1H-pyrazolo[3,4-b]pyridin-5-yl)benzamide | $^1$H NMR (400 MHz, CD$_3$OD) δ 8.59-8.63 (m, 1H), 8.50-8.53 (m, 1H), 7.65-7.72 (m, 1H), 7.09-7.14 (m, 1H), 5.76-6.07 (m, 1H), 4.09 (s, 3H), 3.34-3.43 (m, 2H); m/z (APCI-neg) M − 1 = 461.0 |
| 147 | 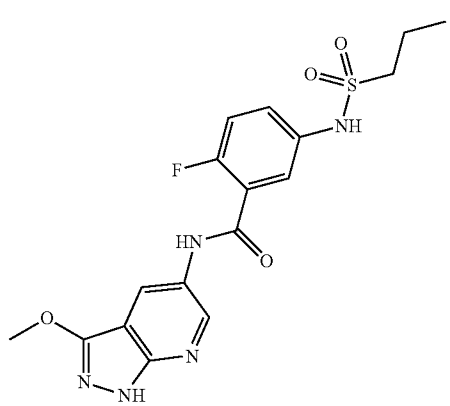 [SMILES: CCCS(=O)(=O)Nc1ccc(F)c(C(=O)Nc2cnc3[nH]nc(OC)c3c2)c1] | 2-fluoro-N-(3-methoxy-1H-pyrazolo[3,4-b]pyridin-5-yl)-5-(propylsulfonamido)benzamide | $^1$H NMR (400 MHz, d$_6$-DMSO) δ 12.06 (s, 1H), 10.61 (s, 1H), 9.97 (brs, 1H), 8.64 (s, 1H), 8.47 (s, 1H), 7.48-7.49 (m, 1H), 7.37-7.39 (m, 2H), 4.01 (s, 3H), 3.08-3.12 (m, 2H), 1.67-1.73 (m, 2H), 0.94-0.97 (m, 3H); m/z (APCI-neg) M − 1 = 406.1 |

TABLE 2-continued

| Ex. # | Structure | Name | MS/NMR |
|---|---|---|---|
| 148 | 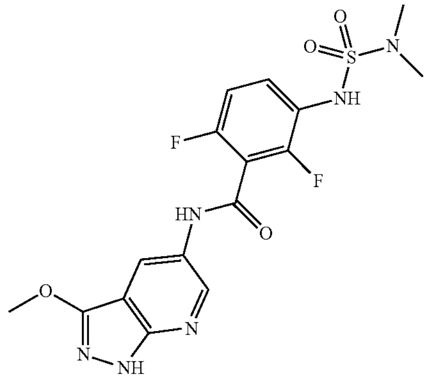 | 3-(N,N-dimethylsulfamoylamino)-2,6-difluoro-N-(3-methoxy-1H-pyrazolo[3,4-b]pyridin-5-yl)benzamide | $^1$H NMR (400 MHz, CD$_3$OD) δ 8.59-8.61 (m, 1H), 8.50-8.52 (m, 1H), 7.65-7.72 (m, 1H), 7.08-7.14 (m, 1H), 4.09 (s, 3H), 2.82 (s, 6H); m/z (APCI-neg) M − 1 = 424.9 |
| 149 | 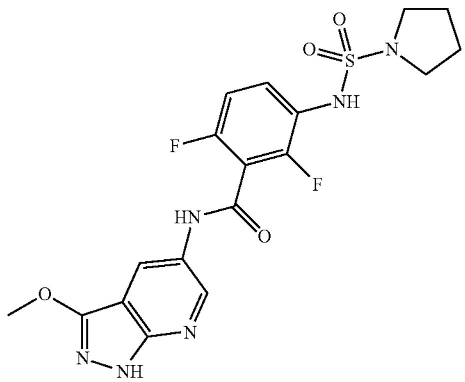 [SMILES: COc1n[nH]c2ncc(NC(=O)c3c(F)ccc(NS(=O)(=O)N4CCCC4)c3F)cc12] | 2,6-difluoro-N-(3-methoxy-1H-pyrazolo[3,4-b]pyridin-5-yl)-3-(pyrrolidine-1-sulfonamido)benzamide | $^1$H NMR (400 MHz, CD$_3$OD) δ 8.58-8.61 (m, 1H), 8.50-8.52 (m, 1H), 7.65-7.75 (m, 1H), 7.08-7.14 (m, 1H), 4.09 (s, 3H), 3.25-3.30 (m, 4H), 1.86-1.91 (m, 4H); m/z (APCI-neg) M − 1 = 451.0 |

Example a

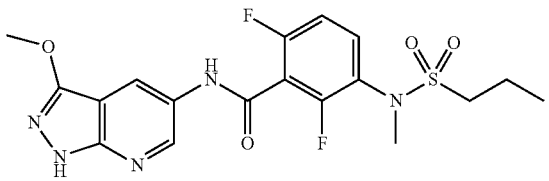 [SMILES: CCCS(=O)(=O)N(C)c1ccc(F)c(C(=O)Nc2cnc3[nH]nc(OC)c3c2)c1F]

2,6-difluoro-N-(3-methoxy-1H-pyrazolo[3,4-b]pyridin-5-yl)-3-(N-methylpropylsulfonamido)benzamide 2,6-Difluoro-N-(3-methoxy-1H-pyrazolo[3,4-b]pyridin-5-yl)-3-(N-methylpropylsulfonamido)benzamide (66.4% yield) was prepared according to Example 1, Step E, substituting 3-methoxy-1H-pyrazolo[3,4-b]pyridin-5-amine for 1H-pyrazolo[3,4-b]pyridin-5-amine and 2,6-difluoro-3-(N-methylpropylsulfonamido)benzoic acid for 2,6-difluoro-3-(propylsulfonamido)benzoic acid. 2,6-Difluoro-3-(N-methylpropylsulfonamido) benzoic acid was isolated by column chromatography in 18% yield as a minor byproduct from Example C. $^1$H NMR (400 MHz, CDCl$_3$) δ 9.86 (br s, 1H), 8.54 (s, 1H), 8.50 (br s, 1H), 8.64 (s, 1H), 8.10 (br s, 1H), 7.54-7.60 (q, 1H), 7.03-7.07 (t, 1H), 4.11 (s, 3H), 3.32 (s, 3H), 3.08-3.12 (t, 2H), 1.89-1.95 (m, 2H), 1.06-1.11 (t, 3H); m/z (APCI-pos) M+1=440.1.

While the invention has been described in conjunction with the enumerated embodiments, it will be understood that they are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A compound selected from Formula I:

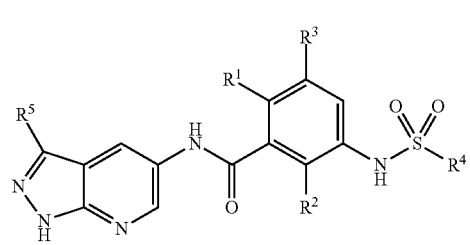

I and stereoisomers, tautomers and pharmaceutically acceptable salts thereof, wherein:

$R^1$ and $R^2$ are independently selected from hydrogen, halogen, CN, $C_1$-$C_3$ alkyl, and $C_1$-$C_3$ alkoxy;

$R^3$ is hydrogen, halogen, or $C_1$-$C_3$ alkyl;

$R^4$ is $C_3$-$C_5$ cycloalkyl, $C_1$-$C_6$ alkyl, $C_2$-$C_6$ alkenyl, or $C_2$-$C_6$ alkynyl, phenyl, a 5-6 membered heteroaryl, or $NR^gR^h$, wherein the cycloalkyl, alkyl, alkenyl, alkynyl, phenyl and heteroaryl are optionally substituted with $OR^c$, halogen, phenyl, $C_3$-$C_4$ cycloalkyl, or $C_1$-$C_4$ alkyl optionally substituted with halogen;

$R^5$ is:
hydrogen,
halogen,
CN,
$NR^cR^d$,
$OR^e$,
$SR^f$,
phenyl optionally substituted with one to three $R^a$ groups,
a 5-6 membered heteroaryl optionally substituted with $C_1$-$C_4$ alkyl,
a saturated or partially unsaturated $C_3$-$C_6$ cycloalkyl optionally substituted with halogen or $C_1$-$C_4$ alkyl,
a saturated or partially unsaturated 4-6 membered heterocyclyl optionally substituted with $C_1$-$C_4$ alkyl,
$C_2$-$C_6$ alkynyl optionally substituted with halogen, $OR^c$, or $NR^cR^d$,
$C_2$-$C_6$ alkenyl optionally substituted with halogen, $OR^c$, or $NR^cR^d$, or
$C_1$-$C_6$ alkyl optionally substituted with one to three $R^b$ groups;

each $R^a$ is independently selected from halogen, $CF_3$, $C_1$-$C_4$ alkyl or —O($C_1$-$C_4$ alkyl), wherein the alkyl or alkoxy are optionally substituted with OH, $NR^cR^d$ or a 5-6 membered heterocyclyl optionally substituted with $C_1$-$C_3$ alkyl;

each $R^b$ is independently selected from halogen, OH, $OCH_3$, oxo, —$NR^cR^d$, or $C_3$-$C_6$ cycloalkyl;

each $R^c$ and $R^d$ are independently selected from hydrogen, phenyl, and $C_1$-$C_4$ alkyl optionally substituted with oxo;

$R^e$ is selected from a 4-6 membered heterocyclyl and $C_1$-$C_6$ alkyl optionally substituted with halogen, OH, $OCH_3$, $C_3$-$C_6$ cycloalkyl or a 4-6 membered heterocyclyl;

$R^f$ is $C_1$-$C_6$ alkyl; and $R^g$ and $R^h$ are independently selected from hydrogen and $C_1$-$C_5$ alkyl optionally substituted with halogen, or $R^g$ and $R^h$ together with the nitrogen to which they are attached form a 4 to 6 membered heterocyclic ring.

2. A compound of claim 1 selected from Formula I:

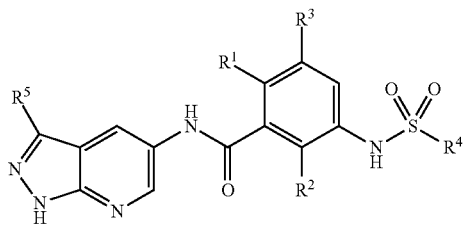

I and stereoisomers, tautomers and pharmaceutically acceptable salts thereof, wherein:
$R^1$ and $R^2$ are independently selected from hydrogen, halogen, CN, $C_1$-$C_3$ alkyl, and $C_1$-$C_3$ alkoxy;
$R^3$ is hydrogen, halogen, or $C_1$-$C_3$ alkyl;
$R^4$ is $C_3$-$C_5$ cycloalkyl, $C_1$-$C_6$ alkyl, $C_1$-$C_6$ alkenyl, or $C_1$-$C_6$ alkynyl, wherein the cycloalkyl, alkyl, alkenyl and alkynyl are optionally substituted with $OR^c$, halogen or $C_3$-$C_4$ cycloalkyl;

$R^5$ is hydrogen, halogen, CN, $NR^cR^d$, $OR^e$, phenyl optionally substituted with one to three $R^a$ groups, a 5-6 membered heteroaryl optionally substituted with $C_1$-$C_4$ alkyl, a saturated or partially unsaturated $C_3$-$C_6$ cycloalkyl optionally substituted with halogen or $C_1$-$C_4$ alkyl, a saturated or partially unsaturated 5-6 membered heterocyclyl, $C_2$-$C_6$ alkynyl optionally substituted with $OR^c$, $C_2$-$C_6$ alkenyl optionally substituted with $OR^c$, or $C_1$-$C_6$ alkyl optionally substituted with one to three $R^b$ groups;

each $R^a$ is independently selected from halogen, $CF_3$, $C_1$-$C_4$ alkyl or —O($C_1$-$C_4$ alkyl), wherein the alkyl or alkoxy are optionally substituted with OH, $NR^cR^d$ or a 5-6 membered heterocyclyl optionally substituted with $C_1$-$C_3$ alkyl;

each $R^b$ is independently selected from halogen, OH, $OCH_3$, oxo or —$NR^cR^d$;

each $R^c$ and $R^d$ are independently selected from hydrogen and $C_1$-$C_4$ alkyl; and $R^e$ is $C_1$-$C_6$ alkyl optionally substituted with halogen or $C_3$-$C_6$ cycloalkyl.

3. A compound of claim 2, wherein:
$R^1$, $R^2$ and $R^3$ are independently selected from hydrogen, halogen or $C_1$-$C_3$ alkyl;
$R^4$ is $C_3$-$C_4$ cycloalkyl or $C_1$-$C_6$ alkyl optionally substituted with OH, halogen or $C_3$-$C_4$ cycloalkyl;
$R^5$ is hydrogen, halogen, CN, $NR^cR^d$, $OR^e$, phenyl optionally substituted with one to three $R^a$ groups, 5 or 6 membered heteroaryl optionally substituted with $C_1$-$C_4$ alkyl, $C_3$-$C_6$ cycloalkyl, 5 or 6 membered heterocyclyl, $C_2$-$C_6$ alkenyl, or $C_1$-$C_6$ alkyl optionally substituted with one to three $R^b$ groups;

each $R^a$ is independently selected from halogen, $CF_3$, $C_1$-$C_4$ alkyl or —O($C_1$-$C_4$ alkyl), wherein the alkyl or alkoxy are optionally substituted with OH, $NR^cR^d$, or a 5-6 membered heterocyclyl optionally substituted with $C_1$-$C_3$ alkyl;

each $R^b$ is independently selected from halogen, OH, $OCH_3$, oxo or —$NR^cR^d$;

$R^c$ and $R^d$ are independently selected from hydrogen and $C_1$-$C_4$ alkyl; and $R^e$ is $C_1$-$C_6$ alkyl optionally substituted with halogen or $C_3$-$C_6$ cycloalkyl.

4. A compound of claim 1, wherein $R^1$, $R^2$ and $R^3$ are independently selected from hydrogen, halogen or $C_1$-$C_3$ alkyl.

5. A compound of claim 1, wherein the residue:

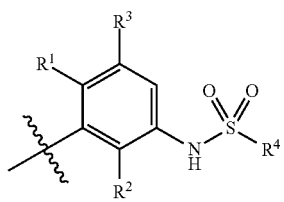

of Formula I, wherein the wavy line represents the point of attachment of the residue in Formula I, is selected from:

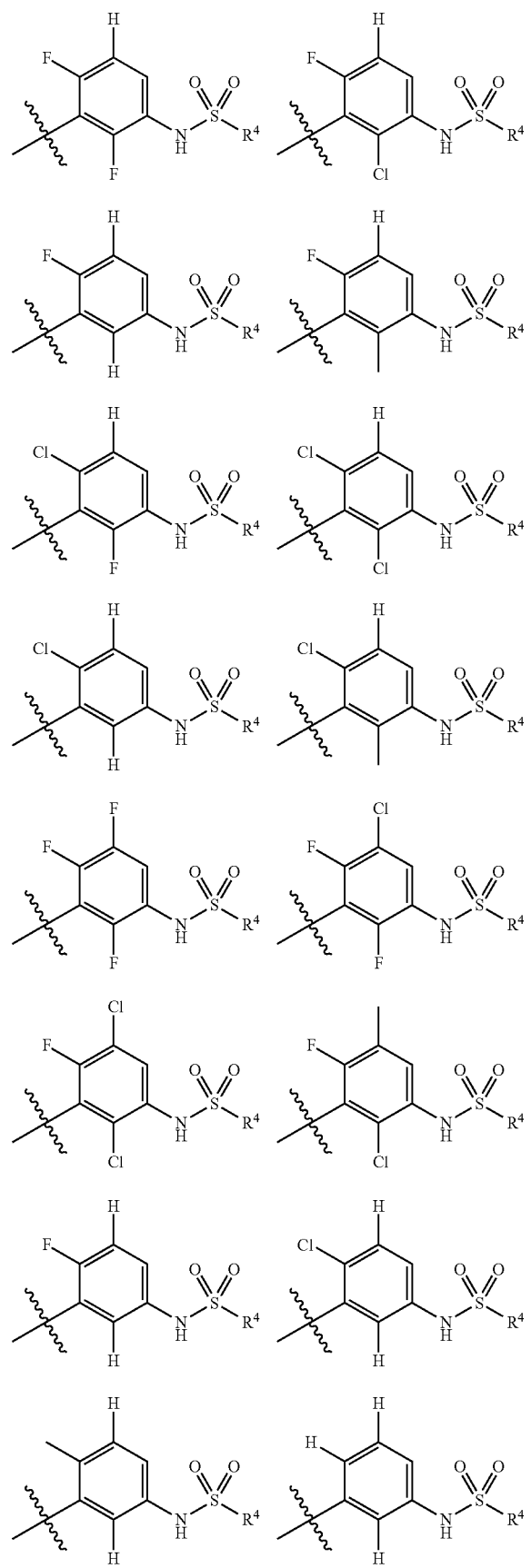
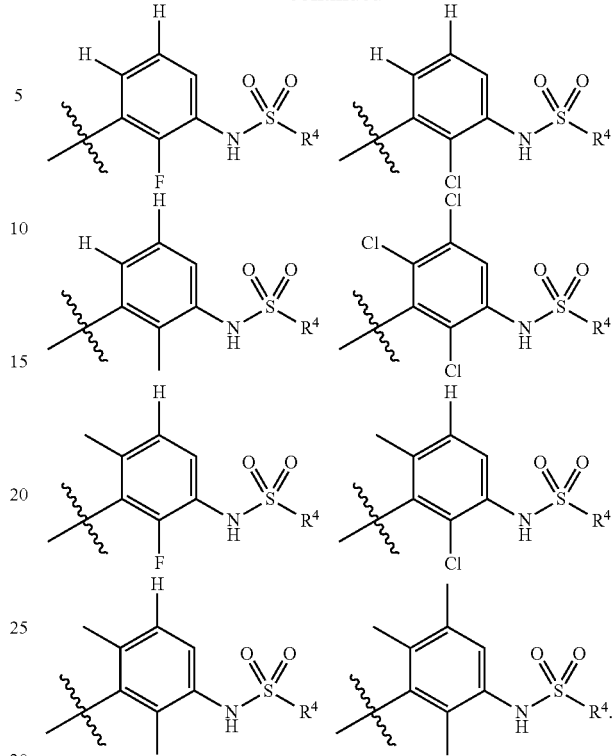

6. A compound of claim 5, wherein $R^1$ and $R^2$ are F and $R^3$ is hydrogen.

7. A compound of claim 5, wherein $R^1$, $R^2$ and $R^3$ are F.

8. A compound of claim 5, wherein $R^1$ is F and $R^2$ is Cl and $R^3$ is hydrogen.

9. A compound of claim 5, wherein $R^1$ is Cl and $R^2$ is F and $R^3$ is hydrogen.

10. A compound of claim 5, wherein $R^1$ is F and $R^2$ is methyl and $R^3$ is hydrogen.

11. A compound of claim 5, wherein $R^1$ is methyl and $R^2$ is F and $R^3$ is hydrogen.

12. A compound of claim 5, wherein $R^1$ is F and $R^2$ and $R^3$ are hydrogen.

13. A compound of claim 5, wherein $R^1$ is Cl and $R^2$ and $R^3$ are hydrogen.

14. A compound of claim 5, wherein $R^2$ is F and $R^1$ and $R^3$ are hydrogen.

15. A compound of claim 5, wherein $R^2$ and $R^3$ are F and $R^1$ is hydrogen.

16. A compound of claim 5, wherein $R^4$ is propyl, butyl, isobutyl, —$CH_2Cl$, —$CH_2CF_3$, —$CH_2CH_2CH_2F$, —$CH_2CH_2CF_3$ or cyclopropylmethyl.

17. A compound of claim 16, wherein $R^4$ is propyl.

18. A compound of claim 5, wherein $R^4$ is —$CF_3$, —$CH_2CF_3$, —$CH_2CH_2CH_2F$, —$CH_2CH_2CF_3$, —$CF_2CF_3$ or —$CF_2CF_2CF_3$.

19. A compound of claim 1, wherein $R^4$ is cyclopropyl, ethyl, propyl, butyl, isobutyl, —$CH_2CH_2CH_2OH$, —$CH_2Cl$, —$CH_2CF_3$, —$CH_2CH_2CH_2F$, —$CH_2CH_2CF_3$, phenylmethyl, cyclopropylmethyl, phenyl, 2-fluorophenyl, 3-fluorophenyl, 4-fluorophenyl, 2,5-difluorophenyl, 4-chloro-3-trifluoromethylphenyl, 1-methyl-1H-imidazol-4-yl, furan-2-yl, pyridin-2-yl, pyridin-3-yl, thiophen-2-yl, —$NHCH_2CH_3$, —$NHCH_2CH_2CH_3$, —$N(CH_3)CH_2CH_3$, —$NHCH(CH_3)_2$, —$NHCH_2CHF_2$, —$N(CH_3)_2$ or pyrrolidin-1-yl.

20. A compound of claim 19, wherein $R^4$ is cyclopropyl, ethyl, propyl, isobutyl, —CH$_2$CH$_2$CH$_2$OH, —CH$_2$CH$_2$CH$_2$F, phenylmethyl, cyclopropylmethyl, phenyl, 2-fluorophenyl, 3-fluorophenyl, 4-fluorophenyl, 2,5-difluorophenyl, 4-chloro-3-trifluoromethylphenyl, 1-methyl-1H-imidazol-4-yl, furan-2-yl, pyridin-2-yl, pyridin-3-yl, thiophen-2-yl or —NHCH$_2$CH$_3$.

21. A compound of claim 1, wherein $R^5$ is hydrogen.
22. A compound of claim 1, wherein $R^5$ is halogen.
23. A compound of claim 1, wherein $R^5$ is NR$^c$R$^d$.
24. A compound of claim 1, wherein $R^5$ is OR$^e$.
25. A compound of claim 1, wherein $R^5$ is phenyl optionally substituted with one to three R$^a$ groups.
26. A compound of claim 1, wherein $R^5$ is a 5-6 membered heteroaryl optionally substituted with C$_1$-C$_4$ alkyl, wherein the heteroaryl is selected from pyridine, pyrazole and furan.
27. A compound of claim 1, wherein $R^5$ is a saturated C$_3$-C$_6$ cycloalkyl selected from cyclopropyl, cyclobutyl and cyclopentyl.
28. A compound of claim 1, wherein $R^5$ is a saturated 5-6 membered heterocyclyl selected from piperidine and morpholine.
29. A compound of claim 1, wherein $R^5$ is C$_2$-C$_6$ alkenyl.
30. A compound of claim 1, wherein $R^5$ is C$_1$-C$_6$ alkyl optionally substituted with one to three R$^b$ groups.
31. A compound of claim 1, wherein $R^5$ is selected from hydrogen, Br, I, CN, methylamino, dimethylamino, diethylamino, isopropylamino, phenylamino, —NHC(=O)CH$_3$, methoxy, ethoxy, propoxy, isopropoxy, 2-methoxyethoxy, 2-fluoroethoxy, 2,2,2-trifluoroethoxy, 2-hydroxyethoxy, oxetan-3-yloxy, 3-hydroxypropoxy, cyclobutylmethoxy, oxetan-3-ylmethoxy, tetrahydrofuran-3yloxy, methylthio, ethylthio, phenyl, 3-chlorophenyl, 4-chlorophenyl, 3-fluorophenyl, 4-fluorophenyl, 4-trifluoromethylphenyl, 3-((dimethylamino)methyl)phenyl, 3-(2-(dimethylamino)ethoxy)phenyl, 4-(2-(dimethylamino)ethoxy)phenyl, 3-((2,2-dimethyl-1,3-dioxolan-4-yl)methoxy)phenyl, 3-(2,3-dihydroxypropoxy)phenyl, 3-(morpholinomethyl)phenyl, 3-(piperidin-1-ylmethyl)phenyl, 2,3-difluorophenyl, 3,4-difluorophenyl, 3,5-difluorophenyl, pyridin-2-yl, pyridin-3-yl, pyridin-4-yl, 1-methyl-1H-pyrazol-4-yl, furan-2-yl, 1H-imidazol-1-yl, cyclopropyl, cyclobutyl, cyclopentyl, 2,2-difluorocyclopropyl, 2-methylcyclopropyl, azetidin-3-yl, 1-methylazetidin-3-yl, tetrahydrofuran-3-yl, pyrrolidin-1-yl, piperidin-4-yl, morpholino, 4-methylpiperazin-1-yl, 1-methyl-1,2,3,6-tetrahydropyridin-4-yl, —C≡CCH$_2$N(CH$_2$CH$_3$)$_2$, —CH=CH$_2$, methyl, ethyl, propyl, isopropyl, isobutyl, —CH$_2$CH$_2$CH$_2$OH, —CH$_2$CH$_2$CH$_2$N(CH$_3$)$_2$, —CH$_2$C(=O)OCH$_3$, CF$_3$, —CH$_2$OH, 2,2,2-trifluoroethyl, —C(=O)CH$_3$, and —C(=O)cyclopropyl.

32. A compound of claim 1, wherein $R^5$ is SR$^f$.
33. A compound of claim 1, wherein $R^5$ is a saturated or partially unsaturated 4-6 membered heterocyclyl optionally substituted with C$_1$-C$_4$ alkyl.
34. A compound of Formula I as defined in claim 1 and having the structure:

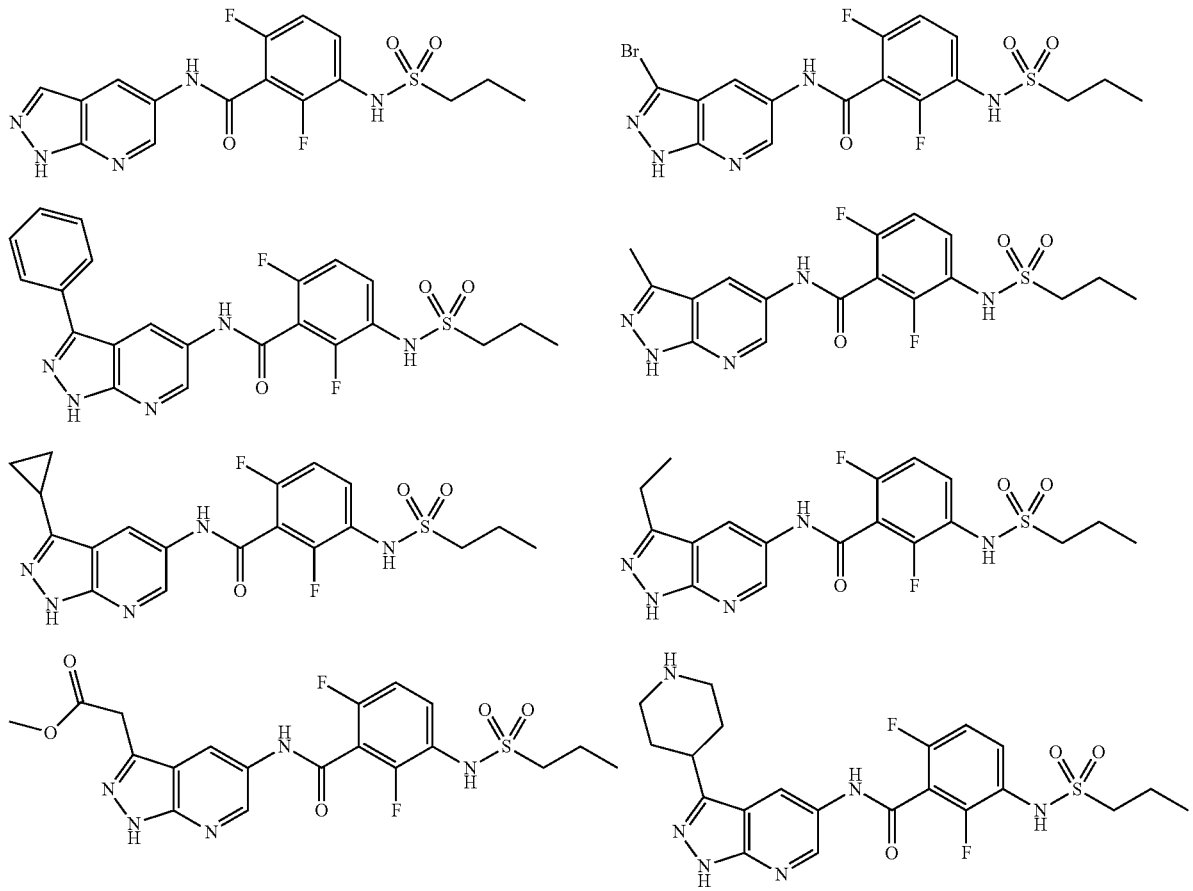

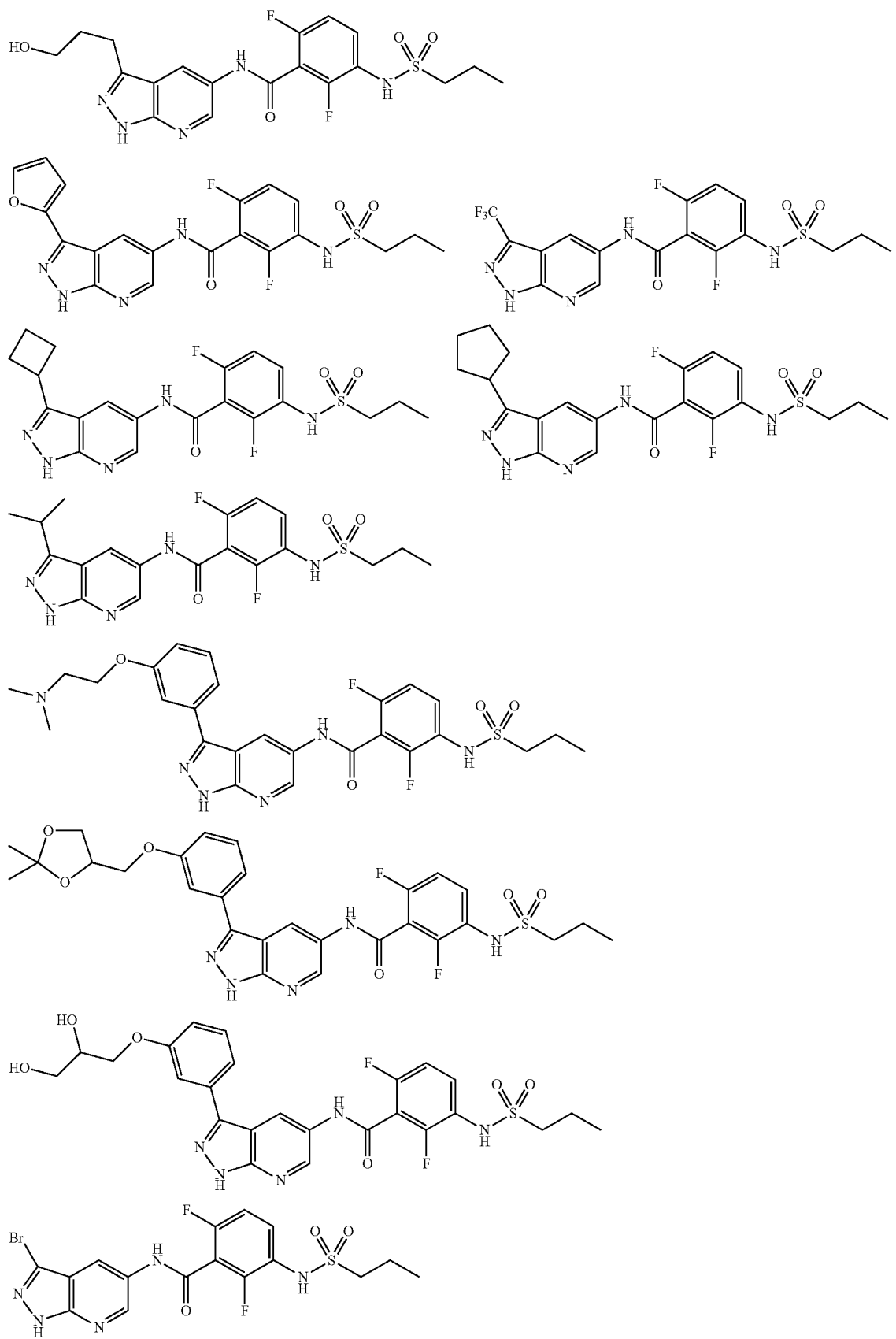

181 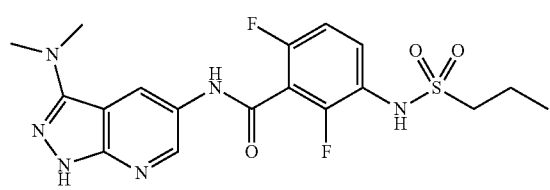 182 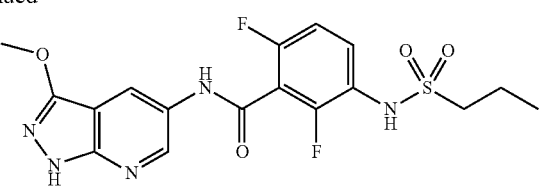
-continued
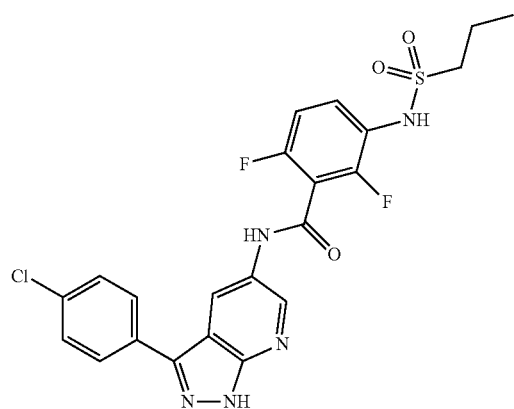 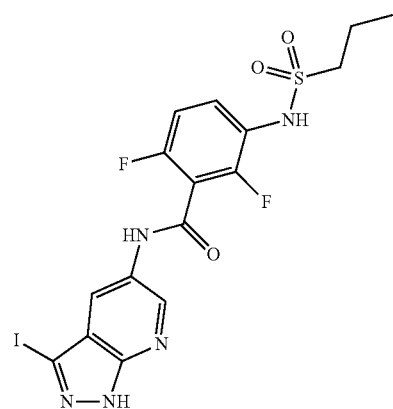
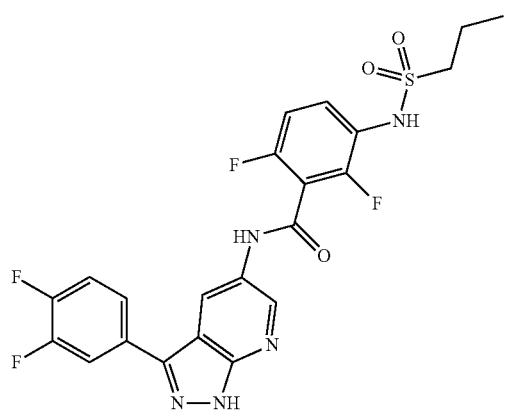 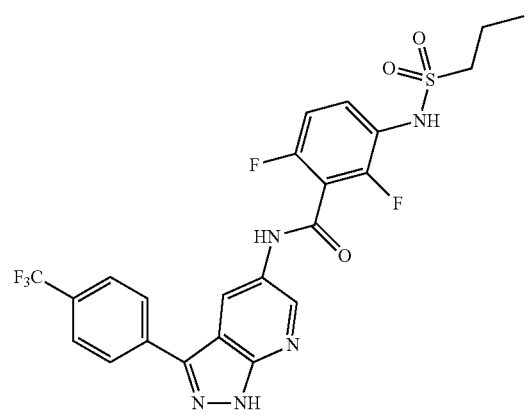
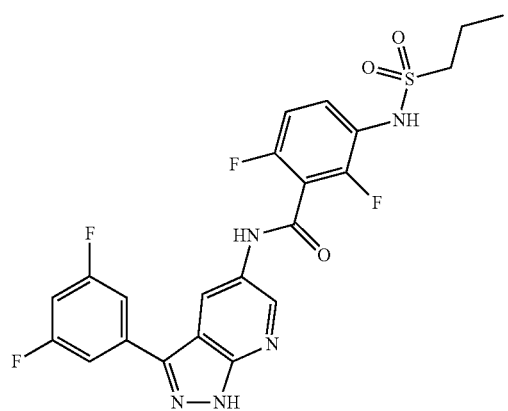 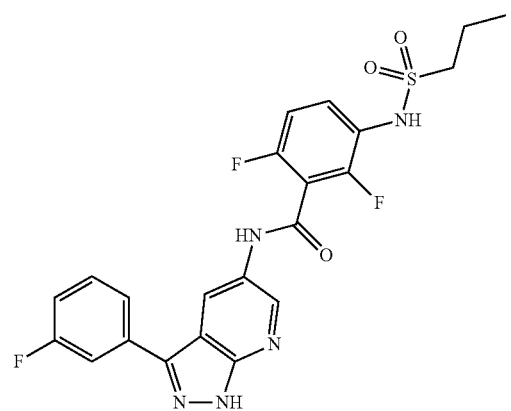

-continued
183 184
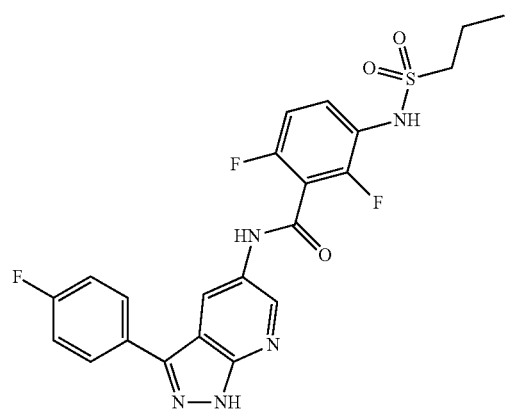
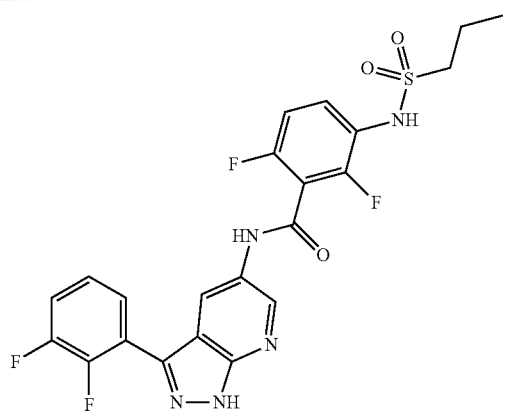
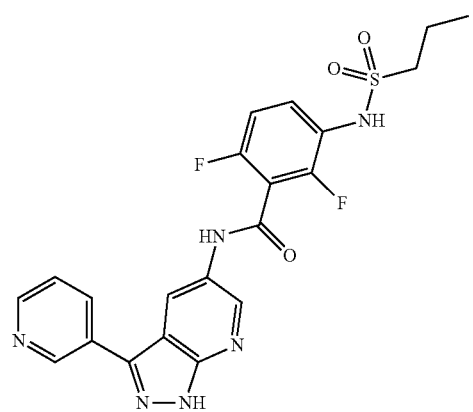
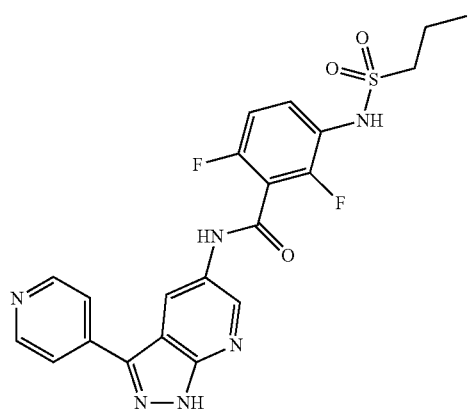
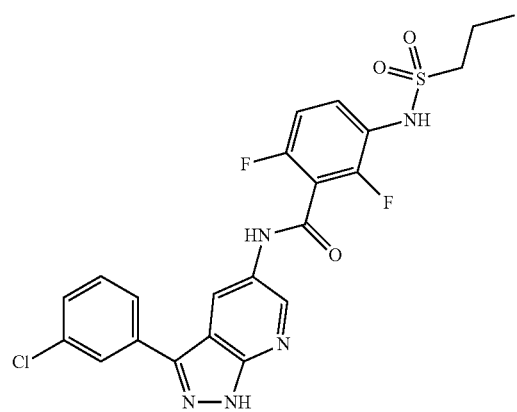
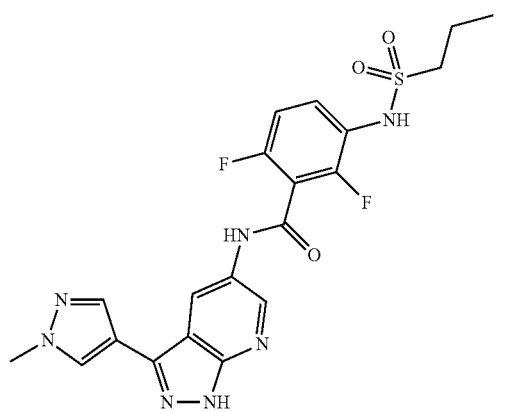
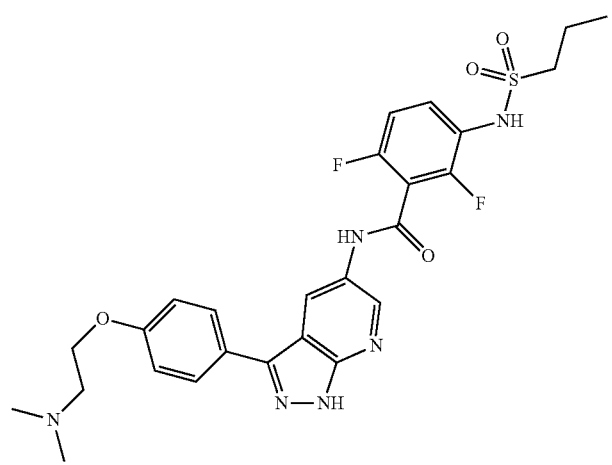
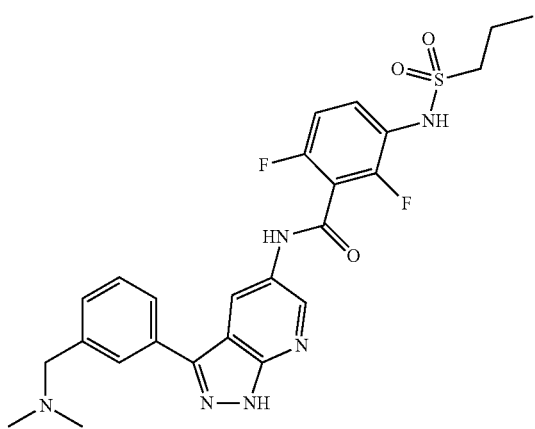

185
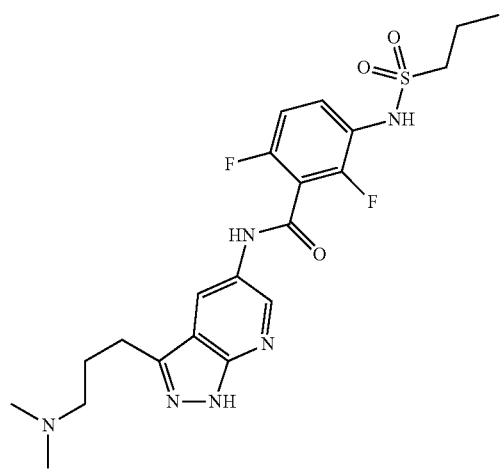
186
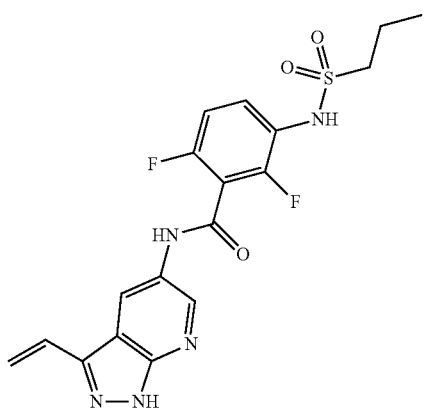
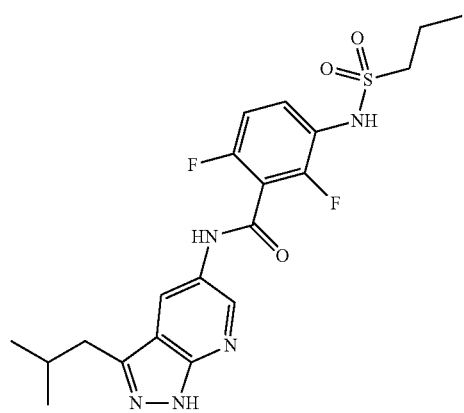
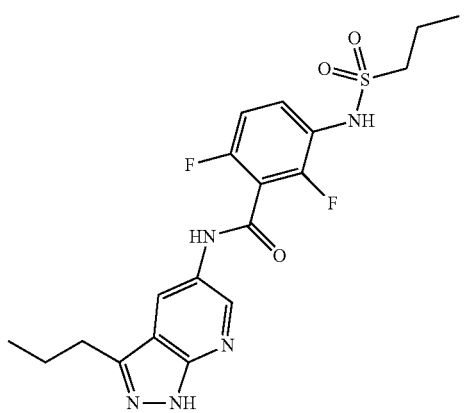
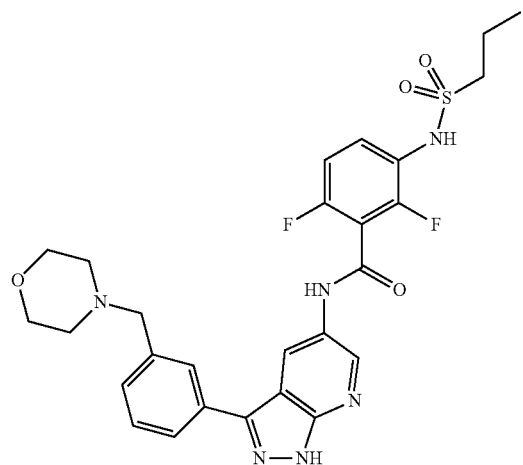
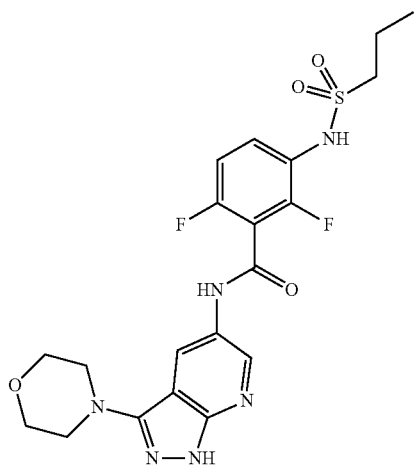

187
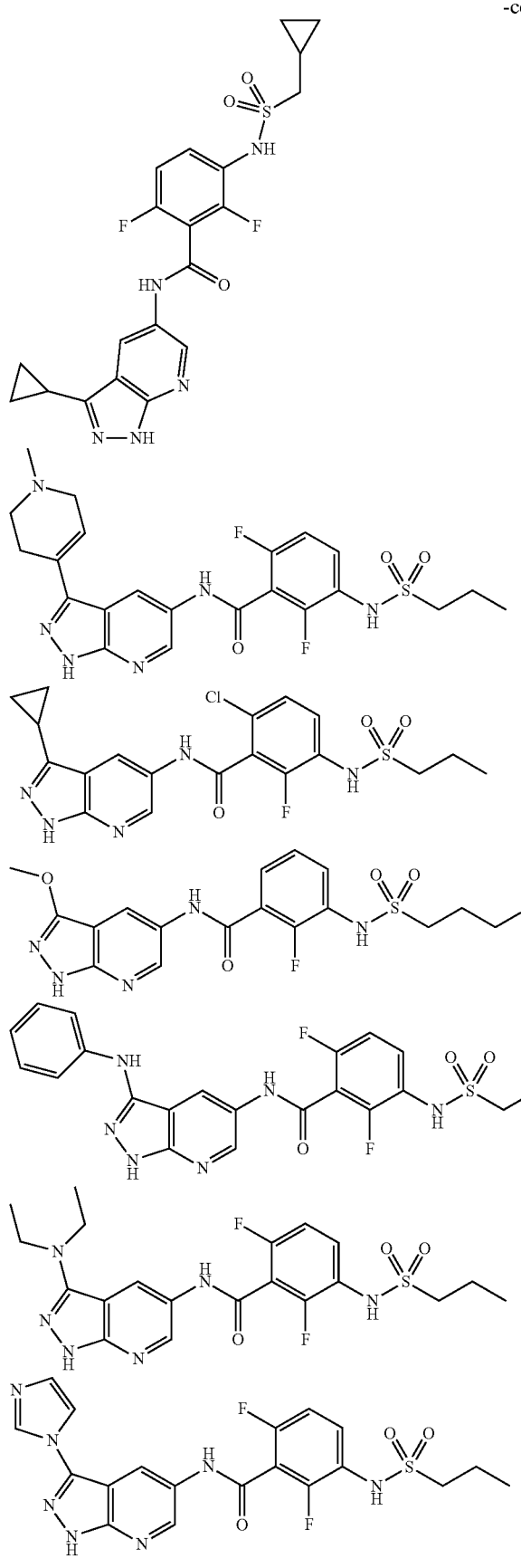
188
-continued
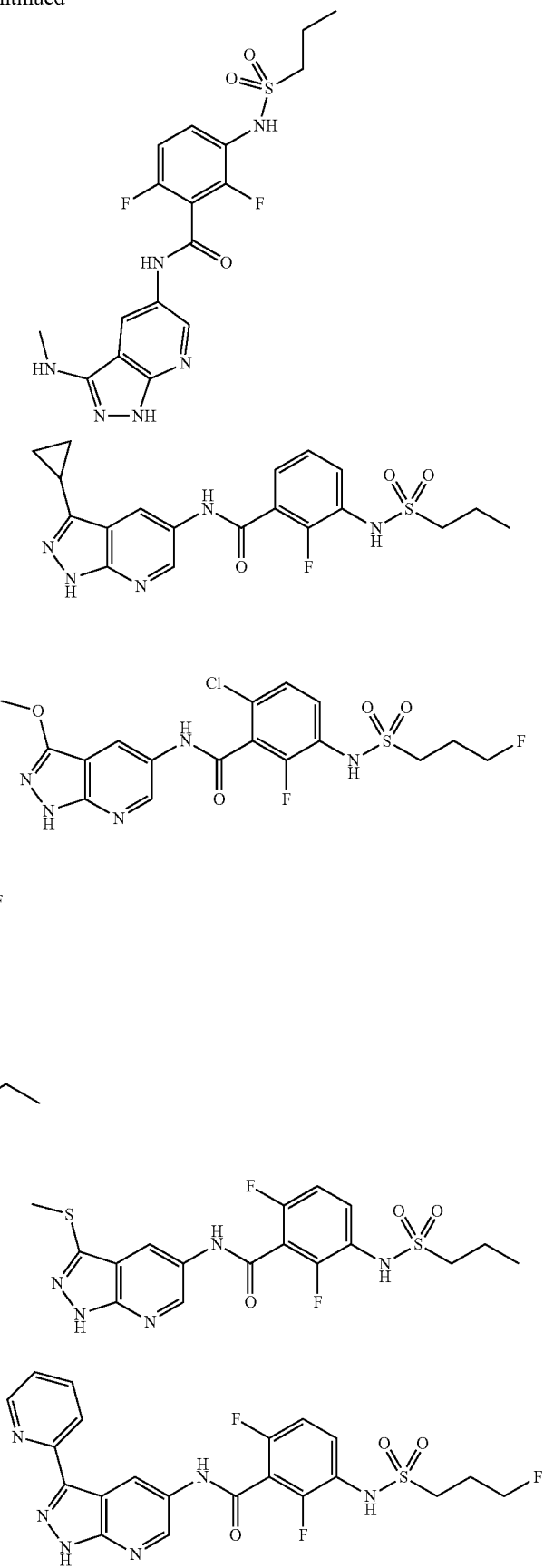

189 190
-continued
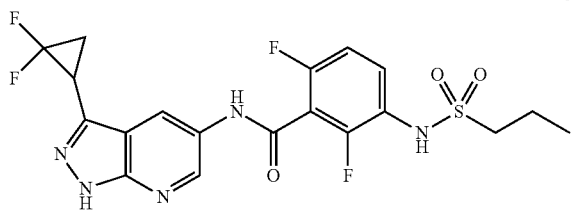
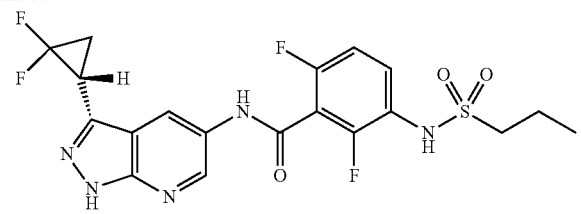
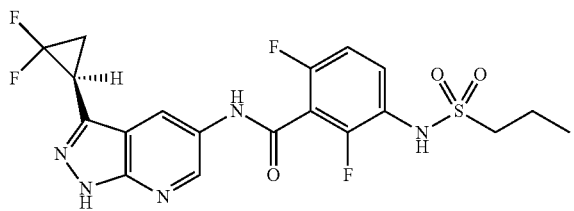
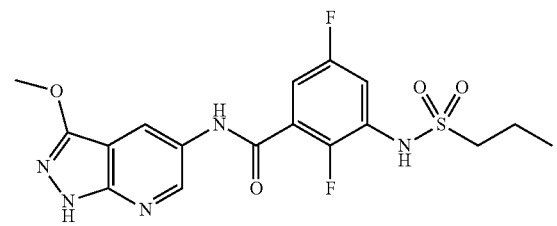
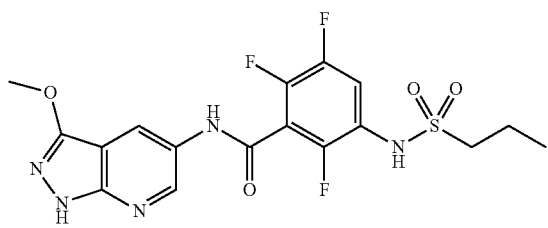
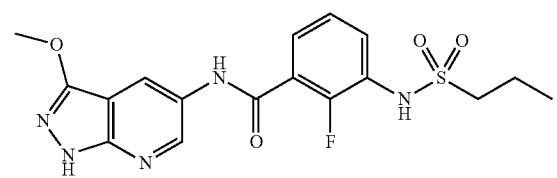
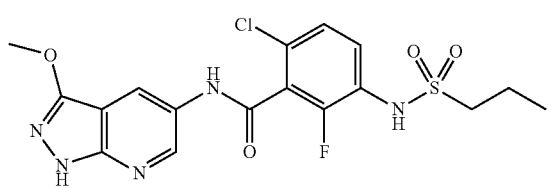
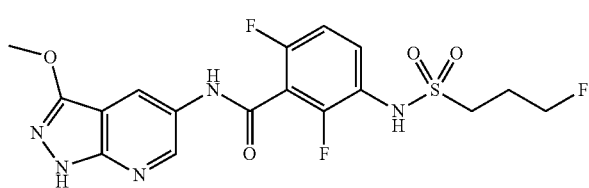
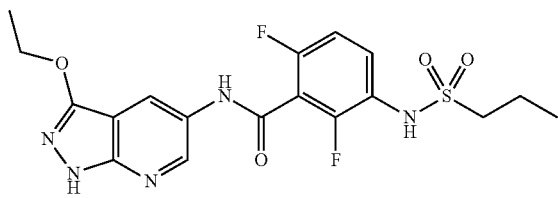
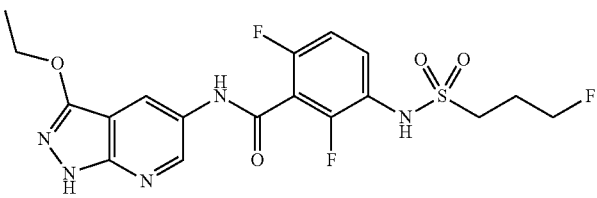
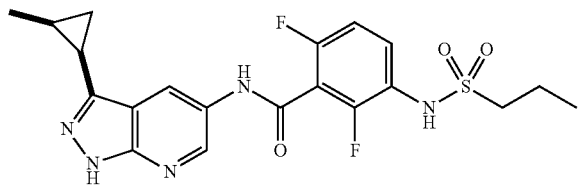
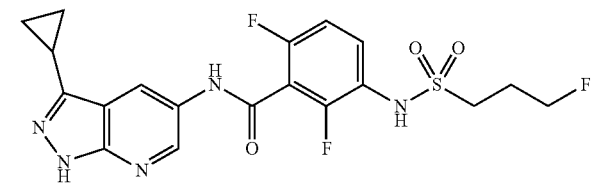
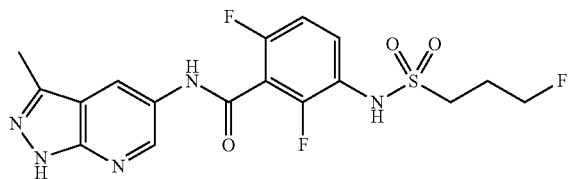
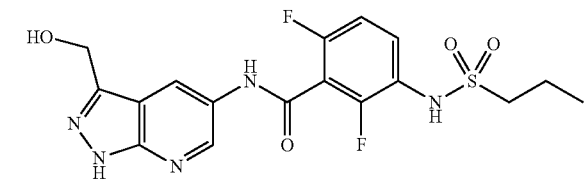
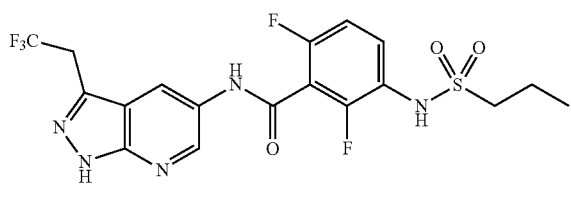
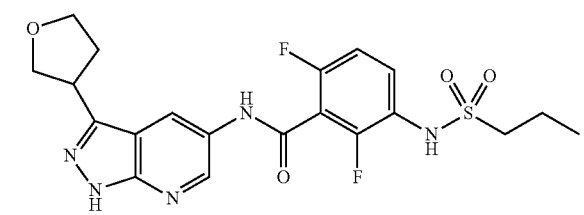

191
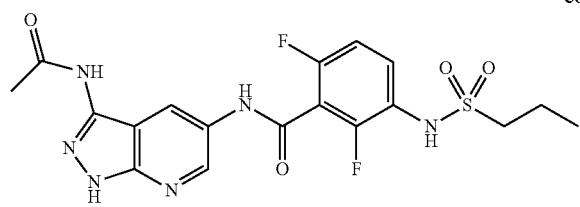
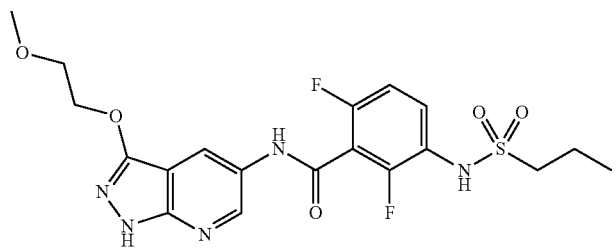
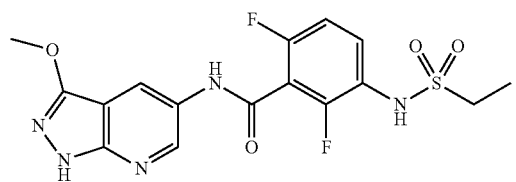
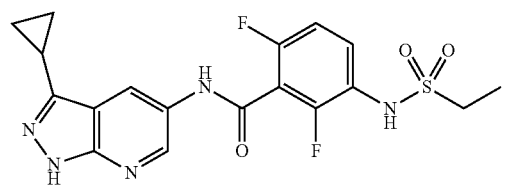
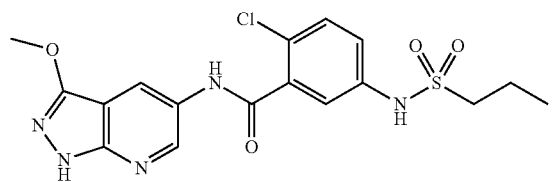
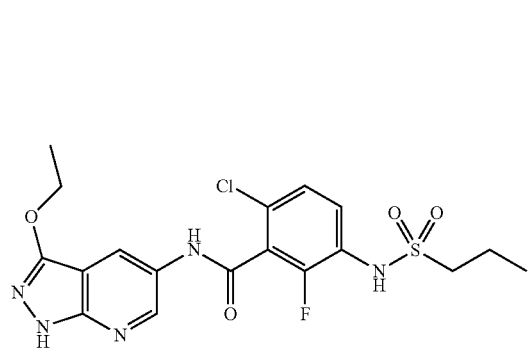
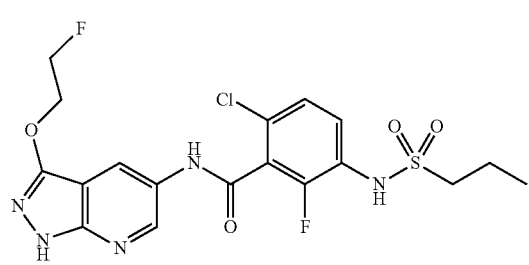
192
-continued
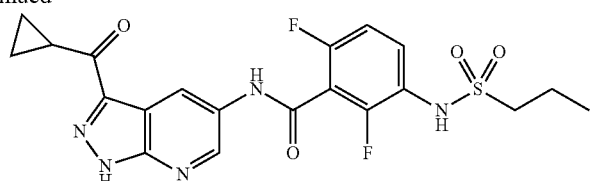
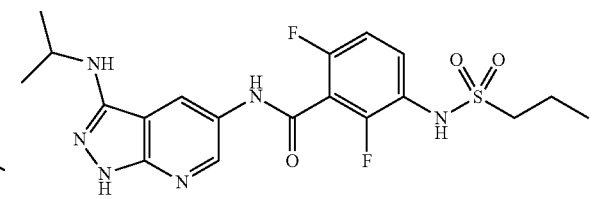
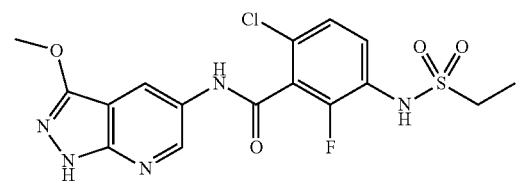
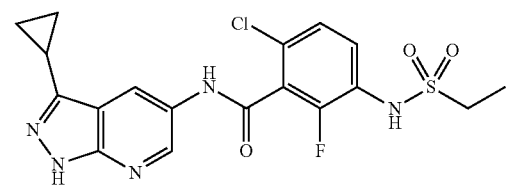
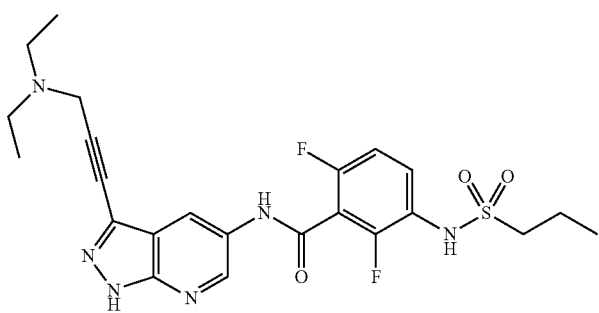
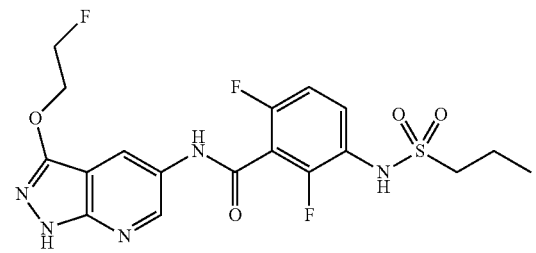
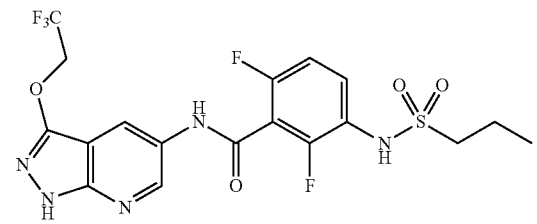

193 194
-continued
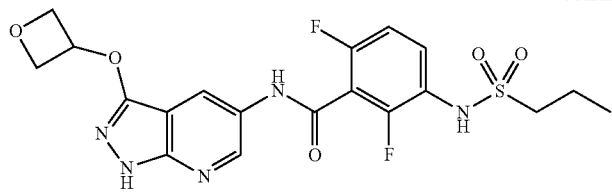
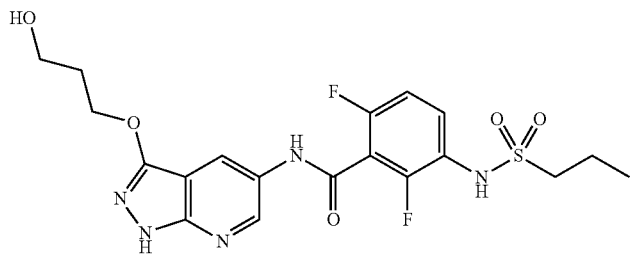
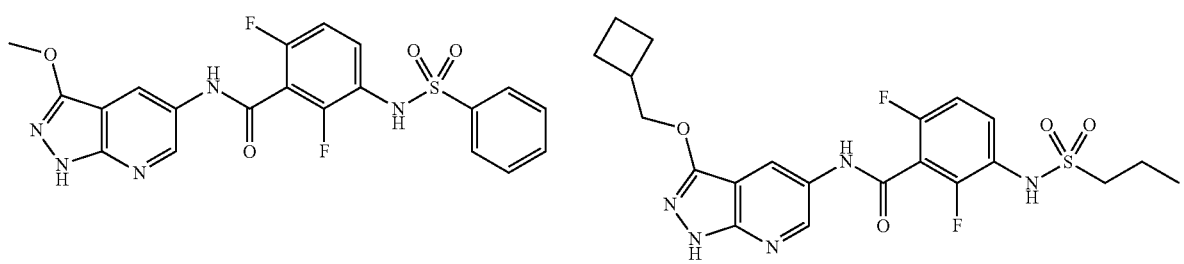
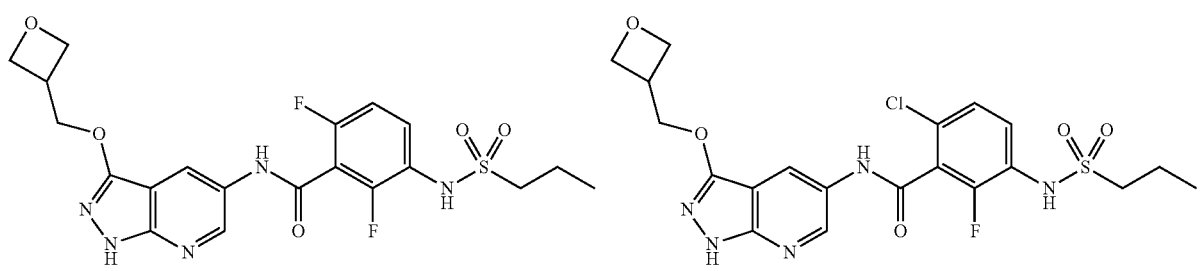
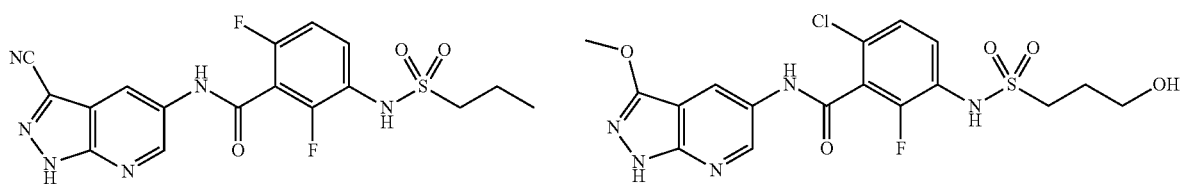
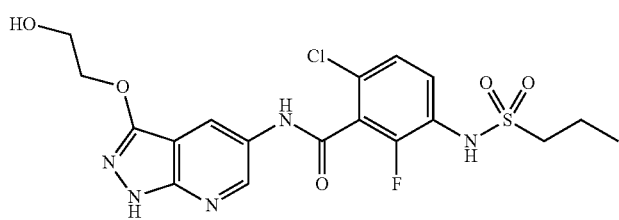
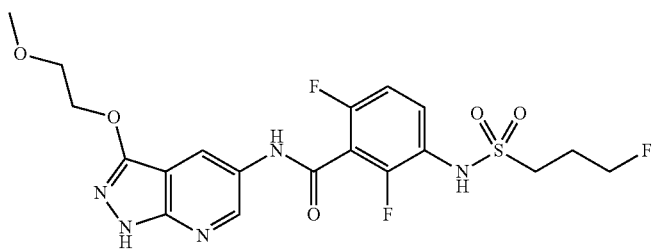

195 196
-continued
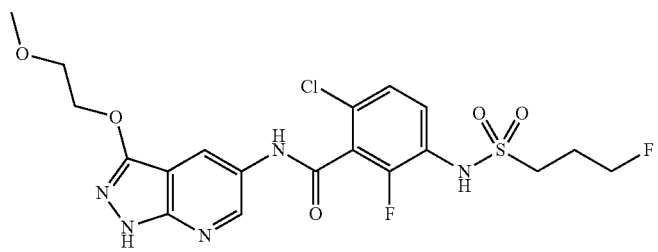
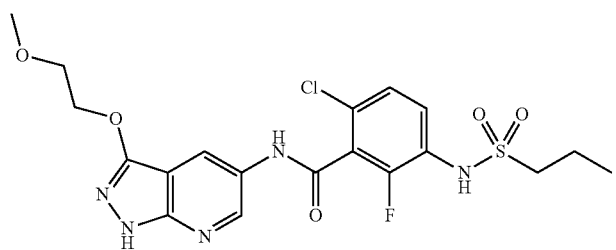
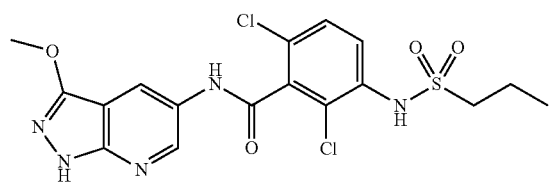
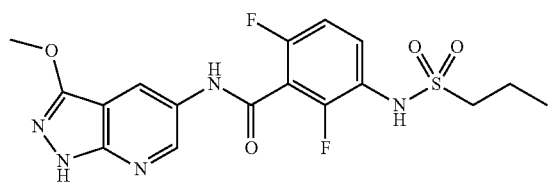
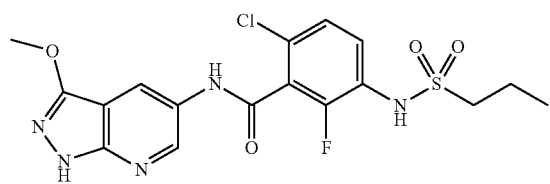
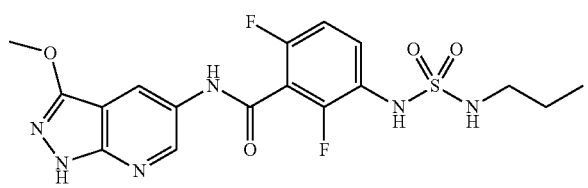
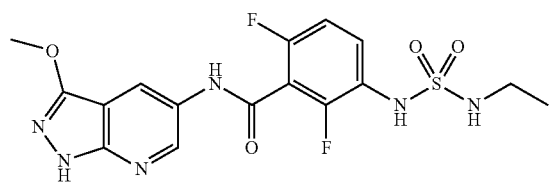
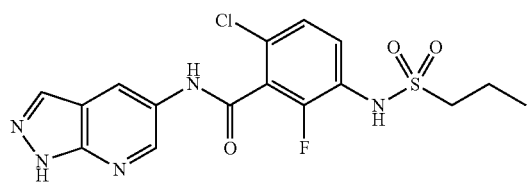
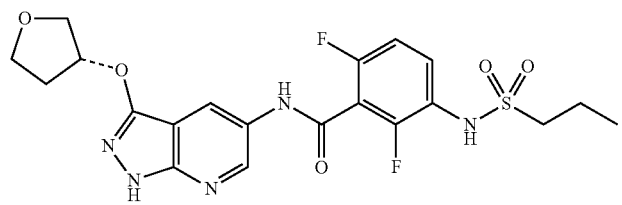
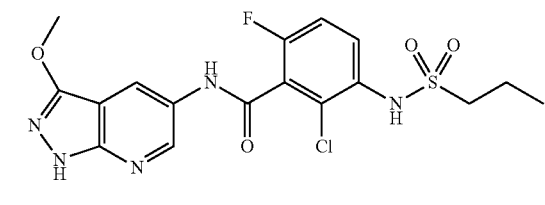
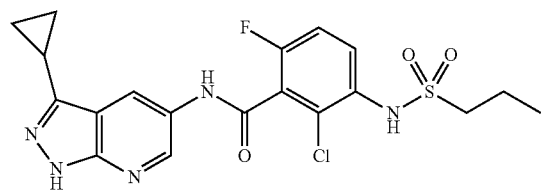
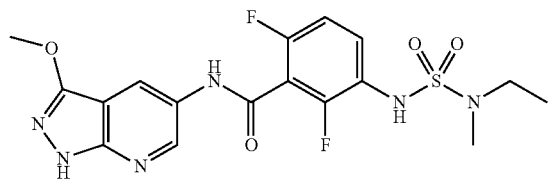

-continued
197
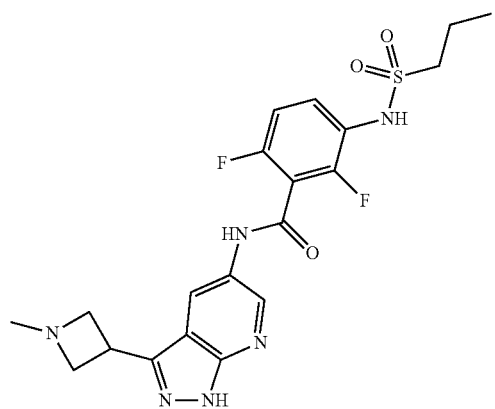
198
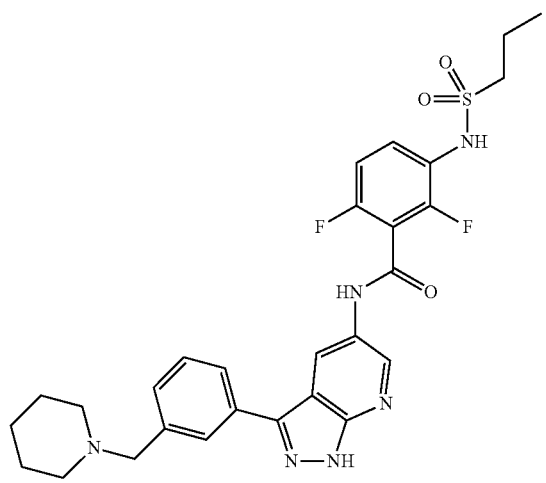
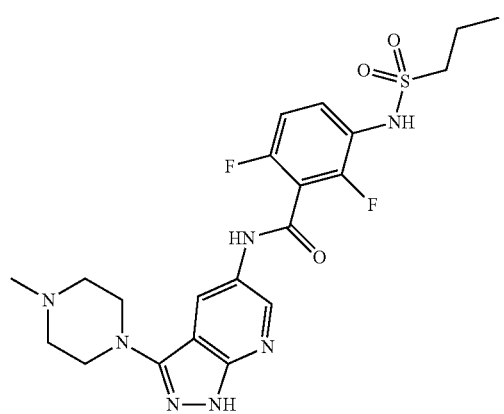
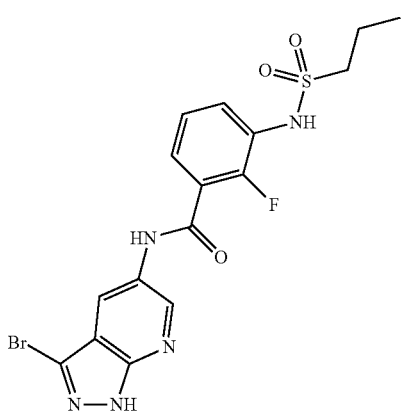
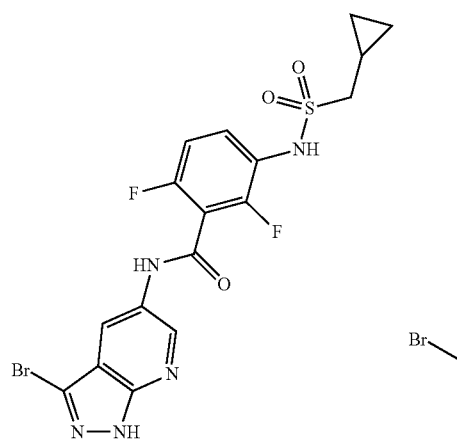
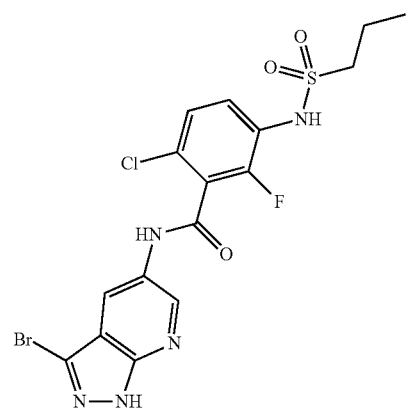
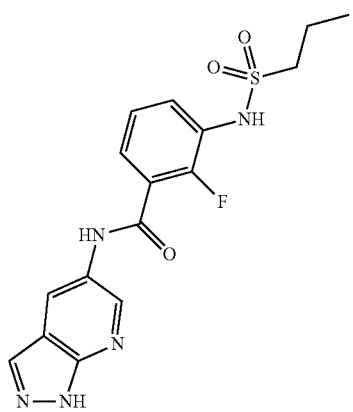

-continued
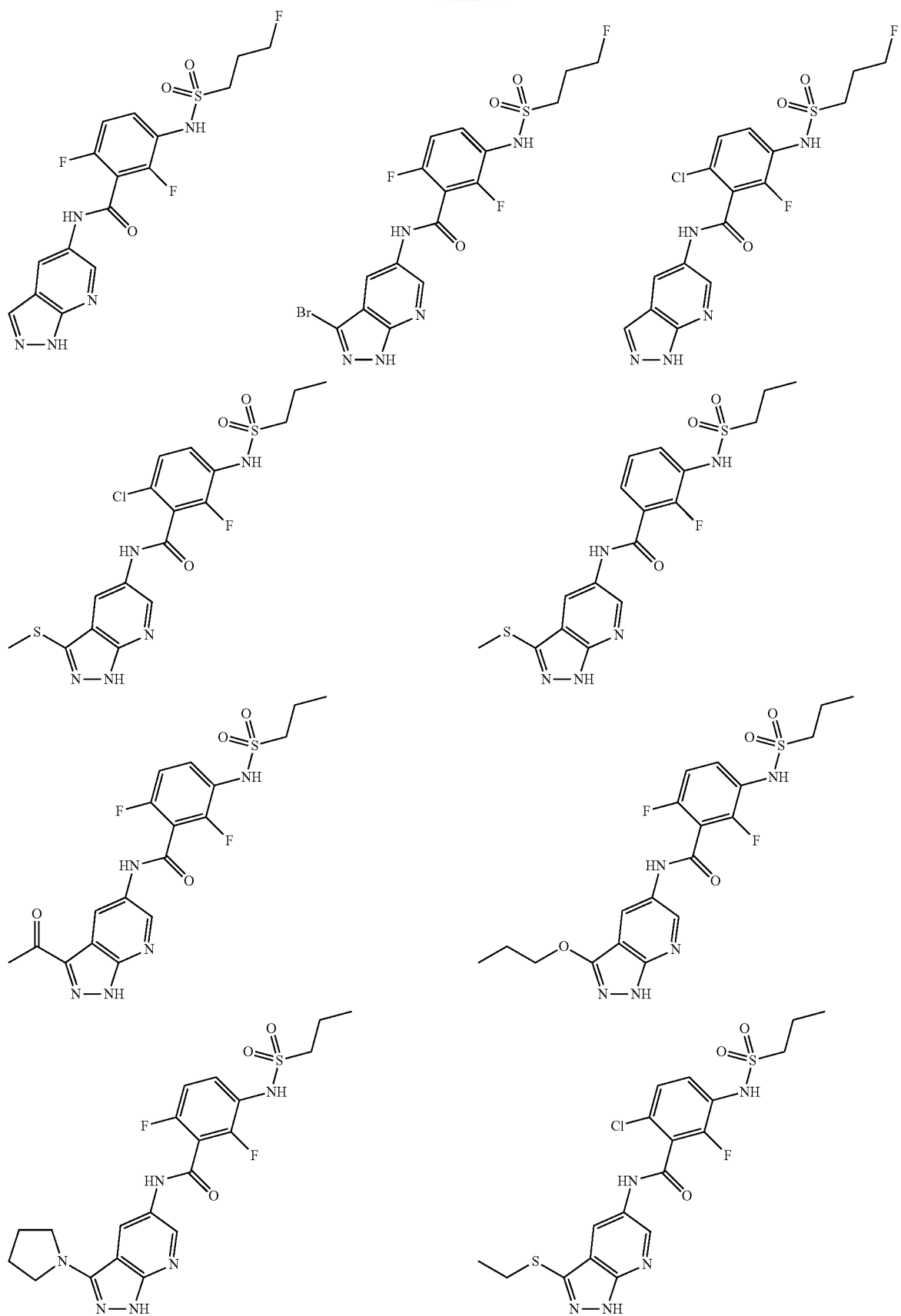

-continued
| 201 | 202 |
|---|---|
| 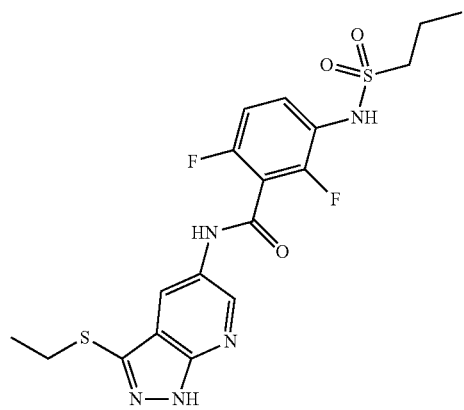 | 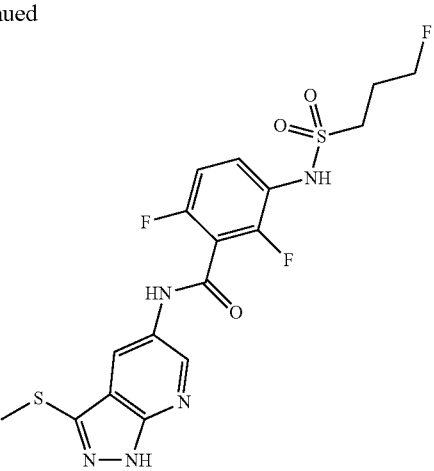 |
| 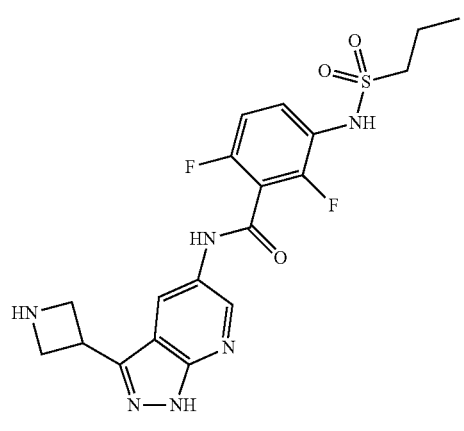 | 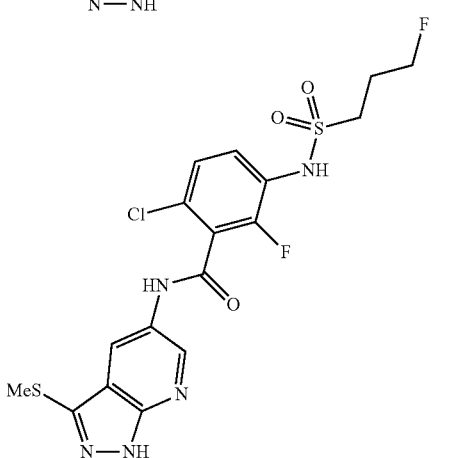 |
| 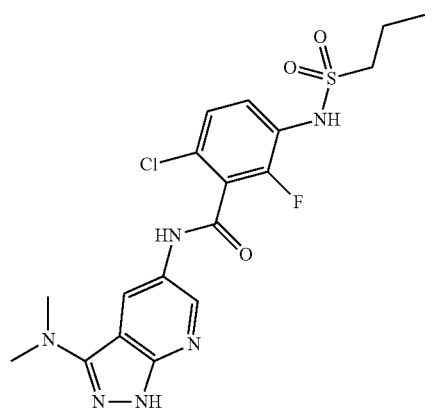 | 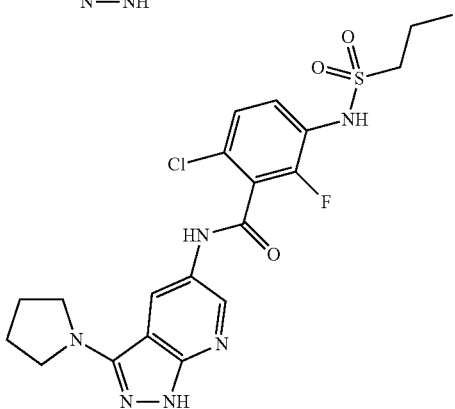 |
| 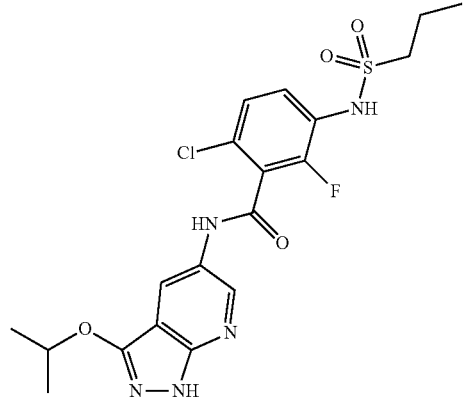 | 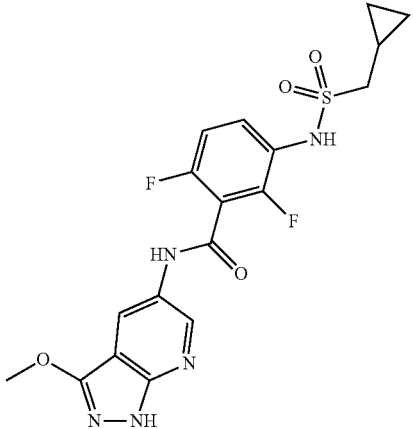 |

-continued
| 203 | 204 |
|---|---|
| 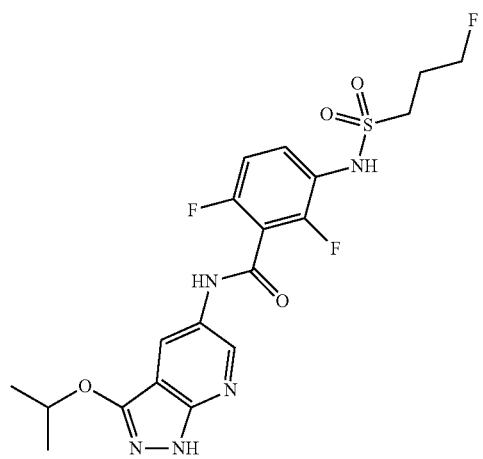 | 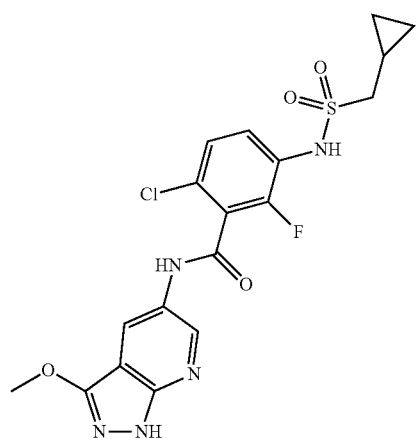 |
| 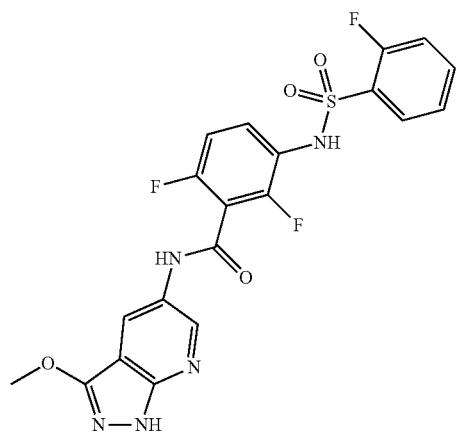 | 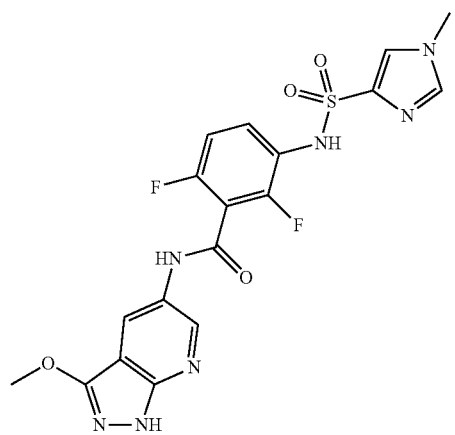 |
| 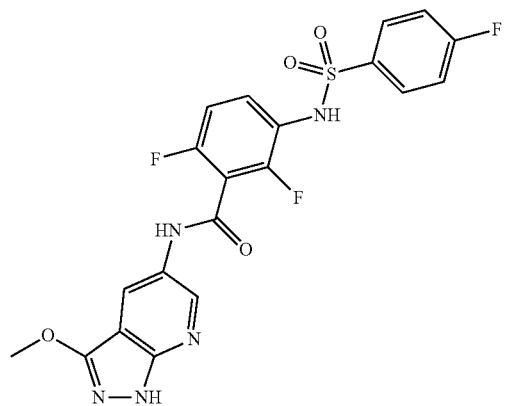 | 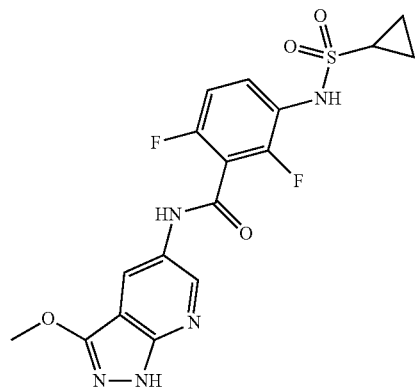 |
| 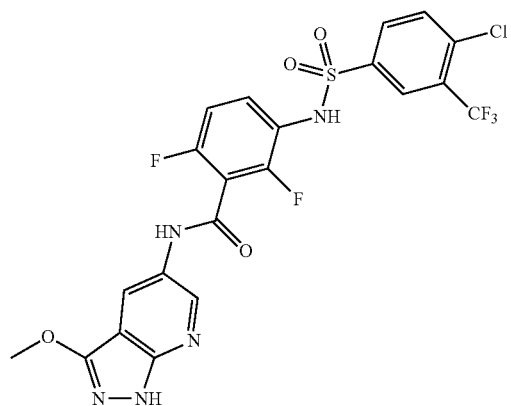 | 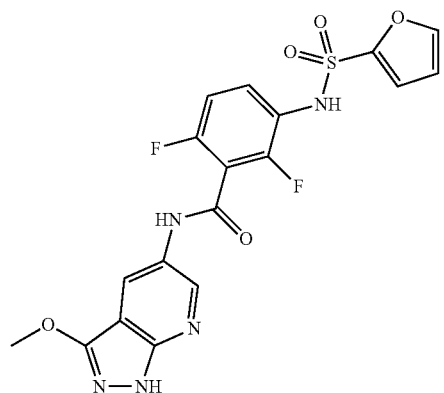 |

205
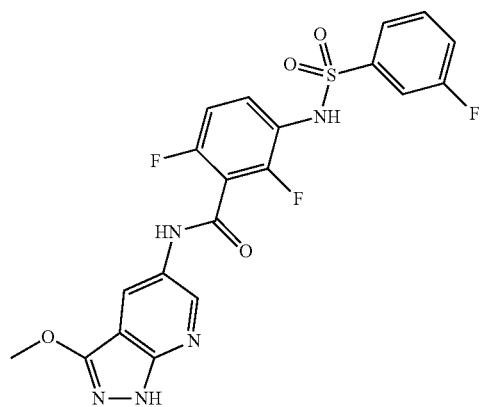
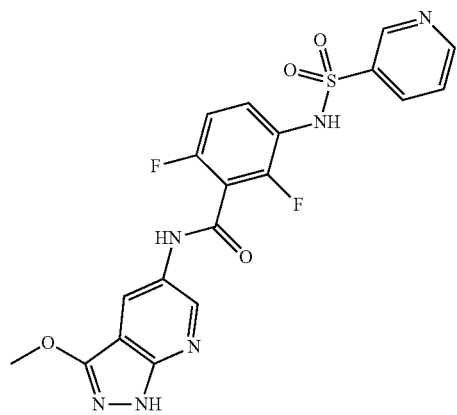
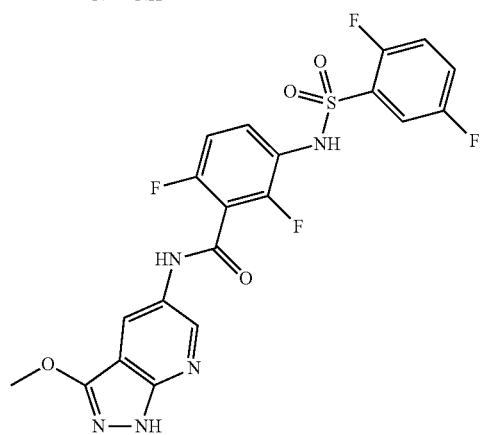
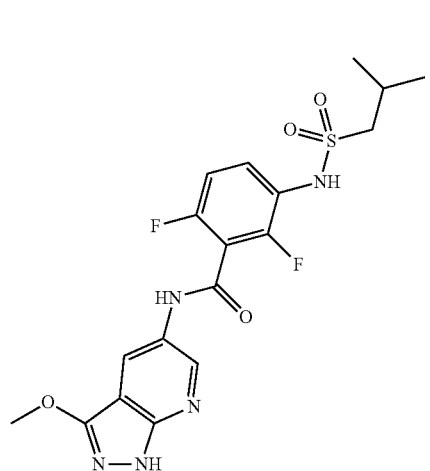
206
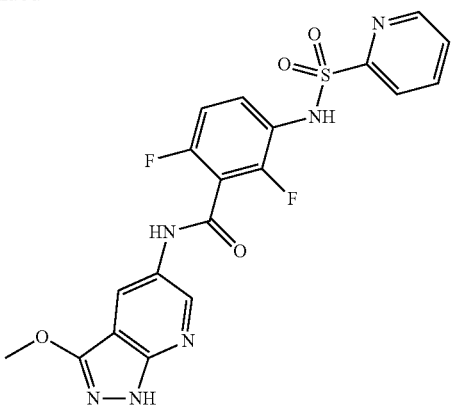
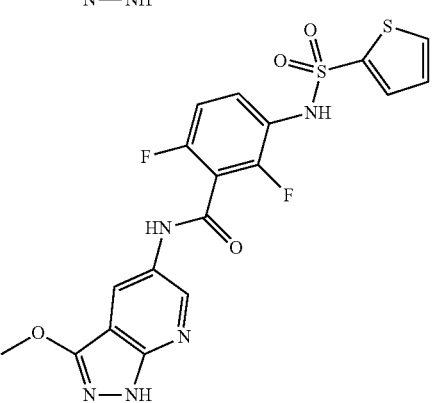
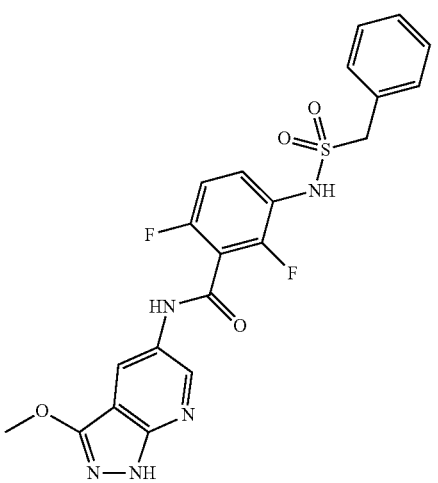
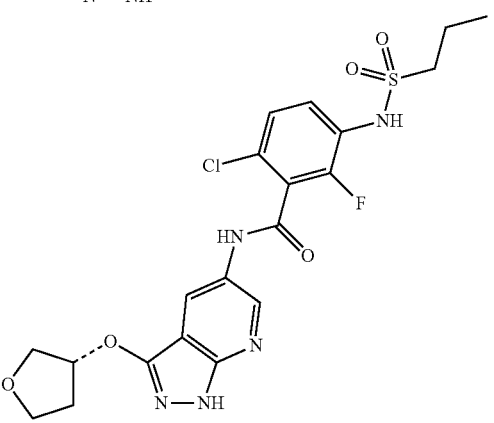

-continued

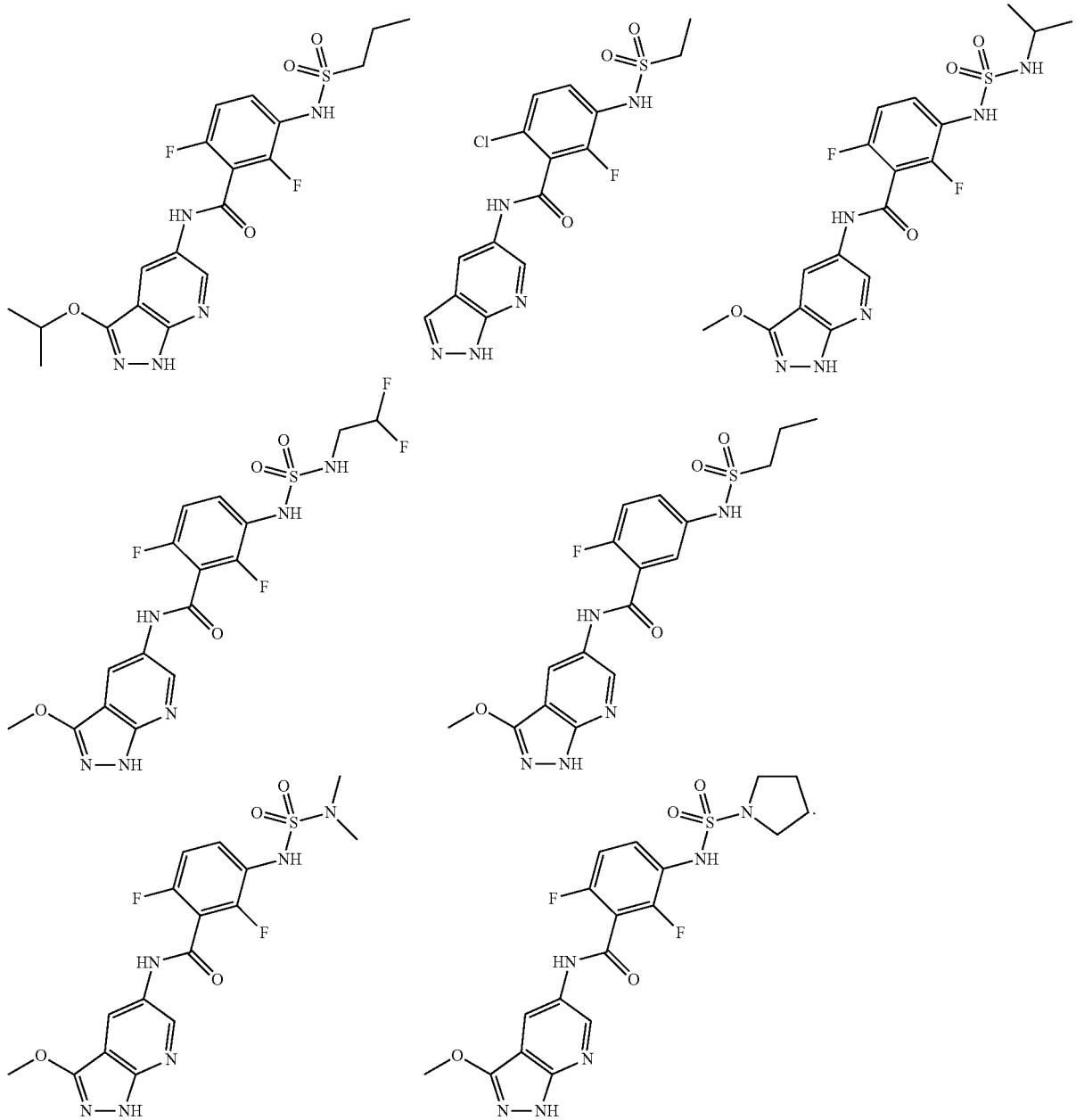

35. A pharmaceutical composition, comprising a compound as claimed in of claim 1, and a pharmaceutically acceptable carrier or excipient.

36. A method of treating a disease or disorder modulated by b-Raf, comprising administering to a mammal having a disease or disorder modulated by b-Raf an effective amount of a compound of claim 1.

37. A method of treating cancer modulated by b-Raf, comprising administering to a mammal having cancer modulated by b-Raf an effective amount of a compound of claim 1, alone or in combination with one or more compounds having anticancer properties.

38. The method of claim 37, wherein the cancer is a sarcoma.

39. The method of claim 37, wherein the cancer is a carcinoma.

40. The method of claim 39, wherein the carcinoma is squamous cell carcinoma.

41. The method of claim 39, wherein the carcinoma is adenoma or adenocarcinoma.

42. The method of claim 37, wherein the cancer is breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

43. A method of treating a hyperproliferative disease modulated by b-Raf in a mammal having a hyperproliferative disease modulated by b-Raf, comprising administering a therapeutically effective amount of a compound of claim 1 to the mammal.

44. A method of treating kidney disease modulated by b-Raf, comprising administering to a mammal having kidney disease modulated by b-Raf an effective amount of a compound of claim 1, or a stereoisomer or pharmaceutically acceptable salt thereof, alone or in combination with one or more compounds.

45. The method of claim 44, wherein the kidney disease is polycystic kidney disease.

\* \* \* \* \*

UNITED STATES PATENT AND TRADEMARK OFFICE
CERTIFICATE OF CORRECTION

PATENT NO. : 8,394,795 B2  Page 1 of 1
APPLICATION NO. : 12/920050
DATED : March 12, 2013
INVENTOR(S) : Ahrendt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 235 days.

Signed and Sealed this
First Day of September, 2015

Michelle K. Lee
*Director of the United States Patent and Trademark Office*